US012503453B2

(12) United States Patent
Buhrlage et al.

(10) Patent No.: US 12,503,453 B2
(45) Date of Patent: Dec. 23, 2025

(54) USP7 INHIBITION

(71) Applicant: Dana-Farber Cancer Institute, Inc., Boston, MA (US)

(72) Inventors: Sara Buhrlage, Somerville, MA (US); Xiaoxi Liu, Burlington, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 910 days.

(21) Appl. No.: 17/286,219

(22) PCT Filed: Oct. 22, 2019

(86) PCT No.: PCT/US2019/057456
§ 371 (c)(1),
(2) Date: Apr. 16, 2021

(87) PCT Pub. No.: WO2020/086595
PCT Pub. Date: Apr. 30, 2020

(65) Prior Publication Data

US 2021/0347761 A1 Nov. 11, 2021

Related U.S. Application Data

(60) Provisional application No. 62/748,910, filed on Oct. 22, 2018.

(51) Int. Cl.
*C07D 401/14* (2006.01)
*A61P 35/00* (2006.01)
*C07D 401/06* (2006.01)
*C07D 417/14* (2006.01)

(52) U.S. Cl.
CPC ............ *C07D 401/14* (2013.01); *A61P 35/00* (2018.01); *C07D 401/06* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 11,465,983 | B2 | 10/2022 | Buhrlage et al. |
| 2009/0170881 | A1 | 7/2009 | Angibaud et al. |
| 2014/0371247 | A1 | 12/2014 | Colland et al. |
| 2016/0229833 | A1 | 8/2016 | Ioannidis et al. |
| 2016/0229872 | A1 | 8/2016 | Ioannidis et al. |
| 2018/0162835 | A1 | 6/2018 | Ioannidis et al. |
| 2020/0347031 | A1 | 11/2020 | Buhrlage et al. |
| 2023/0265070 | A1 | 8/2023 | Buhrlage et al. |

FOREIGN PATENT DOCUMENTS

| | | | |
|---|---|---|---|
| EP | 2565186 | A1 | 3/2013 |
| JP | H11171774 | A | 6/1999 |
| WO | WO-98/033792 | A1 | 8/1998 |
| WO | WO-99/53924 | A1 | 10/1999 |
| WO | WO-2007/147217 | A1 | 12/2007 |
| WO | WO-2013/030218 | A1 | 3/2013 |
| WO | WO-2016/109480 | A1 | 7/2016 |
| WO | WO-2016/109515 | A1 | 7/2016 |
| WO | WO-2016/126926 | A1 | 8/2016 |
| WO | WO-2018/020242 | A1 | 2/2018 |
| WO | WO-2018/073602 | A1 | 4/2018 |
| WO | WO-2020/086595 | A1 | 4/2020 |
| WO | WO-2020/086595 | A8 | 7/2020 |
| WO | WO-2023/003973 | A1 | 1/2023 |

OTHER PUBLICATIONS

Database Registry Chemical Abstracts Service, Accession No. RN 1797702-91-0, Entered STN: Jul. 9, 2015.
Database Registry Chemical Abstracts Service, Accession No. RN 1426340-65-9, Entered STN: Mar. 26, 2013.
International Search Report and Written Opinion for International Application No. PCT/US2018/052797 dated Dec. 11, 2018.
International Search Report and Written Opinion for International Application No. PCT/US19/57456 dated Feb. 6, 2020.
Invitation to Pay Additional Fees for International Application No. PCT/US19/57456 dated Dec. 17, 2019.
Database Registry Chemical Abstracts Service, Accession No. RN 1381443-96-4, Entered STN: Jul. 4, 2012.
Schauer et al., "Selective USP7 inhibition elicits cancer cell killing through a p53-dependent mechanism," Scientific Reports, 10:5324 (2020).
U.S. Appl. No. 16/650,727.
Extended European Search Report for EP Application No. 18862773.1 dated May 19, 2021.
Lamberto et al., "Structure-Guided Development of a Potent and Selective Non-Covalent Active-Site Inhibitor of USP7," Cell Chemical Biology, 24(1): 1490-1500 and e1-11 (2017).
Desroses et al., "The Next Step Forward in Ubiquitin-Specific Protease 7 Selective Inhibition" Cell Chemical Biology, 2017, 24(12), pp. 1429-1431.
Dowd et al., "Identification and Structure-Guided Development of Pyrimidinone Based USP7 Inhibitors", ACS Medicinal Chemistry Letters, vol. 9, No. 3, pp. 238-243 (2018).
Extended European Search Report for EP Application No. 19874929.3 dated Oct. 25, 2022.
Invitation to Pay Additional Fees for Application No. PCT/US2022/037756 dated Oct. 31, 2022.
Database Registry CAS, Accession No. RN 1381178-30-8, Entered STN: Jul. 4, 2012.
Database Registry CAS, Accession No. RN 1381291-50-4, Entered STN: Jul. 4, 2012.

(Continued)

*Primary Examiner* — James H Alstrum-Acevedo
*Assistant Examiner* — Lauren Wells
(74) *Attorney, Agent, or Firm* — Foley Hoag LLP; DeAnn F. Smith

(57) ABSTRACT

Disclosed herein are inhibitors of deubiquitinating (DUB) enzyme USP7 (Ubiquitin Specific Protease 7). Also provided are methods of treating a disease or disorder modulated by USP7.

18 Claims, 21 Drawing Sheets

Specification includes a Sequence Listing.

(56) References Cited

OTHER PUBLICATIONS

Database Registry CAS, Accession No. RN 1381349-24-1, Entered STN: Jul. 4, 2012.
Database Registry CAS, Accession No. RN 1381444-09-2, Entered STN: Jul. 4, 2012.
Database Registry CAS, Accession No. RN 1381507-17-0, Entered STN: Jul. 5, 2012.
Database Registry CAS, Accession No. RN 1381589-44-1, Entered STN: Jul. 5, 2012.
Database Registry CAS, Accession No. RN 1381728-91-1, Entered STN: Jul. 5, 2012.
Database Registry Chemical Abstracts Service, Columbus, Ohio, Accession No. RN 1381349-35-4, Entered STN: Jul. 4, 2012.
Database Registry CAS, Accession No. 1381443-88-4, Entered STN: Jul. 4, 2012.
Database Registry CAS, Accession No. 1381641-90-2, Entered STN: Jul. 5, 2012.
Database Registry CAS, Accession No. 1381642-23-4, Entered STN: Jul. 5, 2012.
Database Registry CAS, Accession No. 1381647-02-4, Entered STN: Jul. 5, 2012.
Database Registry CAS, Accession No. 1381647-21-7, Entered STN: Jul. 5, 2012.
Database Registry CAS, Accession No. 1381736-63-5, Entered STN: Jul. 5, 2012.
Database Registry CAS, Accession No. 1381736-70-4, Entered STN: Jul. 5, 2012.
Database Registry CAS, Accession No. RN 1381291-29-7, Entered STN: Jul. 4, 2012.

*(R)* = 42
*(S)* = 43

*(S)* = 6
*(R)* = 7

USP7 INHIBITION

RELATED APPLICATIONS

This application is the § 371 National Stage of PCT/US2019/057456, filed Oct. 22, 2019, which claims the benefit of U.S. Provisional Application No. 62/748,910, filed Oct. 22, 2018, the contents of both of which are fully incorporated by reference herein.

GOVERNMENT SUPPORT

This invention was made with government support under Grant R01 CA211681 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 15, 2021, is named DFS-25301_SL.txt and is 1,253 bytes in size.

BACKGROUND

Deubiquitinating enzymes (DUBs) have garnered significant attention as drug targets in the last 5-10 years. DUB inhibitors effectively promote degradation of oncogenic proteins, especially proteins that are challenging to directly target because they are stabilized by DUB family members. Highly-optimized and well-characterized DUB inhibitors have thus become highly sought after tools. Most reported DUB inhibitors, however, are polypharmacological agents possessing weak (micromolar) potency toward their primary target, thereby limiting their utility in target validation and mechanism studies. Due to a lack of high resolution DUB-small molecule ligand complex structures, no structure-guided optimization efforts have been reported for a mammalian DUB.

The DUB enzyme USP7 (Ubiquitin Specific Protease 7) has been shown to be involved in regulation of a myriad of cellular processes, including epigenetics, cell cycle, DNA repair, immunity, viral infection and tumorigenesis. USP7, also known as herpes virus-associated ubiquitin specific protease (HAUSP), was first discovered as a protein that plays a role in viral lytic growth. Interest in the enzyme intensified when USP7 was implicated in regulating degradation of the tumor suppressor p53, by stabilizing the major E3 ligase for p53, MDM2.

Consistent with its regulation of diverse substrates and biological processes USP7 has emerged as a drug target in a wide range of malignancies including multiple myeloma, breast cancer, neuroblastoma, glioma, and ovarian cancer. However, known USP7 inhibitors have been shown to exhibit modest potency against USP7 and poor selectivity over other DUBs. In addition to modest potency and selectivity, reported drawbacks of known USP7 inhibitor compounds include poor solubility and general toxicity. Therefore, there is a need for the development of more potent and selective irreversible USP7 inhibitors.

SUMMARY OF THE DISCLOSURE

Disclosed herein are compounds of Formula (I):

(I)

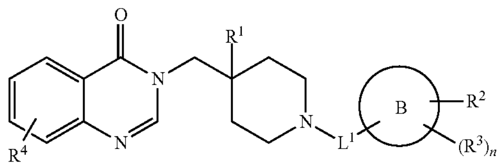

or a pharmaceutically acceptable salt thereof, wherein:

Ring B is cycloalkyl, heterocyclyl, aryl, or heteroaryl;

$L^1$ is a bond, alkyl, —C(═O)alkyl, —C(═O)NR$^5$alkyl, —NR$^5$R$^6$, or —C(═O)alkyl-[NR$^5$C(═O)-alkyl]$_p$—NR$^5$C(═O), wherein each alkyl is independently optionally substituted with one or more $R^7$;

$L^3$ is a bond, —NR$^5$R$^6$, alkyl, cycloalkyl, or heterocyclyl, wherein each alkyl is independently optionally substituted with one or more $R^8$;

Y is O;

$R^1$ is H, —OR$^5$, or —NR$^5$R$^6$;

$R^2$ is

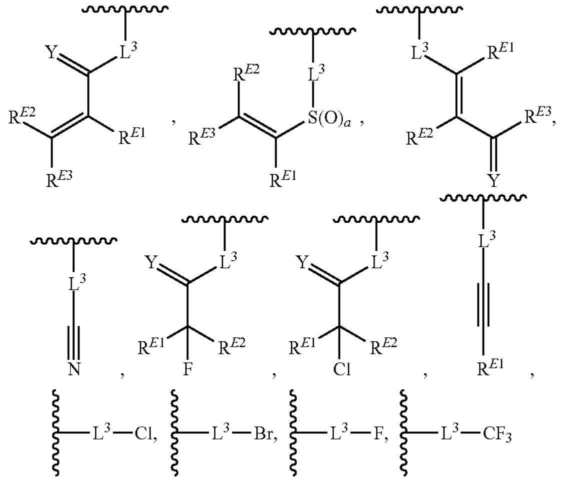

or absent;

$R^3$ is alkyl, hydroxyl, $CF_3$, halo —NR$^5$C(═O)alkyl, —C(═O)NR$^5$alkyl, —NR$^5$R$^6$, cycloalkyl, heteroaryl, or aryl;

$R^4$ is halogen, alkyl, —NR$^5$C(═O)alkyl, —C(═O)NR$^5$alkyl, or —NR$^5$R$^6$, wherein each alkyl is independently optionally substituted with one or more $R^8$; or $R^4$ is alkyl, and two $R^8$ together form cycloalkyl or heterocyclyl, wherein each cycloalkyl or heterocyclyl is independently optionally substituted with one or more $R^9$;

each $R^5$ and $R^6$ is independently H, alkenyl, or alkyl;

each $R^7$ is independently at each occurrence H, —NR$^5$R$^6$, alkylamine, cycloalkyl, carbocycloalkyl, aryl, aralkynyl, heterocyclyl, heterocyclylalkyl, heteroaryl, or heteroaralkyl, wherein each amine, cycloalkyl, aryl, heterocyclyl, or heteroaryl is independently optionally substituted with one or more $R^{10}$;

each $R^8$ is independently at each occurrence —NR$^5$R$^6$, cycloalkyl, or heterocyclyl;

each $R^9$ is independently at each occurrence H, alkenyl, or alkyl;

each $R^{10}$ is independently at each occurrence halogen, —$OR^5$, —$NR^5R^6$, alkenyl, or alkyl;

each $R^{11}$ and $R^{12}$ is independently at each occurrence H, alkyl, cycloalkyl, heterocyclyl, aryl, or heteroaryl;

or $R^{11}$ and $R^{12}$ together form heterocyclyl or heteroaryl;

each $R^{E1}$, $R^{E2}$, and $R^{E3}$ is independently at each occurrence H, alkyl, —$OR^{11}$, —$NR^{11}R^{12}$, cycloalkyl, —$NR^5C$(═O)heterocyclyl, —C(═O)$NR^5$alkyl, C(═O)$NR^5$cycloalkyl, or —C(═O)heterocyclyl;

n is 0, 1, 2, 3, or 4; and p is 0, 1, 2, 3, or 4.

In another aspect, disclosed herein is a method of treating a disease or disorder modulated by USP7, comprising administering to a subject in need thereof any one of the compounds disclosed herein.

In another aspect, disclosed herein is a method of inhibiting USP7, comprising administering to a subject in need thereof any one of the compounds disclosed herein.

In another aspect, disclosed herein is a method of treating cancer, comprising administering to a subject in need thereof any one of the compounds disclosed herein.

In another aspect, disclosed herein is a method of inhibiting USP7, wherein any one of the compounds disclosed herein forms a covalent bond with USP7.

DETAILED DESCRIPTION OF THE DISCLOSURE

Figure 1A:
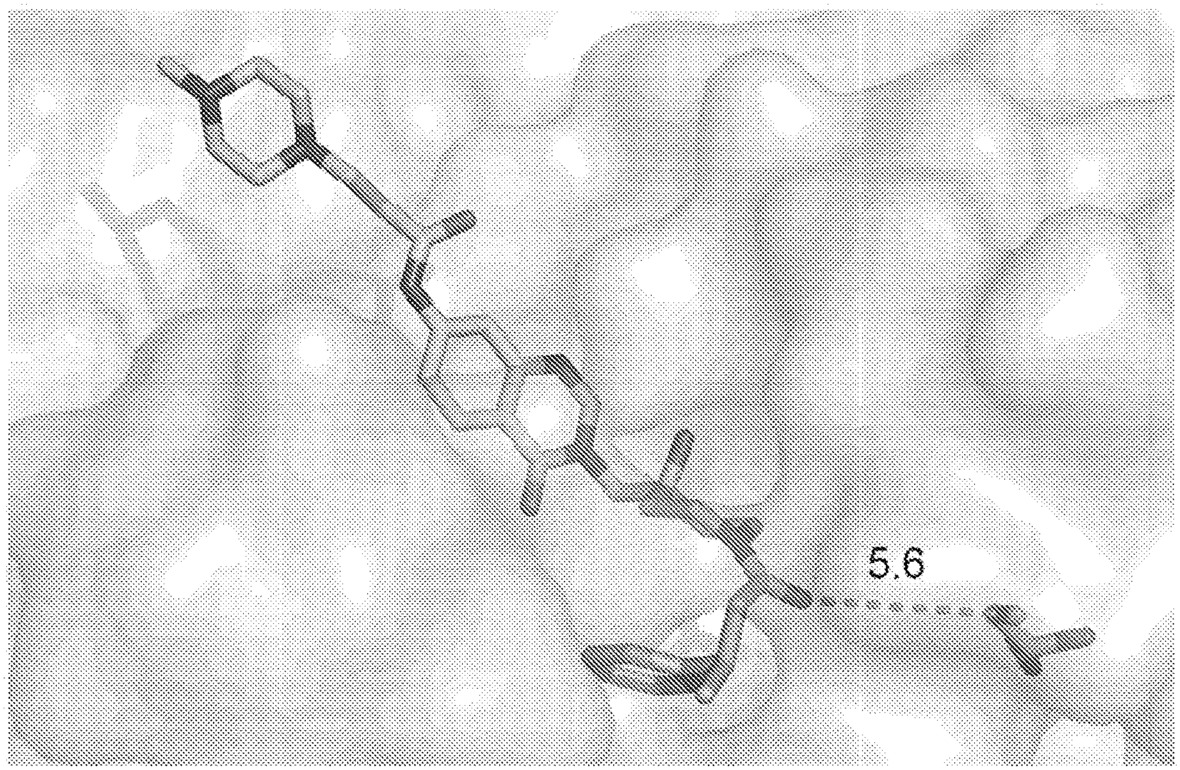
FIG. 1A depicts the co-crystal structure of compound 42 bound to the USP7 catalytic domain, highlighting the ligand's solvent accessibility and distance to the catalytic cysteine (PDB: 5VS6).

USP7 (Ubiquitin Specific Protease 7)/HAUSP (Herpes Associated Ubiquitin Specific Protease) is a 135 kDa protein of the USP family. USP7 has been shown to interact with viral proteins, such as ICP0 (Vmw 110), a herpes simplex virus immediate-early gene stimulating initiation of the viral lytic cycle, and EBNA1 (Epstein-Barr Nuclear Antigen-1). The DUB USP7 has been shown to be involved in regulation of a myriad of cellular processes, including epigenetics, cell cycle, DNA repair, immunity, viral infection and tumorigenesis. Interest in the enzyme intensified when USP7 was implicated in regulating degradation of the tumor suppressor p53, by stabilizing the major E3 ligase for p53, MDM2. Consistent with recent reports, USP7 silencing has also been shown to increase steady-state p53 levels by promoting Mdm2 degradation. Binding of USP7 to p53 was recently shown to be regulated by TSPYL5, a protein potentially involved in breast oncogenesis through a competition with p53 for binding to the same region of USP7. More recently, both upregulation and downregulation of USP7 have been shown to inhibit colon cancer cell proliferation in vitro and tumor growth in vivo, by resulting in constitutively high p53 levels.

Disclosed herein are small molecule USP7 inhibitors. In some embodiments, the small molecule USP7 inhibitors covalently bind to USP7.

Disclosed herein are compounds of Formula (I):

(I)

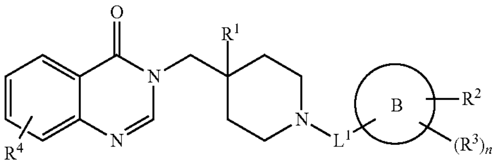

or a pharmaceutically acceptable salt thereof, wherein:

Ring B is cycloalkyl, heterocyclyl, aryl, or heteroaryl;

$L^1$ is a bond, alkyl, —C(═O)alkyl, —C(═O)$NR^5$alkyl, —$NR^5R^6$, or —C(═O)alkyl-[$NR^5$C(═O)-alkyl]$_p$—$NR^5$C(═O), wherein each alkyl is independently optionally substituted with one or more $R^7$;

$L^3$ is a bond, —$NR^5R^6$, alkyl, cycloalkyl, or heterocyclyl, wherein each alkyl is independently optionally substituted with one or more $R^8$.

Y is O;

$R^1$ is H, —$OR^5$, or —$NR^5R^6$;

$R^2$ is

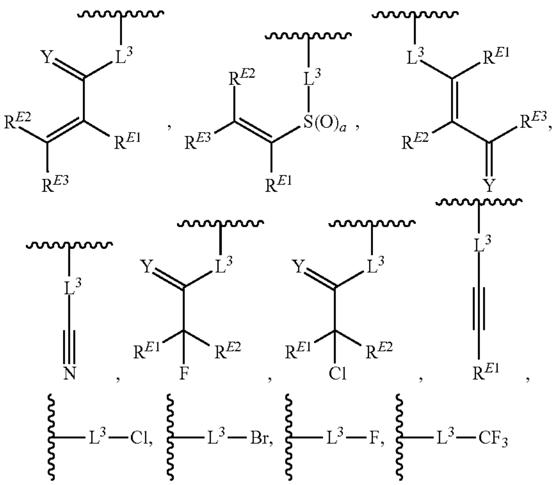

or absent;

$R^3$ is alkyl, hydroxyl, $CF_3$, halo —$NR^5$C(═O)alkyl, —C(═O)$NR^5$alkyl, —$NR^5R^6$, cycloalkyl, heteroaryl, or aryl;

$R^4$ is halogen, alkyl, —$NR^5$C(═O)alkyl, —C(═O)$NR^5$alkyl, or —$NR^5R^6$, wherein each alkyl is independently optionally substituted with one or more R; or $R^4$ is alkyl, and two $R^8$ together form cycloalkyl or heterocyclyl, wherein each cycloalkyl or heterocyclyl is independently optionally substituted with one or more $R^9$;

each $R^5$ and $R^6$ is independently H, alkenyl, or alkyl;

each $R^7$ is independently at each occurrence H, —$NR^5R^6$, alkylamine, cycloalkyl, carbocycloalkyl, aryl, aralkynyl, heterocyclyl, heterocyclylalkyl, heteroaryl, or heteroaralkyl, wherein each amine, cycloalkyl, aryl, heterocyclyl, or heteroaryl is independently optionally substituted with one or more $R^{10}$;

each $R^8$ is independently at each occurrence —$NR^5R^6$, cycloalkyl, or heterocyclyl;

each $R^9$ is independently at each occurrence H, alkenyl, or alkyl;

each $R^{10}$ is independently at each occurrence halogen, —$OR^5$, —$NR^5R^6$, alkenyl, or alkyl;

each $R^{11}$ and $R^{12}$ is independently at each occurrence H, alkyl, cycloalkyl, heterocyclyl, aryl, or heteroaryl;

or $R^{11}$ and $R^{12}$ together form heterocyclyl or heteroaryl;

each $R^{E1}$, $R^{E2}$, and $R^{E3}$ is independently at each occurrence H, alkyl, —$OR^{11}$, —$NR^{11}R^{12}$, cycloalkyl, —$NR^5$C(═O)heterocyclyl, —C(═O)$NR^5$alkyl, C(═O)$NR^5$cycloalkyl, or —C(═O)heterocyclyl;

n is 0, 1, 2, 3, or 4; and p is 0, 1, 2, 3, or 4.

In certain embodiments, the compounds of Formula (I) have the following structural formula:

(Ia)

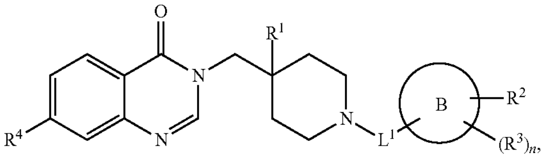

or a pharmaceutically acceptable salt thereof.

In other embodiments, the compounds of Formula (I) have the following structural formula:

(Ib)

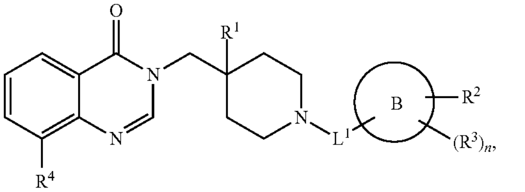

or a pharmaceutically acceptable salt thereof.

In certain embodiments, the compounds of Formula (I) have the following structural formula:

(Ic)

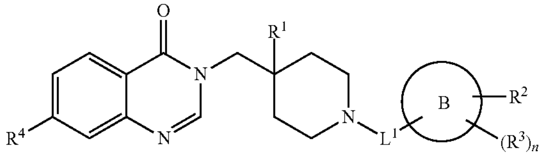

or a pharmaceutically acceptable salt thereof, wherein:

Ring B is cycloalkyl, heterocyclyl, aryl, or heteroaryl;

$L^1$ is a bond, alkyl, —C(═O)alkyl, —C(═O)$NR^5$alkyl, —$NR^5R^6$, or —C(═O)alkyl-[$NR^5$C(═O)-alkyl]$_p$—$NR^5$C(═O), wherein each alkyl is independently optionally substituted with one or more $R^7$;

$L^3$ is a bond, —$NR^5R^6$, alkyl, cycloalkyl, or heterocyclyl, wherein each alkyl is independently optionally substituted with one or more $R^8$.

Y is O;

$R^1$ is H, —$OR^5$, or —$NR^5R^6$;

$R^2$ is

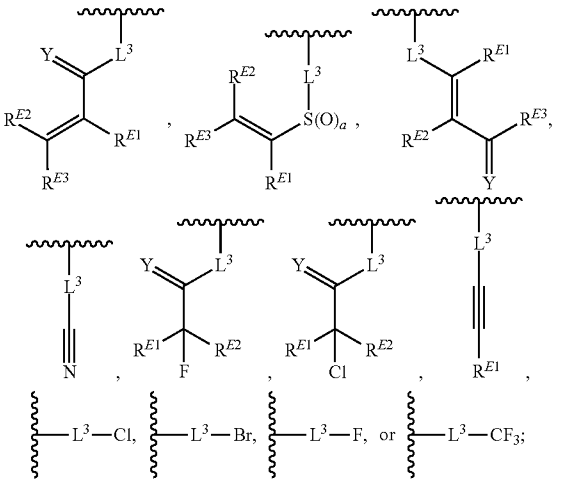

$R^3$ is alkyl, —$NR^5C$(═O)alkyl, —C(═O)$NR^5$alkyl, or —$NR^5R^6$;

$R^4$ is halogen, alkyl, —$NR^5C$(═O)alkyl, —C(═O)$NR^5$alkyl, or —$NR^5R^6$, wherein each alkyl is independently optionally substituted with one or more R; or $R^4$ is alkyl, and two $R^8$ together form cycloalkyl or heterocyclyl, wherein each cycloalkyl or heterocyclyl is independently optionally substituted with one or more $R^9$;

each $R^5$ and $R^6$ is independently H, alkenyl, or alkyl;

each $R^7$ is independently at each occurrence H, —$NR^5R^6$, alkylamine, cycloalkyl, carbocycloalkyl, aryl, aralkynyl, heterocyclyl, heterocyclylalkyl, heteroaryl, or heteroaralkyl, wherein each amine, cycloalkyl, aryl, heterocyclyl, or heteroaryl is independently optionally substituted with one or more $R^{10}$;

each $R^8$ is independently at each occurrence —$NR^5R^6$, cycloalkyl, or heterocyclyl;

each $R^9$ is independently at each occurrence H, alkenyl, or alkyl;

each $R^{10}$ is independently at each occurrence halogen, —$OR^5$, —$NR^5R^6$, alkenyl, or alkyl;

each $R^{11}$ and $R^{12}$ is independently at each occurrence H, alkyl, cycloalkyl, heterocyclyl, aryl, or heteroaryl;

or $R^{11}$ and $R^{12}$ together form heterocyclyl or heteroaryl;

each $R^{E1}$, $R^{E2}$, and $R^{E3}$ is independently at each occurrence H, alkyl, —$OR^{11}$, —$NR^{11}R^{12}$, cycloalkyl, —$NR^5C$(═O)heterocyclyl, —C(═O)$NR^5$alkyl, C(═O)$NR^5$cycloalkyl, or —C(═O)heterocyclyl;

n is 0, 1, 2, 3, or 4; and p is 0, 1, 2, 3, or 4.

In certain embodiments, $R^4$ is not halogen. In certain embodiments, $R^4$ is not chloro.

In certain embodiments, the compounds of Formula (I) have the following structural formula:

(I)

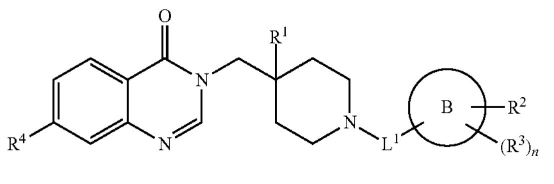

or a pharmaceutically acceptable salt thereof, wherein:

Ring B is cycloalkyl, heterocyclyl, aryl, or heteroaryl;

$L^1$ is a bond, alkyl, —C(═O)alkyl, —C(═O)$NR^5$alkyl, —$NR^5R^6$, or —C(═O)alkyl-[$NR^5C$(═O)-alkyl]$_p$—$NR^5C$(═O), wherein each alkyl is independently optionally substituted with one or more $R^7$;

$L^3$ is a bond, —$NR^5R^6$, alkyl, cycloalkyl, or heterocyclyl, wherein each alkyl is independently optionally substituted with one or more $R^8$.

Y is O;

$R^1$ is H, —$OR^5$, or —$NR^5R^6$;

$R^2$ is

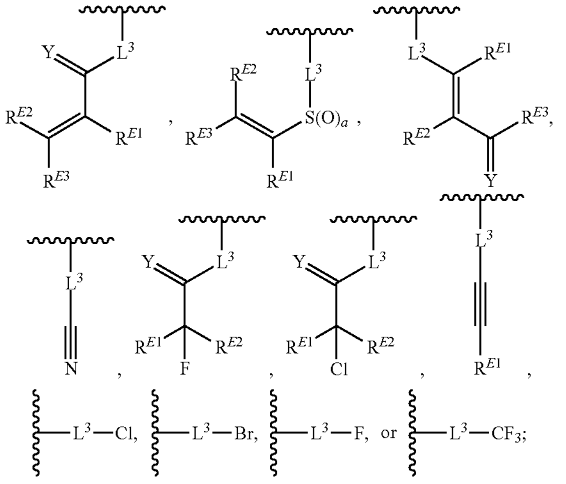

$R^3$ is alkyl, —$NR^5C$(═O)alkyl, —C(═O)$NR^5$alkyl, or —$NR^5R^6$;

$R^4$ is alkyl, —$NR^5C$(═O)alkyl, —C(═O)$NR^5$alkyl, or —$NR^5R^6$, wherein each alkyl is independently optionally substituted with one or more $R^8$; or $R^4$ is alkyl, and two $R^8$ together form cycloalkyl or heterocyclyl, wherein each cycloalkyl or heterocyclyl is independently optionally substituted with one or more $R^9$;

each $R^5$ and $R^6$ is independently H, alkenyl, or alkyl;

each $R^7$ is independently at each occurrence H, —$NR^5R^6$, alkylamine, cycloalkyl, carbocycloalkyl, aryl, aralkynyl, heterocyclyl, heterocyclylalkyl, heteroaryl, or heteroaralkyl, wherein each amine, cycloalkyl, aryl, heterocyclyl, or heteroaryl is independently optionally substituted with one or more $R^{10}$;

each $R^8$ is independently at each occurrence —$NR^5R^6$, cycloalkyl, or heterocyclyl;

each $R^9$ is independently at each occurrence H, alkenyl, or alkyl;

each $R^{10}$ is independently at each occurrence halogen, —$OR^5$, —$NR^5R^6$, alkenyl, or alkyl;

each $R^{11}$ and $R^{12}$ is independently at each occurrence H, alkyl, cycloalkyl, heterocyclyl, aryl, or heteroaryl;

or $R^{11}$ and $R^{12}$ together form heterocyclyl or heteroaryl;

each $R^{E1}$, $R^{E2}$, and $R^{E3}$ is independently at each occurrence H, alkyl, —$OR^{11}$, —$NR^{11}R^{12}$, cycloalkyl, —$NR^5C$(═O)heterocyclyl, —C(═O)$NR^5$alkyl, C(═O)$NR^5$cycloalkyl, or —C(═O)heterocyclyl;

n is 0, 1, 2, 3, or 4; and p is 0, 1, 2, 3, or 4.

In certain embodiments, the compounds of Formula (I) have the structures described herein, provided that the compound is not selected from the following:

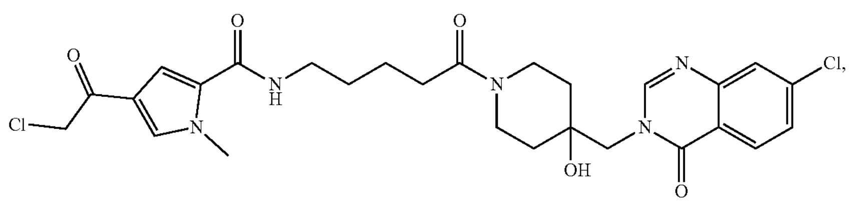
,
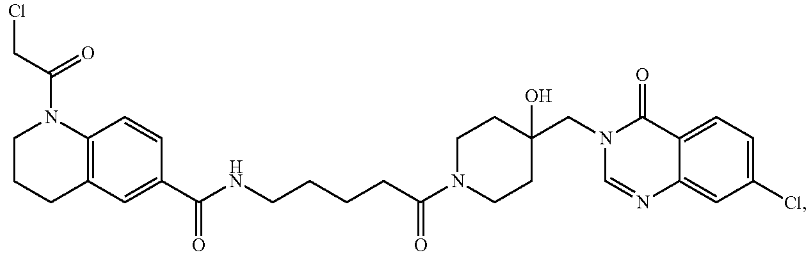
,
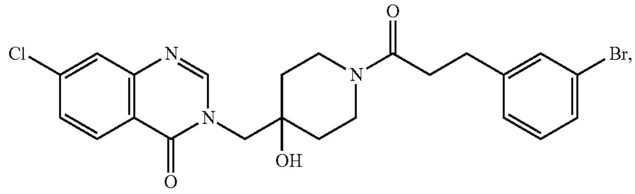
,
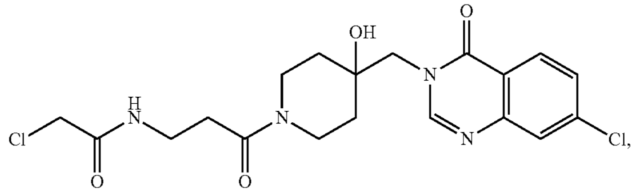
,
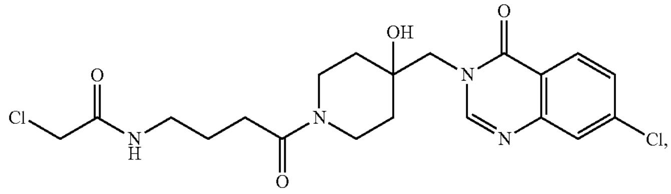
,
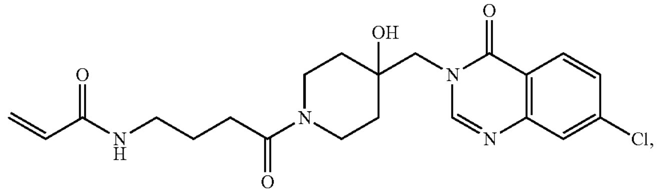
,
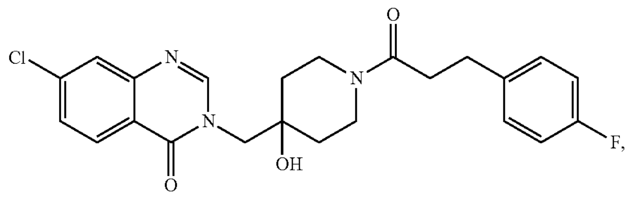
, -continued
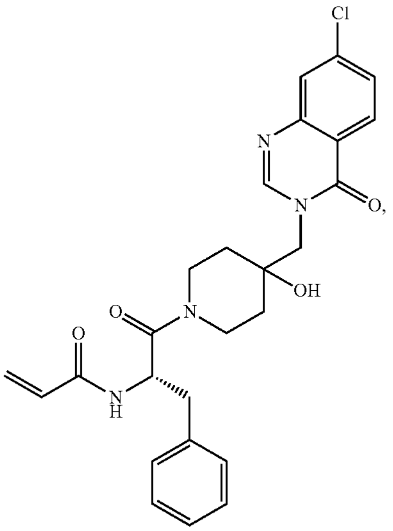
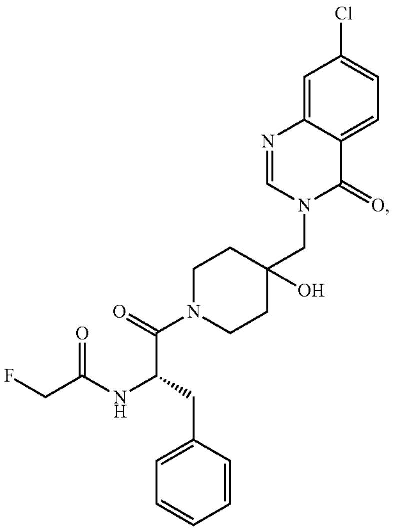
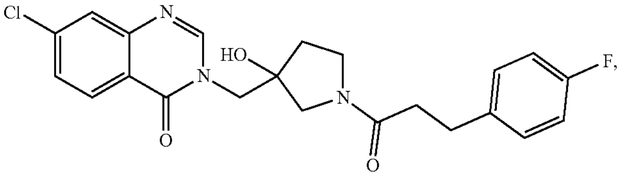
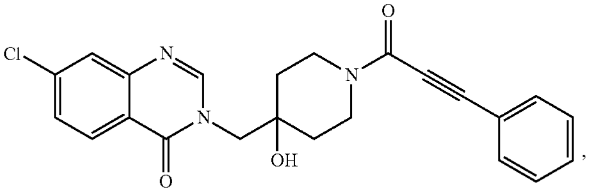
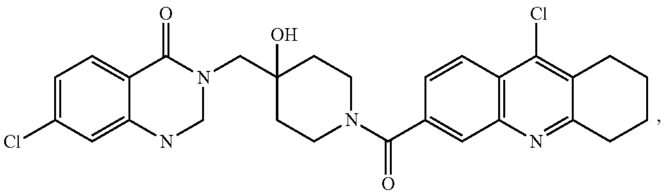
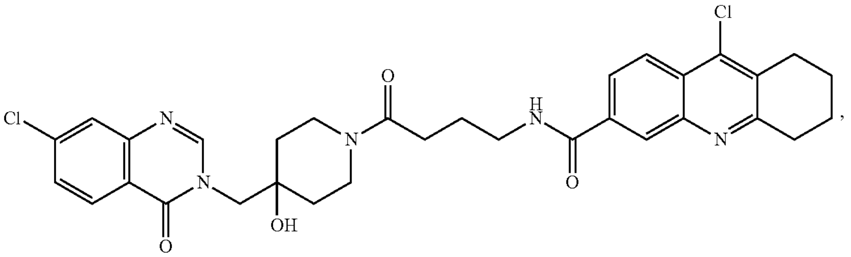
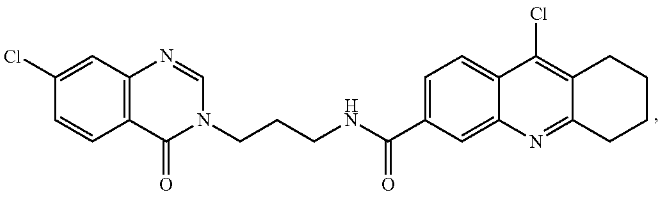

-continued
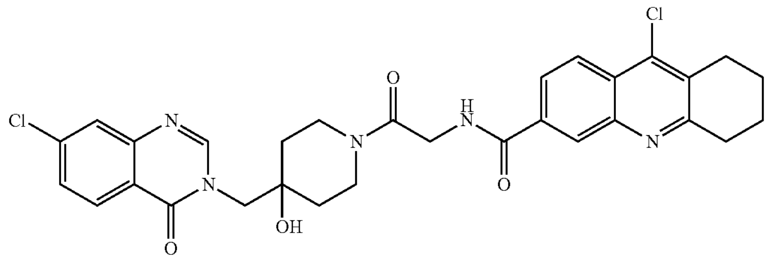
,
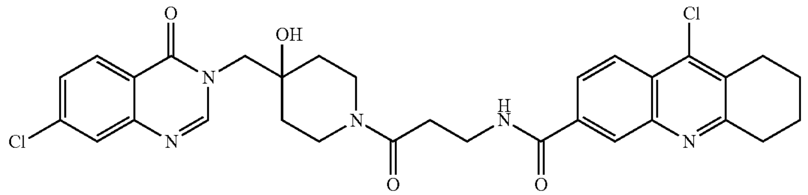
,
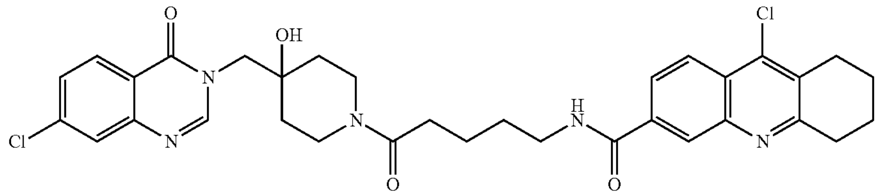
,
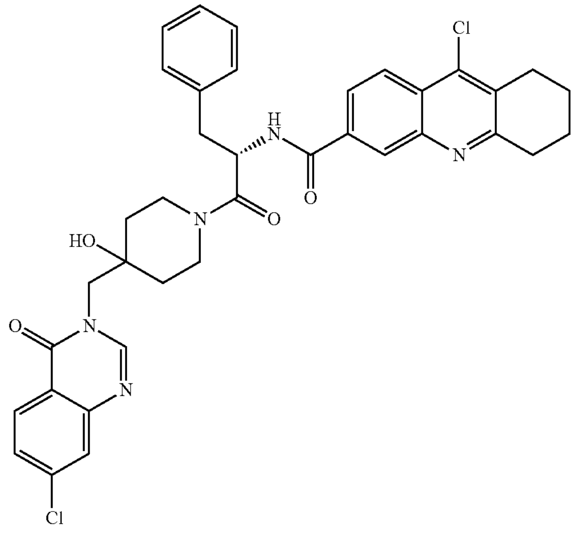
,
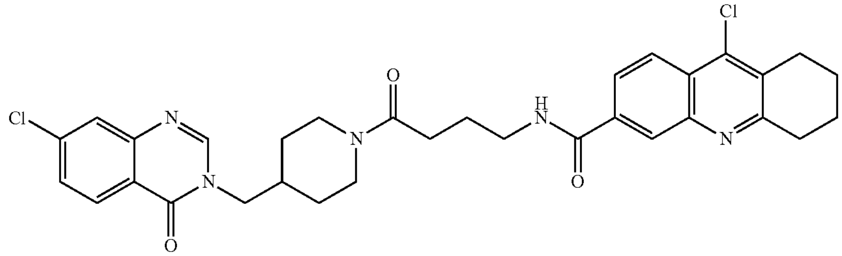
,
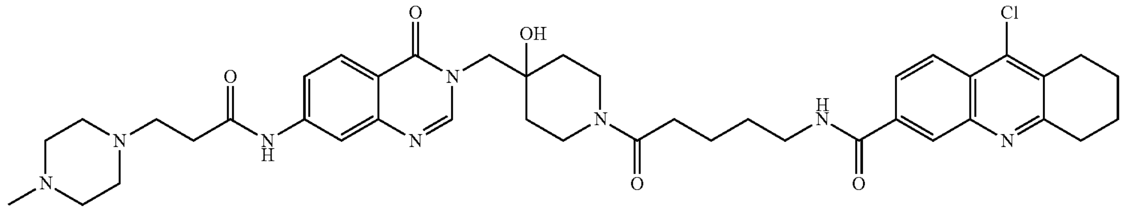
, -continued
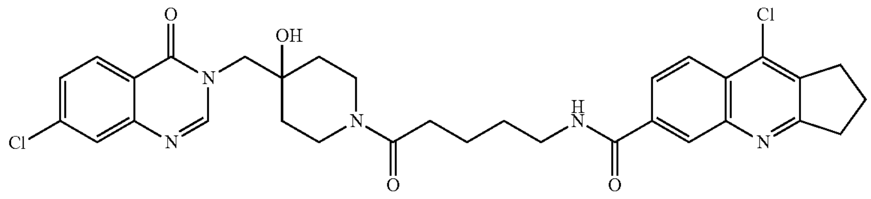
,
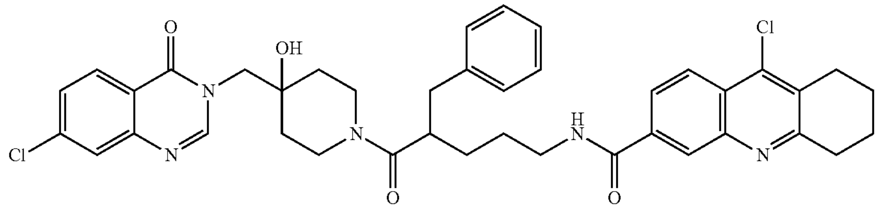
,
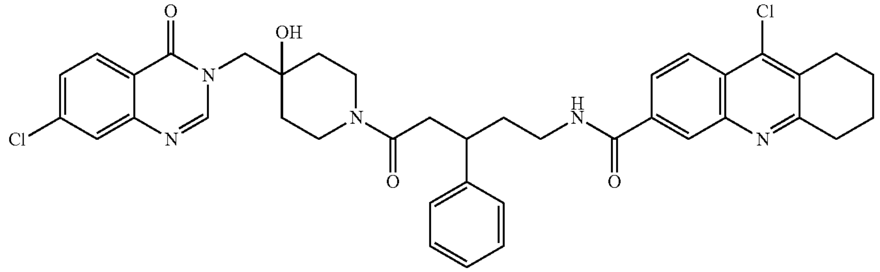
,
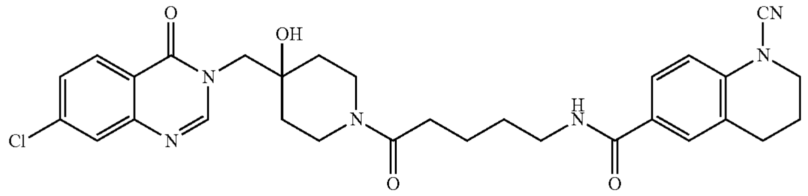
,
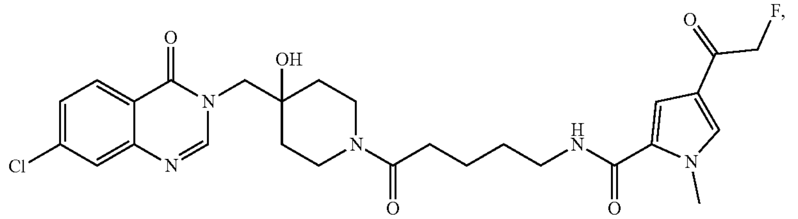
, and
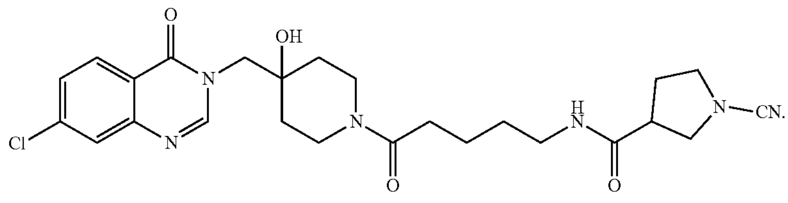
.

In certain embodiments of the compounds disclosed herein, $R^4$ is alkyl, —$NR^5C$(═O)alkyl, —C(═O)$NR^5$alkyl, or —$NR^5R^6$, wherein each alkyl is independently optionally substituted with one or more $R^8$; or $R^4$ is alkyl, and two $R^8$ together form cycloalkyl or heterocyclyl, wherein each cycloalkyl or heterocyclyl is independently optionally substituted with one or more $R^9$. In certain embodiments, the heterocyclyl is methylpiperidinyl or morpholinyl.

In certain embodiments, the compounds of Formula (I) have the following structural formula:

(II)

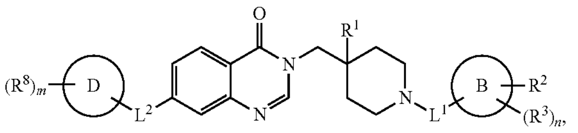

or a pharmaceutically acceptable salt thereof, wherein

Ring D is cycloalkyl, heterocyclyl, aryl, or heteroaryl;

$L^2$ is alkyl, —$NR^5C$(═O)alkyl, —C(═O)$NR^5$alkyl, or —$NR^5R^6$, wherein each alkyl is independently optionally substituted with one or more $R^8$; and m is 0, 1, 2, 3, or 4.

In some embodiments of the compounds disclosed herein, $L^2$ is alkyl or —$NR^5C$(═O)alkyl.

In some embodiments, the compounds of Formula (I) have the following structural formula:

(IIIa)

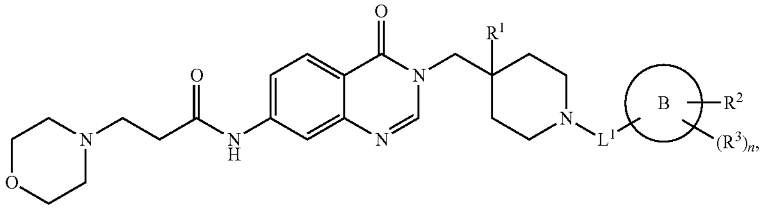

or a pharmaceutically acceptable salt thereof.

In certain embodiments, the compounds of Formula (I) have the following structural formula:

(IIIb)

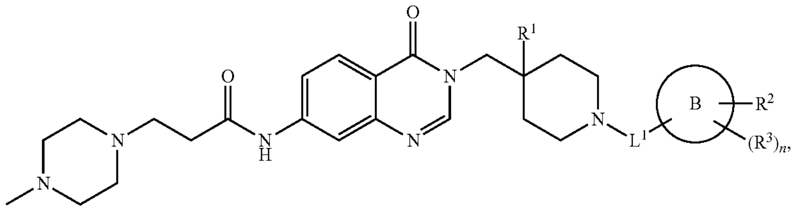

or a pharmaceutically acceptable salt thereof.

In certain embodiments of the compounds disclosed herein, $L^1$ is alkyl, —C(═O)alkyl, or —C(═O)$NR^5$alkyl, —$NR^5R^6$, —C(═O)alkyl-[$NR^5C$(═O)-alkyl]$_p$—$NR^5C$(═O). In some embodiments, $L^1$ is —C(═O)alkyl-[$NR^5C$(═O)-alkyl]$_p$—$NR^5C$(═O). In some embodiments, p is 0, 1, or 2.

In certain embodiments, the compounds of Formula (I) have the following structural formula:

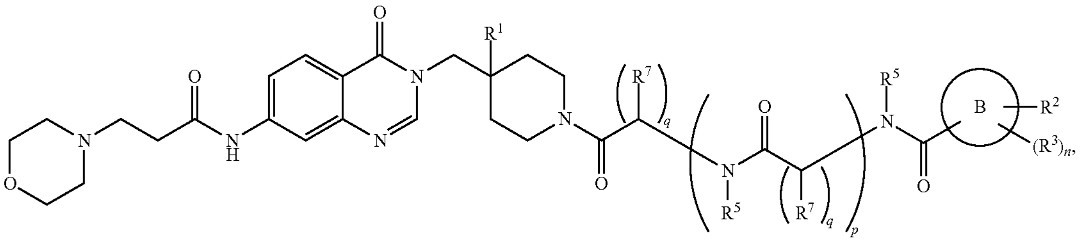

(IVa)

or a pharmaceutically acceptable salt thereof, wherein q is 0, 1, 2, 3, 4, 5, or 6.

In certain embodiments, the compounds of Formula (I) have the following structural formula:

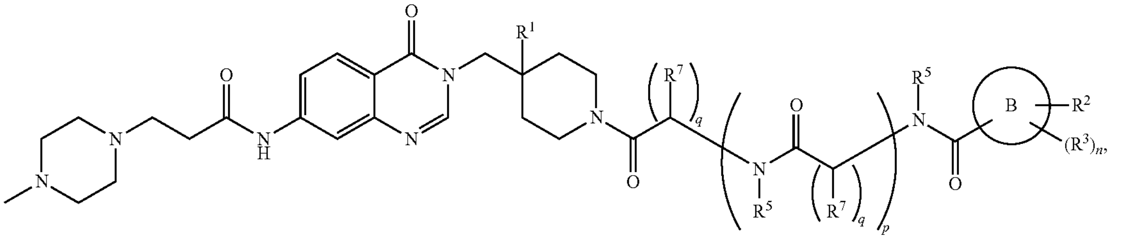

(IVb)

or a pharmaceutically acceptable salt thereof, wherein q is 0, 1, 2, 3, 4, 5, or 6.

In certain embodiments of the compounds of Formula (IVb), $R^1$ is OH; q is 4; one instance of $R^7$ is benzyl; three instances of $R^7$ are H; p is 0; and $R^5$ is H.

In certain embodiments of the compounds disclosed herein, ring B is cycloalkyl, heterocyclyl, or heteroaryl.

In certain embodiments of the compounds disclosed herein, each alkyl is substituted with one or more $R^7$; and each $R^7$ is independently at each occurrence H, aralkynyl, heterocyclylalkyl, or heteroaralkyl.

In certain embodiments of the compounds disclosed herein, each $R^7$ is independently at each occurrence aralkynyl, heterocyclylalkyl, or heteroaralkyl. In certain embodiments, each aryl, heterocyclyl, or heteroaryl of $R^7$ is substituted with one of more $R^{10}$. In certain embodiments, each $R^{10}$ is independently at each occurrence halogen, —$OR^5$, —$NR^5R^6$, or alkyl.

In certain embodiments of the compounds disclosed herein, q is 1, 2, 3, or 4.

In certain embodiments of the compounds disclosed herein, $R^2$ is

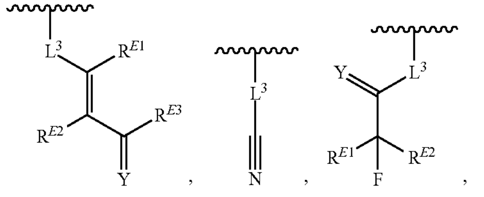

-continued

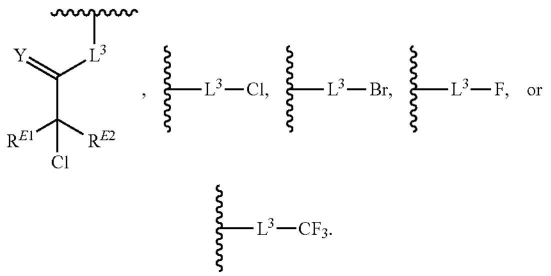

In certain embodiments, $R^2$ is

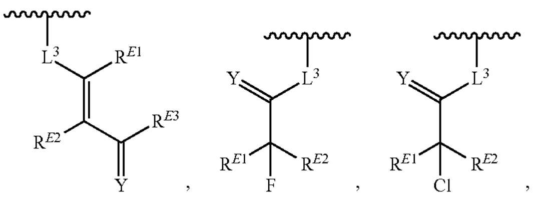

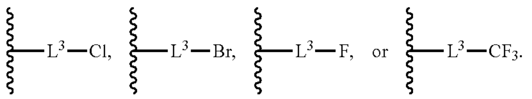

In certain embodiments, $R^2$ is

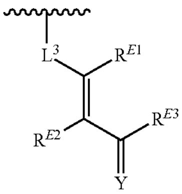
,
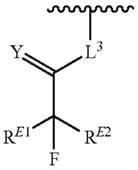
, or
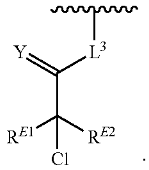
.

In certain embodiments of the compounds disclosed herein, each $R^{E1}$, $R^{E2}$, and $R^{E3}$ is independently at each occurrence H or —$NR^{11}R^{12}$. In certain embodiments, each $R^{11}$ and $R^{12}$ is independently at each occurrence H, alkyl, cycloalkyl, or heterocyclyl; or $R^{11}$ and $R^{12}$ together form heterocyclyl or heteroaryl.

In certain embodiments of the compounds disclosed herein, $L^3$ is a bond, —$NR^5R^6$, or heterocyclyl.

In certain embodiments of the compounds disclosed herein, $R^1$ is H or —$OR^5$.

In certain embodiments of the compounds disclosed herein, n is 0. In other embodiments, n is 1. In certain embodiments, $R^3$ is $CF_3$, alkyl (e.g., methyl), hydroxyl, cycloalkyl (e.g., cyclohexyl), heteroaryl (e.g., thiazolyl), aryl (e.g., phenyl or fluorophenyl).

In certain embodiments of the compounds of Formula (I) disclosed herein,

Ring B is cycloalkyl, heterocyclyl, or heteroaryl;

$L^1$ is alkyl, —C(═O)alkyl, —C(═O)$NR^5$alkyl, —$NR^5R^6$, or —C(═O)alkyl-[$NR^5$C(═O)-alkyl]$_p$—$NR^5$C(═O)), wherein each alkyl is independently optionally substituted with one or more $R^7$;

$L^3$ is a bond, —$NR^5R^6$, or alkyl;

Y is O;

$R^1$ is H or —$OR^5$;

$R^2$ is

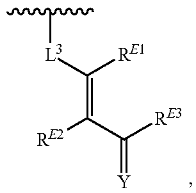
,
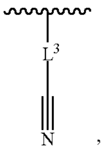
,
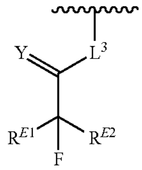
,
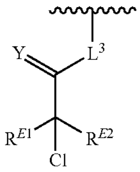
,
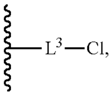
,
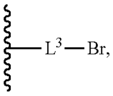
,
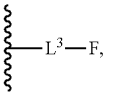
, or
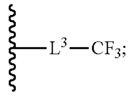
;

$R^3$ is alkyl or —$NR^5R^6$;

$R^4$ is alkyl, —$NR^5$C(═O)alkyl, —C(═O)$NR^5$alkyl, or —$NR^5R^6$, wherein each alkyl is independently optionally substituted with one or more $R^8$; or $R^4$ is alkyl, and two $R^8$ together form cycloalkyl or heterocyclyl, wherein each cycloalkyl or heterocyclyl is independently optionally substituted with one or more $R^9$;

each $R^5$ and $R^6$ is independently H or alkyl;

each $R^7$ is independently at each occurrence H, carbocycloalkyl, aralkynyl, heterocyclylalkyl, or heteroaralkyl, wherein each cycloalkyl, aryl, heterocyclyl, or heteroaryl is independently optionally substituted with one or more $R^{10}$;

each $R^8$ is independently at each occurrence —$NR^5R^6$ or heterocyclyl;

each $R^9$ is independently at each occurrence H or alkyl;

each $R^{10}$ is independently at each occurrence halogen, —$OR^5$, —$NR^5R^6$, or alkyl;

each $R^{11}$ and $R^{12}$ is independently at each occurrence H or alkyl;

or $R^{11}$ and $R^{12}$ together form heterocyclyl or heteroaryl;

each $R^{E1}$, $R^{E2}$, and $R^{E3}$ is independently at each occurrence H, alkyl, —$OR^{11}$, or —$NR^{11}R^{12}$;

n is 0, 1, or 2; and p is 0, 1, or 2.

In certain embodiments of the compounds of Formula (I) disclosed herein,

Ring B is cycloalkyl, heterocyclyl, or heteroaryl;

$L^1$ is alkyl, —C(═O)alkyl, —C(═O)$NR^5$alkyl, —$NR^5R^6$, or —C(═O)alkyl-[$NR^5$C(═O)-alkyl]$_p$—$NR^5$C(═O)), wherein each alkyl is independently optionally substituted with one or more $R^7$;

$L^3$ is a bond, —$NR^5R^6$, or alkyl;

Y is O;

$R^1$ is H or —$OR^5$;

$R^2$ is

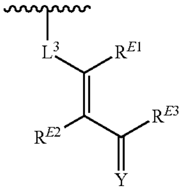
,
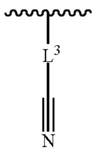
,
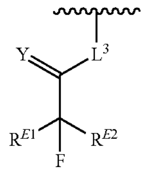
,
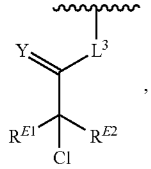
,
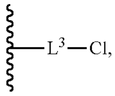
,
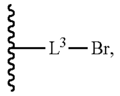
,
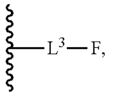
, or
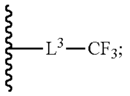
;

$R^3$ is $CF_3$, alkyl (e.g., methyl), hydroxyl, cycloalkyl (e.g., cyclohexyl), heteroaryl (e.g., thiazolyl), aryl (e.g., phenyl or fluorophenyl);

$R^4$ is alkyl, —$NR^5$C(═O)alkyl, —C(═O)$NR^5$alkyl, or —$NR^5R^6$, wherein each alkyl is independently optionally substituted with one or more $R^8$; or $R^4$ is alkyl, and two $R^8$ together form cycloalkyl or heterocyclyl (e.g., methylpiperazinyl or morpholinyl), wherein each cycloalkyl or heterocyclyl is independently optionally substituted with one or more $R^9$;

each $R^5$ and $R^6$ is independently H or alkyl;

each $R^7$ is independently at each occurrence H, carbocycloalkyl, aralkynyl, heterocyclylalkyl, or heteroaralkyl, wherein each cycloalkyl, aryl, heterocyclyl, or heteroaryl is independently optionally substituted with one or more $R^{10}$;

each $R^8$ is independently at each occurrence —$NR^5R^6$ or heterocyclyl;

each $R^9$ is independently at each occurrence H or alkyl;

each $R^{10}$ is independently at each occurrence halogen, —$OR^5$, —$NR^5R^6$, or alkyl;

each $R^{11}$ and $R^{12}$ is independently at each occurrence H or alkyl;

or $R^{11}$ and $R^{12}$ together form heterocyclyl or heteroaryl;

each $R^{E1}$, $R^{E2}$, and $R^{E3}$ is independently at each occurrence H, alkyl, —$OR^{11}$, or —$NR^{11}R^{12}$;

n is 0, 1, or 2; and p is 0, 1, or 2.

In certain embodiments of the compounds of Formula (I) disclosed herein,

Ring B is heterocyclyl or heteroaryl;

$L^1$ is —C(=O)alkyl-[$NR^5$C(=O)-alkyl]$_p$—$NR^5$C(=O)), wherein each alkyl is independently optionally substituted with one or more $R^7$;

$L^3$ is a bond;

Y is O;

$R^1$ is H or —$OR^5$;

$R^2$ is

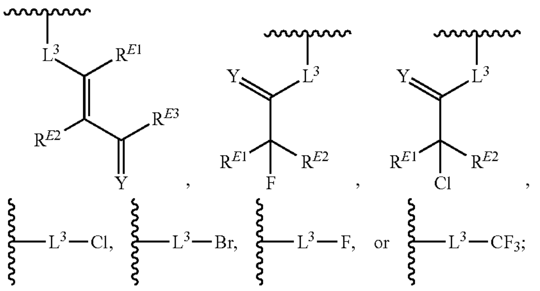

$R^4$ is halogen, alkyl, —$NR^5$C(=O)alkyl, —C(=O)$NR^5$alkyl, or —$NR^5R^6$, wherein each alkyl is independently optionally substituted with one or more $R^8$; or $R^4$ is alkyl, and two $R^8$ together form cycloalkyl or heterocyclyl, wherein each cycloalkyl or heterocyclyl is independently optionally substituted with one or more $R^9$;

each $R^5$ and $R^6$ is H;

each $R^7$ is independently at each occurrence H, carbocycloalkyl, aralkynyl, heterocyclylalkyl, or heteroaralkyl;

each $R^9$ is independently at each occurrence H or alkyl;

each $R^{11}$ and $R^{12}$ is independently at each occurrence H or alkyl;

or $R^{11}$ and $R^{12}$ together form heterocyclyl;

each $R^{E1}$, $R^{E2}$, and $R^{E3}$ is independently at each occurrence H, alkyl, —$OR^{11}$, or —$NR^{11}R^{12}$;

n is 0; and p is 0, 1, or 2.

In certain embodiments of the compounds of Formula (I) disclosed herein,

Ring B is heterocyclyl or heteroaryl;

$L^1$ is —C(=O)alkyl-[$NR^5$C(=O)-alkyl]$_p$—$NR^5$C(=O)), wherein each alkyl is independently optionally substituted with one or more $R^7$;

$L^3$ is a bond;

Y is O;

$R^1$ is H or —$OR^5$;

$R^2$ is

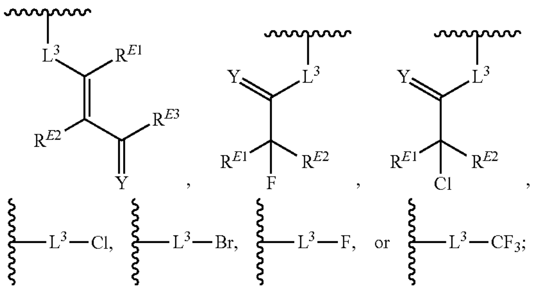

$R^3$ is $CF_3$, alkyl (e.g., methyl), hydroxyl, cycloalkyl (e.g., cyclohexyl), heteroaryl (e.g., thiazolyl), aryl (e.g., phenyl or fluorophenyl);

$R^4$ is halogen, alkyl, —$NR^5$C(=O)alkyl, —C(=O)$NR^5$alkyl, heterocyclyl, or —$NR^5R^6$, wherein each alkyl is independently optionally substituted with one or more $R^8$; or $R^4$ is alkyl, and two $R^8$ together form cycloalkyl or heterocyclyl (e.g., methylpiperazinyl or morpholinyl), wherein each cycloalkyl or heterocyclyl is independently optionally substituted with one or more $R^9$;

each $R^5$ and $R^6$ is H;

each $R^7$ is independently at each occurrence H, carbocycloalkyl, aralkynyl, heterocyclylalkyl, or heteroaralkyl;

each $R^9$ is independently at each occurrence H or alkyl;

each $R^{11}$ and $R^{12}$ is independently at each occurrence H or alkyl;

or $R^{11}$ and $R^{12}$ together form heterocyclyl;

each $R^{E1}$, $R^{E2}$, and $R^{E3}$ is independently at each occurrence H, alkyl, —$OR^{11}$, or —$NR^{11}R^{12}$;

n is 0; and p is 0, 1, or 2.

In certain embodiments the compound of Formula (I) is selected from the group consisting of:

| Compound | |
|---|---|
| 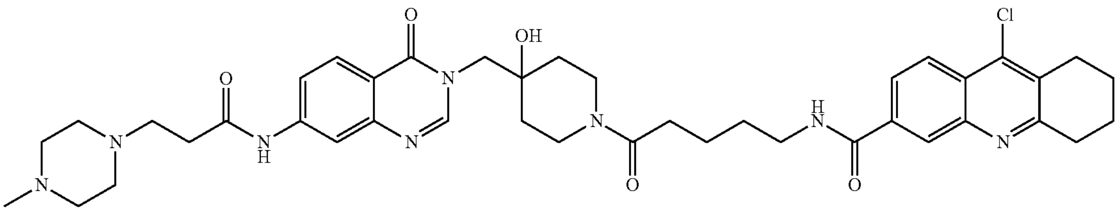 [SMILES: CN1CCN(CCC(=O)Nc2ccc3c(=O)n(CC4(O)CCN(C(=O)CCCCNC(=O)c5ccc6c(Cl)c7c(nc6c5)CCCC7)CC4)cnc3c2)CC1] | 1 |

-continued
| Compound |
|---|
| 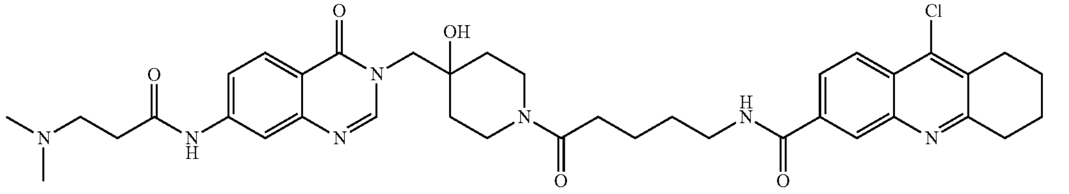 [SMILES: CN(C)CCC(=O)Nc1ccc2c(=O)n(CC3(O)CCN(C(=O)CCCCNC(=O)c4ccc5c(Cl)c6c(nc5c4)CCCC6)CC3)cnc2c1] 2 |
| 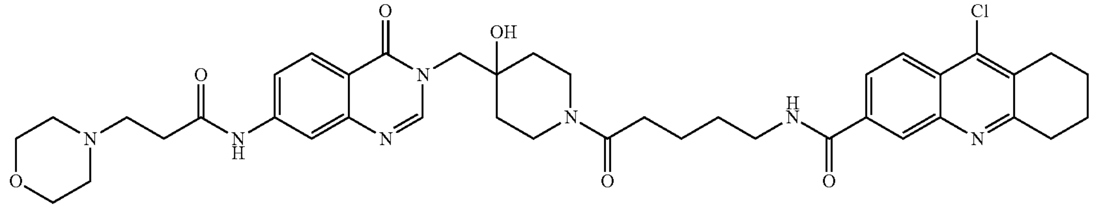 [SMILES: O=C(CCN1CCOCC1)Nc1ccc2c(=O)n(CC3(O)CCN(C(=O)CCCCNC(=O)c4ccc5c(Cl)c6c(nc5c4)CCCC6)CC3)cnc2c1] 3 |
| 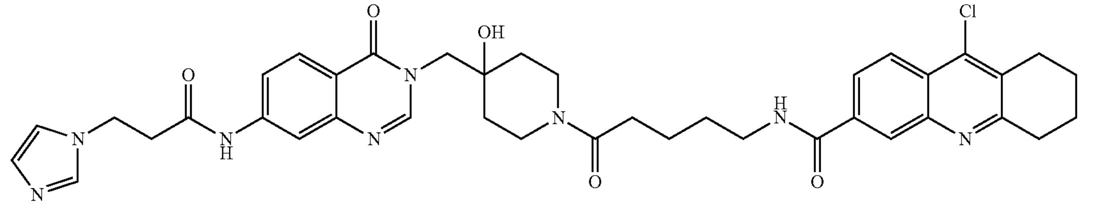 [SMILES: O=C(CCn1ccnc1)Nc1ccc2c(=O)n(CC3(O)CCN(C(=O)CCCCNC(=O)c4ccc5c(Cl)c6c(nc5c4)CCCC6)CC3)cnc2c1] 4 |
| 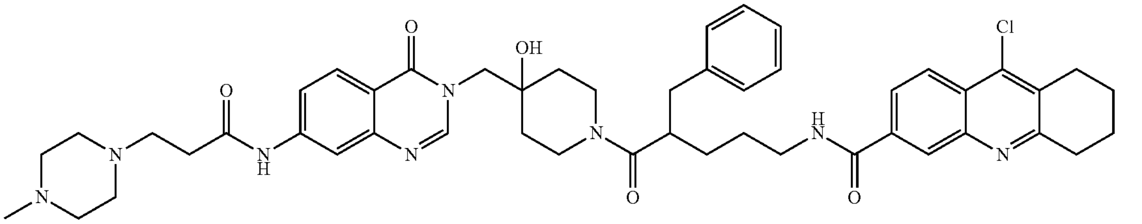 5 |
| 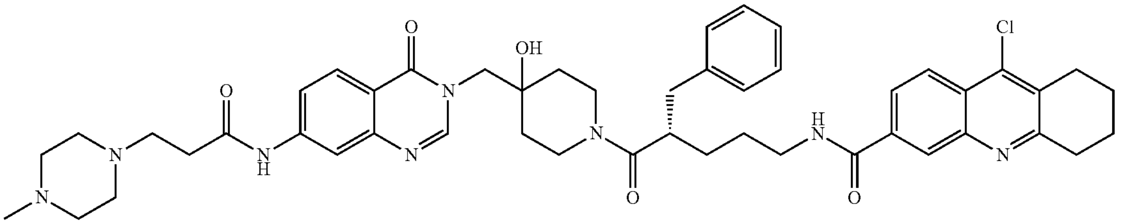 [SMILES: CN1CCN(CCC(=O)Nc2ccc3c(=O)n(CC4(O)CCN(C(=O)[C@@H](CCCNC(=O)c5ccc6c(Cl)c7c(nc6c5)CCCC7)Cc5ccccc5)CC4)cnc3c2)CC1] 6 |
| 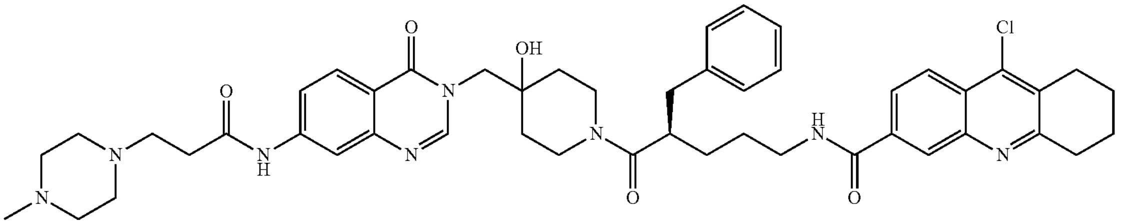 [SMILES: CN1CCN(CCC(=O)Nc2ccc3c(=O)n(CC4(O)CCN(C(=O)[C@H](CCCNC(=O)c5ccc6c(Cl)c7c(nc6c5)CCCC7)Cc5ccccc5)CC4)cnc3c2)CC1] 7 |
| 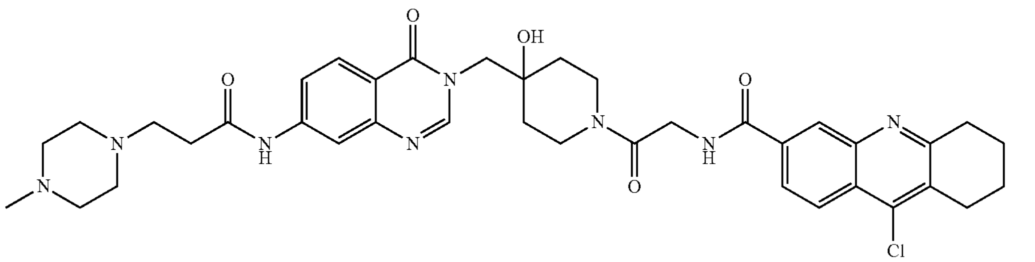 [SMILES: CN1CCN(CCC(=O)Nc2ccc3c(=O)n(CC4(O)CCN(C(=O)CNC(=O)c5ccc6c(Cl)c7c(nc6c5)CCCC7)CC4)cnc3c2)CC1] 8 |

-continued
| Compound |
|---|
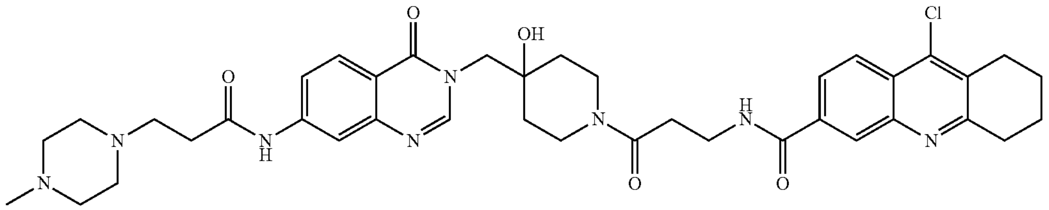 [SMILES: CN1CCN(CCC(=O)Nc2ccc3c(=O)n(CC4(O)CCN(C(=O)CCNC(=O)c5ccc6c(Cl)c7c(nc6c5)CCCC7)CC4)cnc3c2)CC1]
9
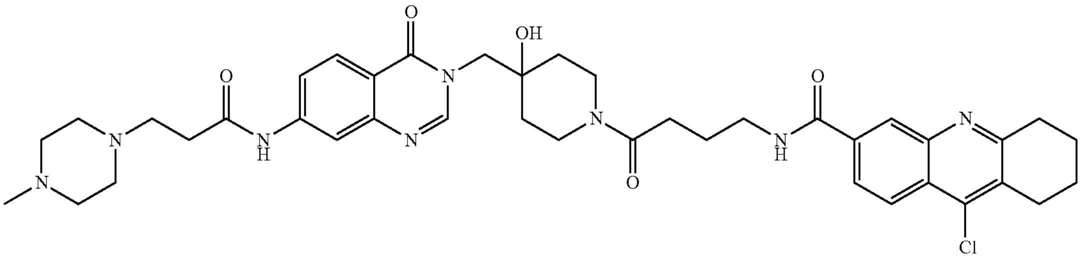 [SMILES: CN1CCN(CCC(=O)Nc2ccc3c(=O)n(CC4(O)CCN(C(=O)CCCNC(=O)c5ccc6c(Cl)c7c(nc6c5)CCCC7)CC4)cnc3c2)CC1]
10
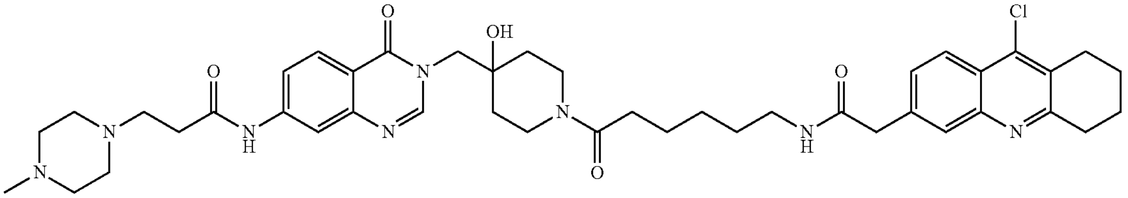 [SMILES: CN1CCN(CCC(=O)Nc2ccc3c(=O)n(CC4(O)CCN(C(=O)CCCCCNC(=O)Cc5ccc6c(Cl)c7c(nc6c5)CCCC7)CC4)cnc3c2)CC1]
11
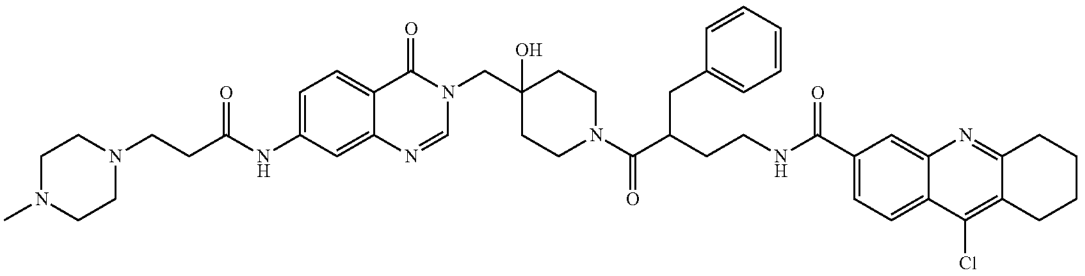 [SMILES: CN1CCN(CCC(=O)Nc2ccc3c(=O)n(CC4(O)CCN(C(=O)C(CCNC(=O)c5ccc6c(Cl)c7c(nc6c5)CCCC7)Cc5ccccc5)CC4)cnc3c2)CC1]
12
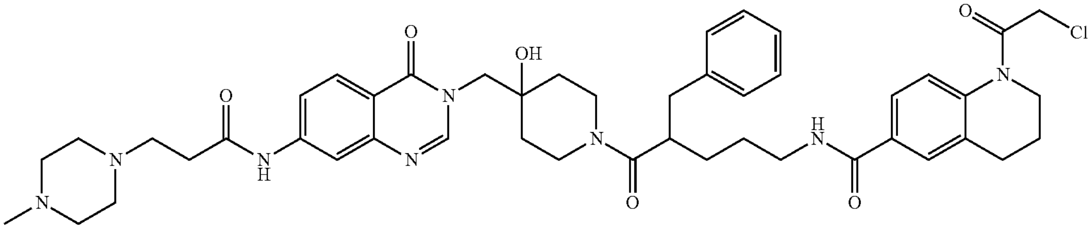 [SMILES: CN1CCN(CCC(=O)Nc2ccc3c(=O)n(CC4(O)CCN(C(=O)C(CCCNC(=O)c5ccc6c(c5)CCCN6C(=O)CCl)Cc5ccccc5)CC4)cnc3c2)CC1]
13
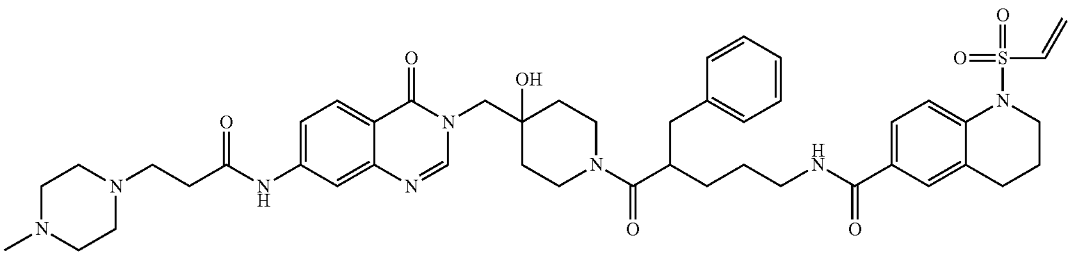 [SMILES: C=CS(=O)(=O)N1CCCc2cc(C(=O)NCCCC(Cc3ccccc3)C(=O)N3CCC(O)(Cn4cnc5cc(NC(=O)CCN6CCN(C)CC6)ccc5c4=O)CC3)ccc21]
14

-continued
| Compound |
|---|
| 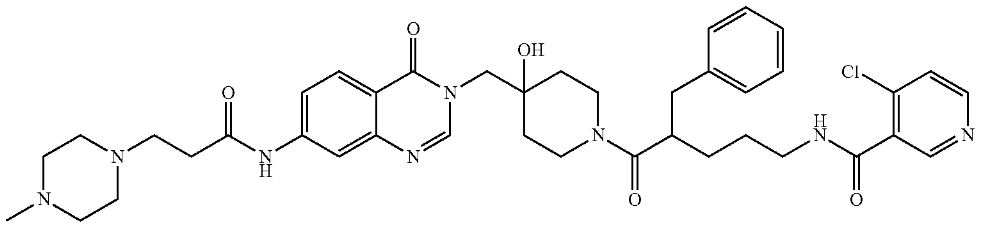 [SMILES: CN1CCN(CCC(=O)Nc2ccc3c(=O)n(CC4(O)CCN(C(=O)C(CCCNC(=O)c5cnccc5Cl)Cc5ccccc5)CC4)cnc3c2)CC1] 15 |
| 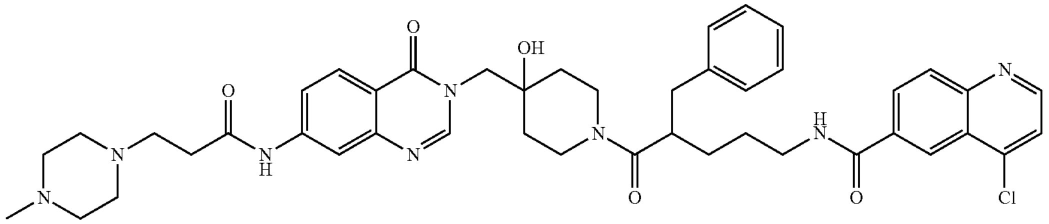 [SMILES: CN1CCN(CCC(=O)Nc2ccc3c(=O)n(CC4(O)CCN(C(=O)C(CCCNC(=O)c5ccc6nccc(Cl)c6c5)Cc5ccccc5)CC4)cnc3c2)CC1] 16 |
| 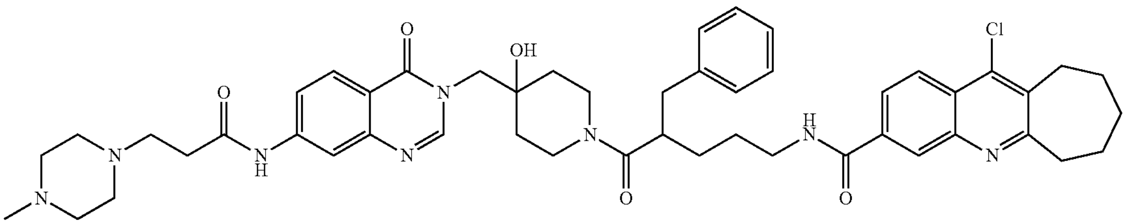 [SMILES: CN1CCN(CCC(=O)Nc2ccc3c(=O)n(CC4(O)CCN(C(=O)C(CCCNC(=O)c5ccc6c(Cl)c7c(nc6c5)CCCCC7)Cc5ccccc5)CC4)cnc3c2)CC1] 17 |
| 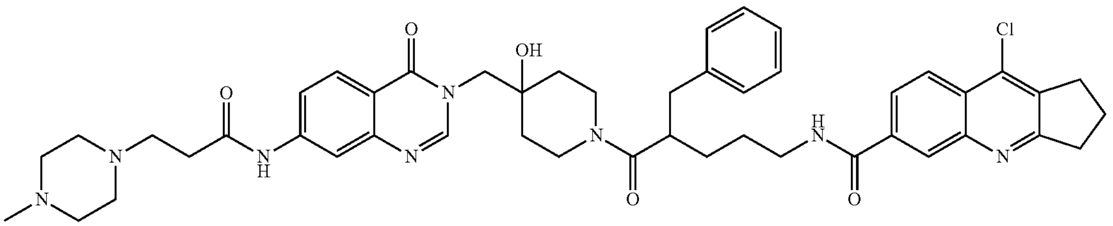 [SMILES: CN1CCN(CCC(=O)Nc2ccc3c(=O)n(CC4(O)CCN(C(=O)C(CCCNC(=O)c5ccc6c(Cl)c7c(nc6c5)CCC7)Cc5ccccc5)CC4)cnc3c2)CC1] 18 |
| 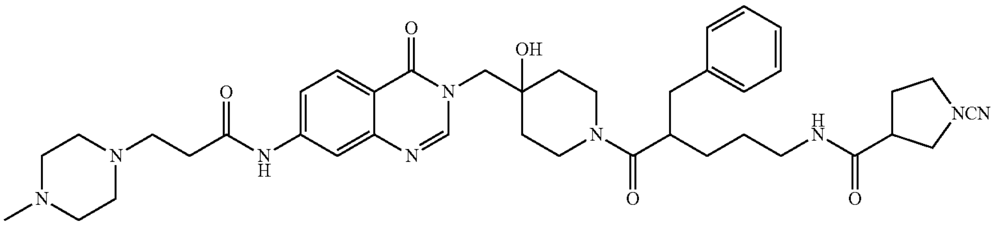 19 |
| 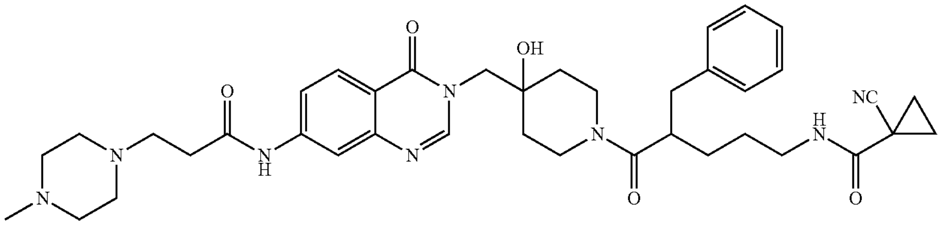 [SMILES: CN1CCN(CCC(=O)Nc2ccc3c(=O)n(CC4(O)CCN(C(=O)C(CCCNC(=O)C5(C#N)CC5)Cc5ccccc5)CC4)cnc3c2)CC1] 20 |

-continued
| Compound | |
| --- | --- |
| 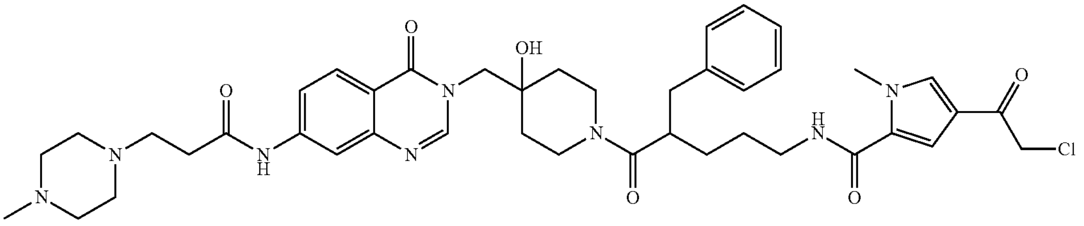 [SMILES: CN1CCN(CCC(=O)Nc2ccc3c(=O)n(CC4(O)CCN(C(=O)C(CCCNC(=O)c5cc(C(=O)CCl)cn5C)Cc5ccccc5)CC4)cnc3c2)CC1] | 21 |
| 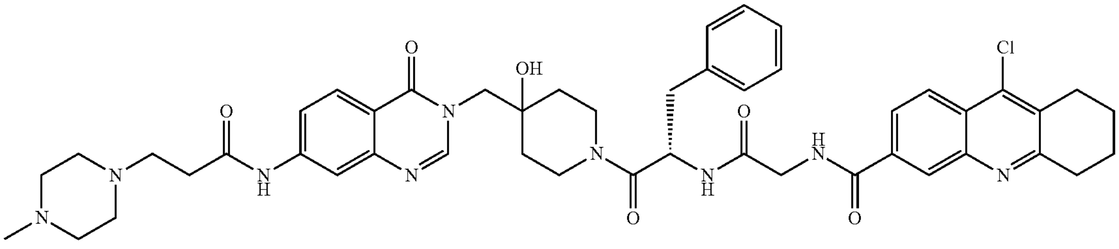 | 22 |
| 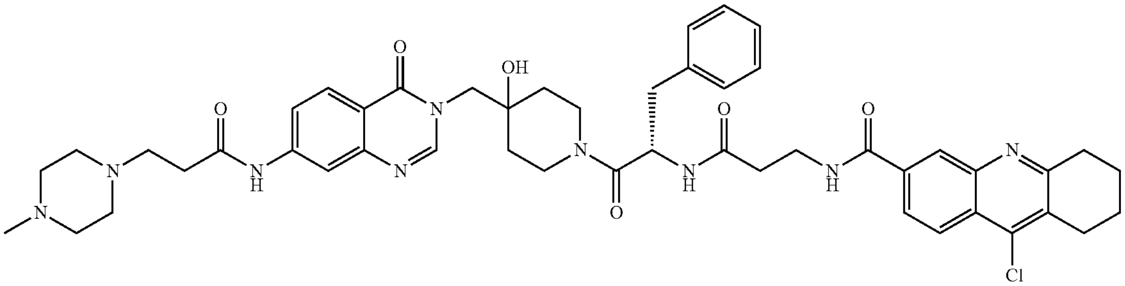 [SMILES: CN1CCN(CCC(=O)Nc2ccc3c(=O)n(CC4(O)CCN(C(=O)[C@H](Cc5ccccc5)NC(=O)CCNC(=O)c5ccc6c(Cl)c7c(nc6c5)CCCC7)CC4)cnc3c2)CC1] | 23 |
| 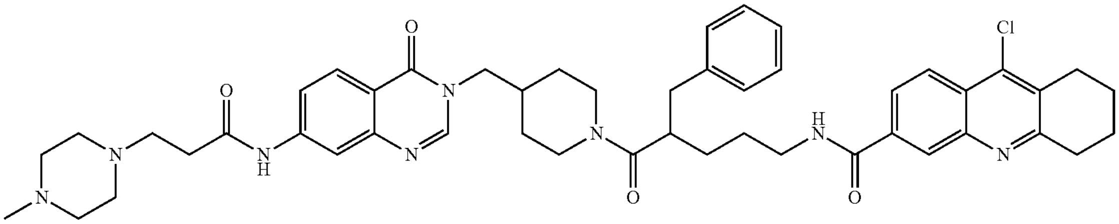 [SMILES: CN1CCN(CCC(=O)Nc2ccc3c(=O)n(CC4CCN(C(=O)C(CCCNC(=O)c5ccc6c(Cl)c7c(nc6c5)CCCC7)Cc5ccccc5)CC4)cnc3c2)CC1] | 24 |
| 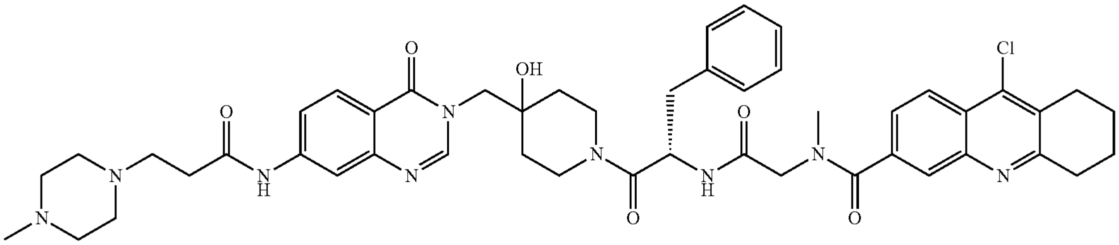 [SMILES: CN1CCN(CCC(=O)Nc2ccc3c(=O)n(CC4(O)CCN(C(=O)[C@H](Cc5ccccc5)NC(=O)CN(C)C(=O)c5ccc6c(Cl)c7c(nc6c5)CCCC7)CC4)cnc3c2)CC1] | 25 |
| 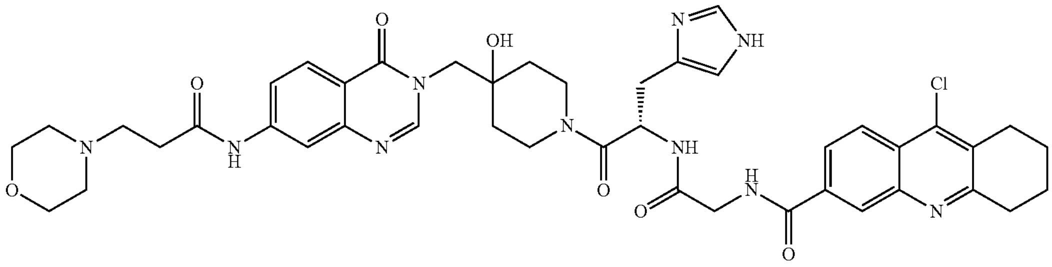 [SMILES: O=C(CCN1CCOCC1)Nc1ccc2c(=O)n(CC3(O)CCN(C(=O)[C@H](Cc4c[nH]cn4)NC(=O)CNC(=O)c4ccc5c(Cl)c6c(nc5c4)CCCC6)CC3)cnc2c1] | 26 |

-continued
| Compound |
|---|
| 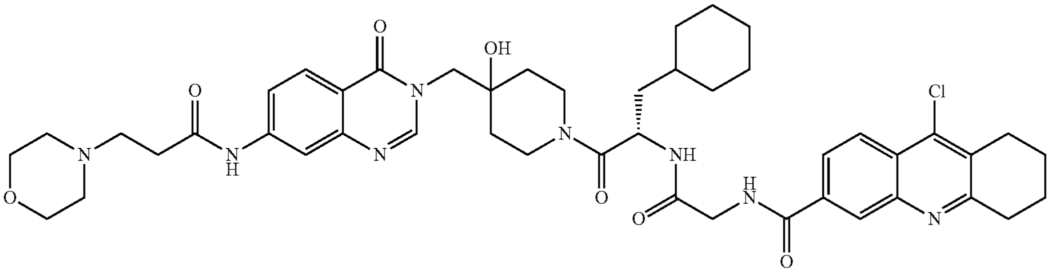 [SMILES: O=C(CCN1CCOCC1)Nc1ccc2c(=O)n(CC3(O)CCN(C(=O)[C@H](CC4CCCCC4)NC(=O)CNC(=O)c4ccc5c(Cl)c6c(nc5c4)CCCC6)CC3)cnc2c1] 27 |
| 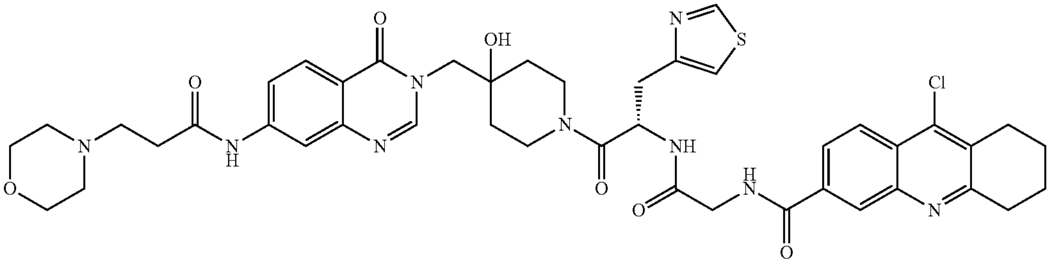 [SMILES: O=C(CCN1CCOCC1)Nc1ccc2c(=O)n(CC3(O)CCN(C(=O)[C@H](Cc4cscn4)NC(=O)CNC(=O)c4ccc5c(Cl)c6c(nc5c4)CCCC6)CC3)cnc2c1] 28 |
| 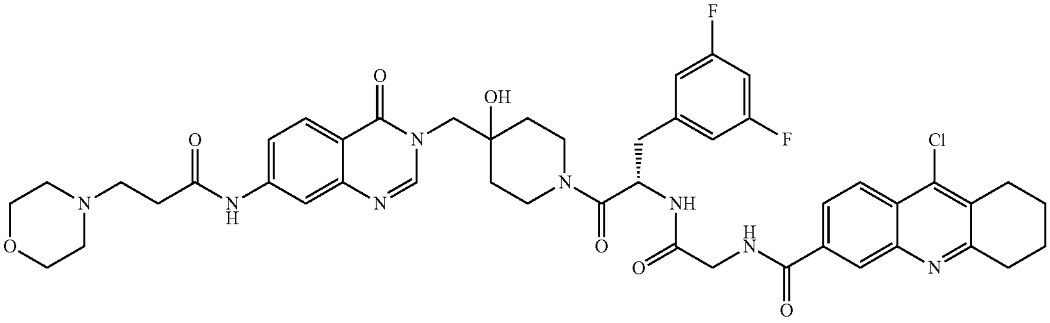 [SMILES: O=C(CCN1CCOCC1)Nc1ccc2c(=O)n(CC3(O)CCN(C(=O)[C@H](Cc4cc(F)cc(F)c4)NC(=O)CNC(=O)c4ccc5c(Cl)c6c(nc5c4)CCCC6)CC3)cnc2c1] 29 |
| 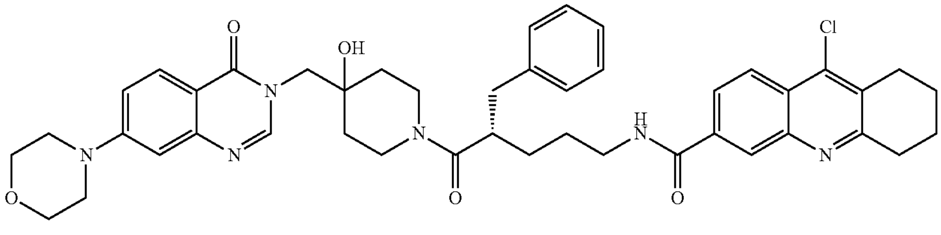 [SMILES: O=C(NCCC[C@@H](Cc1ccccc1)C(=O)N1CCC(O)(Cn2cnc3cc(N4CCOCC4)ccc3c2=O)CC1)c1ccc2c(Cl)c3c(nc2c1)CCCC3] 30 |
| 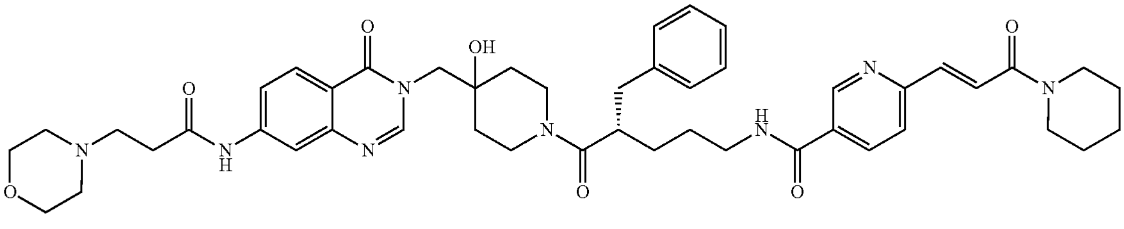 [SMILES: O=C(CCN1CCOCC1)Nc1ccc2c(=O)n(CC3(O)CCN(C(=O)[C@@H](CCCNC(=O)c4ccc(/C=C/C(=O)N5CCCCC5)nc4)Cc4ccccc4)CC3)cnc2c1] 31 |
| 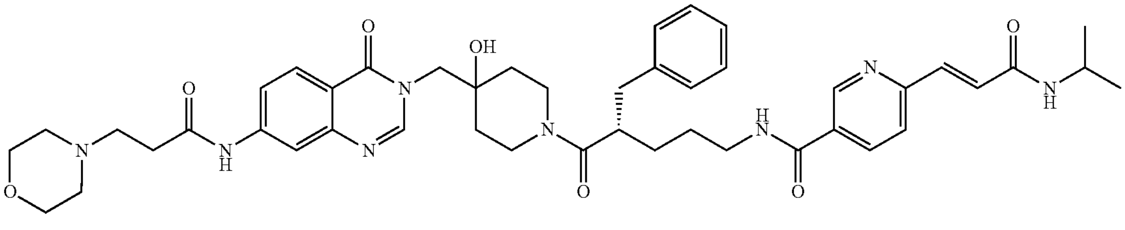 [SMILES: CC(C)NC(=O)/C=C/c1ccc(C(=O)NCCC[C@@H](Cc2ccccc2)C(=O)N2CCC(O)(Cn3cnc4cc(NC(=O)CCN5CCOCC5)ccc4c3=O)CC2)cn1] 32 |

-continued
| Compound |
| --- |
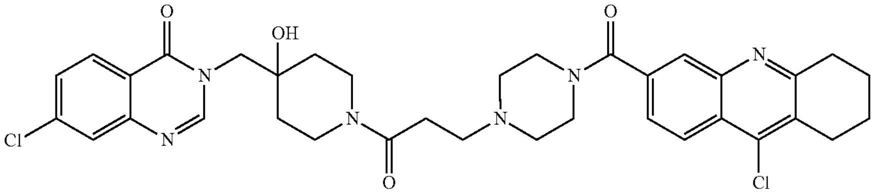 [SMILES: O=C(CCN1CCN(C(=O)c2ccc3c(Cl)c4c(nc3c2)CCCC4)CC1)N1CCC(O)(Cn2cnc3cc(Cl)ccc3c2=O)CC1]
34
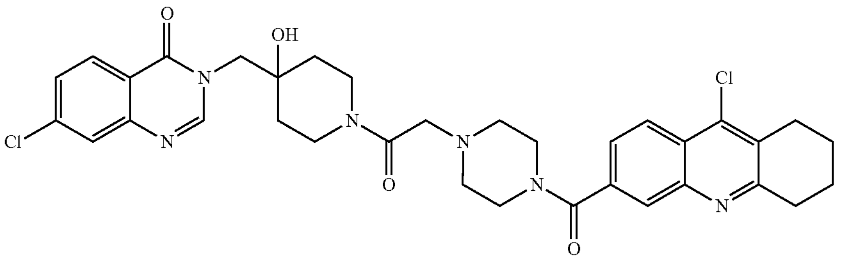 [SMILES: O=C(CN1CCN(C(=O)c2ccc3c(Cl)c4c(nc3c2)CCCC4)CC1)N1CCC(O)(Cn2cnc3cc(Cl)ccc3c2=O)CC1]
35
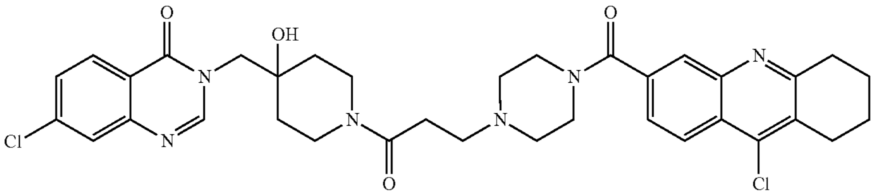 [SMILES: O=C(CCN1CCN(C(=O)c2ccc3c(Cl)c4c(nc3c2)CCCC4)CC1)N1CCC(O)(Cn2cnc3cc(Cl)ccc3c2=O)CC1]
34
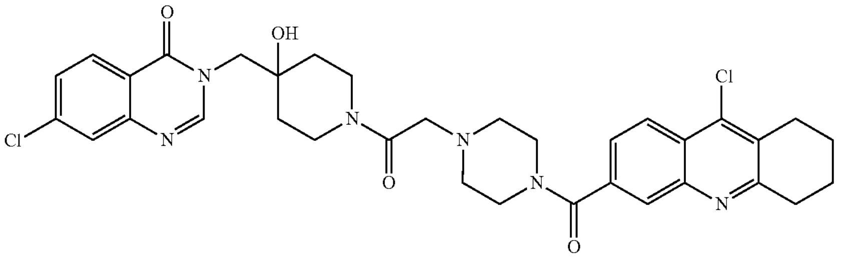 [SMILES: O=C(CN1CCN(C(=O)c2ccc3c(Cl)c4c(nc3c2)CCCC4)CC1)N1CCC(O)(Cn2cnc3cc(Cl)ccc3c2=O)CC1]
35
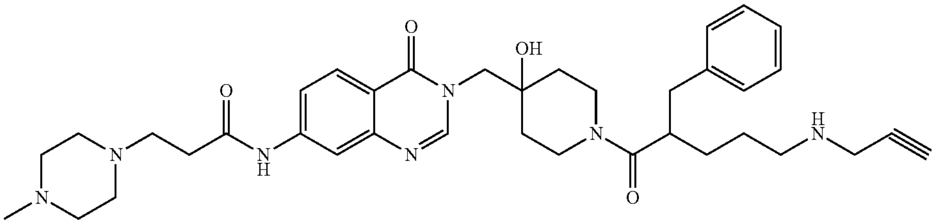 [SMILES: C#CCNCCCC(Cc1ccccc1)C(=O)N1CCC(O)(Cn2cnc3cc(NC(=O)CCN4CCN(C)CC4)ccc3c2=O)CC1]
36
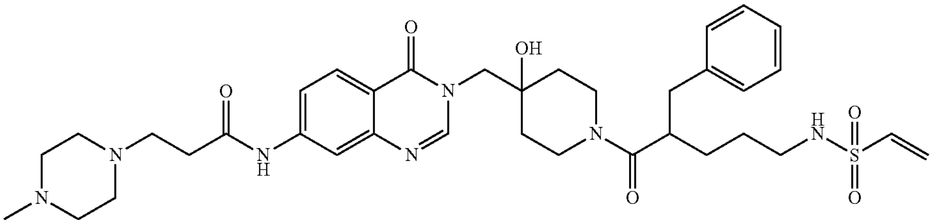 [SMILES: C=CS(=O)(=O)NCCCC(Cc1ccccc1)C(=O)N1CCC(O)(Cn2cnc3cc(NC(=O)CCN4CCN(C)CC4)ccc3c2=O)CC1]
37

-continued
| Compound | |
|---|---|
| 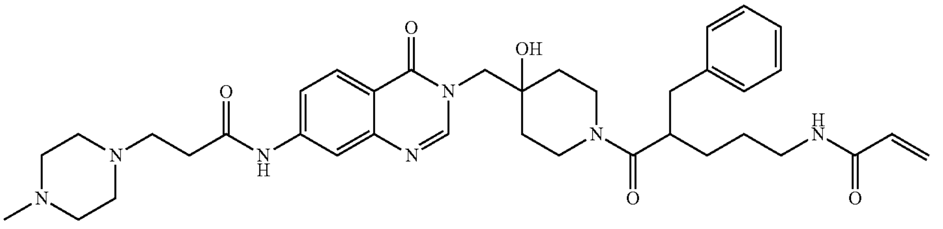 [SMILES: C=CC(=O)NCCCC(Cc1ccccc1)C(=O)N1CCC(O)(Cn2cnc3cc(NC(=O)CCN4CCN(C)CC4)ccc3c2=O)CC1] | 38 |
| 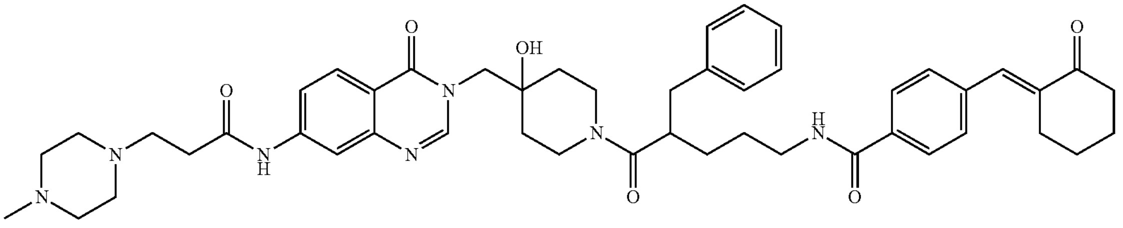 [SMILES: CN1CCN(CCC(=O)Nc2ccc3c(=O)n(CC4(O)CCN(C(=O)C(CCCNC(=O)c5ccc(/C=C6\CCCCC6=O)cc5)Cc5ccccc5)CC4)cnc3c2)CC1] | 39 |
| 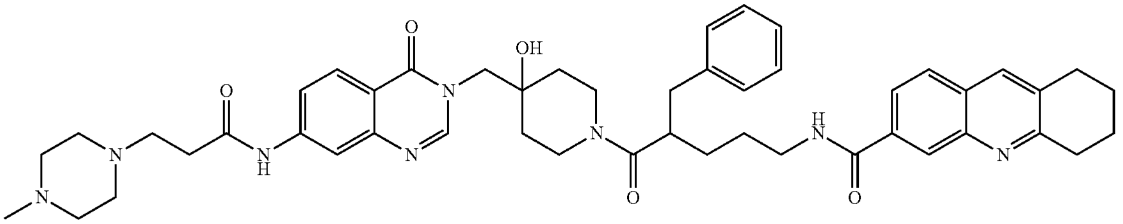 [SMILES: CN1CCN(CCC(=O)Nc2ccc3c(=O)n(CC4(O)CCN(C(=O)C(CCCNC(=O)c5ccc6cc7c(nc6c5)CCCC7)Cc5ccccc5)CC4)cnc3c2)CC1] | 40 |
| 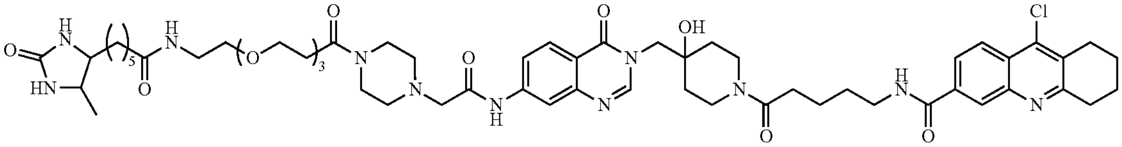 | 41 |
| 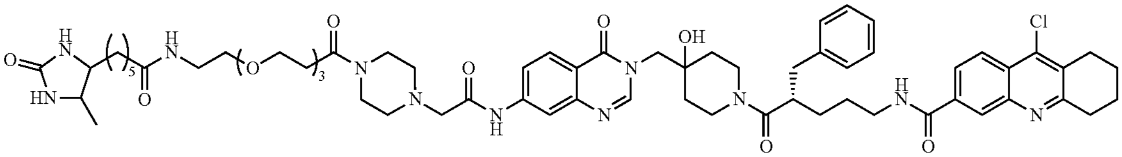 | 42 |
| 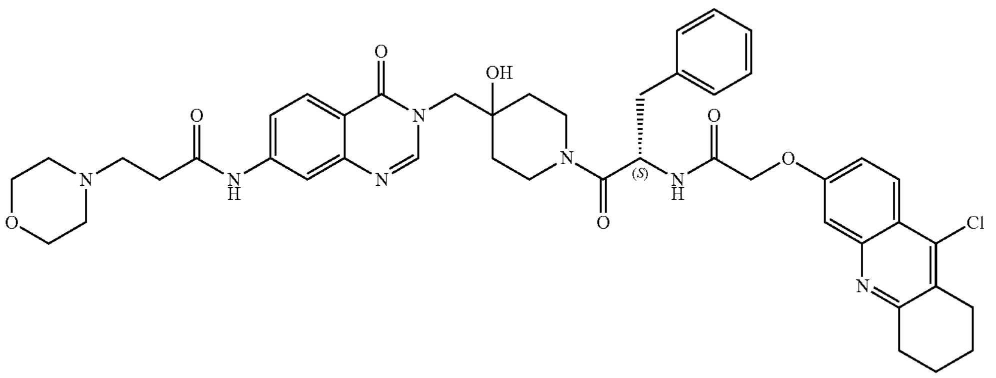 | 43 |

-continued
| Compound |
|---|
| 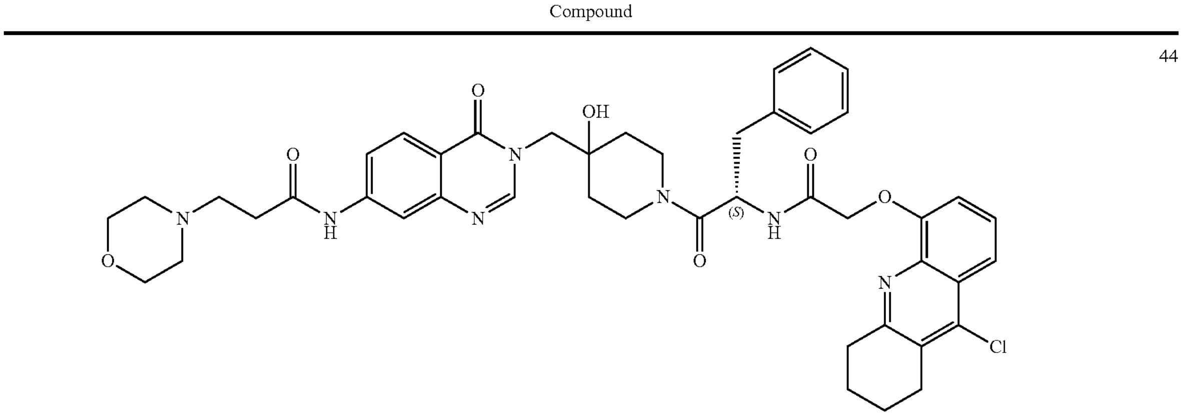 44 |
| 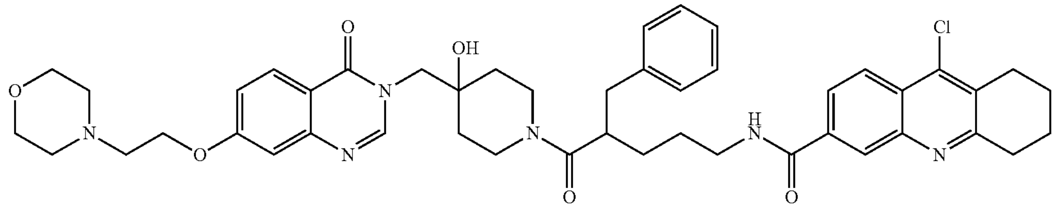 [SMILES: O=C(NCCCC(Cc1ccccc1)C(=O)N1CCC(O)(Cn2cnc3cc(OCCN4CCOCC4)ccc3c2=O)CC1)c1ccc2c(Cl)c3c(nc2c1)CCCC3] 45 |
| 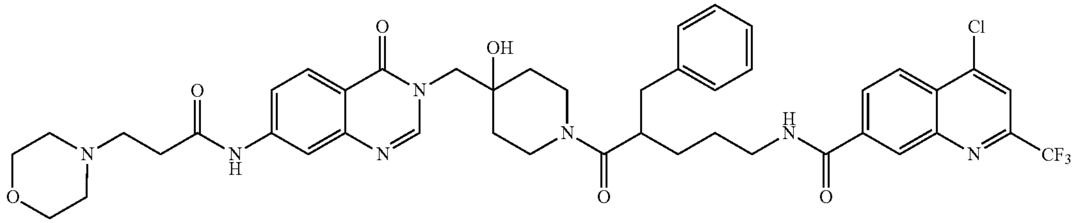 [SMILES: O=C(CCN1CCOCC1)Nc1ccc2c(=O)n(CC3(O)CCN(C(=O)C(CCCNC(=O)c4ccc5c(Cl)cc(C(F)(F)F)nc5c4)Cc4ccccc4)CC3)cnc2c1] 46 |
| 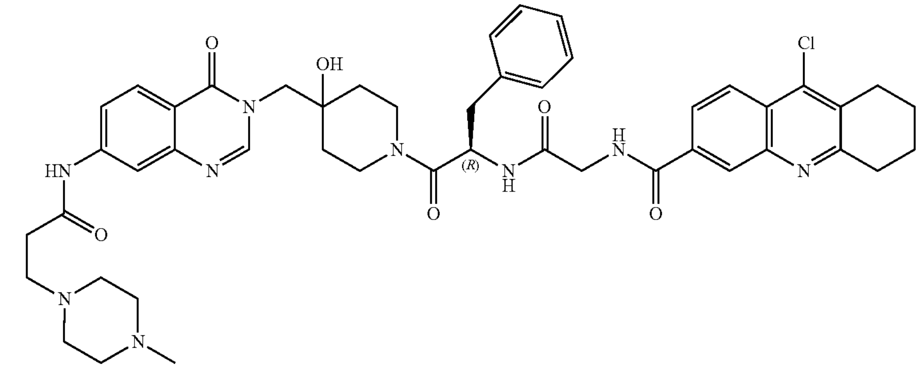 47 |
| 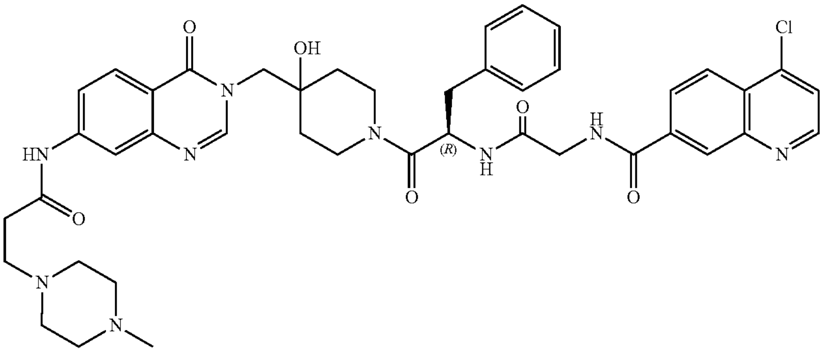 48 |

-continued
| Compound |
|---|
| 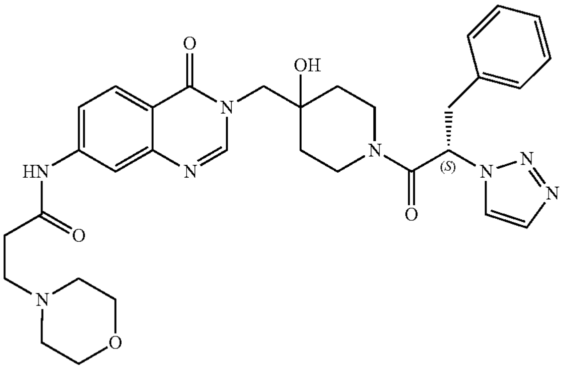 49 |
| 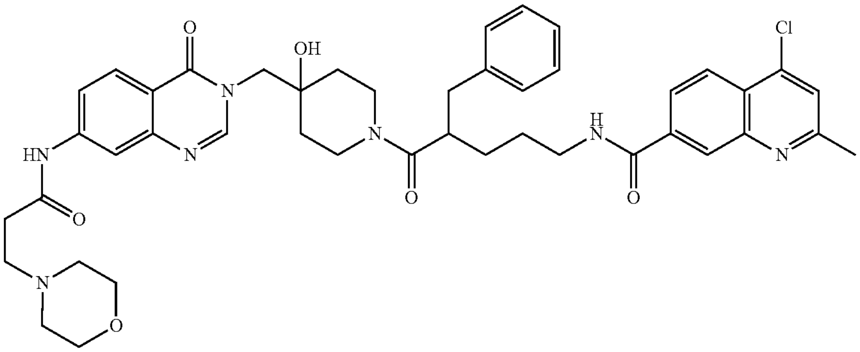 [SMILES: Cc1cc(Cl)c2ccc(C(=O)NCCCC(Cc3ccccc3)C(=O)N3CCC(O)(Cn4cnc5cc(NC(=O)CCN6CCOCC6)ccc5c4=O)CC3)cc2n1] 50 |
| 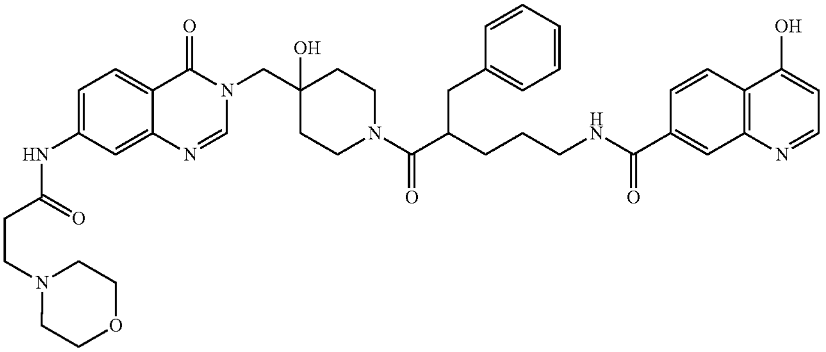 [SMILES: O=C(CCN1CCOCC1)Nc1ccc2c(=O)n(CC3(O)CCN(C(=O)C(CCCNC(=O)c4ccc5c(O)ccnc5c4)Cc4ccccc4)CC3)cnc2c1] 51 |
| 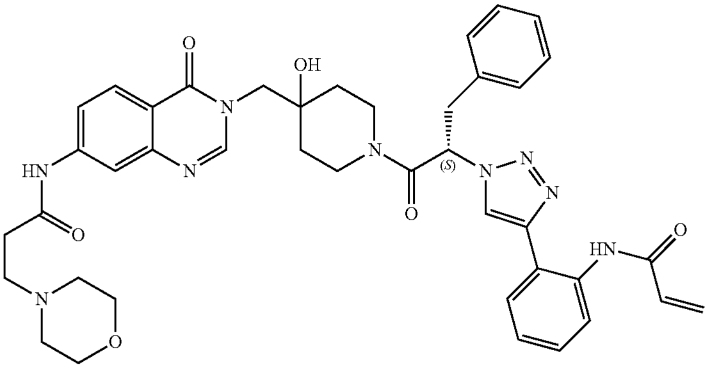 52 |

-continued
Compound
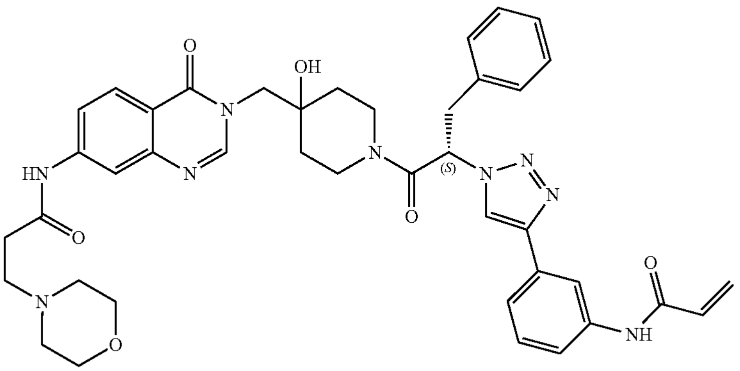
53
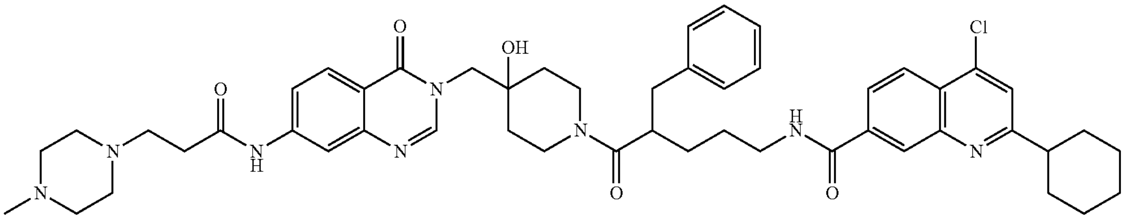 [SMILES: CN1CCN(CCC(=O)Nc2ccc3c(=O)n(CC4(O)CCN(C(=O)C(CCCNC(=O)c5ccc6c(Cl)cc(C7CCCCC7)nc6c5)Cc5ccccc5)CC4)cnc3c2)CC1]
54
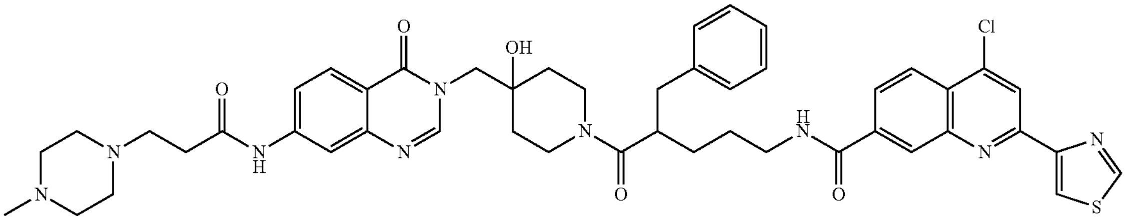 [SMILES: CN1CCN(CCC(=O)Nc2ccc3c(=O)n(CC4(O)CCN(C(=O)C(CCCNC(=O)c5ccc6c(Cl)cc(-c7cscn7)nc6c5)Cc5ccccc5)CC4)cnc3c2)CC1]
55
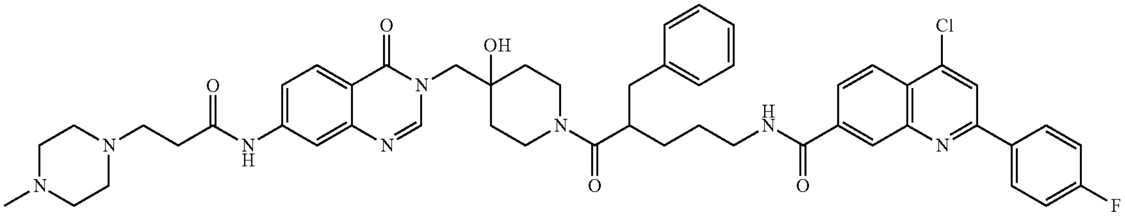 [SMILES: CN1CCN(CCC(=O)Nc2ccc3c(=O)n(CC4(O)CCN(C(=O)C(CCCNC(=O)c5ccc6c(Cl)cc(-c7ccc(F)cc7)nc6c5)Cc5ccccc5)CC4)cnc3c2)CC1]
56
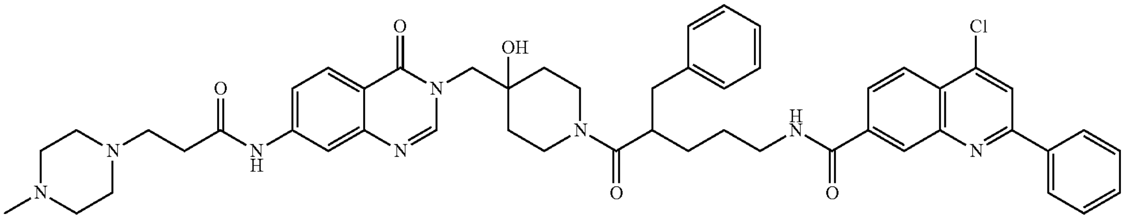 [SMILES: CN1CCN(CCC(=O)Nc2ccc3c(=O)n(CC4(O)CCN(C(=O)C(CCCNC(=O)c5ccc6c(Cl)cc(-c7ccccc7)nc6c5)Cc5ccccc5)CC4)cnc3c2)CC1]
57
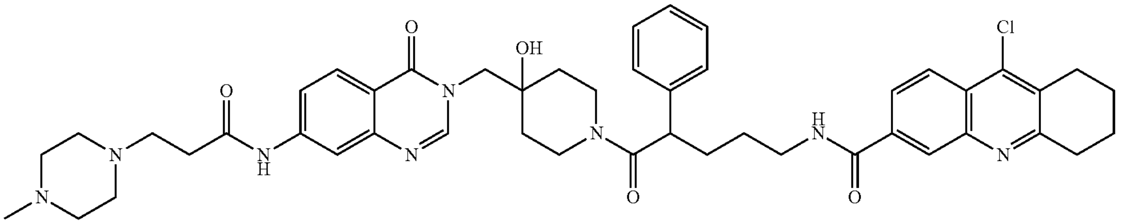 [SMILES: CN1CCN(CCC(=O)Nc2ccc3c(=O)n(CC4(O)CCN(C(=O)C(CCCNC(=O)c5ccc6c(Cl)c7c(nc6c5)CCCC7)c5ccccc5)CC4)cnc3c2)CC1]
58

-continued
Compound
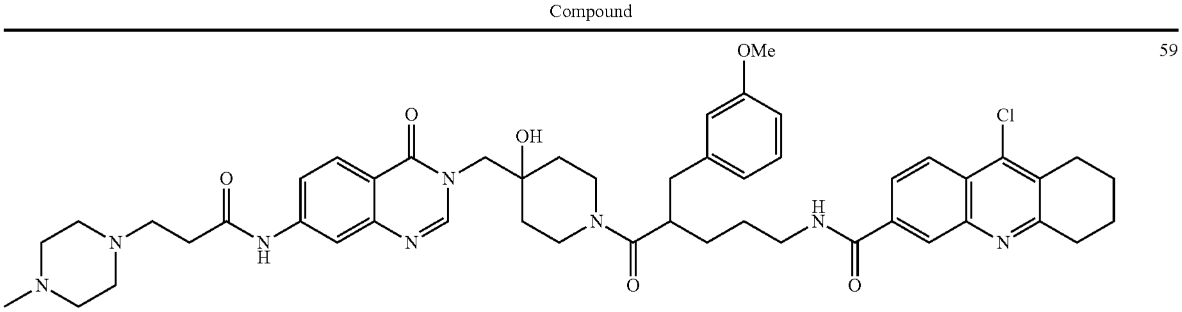
59
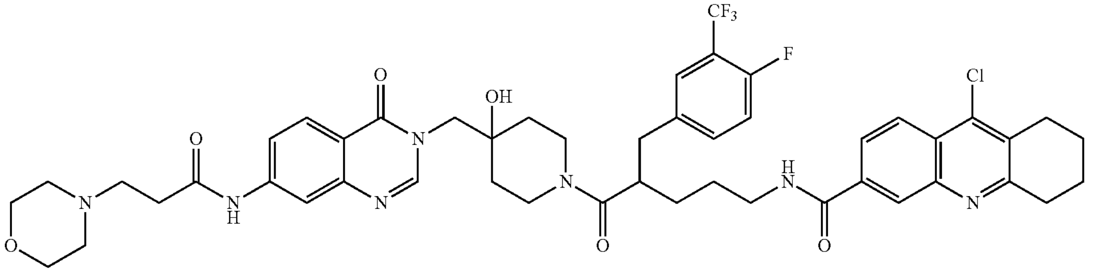 [SMILES: O=C(CCN1CCOCC1)Nc1ccc2c(=O)n(CC3(O)CCN(C(=O)C(CCCNC(=O)c4ccc5c(Cl)c6c(nc5c4)CCCC6)Cc4ccc(F)c(C(F)(F)F)c4)CC3)cnc2c1]
60
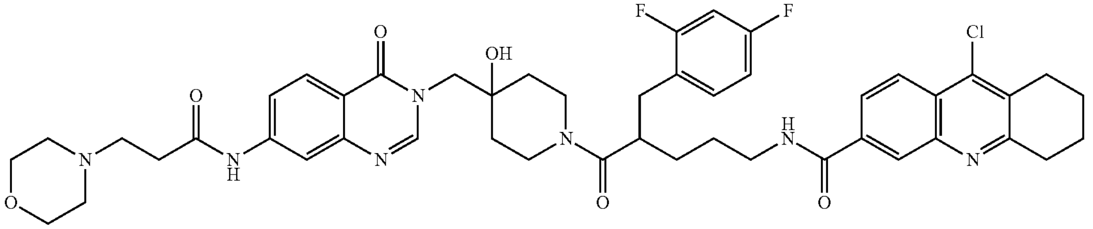 [SMILES: O=C(CCN1CCOCC1)Nc1ccc2c(=O)n(CC3(O)CCN(C(=O)C(CCCNC(=O)c4ccc5c(Cl)c6c(nc5c4)CCCC6)Cc4ccc(F)cc4F)CC3)cnc2c1]
61
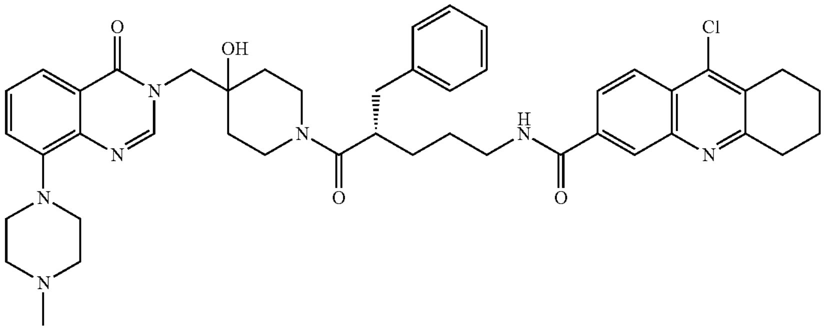 [SMILES: CN1CCN(c2cccc3c(=O)n(CC4(O)CCN(C(=O)[C@@H](CCCNC(=O)c5ccc6c(Cl)c7c(nc6c5)CCCC7)Cc5ccccc5)CC4)cnc23)CC1]
62
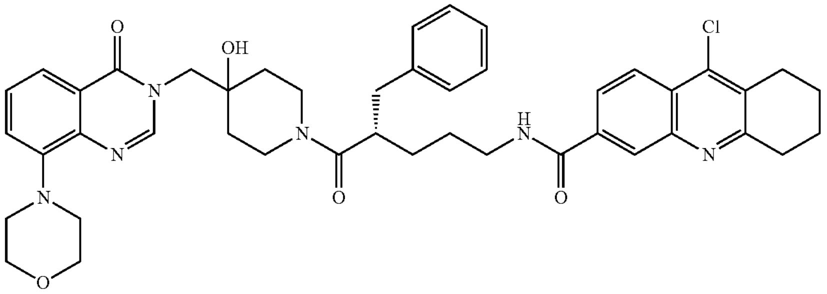 [SMILES: O=C(NCCC[C@@H](Cc1ccccc1)C(=O)N1CCC(O)(Cn2cnc3c(N4CCOCC4)cccc3c2=O)CC1)c1ccc2c(Cl)c3c(nc2c1)CCCC3]
63
or a pharmaceutically acceptable salt thereof.

In certain embodiments, the compound of Formula I is

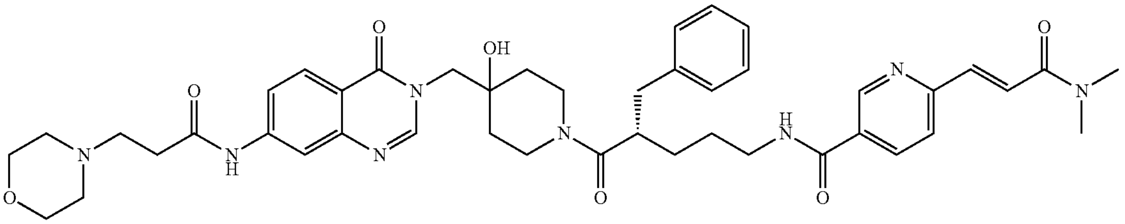 [SMILES: CN(C)C(=O)/C=C/c1ccc(C(=O)NCCC[C@@H](Cc2ccccc2)C(=O)N2CCC(O)(Cn3cnc4cc(NC(=O)CCN5CCOCC5)ccc4c3=O)CC2)cn1]

or a pharmaceutically acceptable salt thereof.

In certain embodiments, the compound of Formula I is not

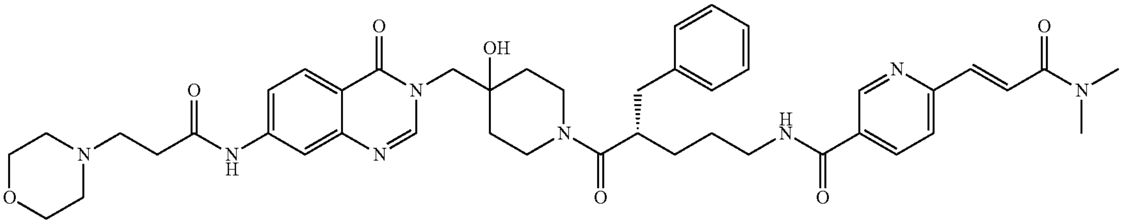 [SMILES: CN(C)C(=O)/C=C/c1ccc(C(=O)NCCC[C@@H](Cc2ccccc2)C(=O)N2CCC(O)(Cn3cnc4cc(NC(=O)CCN5CCOCC5)ccc4c3=O)CC2)cn1]

or a pharmaceutically acceptable salt thereof.

Methods of Use

Ubiquitin is a 76-residue protein that is dynamically conjugated to proteins via an isopeptide bond. Canonically, ubiquitin's C-terminal glycine is linked to a substrate lysine side chain, and ubiquitin can also be conjugated to substrates via cysteine, serine and threonine side chains as well as the N-terminal amine. McDowell, G. S. & Philpott, A. Non-canonical ubiquitylation: Mechanisms and consequences. *Int. J. Biochem. Cell Biol.* 45, 1833-1842 (2013). Ubiquitin itself possesses 7 lysine side chains, and there are naturally occurring linear or mixed chains of ubiquitin conjugated through these lysine side chains or the N-terminal methionine residue. Ubiquitin conjugation is achieved through the concerted action of ubiquitin-activating (E1), conjugating (E2), and ligating (E3) enzymes, and it can be reversed by deubiquitinating enzymes (DUBs). Mono-ubiquitin tags or ubiquitin chains of different topologies mediate protein conformational changes and binding to numerous scaffolding and adaptor proteins, and ubiquitination plays a key role in many cellular processes including proteasomal degradation (Nandi, D., et al., The Ubiquitin-Proteasome System. *J Biosci* 31, 137-155 (2016)), membrane trafficking (Hurley, J. H. & Stenmark, H. Molecular Mechanisms of Ubiquitin-Dependent Membrane Traffic. *Annu. Rev. Biophys.* 40, 119-142 (2011)), chromatin dynamics (Shilatifard, A. Chromatin Modifications by Methylation and Ubiquitination: Implications in the Regulation of Gene Expression. *Annu. Rev. Biochem.* 75, 243-269 (2006)), and DNA repair (Jackson, S. P. & Durocher, D. Review Regulation of DNA Damage Responses by Ubiquitin and SUMO. *Mol. Cell* 49, 795-807 (2013)). Ubiquitin signaling is also implicated in numerous disease settings, including cancer (Senft, D., Qi, J. & Ronai, Z. A. Ubiquitin ligases in oncogenic transformation and cancer therapy. *Nat. Rev. Cancer* 18, 69-88 (2018); Pinto-Fernandez, A. & Kessler, B. M. DUBbing cancer: Deubiquitylating enzymes involved in epigenetics, DNA damage and the cell cycle as therapeutic targets. *Front. Genet.* 7, 1-13 (2016)), infection (Isaacson, M. K. & Ploegh, H. L. Ubiquitination, Ubiquitin-like Modifiers, and Deubiquitination in Viral Infection. *Cell Host Microbe* 5, 559-570 (2009)), and neurodegeneration (Ciechanover, A. & Brundin, P. The ubiquitin proteasome system in neurodegenerative diseases: sometimes the chicken, sometimes the egg. *Neuron* 40, 427-446 The ubiquitin proteasome system in neurodeg (2003)). In particular, the ubiquitin-proteasome system (UPS) has become a target of interest in oncology, as both proteasome inhibitors and bivalent substrate-E3 ligands have been approved as targeted cancer therapies (Manasanch, E. E. & Orlowski, R. Z. Proteasome inhibitors in cancer therapy. *Nat. Rev. Clin. Oncol.* 14, 417-433 (2017); Bartlett, J. B., et al. The evolution of thalidomide and its IMiD derivatives as anticancer agents. *Nat. Rev. Cancer* 4, 314-322 (2004)). There are currently no DUB inhibitors in the clinic, a reality driven in part by a dearth of high quality probe compounds for addressing both explorations of fundamental DUB biology and target validation in preclinical disease models.

There are ~100 human DUBs belonging to seven distinct families, six of which are cysteine proteases (ubiquitin-specific protease [USP], ubiquitin C-terminal hydrolase [UCH], ovarian tumor protease [OTU], Josephin, Mindy, and ZUFSP), and one of which is a family of zinc metalloproteases (JAB/MPN/MOV34 [JAMM/MPN]). Several high quality probes targeting USP7 recently have been developed. These probes share the characteristics of single- or double-digit nM potency against USP7, co-structural confirmation of USP7 catalytic domain binding, and activity profiling verifying selectivity against 40+ DUBs. Lamberto, I. et al. Structure-Guided Development of a Potent and Selective Non-covalent Active-Site Inhibitor of USP7. *Cell Chem. Biol.* 24, 1490-1500 (2017); Kategaya, L. et al. USP7 small-molecule inhibitors interfere with ubiquitin binding. *Nature* 550, 534-538 (2017); Turnbull, A. P. et al. Molecular basis of USP7 inhibition by selective small-molecule inhibitors. *Nature* 550, 481-486 (2017); and Gavory, G. et al. Discovery and characterization of highly potent and selective allosteric USP7 inhibitors. 7, (2017). Collectively, this work represented a sea change in thinking about the druggability of USP7 and DUBs more broadly: prior to 2017, no USP:small molecule co-crystal structures had been published in the Protein Data Bank (PDB), and DUB profiling reported by research had consistently found that previously reported DUB inhibitors typically had weak (>1 μM) affinity and lacked a high degree of selectivity among DUBs. Ritorto, M. S. et al. Screening of DUB activity and specificity by MALDI-TOF mass spectrometry. *Nat. Commun.* 5, 4763 (2014).

USP7 is one of the most widely studied DUBs, and it has been associated with multiple substrates, cellular pathways, and disease states. USP7 was first discovered as an interacting partner and stabilizer of the Herpesvirus E3 ligase ICP0. Everett, R. D. et al. A novel ubiquitin-specific protease is dynamically associated with the PML nuclear domain and binds to a herpesvirus regulatory protein. 16, 1519-1530 (1997). Since then, USP7 has also been reported to interact with and regulate numerous mammalian E3 ligases, including MDM2 (Li, M., et al. A dynamic role of HAUSP in the p53-Mdm2 pathway. *Mol. Cell* 13, 879-886 (2004)), UHRF1 (Ma, H. et al. M phase phosphorylation of the epigenetic regulator UHRF1 regulates its physical association with the deubiquitylase USP7 and stability. *Proc. Natl. Acad. Sci.* 109, 4828-4833 (2012)), TRIM27 (Zaman, M. M.-U. et al. Ubiquitination-Deubiquitination by the TRIM27-USP7 Complex Regulates Tumor Necrosis Factor Alpha-Induced Apoptosis. *Mol. Cell. Biol.* 33, 4971-4984 (2013)), RING1B (de Bie, P. et al. Regulation of the Polycomb protein RING1B ubiquitination by USP7. *Biochem. Biophys. Res. Commun.* 400, 389-395 (2010)), RAD18 (Zlatanou, A. et al. USP7 is essential for maintaining Rad18 stability and DNA damage tolerance. 35, 965-976 (2015)), RNF220 (Ma, P. et al. The Ubiquitin Ligase RNF220 Enhances Canonical Wnt Signaling through USP7-Mediated Deubiquitination of -Catenin. *Mol. Cell. Biol.* 34, 4355-4366 (2014)), MARCH7 (Nathan, J. A. et al. The ubiquitin E3 ligase MARCH7 is differentially regulated by the deubiquitylating enzymes USP7 and USP9X. *Traffic* 9, 1130-1145 (2008)), RNF168 (Zhu, Q., Sharma, N., He, J., Wani, G. & Wani, A. A. USP7 deubiquitinase promotes ubiquitin-dependent DNA damage signaling by stabilizing RNF168. *Cell Cycle* 14, 1413-1425 (2015)), and RNF169 (An, L. et al. Dual-utility NLS drives RNF169-dependent DNA damage responses. *Proc. Natl. Acad. Sci.* 114, E2872-E2881 (2017)). In addition, USP7 has been found in a binary complex with both GMPS and UVSSA, and USP7 binding appears to be essential for these proteins' cellular function. Van Der Knaap, J. A. et al. GMP synthetase stimulates histone H2B deubiquitylation by the epigenetic silencer USP7. *Mol. Cell* 17, 695-707 (2005); Schwertman, P. et al. UV-sensitive syndrome protein UVSSA recruits USP7 to regulate transcription-coupled repair. *Nat. Genet.* 44, 598-602 (2012).

Of all these potential substrates, USP7's interaction with MDM2 has garnered the most interest from a mechanistic and therapeutic standpoint. USP7 binds both MDM2 and p53 through its TRAF domain and has been shown to have DUB activity toward both of these proteins. There is an emerging hypothesis that USP7 acts as a molecular switch, where it deubiquitinates and stabilizes MDM2 during normal cell growth but will change its preferred substrate to p53 in the presence of cellular stress signals. Brazhnik, P. & Kohn, K. W. HAUSP-regulated switch from auto- to p53 ubiquitination by Mdm2 (in silico discovery). *Math. Biosci.* 210, 60-77 (2007); Kim, R. Q. & Sixma, T. K. Regulation of USP7: A high incidence of E3 complexes. *J. Mol. Biol.* 429, 3395-3408 (2017). Given the key role of p53 in tumor suppression, USP7 has been proposed as a therapeutic target in TP53-WT tumors, with a putative mechanism-of-action that involves increasing p53 protein levels, similar to the effects of the MDM2-p53 interaction inhibitor RG-7388 and the MDM2/MDM4 dual inhibitor ATSP-7041, which are both currently under clinical investigation. Ding, Q. et al. Discovery of RG7388, a potent and selective p53-MDM2 inhibitor in clinical development. *J. Med. Chem.* 56, 5979-5983 (2013); Chang, Y. S. et al. Stapled α-helical peptide drug development: A potent dual inhibitor of MDM2 and MDMX for p53-dependent cancer therapy. *Proc. Natl. Acad. Sci.* 110, E3445-E3454 (2013). However, given that USP7 targets multiple substrates, there is an open debate about the relative importance of p53 mutational status in predicting response to USP7 inhibition. Several prior studies on non-selective USP7 inhibitors have indicated that USP7 inhibitors are effective against both p53 WT and mutant disease. Chauhan, D. et al. Article A Small Molecule Inhibitor of Ubiquitin-Specific Protease-7 Induces Apoptosis in Multiple Myeloma Cells and Overcomes Bortezomib Resistance. *Cancer Cell* 22, 345-358 (2012); Wang, M. et al. The USP7 Inhibitor P5091 Induces Cell Death in Ovarian Cancers with Different P53 Status. *Cell. Physiol. Biochem.* 43, 1755-1766 (2018). These results were supported in studies using Genentech's DUB-selective USP7 inhibitor GNE-6640, which did not produce significantly different responses in TP53-WT or mutant cell lines when screened in a 181-cell panel. Kategaya, L. et al. USP7 small-molecule inhibitors interfere with ubiquitin binding. *Nature* 550, 534-538 (2017). On the other hand, it has been found that in the case of the selective USP7 inhibitor compound 42, TP53 status is a key predictor of response in Ewing sarcoma and other cancer cell types. Roti, G. et al., *J. Exp. Med.,* 215, 197-216 (2018).

One of the major missing pieces in previous reports of selective USP7 inhibitors was the spectrum of off targets outside of the DUB family. A well annotated off target profile would help clarify whether the p53-independent effects of a USP7 inhibitor are due to other USP7 substrates or other compound targets. Based on the structure of compound 42 bound to USP7's catalytic domain, a rational synthesis of an irreversible, affinity-taggable analog was designed that would be sufficient for proteome-wide profiling experiments and follow-up studies on USP7/p53 biology. USP7 also alters the level of the $p16_{INK4a}$ tumor suppressor through Bmi1/Mel18 stabilization. Maertens et al., *Embo J.* 29, 2553-2565 (2010). Additional proteins involved in genomic integrity/regulation such as the DNMT1 DNA methylase and the Claspin adaptor are also stabilized by USP7. Du et al., *Science Signaling,* 3(146): ra80 (2010); Faustrup et al., *J. Cell Biol.,* 184(1):13-9 (2009). Importantly, the abundance of USP7 and DNMT1, a protein involved in maintaining epigenetic methylation required to silence genes involved in development and cancer, correlates in human colon cancer (Du et al., 2010). USP7 has also been shown in human cells to deubiquitinate the well-known tumor suppressor gene PTEN, which provokes its nuclear export and hence its inactivation. Song et al., *Nature,* 455(7214), 813-7 (2008). More importantly, USP7 overexpression was reported for the first time in prostate cancer and this overexpression was directly associated with tumour aggressiveness (Song et al., 2008).

Recently, several epigenetic modifiers, including the methyltransferase PHF8 (Wang et al., 2016a), demethylase DNMT1 (Du et al., 2010, Felle et al., *Nucleic Acids Res,* 39, 8355-65, 2011, Qin et al., *J Cell Biochem,* 112, 439-44, 2011), and acetyltransferase Tip60, (Dar et al., *Mol Cell Biol,* 33, 3309-20, 2013), as well as H2B itself (van der Knaap et al., *Mol Cell,* 17, 695-707, 2005) have been identified as direct targets of USP7. Other notable targets of USP7 include the transcription factors FOXP3, which in Treg cells links this DUB enzyme to immune response (van Loosdregt et al., *Immunity,* 39, 259-71, 2013), and N-Myc, which is stabilized in neuroblastoma cells. Tavana et al., *Nat Med,* 22, 1180-1186, 2016. Consistent with its regulation of diverse substrates and biological processes USP7 has emerged as a drug target in a wide range of malignancies including multiple myeloma (Chauhan et al., *Cancer Cell,* 22, 345-58, 2012), breast cancer (Wang et al., 2016a), neuroblastoma (Tavana et al., 2016), glioma (Cheng et al., *Oncol Rep,* 29, 1730-6, 2013), and ovarian cancer (Zhang et al., *Tohoku J Exp Med,* 239, 165-75, 2016). USP7 has also been shown in human cells to deubiquitinate FOXO4, which provokes its nuclear export and hence its inactivation; consequently the oncogenic PI3K/PKB signaling pathway was activated (van der Horst et al., *Nat Cell Biol.* 2006, 8, 1064-1073) Finally, USP7 plays an important role in p53-mediated cellular responses to various types of stress, such as DNA damage and oxidative stress (Marchenko et al., *Embo J.* 2007 26, 923-934, Meulmeester et al., *Mol Cell* 2005, 18, 565-576, van der Horst et al., *Nat Cell Biol.* 2006, 8, 1064-1073).

Multiple myeloma (MM) is an incurable hematological malignancy characterized by the accumulation of abnormal plasma cells in the bone marrow, which impede production of normal blood cells. The average survival of MM patients has improved in recent years as a result of the introduction of proteasome inhibitors and immunomodulatory agents into treatment regimens but is still quite poor at only 5 years. The proteasome inhibitor bortezomib validates the ubiquitin proteasome system as a therapeutic target for MM drug development. USP7 is a therapeutic target in MM due to its role in the degradation of p53. USP7 is highly expressed in MM patient tumor cells and MM cell lines versus normal bone marrow cells. Mutations or deletions in TP53 are late events in MM suggesting that increasing p53 via pharmacological inhibition of USP7 could be an effective therapeutic strategy for this malignancy.

Ewing sarcoma is a rare type of cancer that occurs in bones or in the soft tissue around the bones. Ewing sarcoma is more common in teenagers and young adults. The current standard of care for Ewing sarcoma is chemotherapy, radiation, and surgery.

Disclosed herein are methods for treating and preventing diseases and conditions that benefit from the modulation of USP7, comprising administering to a subject in need thereof any one of the compounds disclosed herein, or a pharmaceutically acceptable salt thereof.

Disclosed herein are methods for treating and preventing diseases and conditions that benefit from the inhibition of USP7, comprising administering to a subject in need thereof any one of the compounds disclosed herein, or a pharmaceutically acceptable salt thereof.

Disclosed herein are methods for inhibiting USP7, comprising administering to a subject in need thereof any one of the compounds disclosed herein, or a pharmaceutically acceptable salt thereof.

In some embodiments, disclosed herein are methods of treating a disease or disorder modulated by USP7, comprising administering to a subject in need thereof any one of the compounds disclosed herein, or a pharmaceutically acceptable salt thereof. In some embodiments, disclosed herein are methods of preventing a disease or a disorder modulated by USP7 comprising administering to a subject in need thereof any one of the compounds disclosed herein, or a pharmaceutically acceptable salt thereof. In some embodiments, the modulation of USP7 involves inhibiting USP7.

In some embodiments, the disease or disorder is selected from cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

Disclosed herein is the use of an inhibitor of USP7 for the preparation of a medicament for treating or preventing a disease or condition modulated by USP7, wherein the medicament comprises any one of the compounds disclosed herein, or a pharmaceutically acceptable salt thereof.

Disclosed herein are any one of the disclosed compounds, or a pharmaceutically acceptable salt thereof, for use in treating a disease or condition modulated by USP7.

Disclosed herein are methods of treating cancer comprising administering to a subject in need thereof any one of the compounds disclosed herein, or a pharmaceutically acceptable salt thereof.

Disclosed herein are methods of inhibiting USP7, wherein any one of the compounds disclosed herein, or a pharmaceutically acceptable salt thereof, forms a covalent bond with USP7.

In some embodiments, the covalent bond forms with a cysteine residue of USP7. In some embodiments, the cysteine residue of USP7 is cysteine 223 (C223).

In some embodiments of the methods and uses disclosed herein, the modulation of USP7 involves inhibiting USP7. In some embodiments, inhibition of USP7 is irreversible. In some embodiments, inhibiting USP7 is a novel treatment for a disease or condition.

In some embodiments, exemplary cancers include, but are not limited to, p53 WT cancers.

In some embodiments, exemplary cancers include, but are not limited to, solid tumors.

In some embodiments, exemplary cancers include, but are not limited to, liposarcoma, neuroblastoma, glioblastoma, breast cancer, bladder cancer, glioma, adrenocortical cancer, multiple myeloma, colorectal cancer, colon cancer, prostate cancer, non-small cell lung cancer, Human Papilloma Virus-associated cervical cancer, oropharyngeal cancer, penis cancer, ovarian cancer, anal cancer, thyroid cancer, vaginal cancer, Epstein-Barr Virus-associated nasopharyngeal carcinoma, gastric cancer, rectal cancer, thyroid cancer, Hodgkin lymphoma, diffuse large B-cell lymphoma, and Ewing sarcoma.

In some embodiments, the cancers are selected from neuroblastoma, multiple myeloma, breast cancer, glioma, colon cancer, prostate cancer, and ovarian cancer. In some embodiments, the cancer is neuroblastoma, breast cancer, glioma, multiple myeloma, or ovarian cancer. In some embodiments, the cancer is multiple myeloma. In some embodiments, the cancer is Ewing sarcoma.

Disclosed herein are methods of treating neurodegenerative diseases comprising administering to a subject in need thereof any one of the compounds disclosed herein, or a pharmaceutically acceptable salt thereof.

In some embodiments, neurodegenerative diseases include, but are not limited to, Alzheimer's disease, multiple sclerosis, Huntington's disease, infectious meningitis, encephalomyelitis, Parkinson's disease, amyotrophic lateral sclerosis, or encephalitis.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulations, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) provides improved efficacy relative to each individual administration of the compound of the invention (e.g., compound of formula I or Ia) or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s). In some embodiments, the conjoint administration provides a synergistic effect. In some embodiments, the combination index is less than 0.6.

In some embodiments, the additional therapeutic agent is a DNA-damaging agent. In some embodiments, the additional therapeutic agent is a p53 stabilizing agent. In some embodiments, the additional therapeutic agent is selected from RG7388, etoposide, GSK2830371, and doxorubicin.

Definitions

Unless defined otherwise, all technical and scientific terms used herein have the meaning commonly understood by a person skilled in the art of the present disclosure. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

In this disclosure, "comprises", "comprising", "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Unless specifically stated or obvious from context, as used herein, the term "or" is understood to be inclusive. Unless specifically stated or obvious from context, as used herein, the terms "a", "an", and "the" are understood to be singular or plural.

The term "and/or" is used in this disclosure to mean either "and" or "or" unless indicated otherwise.

The term "acyl" is art-recognized and refers to a group represented by the general formula hydrocarbylC(═O)—, preferably alkylC(═O)—.

The term "acylamino" is art-recognized and refers to an amino group substituted with an acyl group and may be represented, for example, by the formula hydrocarbylC(═O)NH—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A C1-C6 straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Exemplary substituted alkyls are described below. Cycloalkyls can be further substituted with alkyls, alkenyls, alkoxys, alkylthios, aminoalkyls, carbonyl-substituted alkyls, —CF3, —CN, and the like. Furthermore, as valence permits, "alkyl" also refers to a diradical (e.g., "alkylene").

The term "Cx-y" when used in conjunction with a chemical moiety, such as, acyl, acyloxy, alkyl, alkenyl, alkynyl, or alkoxy is meant to include groups that contain from x to y carbons in the chain. For example, the term “Cx-yalkyl” refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. C0 alkyl indicates a hydrogen where the group is in a terminal position, a bond if internal. The terms “C2-yalkenyl” and “C2-yalkynyl” refer to substituted or unsubstituted unsaturated aliphatic groups analogous in length and possible substitution to the alkyls described above, but that contain at least one double or triple bond respectively.

The term “heteroalkyl”, as used herein, refers to a saturated or unsaturated chain of carbon atoms and at least one heteroatom, wherein no two heteroatoms are adjacent.

Moreover, the term “heteroalkyl” (or “lower heteroalkyl”) as used throughout the specification, examples, and claims is intended to include both “unsubstituted heteroalkyl” and “substituted heteroalkyls”, the latter of which refers to heteroalkyl moieties having substituents replacing a hydrogen on one or more carbons or heteroatoms of the backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the heteroalkyl chain can themselves be substituted, if appropriate. For instance, the substituents of a substituted heteroalkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

The term “alkylamino”, as used herein, refers to an amino group substituted with at least one alkyl group.

The term “alkylthio”, as used herein, refers to a thiol group substituted with an alkyl group and may be represented by the general formula alkylS—.

The term “alkynyl”, as used herein, refers to an aliphatic group containing at least one triple bond and is intended to include both “unsubstituted alkynyls” and “substituted alkynyls”, the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term “amide”, as used herein, refers to a group

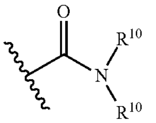

wherein each $R^{10}$ independently represents a hydrogen or hydrocarbyl group, or two $R^{10}$ are taken together with the N atom to which they are attached complete a heterocycle having from 4 to 8 atoms in the ring structure.

The terms “amine” and “amino” are art-recognized and refer to both unsubstituted and substituted amines and salts thereof, e.g., a moiety that can be represented by

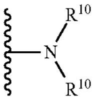
or
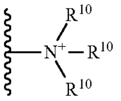

wherein each $R^{10}$ independently represents a hydrogen or a hydrocarbyl group, or two $R^{10}$ are taken together with the N atom to which they are attached complete a heterocycle having from 4 to 8 atoms in the ring structure. The term “aminoalkyl”, as used herein, refers to an alkyl group substituted with an amino group.

The term “aralkyl”, as used herein, refers to an alkyl group substituted with an aryl group.

The term “aryl” as used herein include substituted or unsubstituted single-ring aromatic groups in which each atom of the ring is carbon. Preferably, the ring is a 5- to 7-membered ring, more preferably a 6-membered ring. The term “aryl” also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Furthermore, as valence permits, “aryl” also refers to a diradical (e.g., “arylene”).

The term “carbamate” is art-recognized and refers to a group

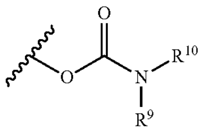
or
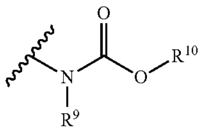

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms “carbocycle”, and “carbocyclic”, as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond.

The term “carbocycle” includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term “fused carbocycle” refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydroacridine, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings.

Cycloalkyl includes bicyclic molecules in which one, two or three or more atoms are shared between the two rings. Furthermore, as valence permits, "cycloalkyl" also refers to a diradical (e.g., "cycloalkylene"). The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The terms "carbocyclylalkyl", as used herein, refers to an alkyl group substituted with a carbocycle group.

The term "carbonate" is art-recognized and refers to a group —OCO2-R10, wherein R10 represents a hydrocarbyl group.

The term "carboxy", as used herein, refers to a group represented by the formula —CO2H.

The term "ester", as used herein, refers to a group —C(O)OR10 wherein R10 represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like. Furthermore, as valence permits, "heteroaryl" also refers to a diradical (e.g., "heteroarylene").

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Furthermore, as valence permits, "heterocyclyl" also refers to a diradical (e.g., "heterocyclylene").

The term "heterocycloalkyl", as used herein, refers to an alkyl group substituted with a heterocycle group.

The term "hydrocarbyl", as used herein, refers to a group that is bonded through a carbon atom that does not have a ═O or ═S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a ═O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO3H, or a pharmaceutically acceptable salt thereof.

The term "sulfonamide" is art-recognized and refers to the group represented by the general formulae

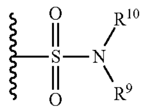

or

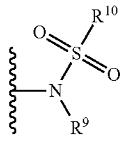

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—R10, wherein R10 represents a hydrocarbyl.

The term "sulfonate" is art-recognized and refers to the group SO3H, or a pharmaceutically acceptable salt thereof.

The term "sulfone" is art-recognized and refers to the group —S(O)2-R10, wherein R10 represents a hydrocarbyl.

The term "thioalkyl", as used herein, refers to an alkyl group substituted with a thiol group.

The term "thioester", as used herein, refers to a group —C(O)SR10 or —SC(O)R10 wherein R10 represents a hydrocarbyl.

The term "thioether", as used herein, is equivalent to an ether, wherein the oxygen is replaced with a sulfur.

The term "urea" is art-recognized and may be represented by the general formula

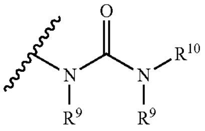

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

The term "protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the subject. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

The present invention includes all pharmaceutically acceptable isotopically-labelled compounds as described herein wherein one or more atoms are replaced by atoms having the same atomic number, but an atomic mass or mass number different from the atomic mass or mass number usually found in nature. In certain embodiments, compounds of the invention are enriched in such isotopically labeled substances (e.g., compounds wherein the distribution of isotopes in the compounds in the composition differ from a natural or typical distribution of isotopes).

Examples of isotopes suitable for inclusion in the compounds of the invention include isotopes of hydrogen, such as $^{2}H$ and $^{3}H$ carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds as disclosed herein, for example, those incorporating a radioactive isotope, are useful in drug and/or substrate tissue distribution studies. The radioactive isotopes tritium, i.e. $^3H$, and carbon-14, i.e. $^{14}C$, are useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron-emitting isotopes, such as $^{11}C$, $^{18}F$, $^{15}O$ and $^{13}N$, can be useful in Positron Emission Tomography (PET) studies for examining substrate receptor occupancy.

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric race mates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms.

Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. "Diastereomers" are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

Diastereomeric purity by weight is the ratio of the weight of one diastereomer or over the weight of all the diastereomers. When the stereochemistry of a disclosed compound is named or depicted by structure, the named or depicted stereoisomer is at least about 60%, about 70%, about 80%, about 90%, about 99% or about 99.9% by weight relative to the other stereoisomers. When a single enantiomer is named or depicted by structure, the depicted or named enantiomer is at least about 60%, about 70%, about 80%, about 90%, about 99% or about 99.9% by weight optically pure. When a single diastereomer is named or depicted by structure, the depicted or named diastereomer is at least about 60%, about 70%, about 80%, about 90%, about 99% or about 99.9% by weight pure. Percent optical purity is the ratio of the weight of the enantiomer or over the weight of the enantiomer plus the weight of its optical isomer.

Percent purity by mole fraction is the ratio of the moles of the enantiomer (or diastereomer) or over the moles of the enantiomer (or diastereomer) plus the moles of its optical isomer. When the stereochemistry of a disclosed compound is named or depicted by structure, the named or depicted stereoisomer is at least about 60%, about 70%, about 80%, about 90%, about 99% or about 99.9% by mole fraction pure relative to the other stereoisomers. When a single enantiomer is named or depicted by structure, the depicted or named enantiomer is at least about 60%, about 70%, about 80%, about 90%, about 99% or about 99.9% by mole fraction pure. When a single diastereomer is named or depicted by structure, the depicted or named diastereomer is at least about 60%, about 70%, about 80%, about 90%, about 99% or about 99.9% by mole fraction pure.

When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

As used herein, the term "pharmaceutically acceptable salt" means any pharmaceutically acceptable salt of the compound of formula (I). For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

In treatment, the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease.

Treatment includes eliciting a clinically significant response without excessive levels of side effects. Treatment also includes prolonging survival as compared to expected survival if not receiving treatment.

EXAMPLES

Example 1: Preparation of Exemplary Compounds of the Disclosure

Analytical Methods, Materials, and Instrumentation

Unless otherwise noted, reagents and solvents were used as received from commercial suppliers. All commercially available starting materials were purchased from Sigma Aldrich, Fisher Scientific, Oakwood Chemical and Combi Block. All reagents were used as received without further purification. Known compounds were synthesized according to published literature procedures and any modifications are noted. Anhydrous solvents, such as tetrahydrofuran (THF), dichloromethane (DCM), dimethyl formamide (DMF), and dimethylsulfoxide were purchased from Fisher Scientific, and used as received. If necessary, air or moisture sensitive reactions were carried out under an inert atmosphere of nitrogen.

Removal of solvents was accomplished on a Büchi R-300 rotary evaporator and further concentration was done under a Welch 1400B-01 vacuum line, and Labconco FreeZone 6 plus system. Purification of compounds was performed by normal phase column chromatography using Teledyne CombiFlash chromatography system, and/or reversed phase chromatography on Waters Micromass ZQ preparative system with SUNFIRE® Prep C18 OBD™ 5 μM column. The purity was analyzed on Waters Acquity UPLC system. Analytical thin layer chromatography (TLC) plates were purchased from Fisher Scientific (EMD Millipore TLC Silica Gel60 F254). Visualization was accomplished by irradiation under UV light (254 nm).

All $^{1}$H-NMR spectra were recorded at 298K on a Bruker ARX 500 (500 MHz) spectrometer. $^{3}$C-NMR spectra were recorded on a Bruker ARX 500 (126 MHz) spectrometer. Samples were dissolved in CDCl3, DMSO-d6, or CD3OD. The spectra were referenced to the residual solvent peak (chloroform-d: 7.26 ppm for 1H-NMR and 77.16 ppm for 13C-NMR; DMSO-d6: 2.50 ppm for 1H-NMR and 39.25 ppm for 13C-NMR, CD3OD: 3.31 ppm for 1H NMR and 49.00 ppm for 13C NMR or tetramethylsilane (TMS) as the internal standard. Chemical shift, multiplicity (s=singlet, d=doublet, dd=doublet of doublets, t=triplet, q=quartet, m=multiplet, br=broad peak), coupling constants (Hz), and number of protons. Mass spectrometry (LCMS) data were obtained on Waters Acquity UPLC system in positive ESI mode.

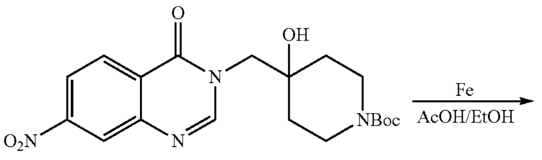

S1

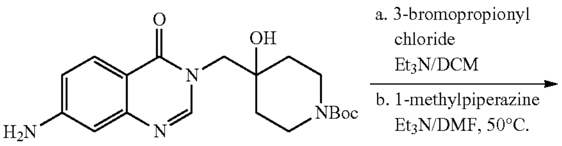

S2

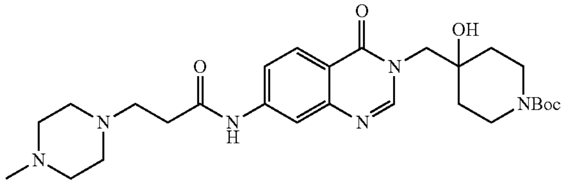

S3

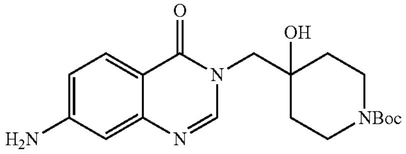

S2

Tert-butyl 4-hydroxy-4-((7-nitro-4-oxoquinazolin-3(4H)-yl)methyl)piperidine-1-carboxylate (S1, 2.4 g, 6.0 mmol) was suspended in 20 mL solvent (EtOH/AcOH=1:1). 4 eq. of iron (Fe) powder was added in portions. The mixture was stirred for 1 hour at 55° C. Then the reaction was cooled down to room temperature, and filtered through a pad of Celite. The filtrate was concentrated under reduced pressure to afford the crude product, which was then purified by flash chromatography (10% MeOH in EtOAc) to afford 2.1 g of tert-butyl 4-((7-amino-4-oxoquinazolin-3(4H)-yl)methyl)-4-hydroxypiperidine-1-carboxylate (compound S2, 93%)$^1$H NMR (500 MHz, DMSO) δ 8.04 (s, 1H), 7.79 (d, J=8.7 Hz, 1H), 6.72 (dd, J=8.7, 1.9 Hz, 1H), 6.61 (d, J=2.0 Hz, 1H), 6.09 (s, 2H), 4.87 (s, 1H), 3.89 (s, 2H), 3.64 (d, J=12.0 Hz, 2H), 3.05 (s, 2H), 1.54-1.24 (m, 13H). LCMS (ESI) m/z 374.97 [$(M+H)^+$ $C_{19}H_{27}N_4O_4^+$ calcd for 375.20].

Compound S2 (2.1 g, 5.6 mmol) was dissolved in 10 mL of anhydrous dichloromethane under $N_2$ at 0° C. 3.0 eq. of $Et_3N$ was added. Then 3-bromopropionyl chloride (1.15 g, 6.7 mmol) was added dropwise. The mixture was stirred at 0° C. for 1 hour, then quenched with MeOH, and concentrated under reduced pressure. The solid residue was directly used for the following step without further purification.

The crude product from last step was dissolved in 10 mL DMF, then 3.0 eq. of $Et_3N$ was added. Into the stirred mixture was added 1-methylpiperazine (0.67 g, 6.7 mmol) dropwise. After the addition completed, the mixture was stirred for 1 hour at 50° C. Then the reaction mixture was cooled down to room temperature, and directly subjected to HPLC purification ($MeOH/H_2O$ with 4% TFA) to afford 2.1 g of product S3 (73% in two steps) $^1$H NMR (500 MHz, MeOD) δ 8.28 (s, 1H), 8.20 (d, J=8.8 Hz, 1H), 8.12 (d, J=1.9 Hz, 1H), 7.69 (dd, J=8.7, 2.0 Hz, 1H), 4.11 (s, 2H), 3.82 (d, J=13.4 Hz, 2H), 3.23 (m, 2H), 2.85 (t, J=7.0 Hz, 2H), 2.79-2.50 (m, 10H), 2.37 (s, 3H), 1.72-1.62 (m, 2H), 1.50 (d, J=17.4 Hz, 11H). LCMS (ESI) m/z 529.08 [$(M+H)^+$ $C_{27}H_{41}N_6O_5^+$ calcd for 529.31].

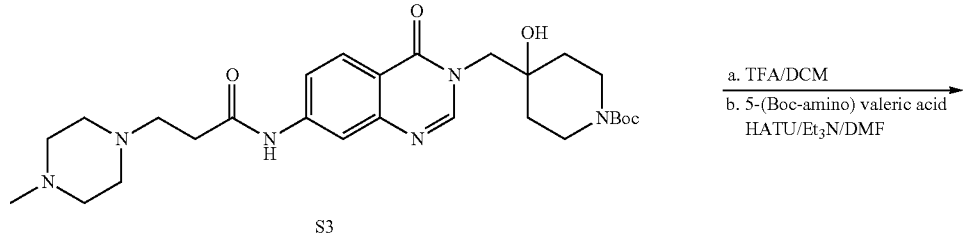

S3

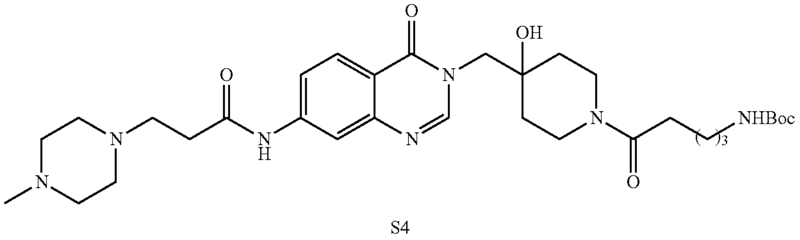

S4

Compound S3 was dissolved in 3 mL DCM, then 5 mL TFA was added in portions. The solution was stirred for 1 hour at room temperature. Then the mixture was concentrated under reduced pressure, and left on high vacuum overnight to remove residual acid. Then the product (0.46 g, 1.0 mmol) was dissolved in 5 mL DMF, and base was added (5 eq. of $Et_3N$). The solution was then added into a premixed solution of 5-(Boc-amino) valeric acid (0.25 g, 1.2 mmol) and HATU (0.76 g, 2.0 mmol) with 2 eq. of $Et_3N$. The resultant solution was stirred overnight. Then the mixture was directly subjected to HPLC purification (MeOH/$H_2O$ with 4% TFA) to afford 514 mg of product S4 (82%) LCMS (ESI) m/z 628.50 $[(M+H)^+$ $C_{32}H_{50}N_7O_6^+$ calcd for 628.38].

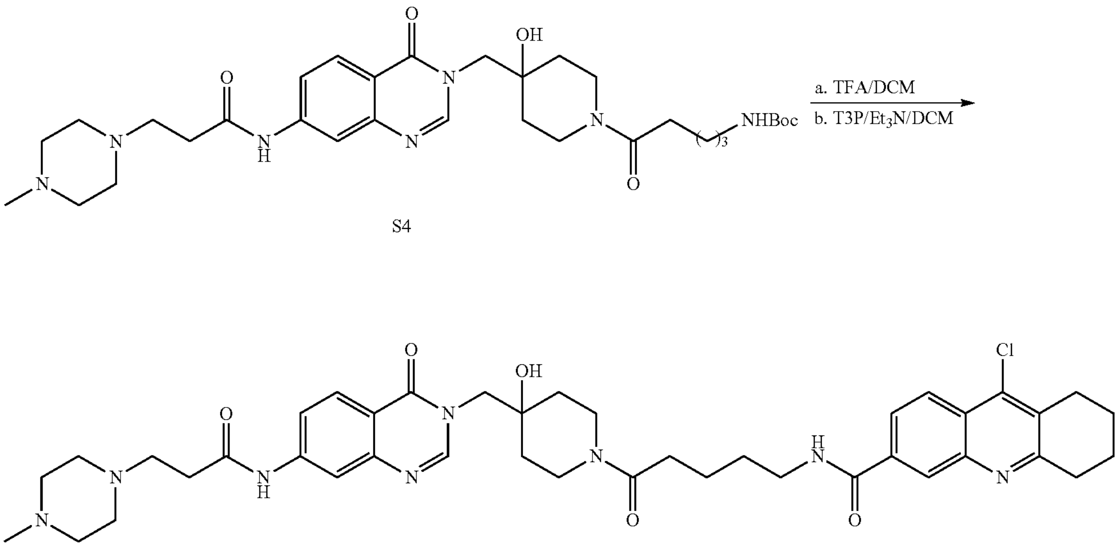

S4

1

Compound S4 (125 mg, 0.2 mmol) was dissolved in 4 M HCl in dioxane/$H_2O$, and stirred for 1 h at room temperature. Then the mixture was concentrated under reduced pressure, and left on high vacuum overnight to remove residual solvent. Then the product (0.10 g, 0.2 mmol) was dissolved in 5 mL DCM with 10 eq. of $Et_3N$. Into the solution was added 9-chloro-5,6,7,8-tetrahydroacridine-3-carboxylic acid (0.078 g, 0.3 mmol), and T3P (propylphosphonic anhydride, 50% in EtOAc) (0.64 g, 1.0 mmol). The solution was stirred at room temperature under nitrogen overnight. Then the mixture was concentrated under reduced pressure, and purified sequentially by flash chromatography and HPLC (MeOH/$H_2O$ with 4% TFA) to afford 75 mg product (1, 49%).

9-chloro-N-(5-(4-hydroxy-4-((7-(3-(4-methylpiperazin-1-yl)propanamido)-4-oxoquinazolin-3(4H)-yl)methyl)piperidin-1-yl)-5-oxopentyl)-5,6,7,8-tetrahydroacridine-3-carboxamide (compound 1). $^1$H NMR (500 MHz, DMSO) δ 10.60 (s, 1H), 8.79 (t, J=5.0 Hz, 1H), 8.46 (s, 1H), 8.22 (s, 1H), 8.15 (d, J=8.7 Hz, 1H), 8.06 (dd, J=14.6, 8.7 Hz, 3H), 7.64 (d, J=8.8 Hz, 1H), 4.11-3.90 (m, 4H), 3.65 (d, J=13.0 Hz, 1H), 3.38-3.20 (m, 6H), 3.07 (m, 5H), 2.96 (m, 4H), 2.77 (m, 6H), 2.36 (m, 2H), 1.88 (s, 3H), 1.55 (d, J=26.5 Hz, 6H), 1.48-1.31 (m, 4H). $^{13}$C NMR (126 MHz, DMSO) δ 170.76, 170.28, 165.81, 160.83, 160.63, 149.94, 149.38, 145.93, 144.60, 140.44, 135.78, 130.56, 127.77, 127.74, 126.26, 125.85, 123.90, 118.84, 117.12, 115.34, 69.80, 53.86, 52.38, 51.73, 49.40, 42.61, 41.48, 39.60, 37.41, 35.58, 34.82, 33.98, 33.18, 32.45, 29.17, 27.54, 22.89, 22.33. LCMS (ESI) m/z 771.47 $[(M+H)^+$; $C_{41}H_{52}ClN_8O_5^+$ calcd for 771.37].

2

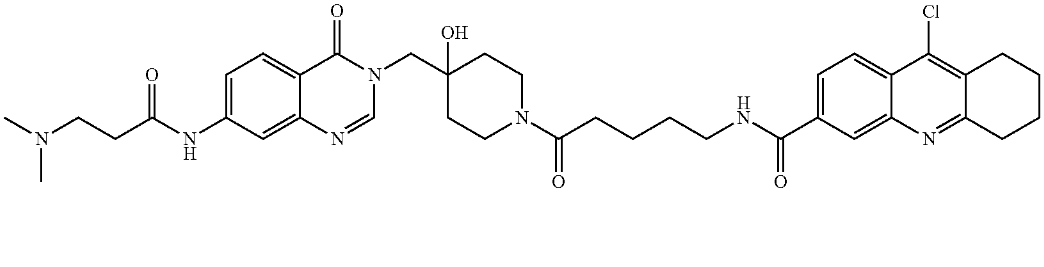

9-chloro-N-(5-(4-((7-(3-(dimethylamino)propanamido)-4-oxoquinazolin-3(4H)-yl)methyl)-4-hydroxypiperidin-1-yl)-5-oxopentyl)-5,6,7,8-tetrahydroacridine-3-carboxamide (compound 2). LCMS (ESI) m/z 715.80 [(M+H)$^+$; $C_{38}H_{47}ClN_7O_5^+$ calcd for 716.33].

3

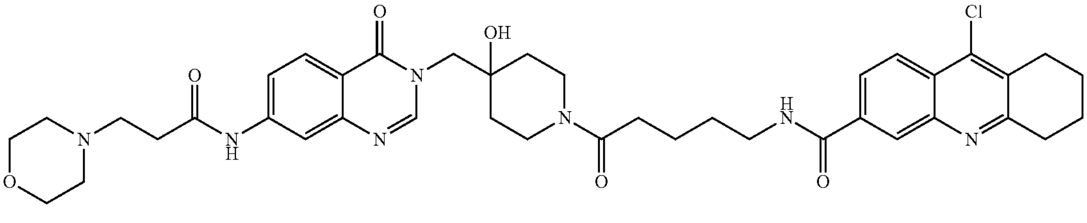

9-chloro-N-(5-(4-hydroxy-4-((7-(3-morpholinopropanamido)-4-oxoquinazolin-3(4H)-yl)methyl)piperidin-1-yl)-5-oxopentyl)-5,6,7,8-tetrahydroacridine-3-carboxamide (compound 3). LCMS (ESI) m/z 757.71 [(M+H)$^+$; $C_{40}H_{49}ClN_7O_6^+$ calcd for 758.34].

4

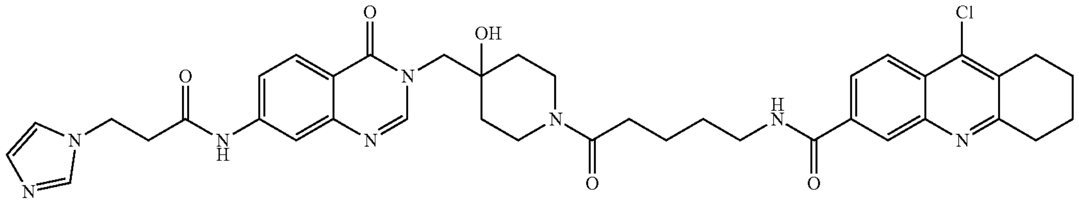

N-(5-(4-((7-(3-(1H-imidazol-1-yl)propanamido)-4-oxoquinazolin-3(4H)-yl)methyl)-4-hydroxypiperidin-1-yl)-5-oxopentyl)-9-chloro-5,6,7,8-tetrahydroacridine-3-carboxamide (compound 4). LCMS (ESI) m/z 738.81 [(M+H)$^+$ $C_{39}H_{44}ClN_8O_5^+$ calcd for 739.31].

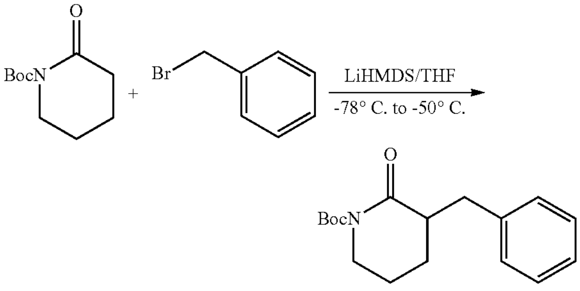

S5

1-Boc-2-piperidone (0.60 g, 3.0 mmol) was dissolved in 10 mL THF under $N_2$. The solution was cooled down at −78° C. 1.1 eq. of LiHMDS was added dropwise, then stirred for 0.5 h at this temperature. 1.0 eq. of benzylbromide was added in portions. After completion of addition, the solution was stirred at −78° C. for 1 h, then −50° C. for 4 h. Then the reaction was quenched by addition of saturated $NH_4Cl$ solution. The mixture was then extracted with EtOAc (×2). Organic layer was then washed with brine, dried over $MgSO_4$, filtered, and concentrated under reduced pressure. The crude material was purified by flash chromatography (5% to 10% EtOAc in hexanes) to afford 0.42 g product S5 (48%). Compound S5 is tert-butyl 3-benzyl-2-oxopiperidine-1-carboxylate. $^1$H NMR (500 MHz, $CDCl_3$) δ 7.30-7.23 (m, 2H), 7.18 (dd, J=14.1, 7.1 Hz, 3H), 3.69 (ddd, J=12.8, 7.8, 4.7 Hz, 1H), 3.60-3.49 (m, 1H), 3.44-3.34 (m, 1H), 2.67-2.55 (m, 2H), 1.87-1.74 (m, 2H), 1.74-1.62 (m, 1H), 1.52 (s, 9H), 1.48-1.35 (m, 1H). LCMS (ESI) m/z 289.97 [(M+H)$^+$ $C_{17}H_{24}NO_3^+$ calcd for 290.18].

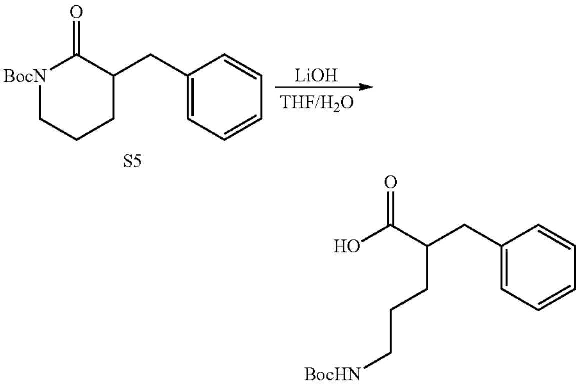

S5

S6

Compound S5 (145 mg, 0.5 mmol) was dissolved in 3 mL THF/$H_2O$. 2 eq. of LiOH was added. The mixture was stirred at room temperature for 2 hours. Then the solution was acidified by 1 M HCl, and extracted with EtOAc (×2). Organic layer was washed with brine, dried over $MgSO_4$, filtered, and evaporated under reduced pressure to afford 0.154 g crude material S6, which was used without further purification. LCMS (ESI) m/z 330.37 [(M+Na)$^+$ $C_{17}H_{25}NNaO_4^+$ calcd for 330.17].

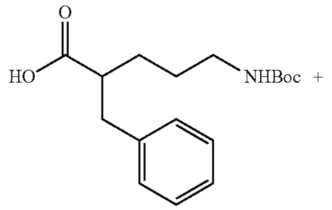

S6

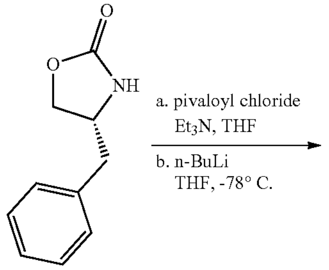

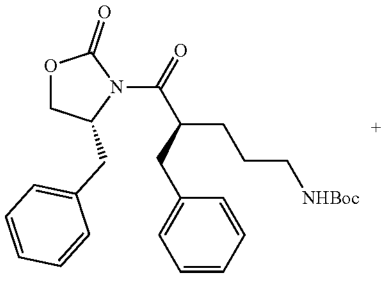

+

S7

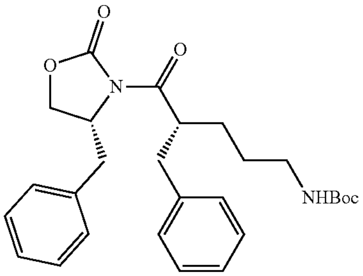

S8

2-benzyl-5-((tert-butoxycarbonyl)amino)pentanoic acid (compound S6, 0.18 g, 0.58 mmol) was dissolved in 5 mL anhydrous THF, and stirred at 0° C. under $N_2$. Into the solution was added trimethylacetyl chloride (74 μL, 0.6 mmol). The mixture was stirred for 3 hours when warming up from 0° C. to room temperature to form anhydride intermediate. (R)-4-benzyloxazolidin-2-one (0.12 g, 0.7 mmol) was dissolved in 3 mL THF and cooled to −78° C. in a separate flask. The solution was treated with 2.5 M n-butyllithium (n-BuLi) solution (0.26 mL, 0.65 mmol) and allowed to stir for one hour. The prepared anhydride solution was added to the lithium-oxazolidinone, and the mixture was allowed to warm to room temperature overnight. Then the mixture was quenched with saturated ammonium chloride solution, then extracted with EtOAc (×2). Organic layer was washed with brine, dried over $MgSO_4$, filtered, and concentrated under reduced pressure. The crude product was purified to separate two diastereomers by flash chromatography to afford the completely separated diastereomers.

S7

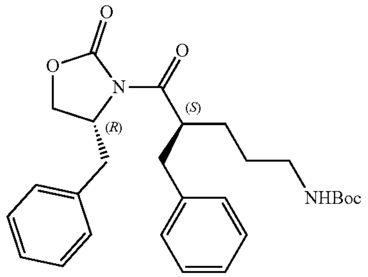

tert-butyl ((S)-4-benzyl-5-((R)-4-benzyl-2-oxooxazolidin-3-yl)-5-oxopentyl)carbamate, (compound S7, 98 mg, 73%). $^1H$ NMR (500 MHz, $CDCl_3$) δ 7.30 (t, J=7.3 Hz, 2H), 7.27-7.20 (m, 3H), 7.16 (dd, J=12.0, 5.7 Hz, 5H), 4.56 (s, 1H), 4.44-4.32 (m, 1H), 4.22-4.11 (m, 1H), 3.98 (dd, J=8.9, 2.1 Hz, 1H), 3.74 (t, J=8.3 Hz, 1H), 3.22 (dd, J=13.3, 3.2 Hz, 1H), 3.11 (s, 2H), 2.89 (dd, J=13.2, 9.0 Hz, 1H), 2.80 (dd, J=13.2, 6.4 Hz, 1H), 2.72-2.61 (m, 1H), 1.89-1.76 (m, 1H), 1.61-1.49 (m, 3H), 1.42 (s, 9H). LCMS (ESI) m/z 367.27 [(M+H-Boc)$^+$ $C_{22}H_{27}N_2O_3^+$ calcd for 367.19].

S8

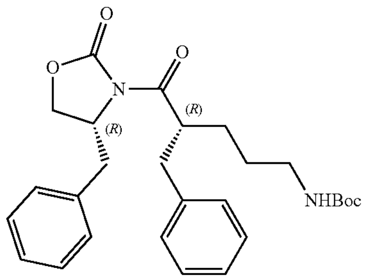

tert-butyl ((R)-4-benzyl-5-((R)-4-benzyl-2-oxooxazolidin-3-yl)-5-oxopentyl)carbamate (compound S8, 97 mg, 73%). $^1H$ NMR (500 MHz, $CDCl_3$) δ 7.29-7.21 (m, 7H), 7.21-7.14 (m, 1H), 7.00 (d, J=6.5 Hz, 2H), 4.66-4.58 (m, 1H), 4.54 (s, 1H), 4.26-4.17 (m, 1H), 4.14 (t, J=8.5 Hz, 1H), 4.03 (dd, J=9.0, 2.7 Hz, 1H), 3.13-3.00 (m, 3H), 2.97 (dd, J=13.5, 3.1 Hz, 1H), 2.78 (dd, J=13.3, 6.7 Hz, 1H), 2.37 (dd, J=13.5, 9.4 Hz, 1H), 1.84-1.69 (m, 1H), 1.59-1.46 (m, 3H), 1.41 (s, 9H). LCMS (ESI) m/z 367.27 [(M+H-Boc)$^+$ $C_{22}H_{27}N_2O_3^+$ calcd for 367.19].

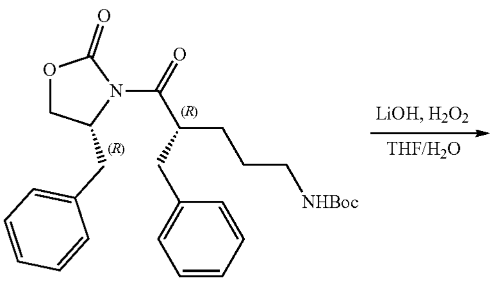

S8

-continued

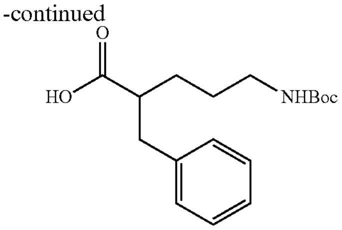

(S)-S6

Lithium hydroxide monohydrate (17 mg, 0.42 mmol) was added to a stirring solution of THF (3 mL) and $H_2O$ (1 mL) until dissolved. Into the solution was added hydrogen peroxide (30%) (80 μL, 0.84 mmol) and allowed to stir at room temperature for 10 min. The reaction was then cooled to 0° C. and THF solution of oxazolidinone adduct S8 (98 mg, 0.21 mmol) was added dropwise. The mixture was stirred at room temperature overnight. Then the solution was diluted with EtOAc, and washed with ice-cold 0.1 M HCl aqueous solution (20 mL×2). The aqueous layer was then extracted with more EtOAc. Combined organic layer was washed with brine, dried over $MgSO_4$, filtered, and concentrated under reduced pressure to afford enantiomerically pure 2-benzyl-5-((tert-butoxycarbonyl)amino)pentanoic acid (compound (S)—S6), which is used without further purification. LCMS (ESI) m/z 329.87 $[(M+Na)^+$ $C_{17}H_{25}NNaO_4^+$ calcd for 330.17].

5

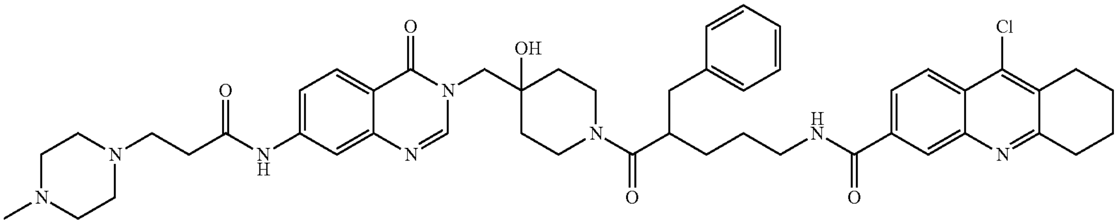

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-9-chloro-5,6,7,8-tetrahydroacridine-3-carboxamide (compound 5). $^1H$ NMR (500 MHz, DMSO) δ 10.50 (d, J=5.5 Hz, 1H), 8.82-8.70 (m, 1H), 8.46 (d, J=13.8 Hz, 1H), 8.22-7.93 (m, 5H), 7.60 (dd, J=16.4, 9.4 Hz, 1H), 7.29-7.03 (m, 5H), 4.82 (s, 1H), 4.06 (dd, J=62.6, 12.8 Hz, 1H), 3.94-3.73 (m, 1H), 3.62 (m, 2H), 3.28 (m, 4H, overlapped with $H_2O$), 3.13 (t, J=11.0 Hz, 2H), 3.05 (m, 2H), 2.96 (d, J=11.0 Hz, 2H), 2.85 (m, 1H), 2.79-2.71 (m, 2H), 2.70-2.60 (m, 4H), 2.53 (m, 3H), 2.14 (s, 4H), 1.88 (d, J=3.1 Hz, 4H), 1.71-1.34 (m, 5H), 1.33-1.03 (m, 4H), 0.39 (m, 1H). $^{13}C$ NMR (126 MHz, DMSO) δ 172.74/172.69 (conformer), 171.51, 165.80/165.76 (conformer), 160.89/160.84 (conformer), 160.58/160.52 (conformer), 149.82/149.78 (conformer), 149.46, 146.10/146.07 (conformer), 144.75, 140.47, 140.32/140.25 (conformer), 135.68, 130.58/130.53 (conformer), 129.43/129.29 (conformer), 128.63/128.51 (conformer), 127.93/127.87 (conformer), 127.77/127.70 (conformer), 126.50/126.44 (conformer), 126.29, 125.87/125.83 (conformer), 123.90, 118.75, 117.07/116.95 (conformer), 115.17, 69.67/69.59 (conformer), 55.22, 54.04/53.84 (conformer), 53.99, 52.82, 46.19, 41.97/41.74 (conformer), 41.41/41.19 (conformer), 39.15, 37.51/37.46 (conformer), 35.73, 35.13, 34.97, 34.78, 34.47, 34.06, 30.97, 30.16, 29.48, 27.56, 27.26/27.23 (conformer), 22.36. LCMS (ESI) m/z 860.72 $[(M+H)^+$; $C_{48}H_{58}ClN_8O_5^+$ calcd for 861.42].

6

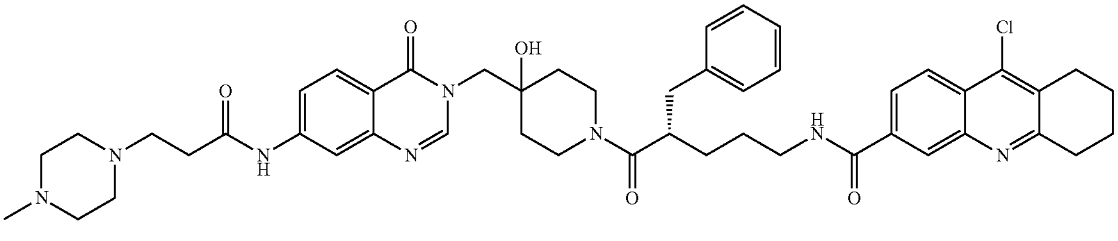

(S)—N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-9-chloro-5,6,7,8-tetrahydroacridine-3-carboxamide (compound 6). $^1H$ NMR (500 MHz, DMSO) δ 10.50 (d, J=5.5 Hz, 1H), 8.85-8.69 (m, 1H), 8.46 (d, J=14.0 Hz, 1H), 8.22-7.93 (m, 5H), 7.61 (dd, J=16.4, 9.3 Hz, 1H), 7.17 (ddt, J=32.3, 19.2, 7.4 Hz, 5H), 4.82 (d, J=4.5 Hz, 1H), 4.20-3.93 (m, 1H), 3.93-3.74 (m, 2H), 3.62 (m, 2H), 3.30 (m, 4H, overlapped with $H_2O$), 3.20-3.09 (m, 2H), 3.05 (m, 2H), 2.96 (m, 2H), 2.85 (m, 1H), 2.80-2.70 (m, 2H), 2.66 (m, 4H), 2.58-2.51 (m, 3H), 2.17 (s, 4H), 1.88 (d, J=3.2 Hz, 4H), 1.71-1.35 (m, 5H), 1.34-1.02 (m, 4H), 0.41 (t, J=10.5 Hz, 1H). $^{13}C$ NMR (126 MHz, DMSO) δ 172.24/172.19 (conformer), 170.98, 165.30/165.25 (conformer), 160.38/160.33 (conformer), 160.08/160.01 (conformer), 149.32/149.27 (conformer), 148.95, 145.59/145.56 (conformer), 144.24, 139.97, 139.81/139.75 (conformer), 135.19/135.17 (conformer), 130.07/130.02 (conformer), 128.93/128.79 (conformer), 128.12/128.00 (conformer), 127.43/127.37 (conformer), 127.26/127.20 (conformer), 125.99/125.94 (conformer), 125.78, 125.37/125.32 (conformer), 123.39, 118.25/118.20 (conformer) 116.56/116.45 (conformer), 114.67, 69.16/69.08 (conformer), 54.62, 53.53/53.33 (conformer), 53.44, 52.20, 45.54, 41.47/41.24 (conformer), 40.90/40.68 (conformer), 38.65, 37.01/36.96 (conformer), 35.22, 34.63, 34.47, 34.26, 33.96, 33.56, 30.46, 29.66, 28.98, 27.05, 26.76, 21.86. LCMS (ESI) m/z 860.82 [$(M+H)^+$; $C_{48}H_{58}ClN_8O_5^+$ calcd for 861.42].

7

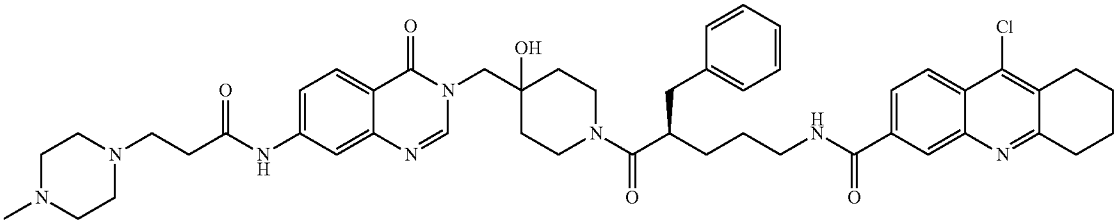

-

(R)-N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-9-chloro-5,6,7,8-tetrahydroacridine-3-carboxamide (compound 7). $^1H$ NMR (500 MHz, DMSO) δ 10.49 (d, J=5.6 Hz, 1H), 8.82-8.69 (m, 1H), 8.46 (d, J=14.0 Hz, 1H), 8.20-7.95 (m, 5H), 7.66-7.55 (m, 1H), 7.30-7.05 (m, 5H), 4.82 (d, J=4.8 Hz, 1H), 4.06 (dd, J=62.9, 12.9 Hz, 1H), 3.95-3.75 (m, 1H), 3.61 (m, 2H), 3.31-3.21 (m, 4H, overlapped with $H_2O$), 3.12 (m, 2H), 3.04 (m, 2H), 2.95 (m, 2H), 2.83 (m, 1H), 2.79-2.70 (m, 2H), 2.70-2.60 (m, 4H), 2.53 (m, 3H), 2.20 (s, 4H), 1.94-1.81 (m, 4H), 1.70-1.34 (m, 5H), 1.34-1.00 (m, 4H), 0.40 (dt, J=12.0, 9.1 Hz, 1H). $^{13}C$ NMR (126 MHz, DMSO) δ 172.75/172.70 (conformer), 171.45, 165.81/165.77 (conformer), 160.89/160.84 (conformer), 160.58/160.52 (conformer), 149.82/149.78 (conformer), 149.45, 146.09/146.06 (conformer), 144.74, 140.47, 140.32/140.25 (conformer), 135.69/135.67 (conformer), 130.58/130.53 (conformer), 129.43/129.29 (conformer), 128.63/128.51 (conformer), 127.93/127.87 (conformer), 127.77/127.70 (conformer), 126.50/126.44 (conformer), 126.28, 125.87/125.82 (conformer), 123.90, 118.76, 117.07/116.96 (conformer), 115.18, 69.67/69.59 (conformer), 54.98, 54.04, 53.88, 52.52, 45.83, 41.97/41.75 (conformer), 41.41/41.19 (conformer), 39.15, 37.52/37.46 (conformer), 35.73, 35.13, 34.97, 34.74, 34.46, 34.06, 30.97, 30.16, 29.48, 27.56, 27.26, 22.36. LCMS (ESI) m/z 860.72 $[(M+H)^+$ $C_{48}H_{58}ClN_8O_5^+$ calcd for 861.42].

8

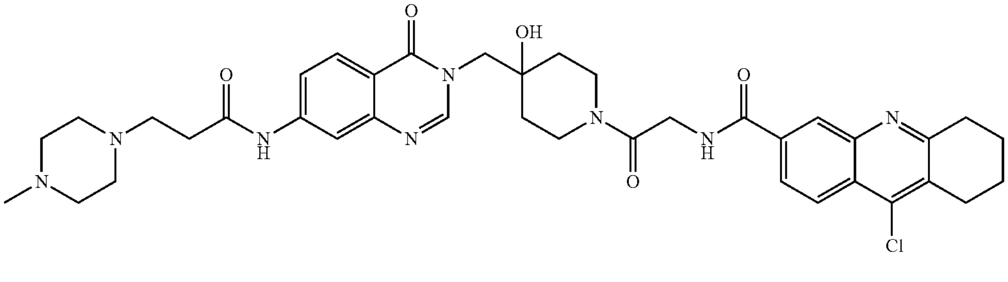

9-chloro-N-(2-(4-hydroxy-4-((7-(3-(4-methylpiperazin-1-yl)propanamido)-4-oxoquinazolin-3(4H)-yl)methyl)piperidin-1-yl)-2-oxoethyl)-5,6,7,8-tetrahydroacridine-3-carboxamide (compound 8). $^{1}H$ NMR (500 MHz, DMSO) δ 10.67 (s, 1H), 8.90 (t, J=5.6 Hz, 1H), 8.49 (s, 1H), 8.25 (s, 1H), 8.20 (d, J=8.8 Hz, 1H), 8.14-7.97 (m, 3H), 7.65 (d, J=7.8 Hz, 1H), 4.18 (p, J=10.8 Hz, 1.5H), 3.96-4.07 (m, 2.5H), 3.76-3.68 (m, 1H), 3.39-3.22 (m, 2H), 3.11-2.94 (m, 5H), 2.84 (s, 4H), 1.90 (s, 4H), 1.78-1.36 (m, 10H), 1.13-1.00 (m, 1H), 0.98-0.87 (m, 5H). $^{13}C$ NMR (126 MHz, DMSO) δ 169.83, 167.04, 166.06, 160.98, 160.64, 150.01, 149.31, 145.59, 144.54, 140.72, 135.48, 130.84, 127.82, 126.44, 125.85, 124.10, 118.90, 117.18, 115.51, 115.35, 69.78, 54.02, 51.85, 50.59, 49.01, 46.78, 42.43, 41.52, 37.99, 35.38, 34.73, 33.90, 32.34, 30.72, 29.62, 27.56, 22.28, 16.77, 16.44, 15.77, 15.64, 15.51. LCMS (ESI) m/z 728.91 [(M+H)$^{+}$; calcd for $C_{38}H_{45}ClN_8O_5^{+}$: 729.28].

9

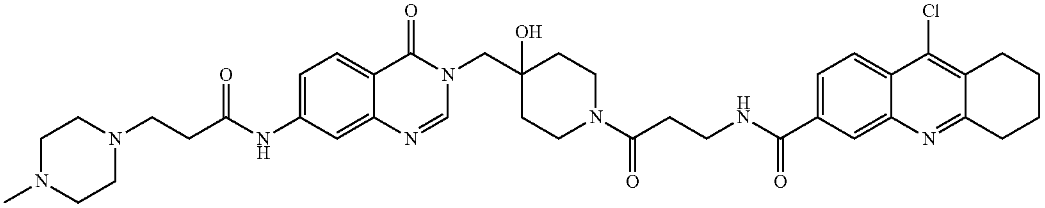

9-chloro-N-(3-(4-hydroxy-4-((7-(3-(4-methylpiperazin-1-yl)propanamido)-4-oxoquinazolin-3(4H)-yl)methyl)piperidin-1-yl)-3-oxopropyl)-5,6,7,8-tetrahydroacridine-3-carboxamide (compound 9). $^{1}H$ NMR (500 MHz, DMSO) δ 10.68 (s, 1H), 8.81 (t, J=5.3 Hz, 1H), 8.45 (s, 1H), 8.24 (s, 1H), 8.18 (d, J=8.7 Hz, 1H), 8.10-8.04 (m, 3H), 7.64 (d, J=7.4 Hz, 1H), 4.08 (d, J=12.8 Hz, 1H), 3.98 (q, J=13.8 Hz, 2H), 3.67 (d, J=13.4 Hz, 1H), 3.56-3.48 (m, 2H), 3.38-3.22 (m, 3H), 3.13-3.03 (m, 2H), 2.97-2.94 (m, 3H), 2.85 (s, 3H), 2.65 (t, J=7.2 Hz, 2H), 1.89 (s, 4H), 1.79-1.66 (m, 1H), 1.65-1.35 (m, 8H), 1.18 (t, J=7.3 Hz, 1H), 1.13-0.99 (m, 1H), 0.99-0.89 (m, 4H). $^{13}C$ NMR (126 MHz, DMSO) δ 169.65, 169.17, 165.82, 160.88, 160.60, 150.03, 149.22, 145.54, 144.50, 140.78, 135.72, 130.77, 127.81, 127.55, 126.34, 125.85, 124.04, 118.89, 117.71, 117.19, 115.30, 69.78, 54.07, 51.80, 50.38, 48.85, 46.16, 42.42, 41.34, 37.38, 36.73, 35.46, 34.70, 33.83, 32.76, 32.11, 30.69, 29.61, 27.53, 22.26, 16.77, 16.43, 15.76, 15.63, 15.50, 9.03. LCMS (ESI) m/z 742.91 [(M+H)$^{+}$; calcd for $C_{39}H_{47}ClN_8O_5^{+}$: 743.31].

10

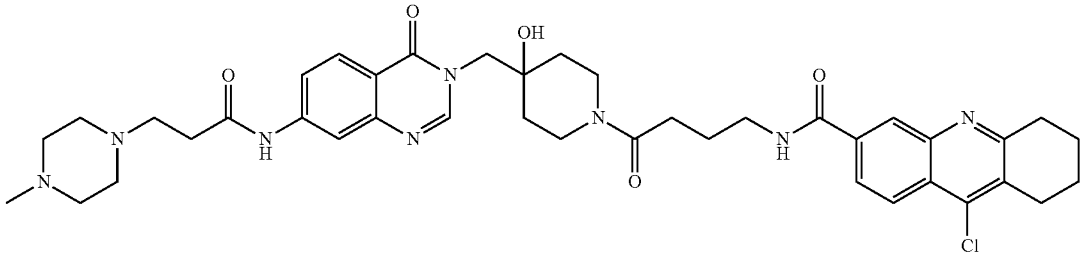

9-chloro-N-(3-(4-hydroxy-4-((7-(3-(4-methylpiperazin-1-yl)propanamido)-4-oxoquinazolin-3 (4H)-yl)methyl)piperidin-1-yl)-3-oxopropyl)-5,6,7,8-tetrahydroacridine-3-carboxamide (compound 10). $^{1}H$ NMR (500 MHz, DMSO) δ 10.68 (s, 1H), 8.80 (t, J=5.2 Hz, 1H), 8.47 (s, 1H), 8.24 (s, 1H), 8.17 (d, J=8.7 Hz, 1H), 8.13-7.98 (m, 3H), 7.64 (d, J=7.6 Hz, 1H), 4.07-3.94 (m, 3H), 3.64 (d, J=13.2 Hz, 1H), 3.39-3.22 (m, 5H), 3.14-3.02 (m, 3H), 3.01-2.77 (m, 7H), 2.40 (t, J=6.2 Hz, 2H), 1.89 (s, 4H), 1.85-1.76 (m, 2H), 1.75-1.69 (m, 1H), 1.62-1.33 (m, 7H), 1.18 (t, J=7.3 Hz, 1H), 1.12-0.99 (m, 1H), 0.99-0.89 (m, 3H). $^{13}C$ NMR (126 MHz, DMSO) δ 170.53, 169.59, 165.83, 160.80, 160.59, 150.04, 149.20, 145.32, 144.49, 140.88, 135.97, 130.71, 127.82, 127.45, 126.29, 126.00, 123.98, 118.89, 117.64, 117.19, 115.30, 69.80, 54.06, 51.70, 50.50, 48.90, 46.17, 42.42, 41.31, 37.45, 35.46, 34.77, 33.77, 32.01, 30.70, 30.32, 29.61, 27.52, 25.21, 22.26, 16.81, 16.77, 16.43, 15.76, 15.63. LCMS (ESI) m/z 756.91 [(M+H)$^+$; calcd for $C_{40}H_{49}ClN_8O_5^+$: 757.33].

11

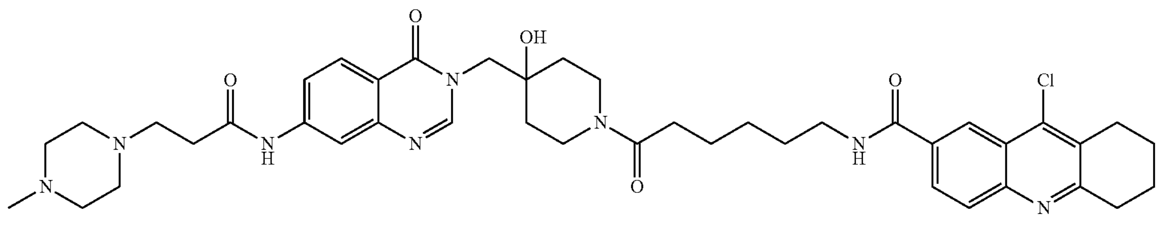

9-chloro-N-(6-(4-hydroxy-4-((7-(3-(4-methylpiperazin-1-yl)propanamido)-4-oxoquinazolin-3(4H)-yl)methyl)piperidin-1-yl)-6-oxohexyl)-5,6,7,8-tetrahydroacridine-2-carboxamide (compound 11). $^1$H NMR (500 MHz, DMSO) δ 10.67 (s, 1H), 8.77 (t, J=5.5 Hz, 1H), 8.47 (s, 1H), 8.23 (s, 1H), 8.16 (d, J=8.7 Hz, 1H), 8.11-7.99 (m, 3H), 7.64 (d, J=8.0 Hz, 1H), 4.04-3.91 (m, 3H), 3.63 (d, J=13.5 Hz, 1H), 3.35-3.24 (m, 7H), 3.12-3.02 (m, 3H), 3.00-2.77 (m, 8H), 2.30 (dd, J=7.3, 4.9 Hz, 2H), 1.88 (s, 4H), 1.76-1.67 (m, 1H), 1.60-1.27 (m, 12H), 0.94 (q, J=6.9 Hz, 2H). $^{13}$C NMR (126 MHz, DMSO) δ 170.81, 169.65, 165.70, 160.78, 160.57, 150.03, 149.19, 145.49, 144.49, 140.93, 135.99, 130.68, 127.82, 127.41, 126.28, 125.98, 123.98, 118.88, 117.65, 117.18, 115.29, 69.79, 54.04, 51.76, 50.39, 48.93, 42.42, 41.38, 37.40, 35.61, 34.79, 33.75, 32.70, 32.05, 30.70, 29.62, 29.31, 27.51, 26.74, 25.09, 22.26, 16.81, 15.77, 15.63. LCMS (ESI) m/z 784.91 [(M+H)$^+$; calcd for $C_{42}H_{53}ClN_8O_5^+$: 785.39].

12

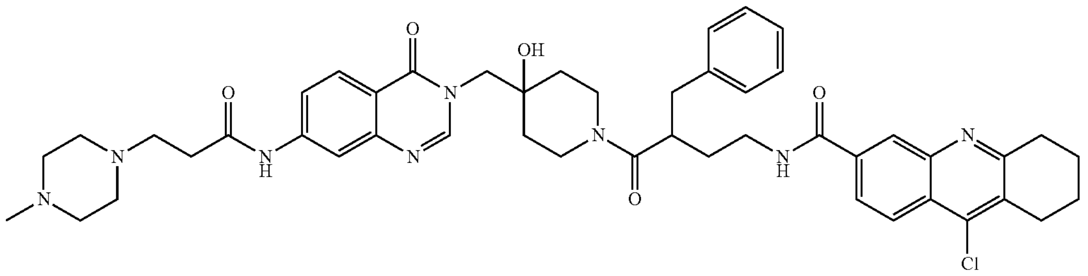

N-(3-benzyl-4-(4-hydroxy-4-((7-(3-(4-methylpiperazin-1-yl)propanamido)-4-oxoquinazolin-3(4H)-yl)methyl)piperidin-1-yl)-4-oxobutyl)-9-chloro-5,6,7,8-tetrahydroacridine-3-carboxamide (compound 12). $^1$H NMR (500 MHz, DMSO) δ 10.63 (s, 1H), 8.75 (dt, J=32.4, 5.3 Hz, 1H, conformer), 8.45 (d, J=13.6 Hz, 1H, conformer), 8.21-7.97 (m, 5H), 7.64 (t, J=9.4 Hz, 1H), 7.32-7.07 (m, 5H), 4.06 (dd, J=50.9, 12.8 Hz, 1H, conformer), 3.91 (dd, J=33.3, 13.8 Hz, 1H), 3.84-3.62 (dd, J=92.0, 13.5 Hz, 1H), 3.54 (d, J=14.0 Hz, 2H), 3.39-3.15 (m, 8H), 3.06 (m, 6H), 2.90-2.61 (m, 9H), 1.99-1.82 (m, 6H), 1.72 (m, 1H), 1.52-1.32 (m, 1H), 1.30-1.00 (m, 3H), 0.39 (t, J=10.6 Hz, 1H). $^{13}$C NMR (126 MHz, DMSO) δ 172.44, 171.51/171.49 (conformer), 165.87, 160.89/160.85 (conformer), 160.56/160.51 (conformer), 149.83/149.77 (conformer), 149.45, 146.09/146.05 (conformer), 144.75, 140.32, 140.12, 135.69/135.66 (conformer), 130.58/130.55 (conformer), 129.49/129.36 (conformer), 128.66/128.55 (conformer), 127.88, 127.76/127.67 (conformer), 126.58/126.52 (conformer), 126.32/126.28 (conformer), 125.91/125.83 (conformer), 123.92/123.89 (conformer), 118.73/118.68 (conformer), 117.05/116.96 (conformer), 115.15, 69.65, 69.56, 55.23, 54.00, 53.80, 52.84, 46.20, 41.41, 41.13, 38.88, 37.99, 37.48, 35.37, 35.04, 34.87, 34.79, 34.46, 34.05, 33.02, 32.48, 27.56, 22.37. LCMS (ESI) m/z 846.92 [(M+H)$^+$; $C_{47}H_{56}ClN_8O_5^+$ calcd for 847.41].

13

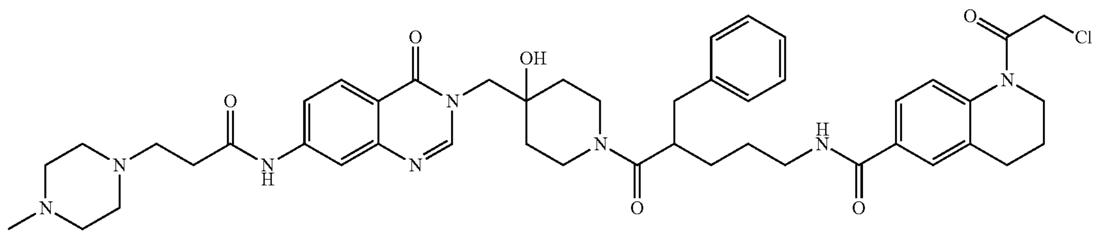

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-1-(2-chloroacetyl)-1,2,3,4-tetrahydroquinoline-6-carboxamide (compound 13). LCMS (ESI) m/z 852.92 $[(M+H)^+$ $C_{46}H_{58}ClN_8O_6^+$ calcd for 853.42].

14

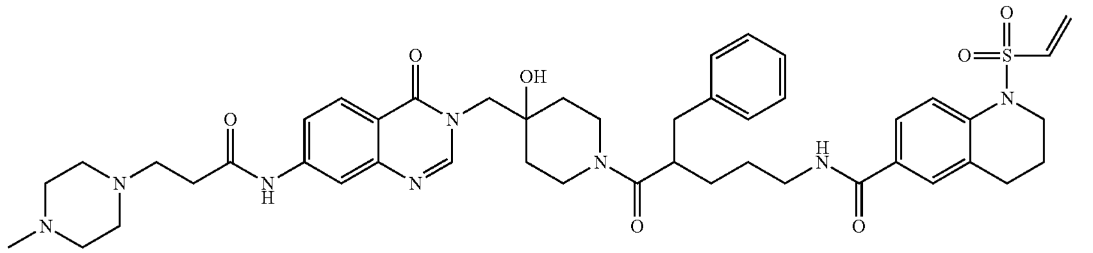

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-1-(vinylsulfonyl)-1,2,3,4-tetrahydroquinoline-6-carboxamide (compound 14). LCMS (ESI) m/z 866.72 $[(M+H)^+$ $C_{46}H_{59}N_8O_7S^+$ calcd for 867.42].

15

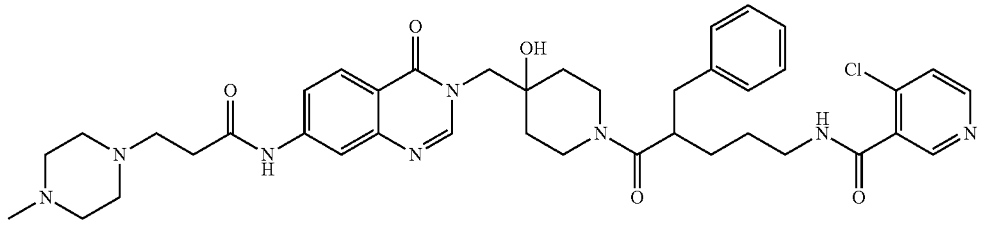

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-4-chloronicotinamide (compound 15). LCMS (ESI) m/z 756.91 $[(M+H)^+$ $C_{40}H_{50}ClN_8O_5^+$ calcd for 757.36].

16

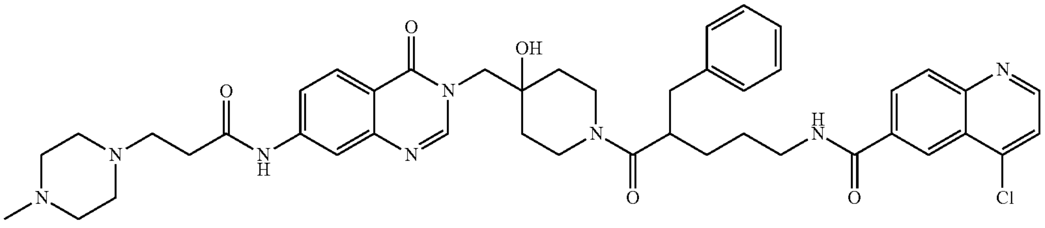

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-4-chloroquinoline-6-carboxamide (compound 16). $^1H$ NMR (500 MHz, DMSO-d6) δ 10.68 (s, 1H), 9.00-8.79 (m, 2H), 8.60 (d, J=13.6 Hz, 1H), 8.32-8.22 (m, 1H), 8.22-7.95 (m, 4H), 7.85 (d, J=4.6 Hz, 1H), 7.66 (br, 1H), 7.33-7.01 (m, 5H), 4.07 (dd, J=61.0, 12.8 Hz, 1H), 3.96-3.75 (m, 2H), 3.74-3.20 (m, 10H), 3.11 (dd, J=16.9, 9.7 Hz, 3H), 3.00-2.57 (m, 7H), 1.79-1.24 (m, 7H), 1.11 (m, 2H), 0.95 (dd, J=13.7, 6.9 Hz, 2H). LCMS (ESI) m/z 806.91 $[(M+H)^+$ $C_{44}H_{52}ClN_8O_5^+$ calcd for 807.37].

17

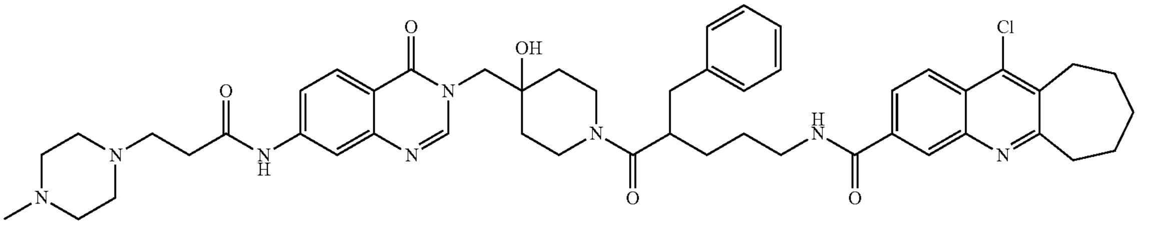

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-11-chloro-7,8,9,10-tetrahydro-6H-cyclohepta[b]quinoline-3-carboxamide (compound 17). LCMS (ESI) m/z 874.82 $[(M+H)^+$ $C_{49}H_{60}ClN_8O_5^+$ calcd for 875.44].

18

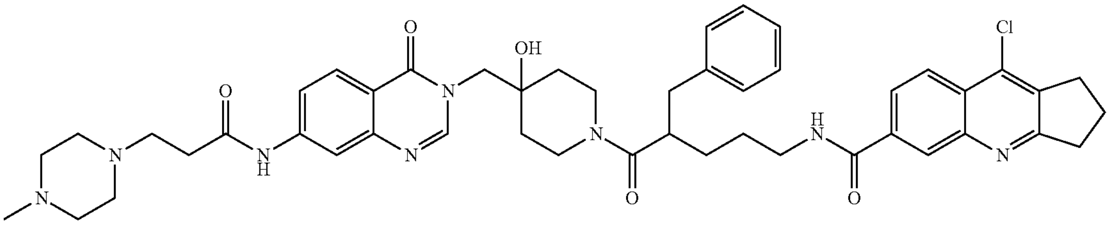

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-9-chloro-2,3-dihydro-1H-cyclopenta[b]quinoline-6-carboxamide (compound 18). LCMS (ESI) m/z 846.82 $[(M+H)^+$ $C_{47}H_{56}ClN_8O_5^+$ calcd for 847.41].

19

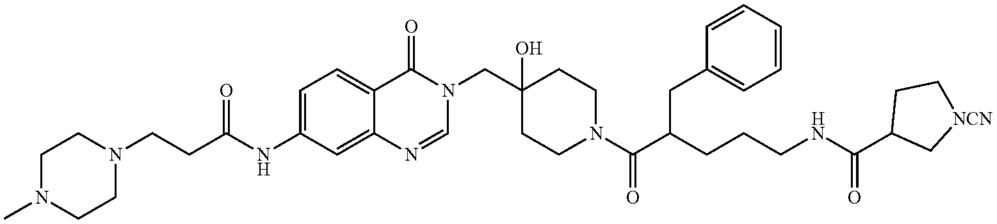

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-1-cyanopyrrolidine-3-carboxamide (compound 19). LCMS (ESI) m/z 739.91 [(M+H)$^+$ $C_{40}H_{54}N_9O_5^+$ calcd for 740.42].

20

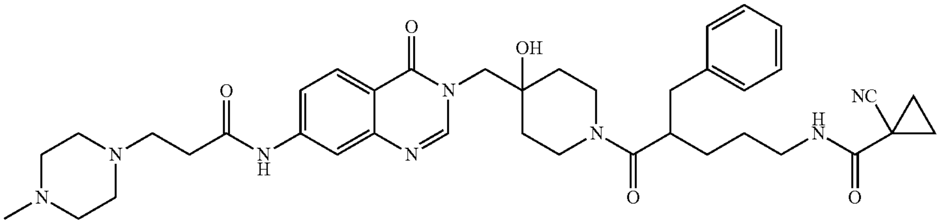

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-1-cyanocyclopropanecarboxamide (compound 20). LCMS (ESI) m/z 710.90 [(M+H)$^+$ $C_{39}H_{51}N_8O_5^+$ calcd for 711.40].

21

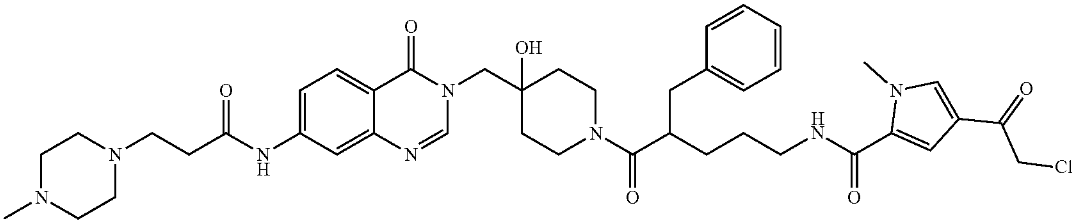

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-4-(2-chloroacetyl)-1-methyl-1H-pyrrole-2-carboxamide (compound 21). LCMS (ESI) m/z 800.81 [(M+H)$^+$ $C_{42}H_{54}ClN_8O_6^+$ calcd for 801.38].

22

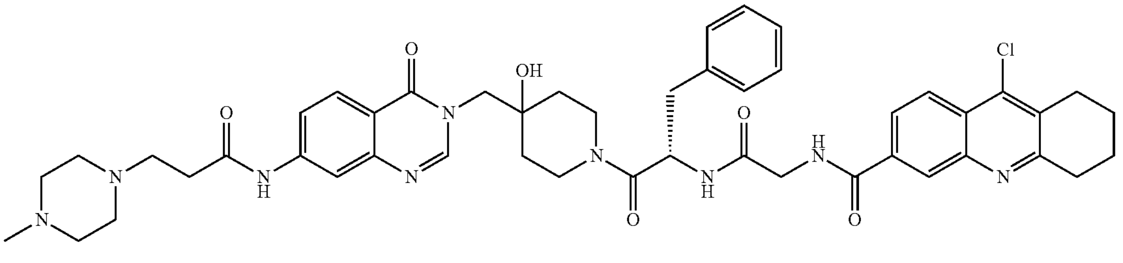

(S)-9-chloro-N-(2-((1-(4-hydroxy-4-((7-(3-(4-methylpiperazin-1-yl)propanamido)-4-oxoquinazolin-3(4H)-yl)methyl)piperidin-1-yl)-1-oxo-3-phenylpropan-2-yl)amino)-2-oxoethyl)-5,6,7,8-tetrahydroacridine-3-carboxamide (compound 6). LCMS (ESI) m/z 876.32 [(M+H)$^+$ $C_{47}H_{55}ClN_9O_6^+$ calcd for 876.40].

23

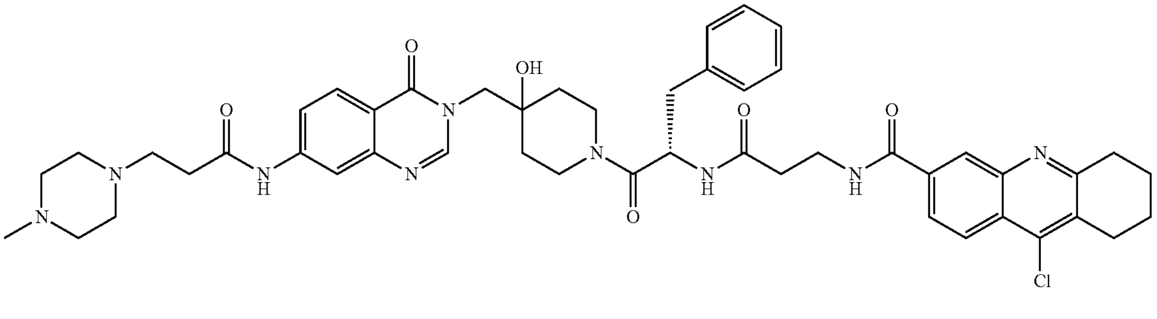

(S)-9-chloro-N-(3-((1-(4-hydroxy-4-((7-(3-(4-methylpiperazin-1-yl)propanamido)-4-oxoquinazolin-3(4H)-yl)methyl)piperidin-1-yl)-1-oxo-3-phenylpropan-2-yl)amino)-3-oxopropyl)-5,6,7,8-tetrahydroacridine-3-carboxamide (compound 23). LCMS (ESI) m/z 890.42 [(M+H)$^+$ $C_{48}H_{57}ClN_9O_6^+$ calcd for 890.41].

24

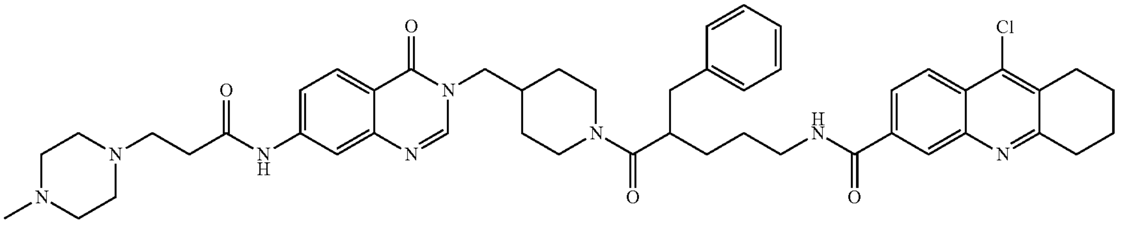

N-(4-benzyl-5-(4-((7-(3-(4-methylpiperazin-1-yl)propanamido)-4-oxoquinazolin-3(4H)-yl)methyl)piperidin-1-yl)-5-oxopentyl)-9-chloro-5,6,7,8-tetrahydroacridine-3-carboxamide (compound 24). $^1H$ NMR (500 MHz, DMSO) δ 10.52 (d, J=4.2 Hz, 1H, conformer), 8.78 (dt, J=18.3, 5.4 Hz, 1H, conformer), 8.48 (d, J=18.1 Hz, 1H, conformer), 8.23-8.11 (m, 2H), 8.11-7.99 (m, 3H), 7.62 (m, 1H), 7.19 (m, 5H), 4.39 (dd, J=39.4, 12.8 Hz, 1H, conformer), 3.78 (m, 2H), 3.61 (ddd, J=43.3, 13.4, 7.0 Hz, 1H), 3.29 (m, 2H), 3.13 (s, 1H), 3.06 (m, 2H), 2.99 (m, 2H), 2.88-2.71 (m, 2H), 2.71-2.59 (m, 4H), 2.58-2.52 (m, 3H), 2.39 (m, 4H), 2.15 (s, 3H), 2.00-1.83 (m, 5H), 1.74-1.35 (m, 6H), 1.23 (m, 1H), 1.05 (td, J=23.0, 11.6 Hz, 1H), 0.72 (dt, J=12.3, 8.8 Hz, 1H). $^{13}C$ NMR (126 MHz, DMSO) δ 172.78/172.70 (conformer), 171.53, 165.81/165.75 (conformer), 160.91, 160.17, 149.45, 148.92, 146.06, 144.77, 140.50, 140.33/140.28 (conformer), 135.68, 130.59, 129.58/129.32 (conformer), 128.69/128.51 (conformer), 127.89/127.87 (conformer), 127.54/127.49 (conformer), 126.51/126.44 (conformer), 126.32/126.29 (conformer), 125.87/125.84 (conformer), 123.96/123.91 (conformer), 118.94, 117.03/116.98 (conformer), 115.25, 55.23, 54.00, 52.84, 50.97/50.80 (conformer), 46.20, 45.31, 44.72, 42.09/41.83 (conformer), 41.54, 41.16, 39.01, 35.56/35.39 (conformer), 34.79, 34.07, 30.92, 30.30, 29.98, 29.61, 29.35, 27.56, 27.28/27.18 (conformer), 22.36. LCMS (ESI) m/z 844.82 [(M+H)$^+$ $C_{48}H_{58}ClN_8O_4^+$ calcd for 845.43].

25

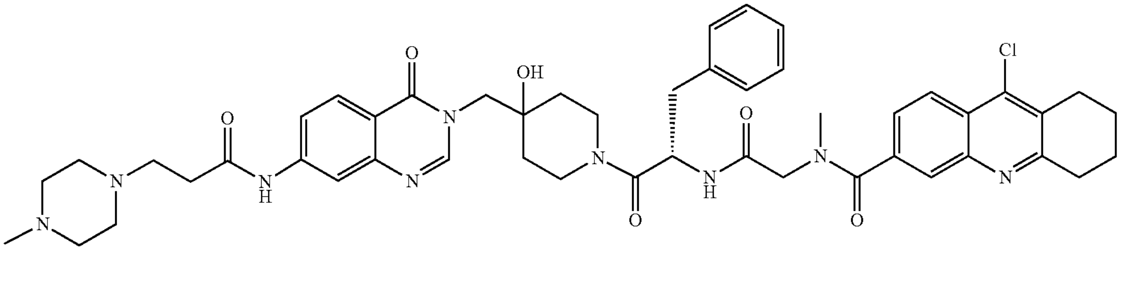

(S)-9-chloro-N-(2-((1-(4-hydroxy-4-((7-(3-(4-methylpiperazin-1-yl)propanamido)-4-oxoquinazolin-3(4H)-yl) methyl)piperidin-1-yl)-1-oxo-3-phenylpropan-2-yl)amino)-2-oxoethyl)-N-methyl-5,6,7,8-tetrahydroacridine-3-carboxamide (compound 25). LCMS (ESI) m/z 890.42 $[(M+H)^+$ $C_{48}H_{57}ClN_9O_6^+$ calcd for 890.41].

34

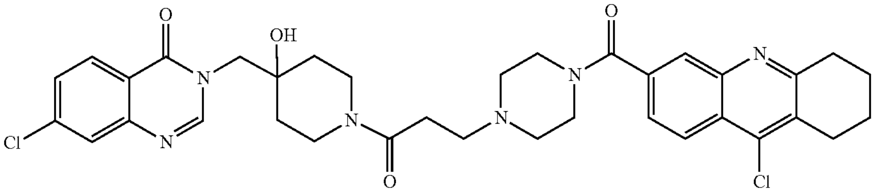

7-chloro-3-((1-(3-(4-(9-chloro-5,6,7,8-tetrahydroacridine-3-carbonyl)piperazin-1-yl)propanoyl)-4-hydroxypiperidin-4-yl)methyl)quinazolin-4(3H)-one (compound 34). $^1H$ NMR (500 MHz, MeOD) δ 8.20 (d, J=7.3 Hz, 2H), 8.08 (d, J=8.6 Hz, 1H), 7.87 (d, J=1.3 Hz, 1H), 7.59 (d, J=2.0 Hz, 1H), 7.55 (dd, J=8.6, 1.5 Hz, 1H), 7.43 (dd, J=8.6, 2.0 Hz, 1H), 4.13 (d, J=13.5 Hz, 1H), 4.08 (d, J=14.0 Hz, 1H), 3.93 (d, J=14.0 Hz, 1H), 3.81-3.64 (m, 3H), 3.06-2.92 (m, 5H), 2.72-2.36 (m, 8H), 1.88 (dd, J=6.5, 3.1 Hz, 4H), 1.73-1.62 (m, 1H), 1.61-1.50 (m, 1H), 1.45 (d, J=13.2 Hz, 2H). $^{13}C$ NMR (126 MHz, MeOD) δ 170.90, 169.71, 161.05, 161.03, 150.08, 148.76, 145.37, 141.56, 140.29, 136.64, 130.53, 128.15, 127.46, 126.03, 125.94, 125.71, 124.98, 124.35, 120.25, 69.71, 54.31, 53.77, 52.94, 52.38, 41.81, 41.52, 37.43, 34.99, 34.23, 33.38, 29.97, 27.16, 21.98. LCMS (ESI) m/z 677.50 $[(M+H)^+$ $C_{35}H_{39}Cl_2N_6O_4^+$ calcd for 677.24]

35

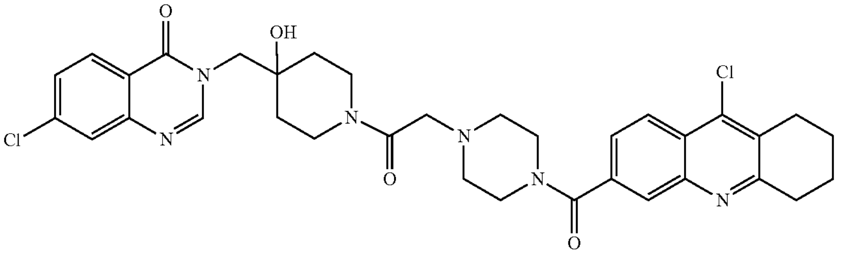

7-chloro-3-((1-(2-(4-(9-chloro-5,6,7,8-tetrahydroacridine-3-carbonyl)piperazin-1-yl)acetyl)-4-hydroxypiperidin-4-yl)methyl)quinazolin-4(3H)-one (compound 35). $^1H$ NMR (500 MHz, MeOD) δ 8.31 (t, J=4.3 Hz, 2H), 8.22 (d, J=8.6 Hz, 1H), 7.98 (s, 1H), 7.69 (d, J=1.8 Hz, 1H), 7.66 (d, J=8.6 Hz, 1H), 7.55 (dd, J=8.6, 1.9 Hz, 1H), 4.19 (m, 2H), 4.05 (d, J=14.0 Hz, 1H), 3.91 (m, 3H), 3.54 (br, 2H), 3.43 (m, 2H), 3.24 (d, J=14.0 Hz, 1H), 3.18-3.10 (m, 3H), 3.08 (m, 2H), 2.78-2.43 (m, 4H), 2.04-1.94 (m, 4H), 1.88-1.75 (m, 1H), 1.71-1.53 (m, 3H). $^{13}C$ NMR (126 MHz, MeOD) δ 169.71, 168.40, 161.07, 161.03, 150.08, 148.75, 145.37, 141.54, 140.29, 136.63, 130.52, 128.14, 127.47, 126.01, 125.94, 125.70, 124.96, 124.35, 120.23, 69.73, 59.83, 54.29, 52.82, 52.37, 41.93, 41.42, 37.60, 35.03, 34.35, 33.38, 27.17, 21.98. LCMS (ESI) m/z 663.30 $[(M+H)^+$; $C_{34}H_{37}Cl_2N_6O_4^+$ calcd for 663.22].

36

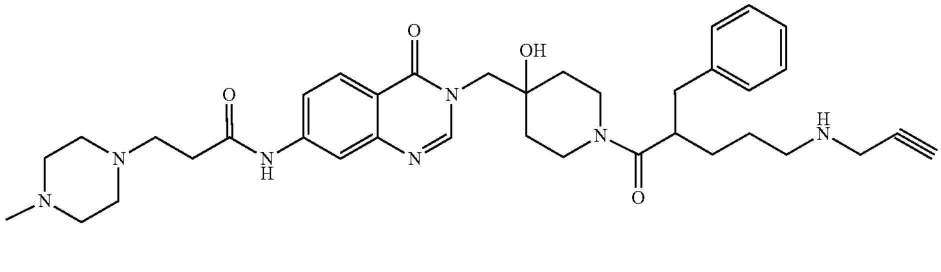

N-(3-((1-(2-benzyl-5-(prop-2-yn-1-ylamino)pentanoyl)-4-hydroxypiperidin-4-yl)methyl)-4-oxo-3,4-dihydroquinazolin-7-yl)-3-(4-methylpiperazin-1-yl)propenamide (compound 36). $^{1}$H NMR (500 MHz, DMSO) δ 10.70 (s, 1H), 8.29-8.00 (m, 3H), 7.81 (d, J=17.1 Hz, 3H), 7.67 (t, J=8.4 Hz, 1H), 7.32-7.20 (m, 2H), 7.20-7.05 (m, 3H), 4.59 (s, 2H), 4.19-3.90 (m, 3H), 3.84 (d, J=13.6 Hz, 1H), 3.75-3.52 (m, 6H), 3.47-3.26 (m, 4H), 3.17-3.05 (m, 2H), 2.93-2.57 (m, 8H), 1.71-1.54 (m, 1H), 1.56-1.26 (m, 4H), 1.22 (d, J=12.6 Hz, 1H), 1.18-1.00 (m, 1H), 0.41 (t, J=10.6 Hz, 1H). $^{13}$C NMR (126 MHz, DMSO) δ 177.67, 172.45, 170.08, 160.62, 160.48, 149.99, 149.91, 149.16, 144.61, 140.19, 139.88, 129.46, 129.32, 128.66, 128.55, 127.80, 127.73, 127.63, 126.59, 118.92, 117.18, 117.05, 116.97, 115.25, 84.30, 71.99, 69.62, 69.54, 57.49, 54.08, 53.78, 51.96, 45.70, 41.80, 41.66, 41.37, 41.16, 37.47, 35.69, 35.06, 34.90, 34.36, 32.84, 30.23, 29.52, 25.41, 25.29. LCMS (ESI) m z 656.50 [(M+H)$^{+}$; calcd for $C_{37}H_{49}N_{7}O_{4}^{+}$: 655.84].

37

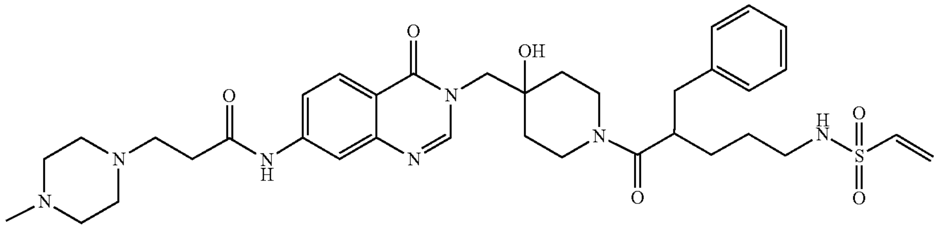

N-(3-((1-(2-benzyl-5-(vinylsulfonamido)pentanoyl)-4-hydroxypiperidin-4-yl)methyl)-4-oxo-3,4-dihydroquinazolin-7-yl)-3-(4-methylpiperazin-1-yl)propenamide (compound 37). $^{1}$H NMR (500 MHz, DMSO) δ 10.51 (s, 1H), 8.25-7.93 (m, 3H), 7.64 (t, J=8.4 Hz, 1H), 7.34-7.18 (m, 3H), 7.15-7.09 (m, 3H), 6.67 (td, J=15.9, 10.3 Hz, 1H), 6.13-5.85 (m, 2H), 4.86 (s, 1H), 4.16-3.88 (m, 2H), 3.81 (d, J=13.6 Hz, 1H), 3.63 (d, J=13.7 Hz, 1H), 3.56 (d, J=12.3 Hz, 1H), 3.20-2.57 (m, 21H), 1.63-1.51 (m, 1H), 1.47-1.26 (m, 4H), 1.19 (d, J=12.6 Hz, 1H), 1.15-0.98 (m, 1H), 0.41 (d, J=9.9 Hz, 1H). $^{13}$C NMR (126 MHz, DMSO) δ 172.64, 160.66, 160.52, 149.92, 149.83, 149.43, 144.66, 140.42, 140.13, 137.42, 129.44, 129.30, 128.63, 128.53, 127.77, 126.51, 125.77, 125.69, 118.83, 117.16, 117.06, 115.31, 69.67, 69.57, 54.02, 53.85, 52.77, 52.51, 49.77, 42.86, 42.78, 41.81, 41.59, 41.38, 41.15, 39.34, 37.46, 35.71, 35.12, 34.96, 34.42, 30.64, 29.97, 27.61. LCMS (ESI) m z 708.40 [(M+H)$^{+}$; calcd for $C_{36}H_{49}N_{7}O_{6}S^{+}$: 707.89].

38

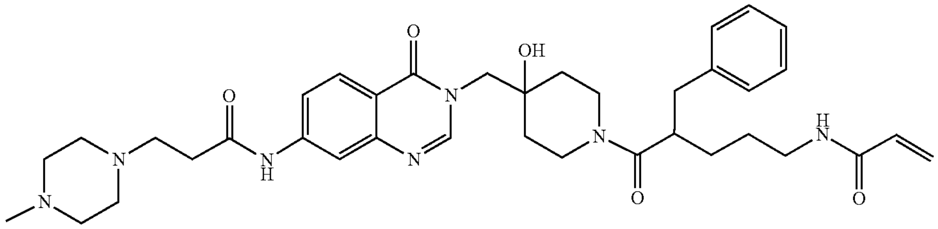

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)acrylamide (compound 38). $^{1}H$ NMR (500 MHz, DMSO) δ 10.64 (s, 1H), 8.29-7.98 (m, 4H), 7.68 (td, J=8.6, 1.9 Hz, 1H), 7.31-7.19 (m, 2H), 7.18-7.06 (m, 3H), 6.26-6.14 (m, 1H), 6.12-6.00 (m, 1H), 5.61-5.49 (m, 1H), 4.90 (s, 1H), 4.13-3.91 (m, 2H), 3.82 (d, J=13.6 Hz, 1H), 3.64 (d, J=13.7 Hz, 1H), 3.58 (d, J=12.6 Hz, 1H), 3.16-3.01 (m, 4H), 2.93-2.56 (m, 15H), 2.53-2.49 (m, 2H), 1.60-1.52 (m, 1H), 1.49-1.27 (m, 4H), 1.22 (d, J=12.6 Hz, 1H), 1.16-0.99 (m, 1H), 0.38 (dd, J=12.1, 9.0 Hz, 1H). $^{13}C$ NMR (126 MHz, DMSO) δ 172.70, 172.65, 171.19, 164.94, 164.89, 160.67, 160.53, 149.88, 149.79, 149.44, 144.79, 140.45, 140.19, 132.38, 132.35, 129.43, 129.28, 128.64, 128.51, 127.69, 126.50, 125.27, 118.81, 117.08, 116.98, 115.24, 69.68, 69.58, 53.95, 53.76, 53.62, 53.37, 50.89, 45.93, 43.95, 41.95, 41.67, 41.40, 41.15, 40.90, 39.24, 38.92, 37.47, 35.69, 35.12, 34.94, 34.44, 31.01, 30.22, 27.34, 9.00. LCMS (ESI) m z 672.50 [(M+H)$^{+}$; calcd for $C_{37}H_{49}N_{7}O_{5}^{+}$: 671.84].

39

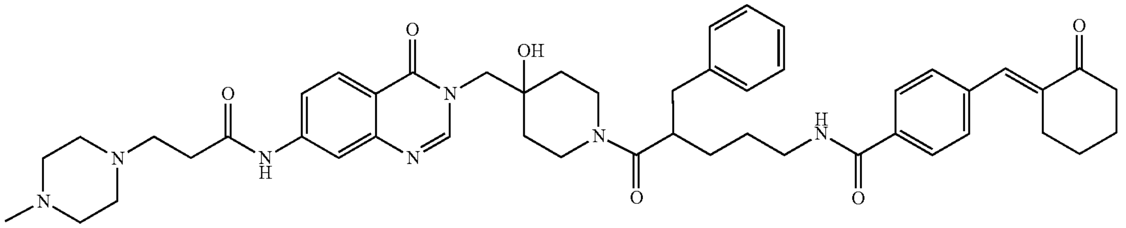

(E)-N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-4-((2-oxocyclohexylidene)methyl)-benzamide (compound 39). LCMS (ESI) m/z 830.71 [(M+H)$^{+}$ $C_{48}H_{60}N_{7}O_{6}^{+}$ calcd for 830.46].

40

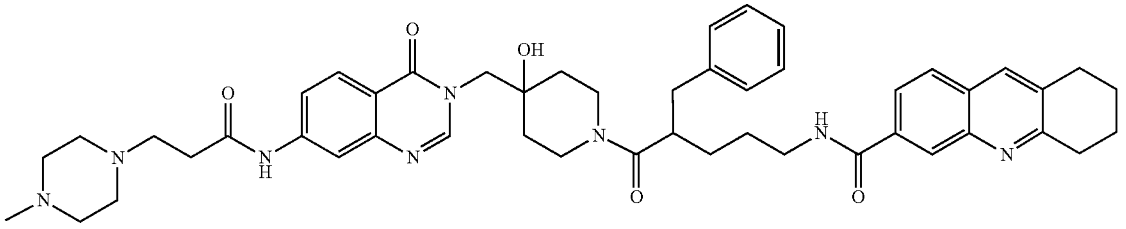

N-(4-benzyl-5-(4-hydroxy-4-((7-(3-(4-methylpiperazin-1-yl)propanamido)-4-oxoquinazolin-3(4H)-yl)methyl)piperidin-1-yl)-5-oxopentyl)-5,6,7,8-tetrahydroacridine-3-carboxamide (compound 40). $^{1}H$ NMR (500 MHz, DMSO) δ 10.50 (d, J=4.4 Hz, 1H, conformer), 8.74-8.60 (m, 1H), 8.40 (d, J=14.3 Hz, 1H, conformer), 8.11 (m, 2H), 8.07-7.96 (m, 2H), 7.92-7.81 (m, 2H), 7.69-7.52 (m, 1H), 7.16 (m, 5H), 4.82 (s, 1H, conformer), 4.06 (dd, J=61.0, 12.9 Hz, 1H, conformer), 3.88 (q, J=13.9 Hz, 1H), 3.71 (dd, J=88.4, 13.6 Hz, 3H), 3.27 (m, 2H), 3.13 (m, 2H), 3.03 (dd, J=7.9, 4.8 Hz, 2H), 2.96 (m, 2H), 2.83 (m, 1H), 2.80-2.69 (m, 2H), 2.69-2.59 (m, 4H), 2.59-2.52 (m, 3H), 2.16 (d, J=18.6 Hz, 3H), 1.98-1.87 (m, 2H), 1.87-1.77 (m, 2H), 1.60 (d, J=29.3 Hz, 1H), 1.43 (m, 4H), 1.35-1.00 (m, 4H), 0.40 (t, J=10.7 Hz, 1H). $^{13}C$ NMR (126 μMHz, DMSO) δ 172.76/172.70 (conformer), 171.52, 166.30, 160.61/160.52 (conformer), 160.32/160.30 (conformer), 149.84/149.79 (conformer), 149.46, 145.88/145.85 (conformer), 144.75, 140.49, 140.25, 134.81, 134.75, 132.73/132.70 (conformer), 129.44/129.30 (conformer), 128.62/128.51 (conformer), 127.78/127.75 (conformer), 127.62, 127.42/127.37 (conformer), 126.49/126.44 (conformer), 124.42/124.38 (conformer), 118.76, 117.07/116.97 (conformer), 115.17, 69.67/69.59 (conformer), 55.23, 54.04/53.84 (conformer), 54.00, 52.84, 46.20, 41.97/41.74 (conformer), 41.40/41.17 (conformer), 39.18, 37.46, 35.72, 35.13, 34.95, 34.79, 34.47, 33.46, 30.97, 30.17, 29.03, 27.31, 23.05, 22.75. LCMS (ESI) m/z 827.61 [(M+H)$^+$ $C_{48}H_{59}N_8O_5^+$ calcd for 827.46].

structure of compound 42 and the USP7 catalytic domain shows the compound bound within the S4-S5 pocket of enzyme about 5 Å removed from the catalytic cysteine (FIG. 1A). Without being bound by any theory, given the proximity of the compound to the catalytic triad, it was hypothesized that the compound could be modified to develop covalent inhibitors that bind to the catalytic residue. In terms of rational design of such a compound, one challenge is the dynamics of the USP7 DUB domain. Crystallographic studies show that the catalytic triad resides in an inactive conformation, where the catalytic cysteine is 12 Å away from the Asp and His triad residues, in the apo- and compound 42-bound states but rearranges to bring the catalytic triad residues into a conformation conducive to catalysis upon ubiquitin binding. Hu, M. et al. Crystal structure of a UBP-family deubiquitinating enzyme in isolation and in complex with ubiquitin aldehyde. *Cell* 111, 1041-1054 (2002). The rearrangement involves the catalytic cysteine moving approximately 9 Å, meaning the distance from a fixed point in the compound to nucleophilic cysteine will change significantly depending on conformation.

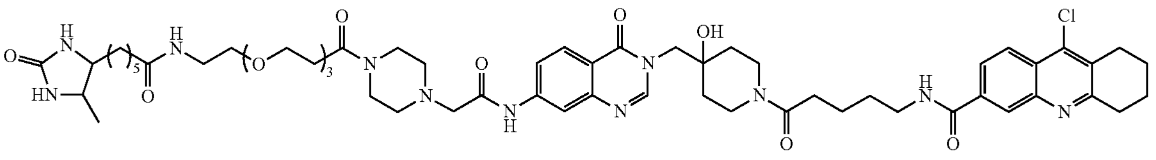

41

9-chloro-N-(5-(4-hydroxy-4-((7-(2-(4-(19-((4R,5S)-5-methyl-2-oxoimidazolidin-4-yl)-14-oxo-4,7,10-trioxa-13-azanonadecanoyl)piperazin-1-yl)acetamido)-4-oxoquinazolin-3(4H)-yl)methyl)piperidin-1-yl)-5-oxopentyl)-5,6,7,8-tetrahydroacridine-3-carboxamide (compound 41). $^1H$ NMR (500 MHz, DMSO) δ 8.78 (t, J=5.6 Hz, 1H), 8.47 (d, J=1.5 Hz, 1H), 8.22 (s, 1H), 8.17 (d, J=8.8 Hz, 1H), 8.10 (d, J=8.6 Hz, 1H), 8.08-8.02 (m, 2H), 7.81 (t, J=5.6 Hz, 1H), 7.69 (s, 1H), 6.29 (s, 1H), 6.12 (s, 1H), 4.96 (s, 1H), 4.10-3.88 (m, 4H), 3.70-3.55 (m, 6H), 3.54-3.43 (m, 11H), 3.39 (t, J=6.0 Hz, 4H), 3.31-3.23 (m, 3H), 3.22-3.14 (m, 3H), 3.06-2.90 (m, 6H), 2.64-2.56 (m, 3H), 2.40-2.30 (m, 2H), 2.05 (t, J=7.4 Hz, 2H), 1.89 (t, J=2.9 Hz, 4H), 1.64-1.52 (m, 5H), 1.50-1.09 (m, 11H), 0.95 (d, J=6.4 Hz, 3H). $^{13}C$ NMR (126 MHz, DMSO) δ 172.97, 170.98, 169.54, 166.02, 163.40, 160.99, 160.68, 150.01, 149.33, 145.97, 143.83, 140.42, 135.73, 130.67, 127.82, 126.31, 125.77, 123.99, 119.19, 117.51, 115.84, 70.19, 70.15, 70.11, 70.00, 69.81, 69.53, 67.13, 55.46, 54.02, 52.98, 52.60, 50.74, 41.42, 38.92, 37.44, 35.70, 35.52, 34.78, 34.00, 33.13, 32.46, 29.91, 29.10, 27.55, 25.99, 25.61, 22.85, 22.32, 22.31, 15.89. LCMS (ESI) m z 1142.60 [(M+H)$^+$; calcd for $C_{58}H_{80}ClN_{11}O_{11}^+$: 1142.79].

Example 2: In Vitro Assays Using Exemplary Compounds of the Disclosure

Enzymatic Assays with Exemplary USP7 Irreversible Inhibitors

Figure 1B:
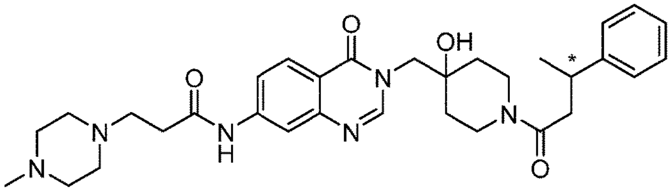
FIG. 1B depicts the chemical structures of compound 42, compound 43, compound 6, and compound 7.
Figure 1B:
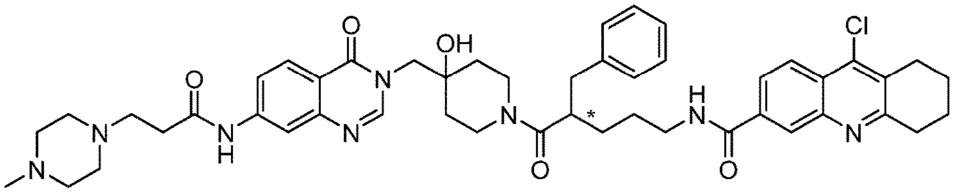
Figure 1C:
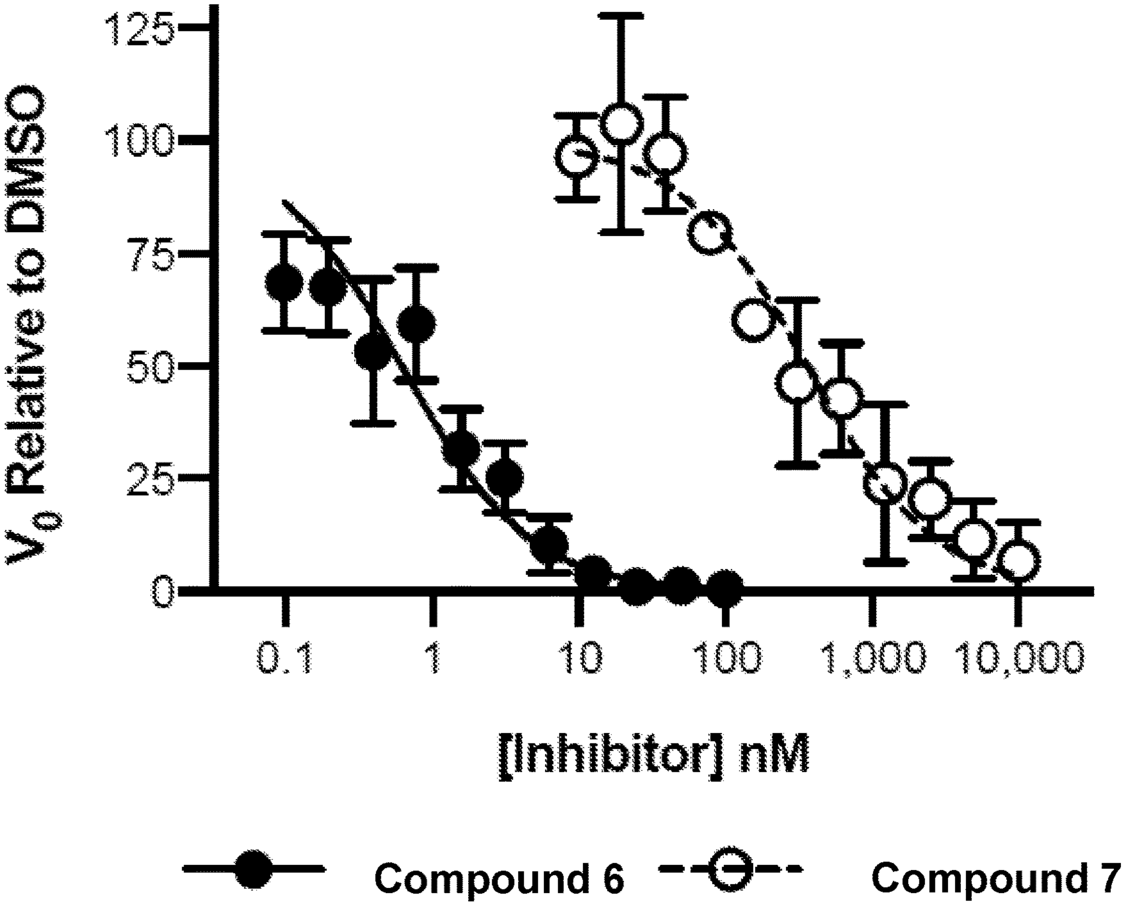
FIG. 1C depicts exemplary Michaelis-Menten plots of full-length USP7 cleavage of Ub-AMC following 6-hour pre-treatment with compound 6 or compound 7.

Compound 42 is a noncovalent inhibitor of USP7 that binds in the thumb-palm cleft that guides the ubiquitin C-terminus into the active site. Specifically, a co-crystal Iterative rounds of analog synthesis culminated in development of compound 6 as a highly potent and selective irreversible inhibitor of USP7 (FIG. 1B). In an enzymatic assay using full-length USP7 and fluorogenic substrate ubiquitin-7-amino-4-methylcoumarin (Ub-AMC), compound 6 inhibited USP7 with an $IC_{50}$ in the subnanomolar range (FIG. 1C). An accurate measure of the enzyme inactivation rate ($k_{inact}$) and inhibition constant ($K_i$) for compound 6 was not feasible due to rapid and complete labeling of USP7 by the compound. However, determination of these parameters for compound 1, a precursor compound containing the same electrophilic warhead, confirmed an irreversible mode of inhibition for the compound series. For compound 1, the enzyme rate ($k_{inact}$) was 0.22±0.07 mini, and the inhibition constant ($K_i$) was 2.8±1.8 nM. A covalent binding mode was also confirmed for compound 6 using mass spectrometry. Purified USP7 catalytic domain was incubated with vehicle (DMSO) or compound 6 for 15 minutes, and samples were analyzed using capillary electrophoresis-mass spectrometry (CE-MS). Quantitative labeling of USP7 by compound 6 with a mass shift corresponding to inhibitor mass minus the chloro-atom, was observed (data not shown). MS/MS analysis confirmed binding to the catalytic residue, C223. An analog of compound 6 without the chloride leaving group, compound 40, showed reduced activity against USP7 in the nanomolar range and was unable to label the USP7 catalytic domain by MS. No mass shift was detected when compound 6 was incubated with USP7 C223A, where the catalytic cysteine residue was replaced with an alanine residue.

TABLE 1
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (nM) |
|---|---|
| 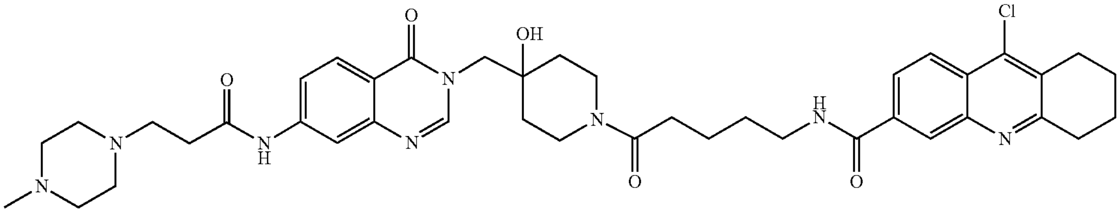 1 | +++ |
| 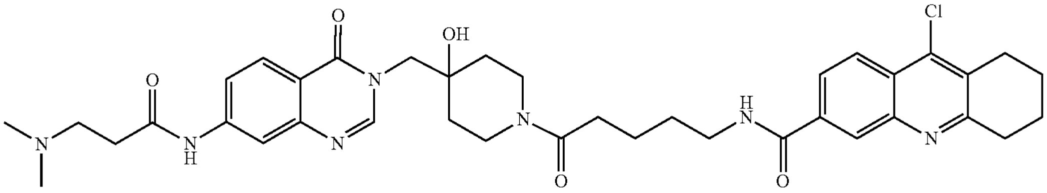 2 | +++ |
| 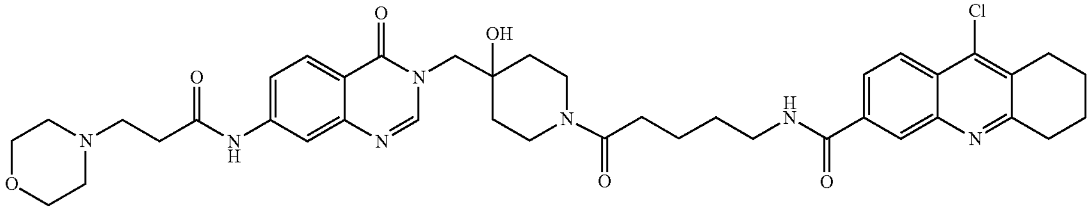 3 | ++ |
| 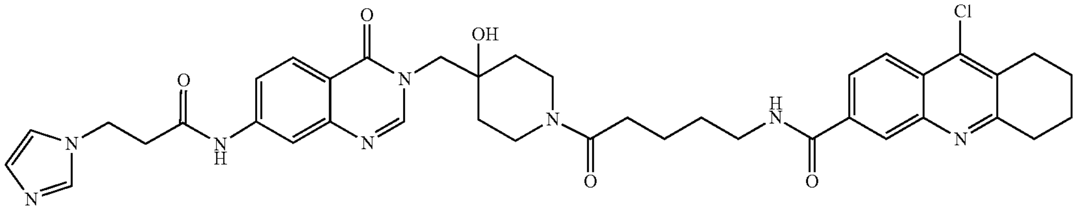 4 | +++ |
| 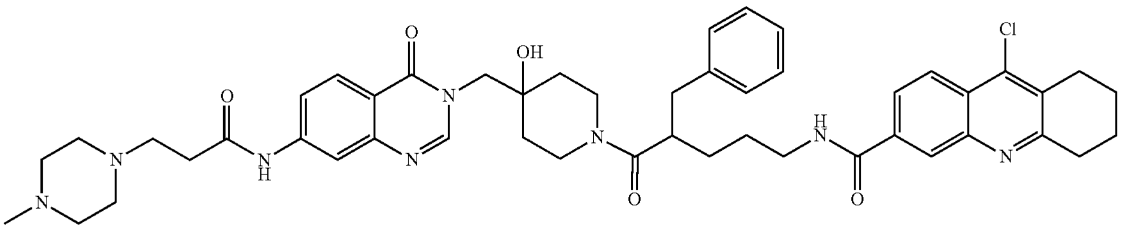 5 | ++++ |

TABLE 1-continued
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (nM) |
|---|---|
| 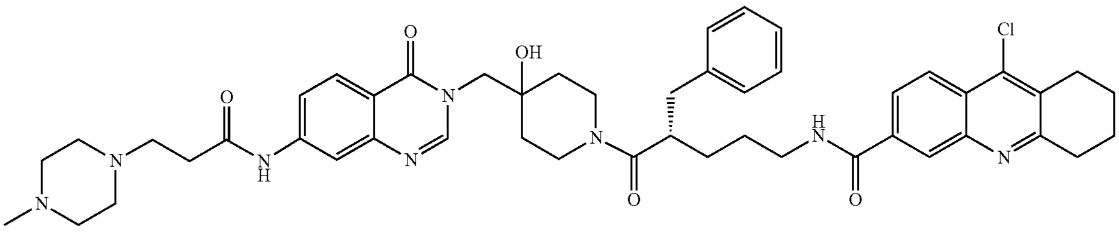 6 | ++++ |
| 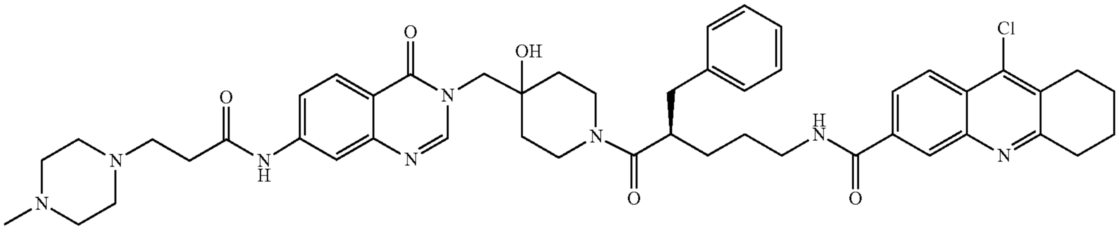 7 | ++ |
| 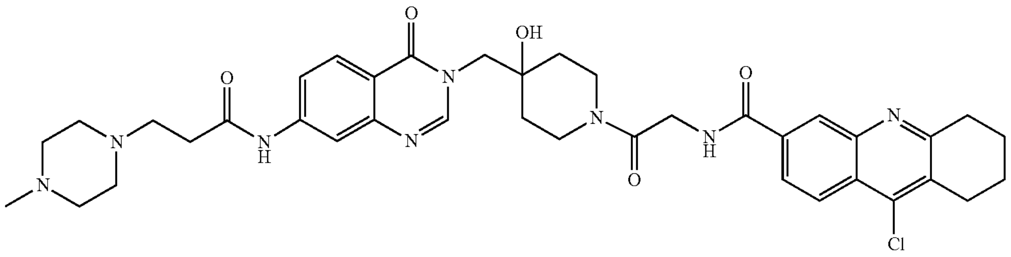 8 | + |
| 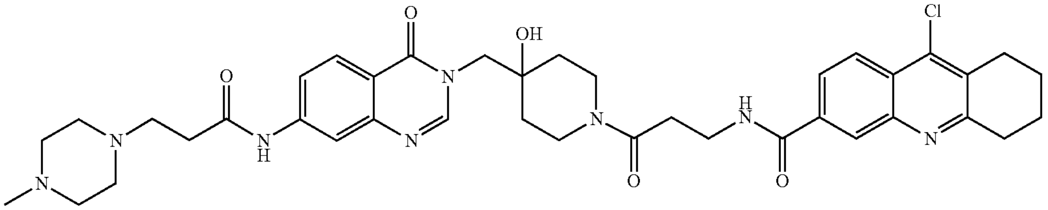 9 | ++ |
| 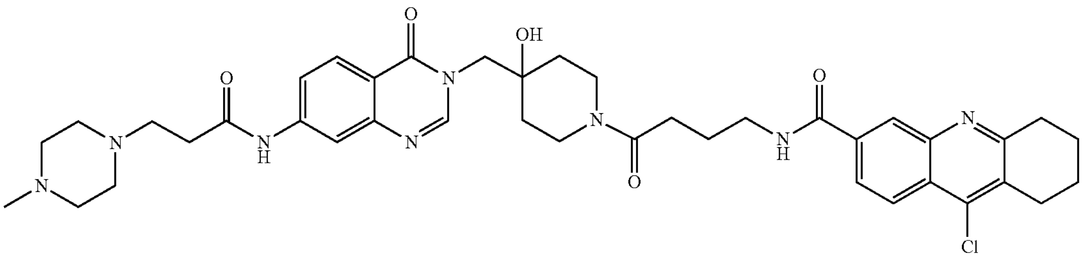 10 | +++ |

TABLE 1-continued
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (nM) |
| --- | --- |
| 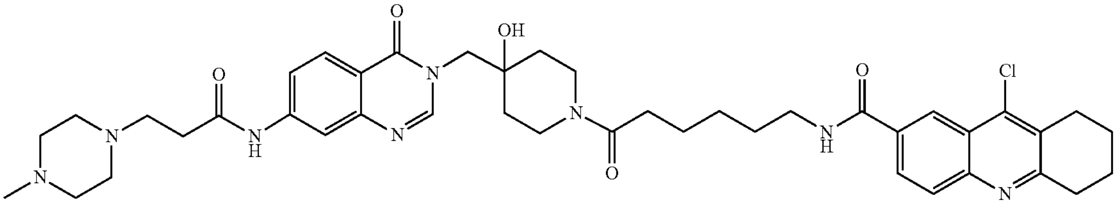 11 | +++ |
| 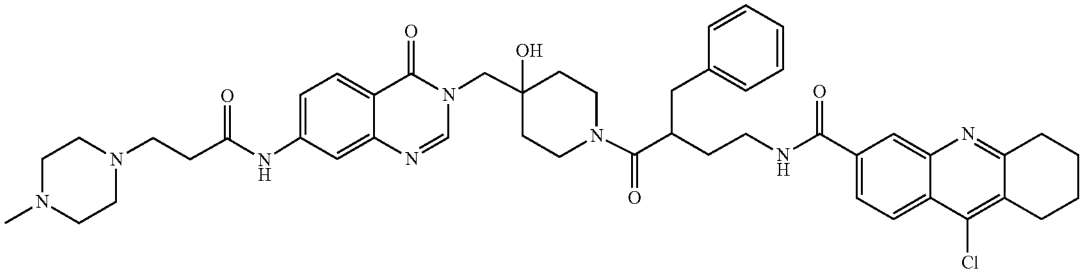 12 | ++++ |
| 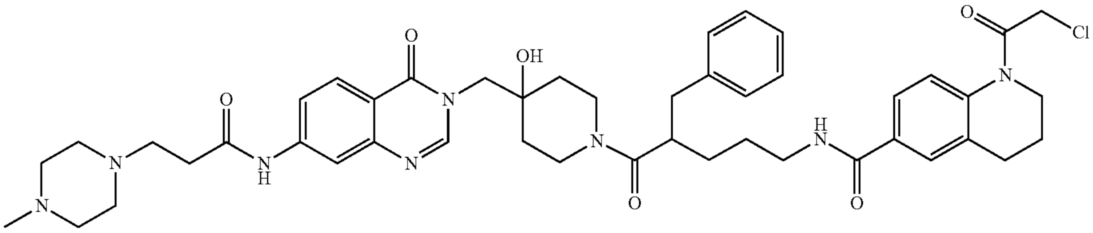 13 | +++ |
| 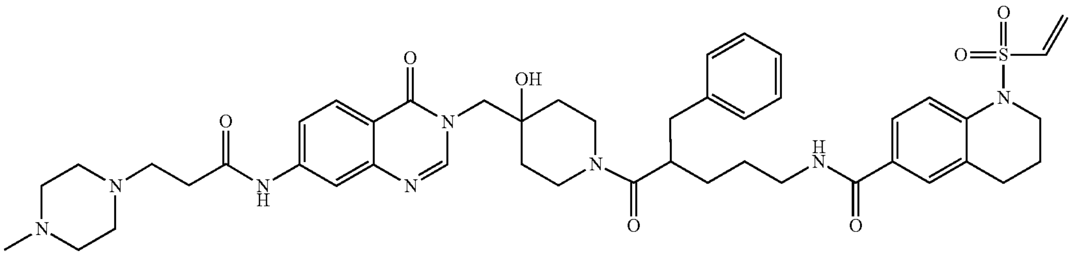 14 | +++ |
| 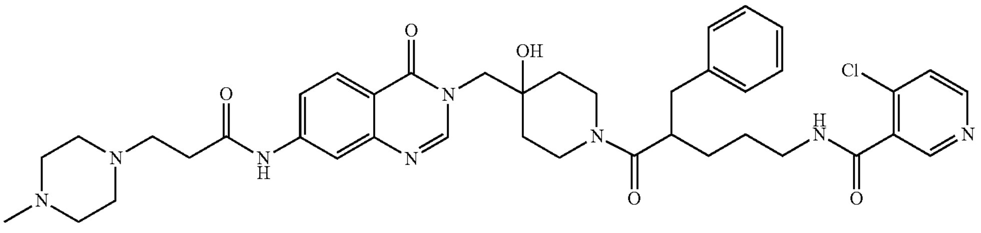 15 | + |

TABLE 1-continued
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (nM) |
|---|---|
| 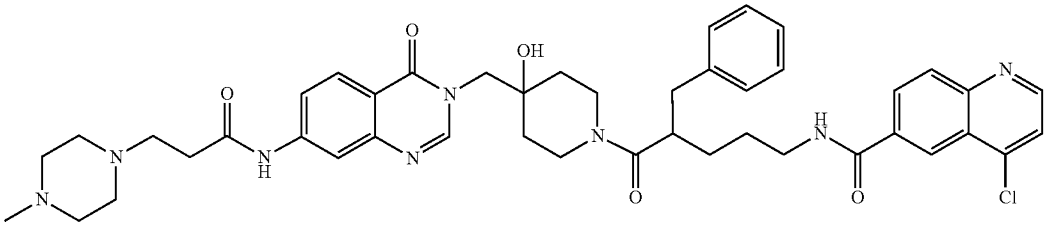 16 | ND |
| 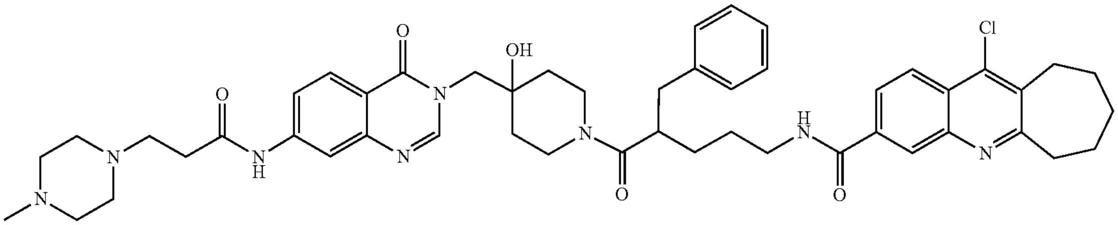 17 | ++++ |
| 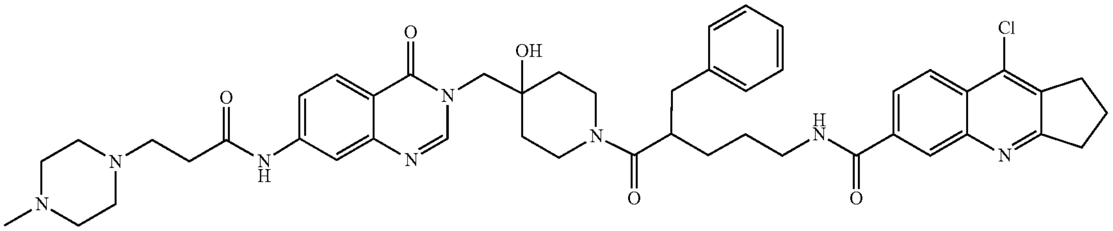 18 | ++++ |
| 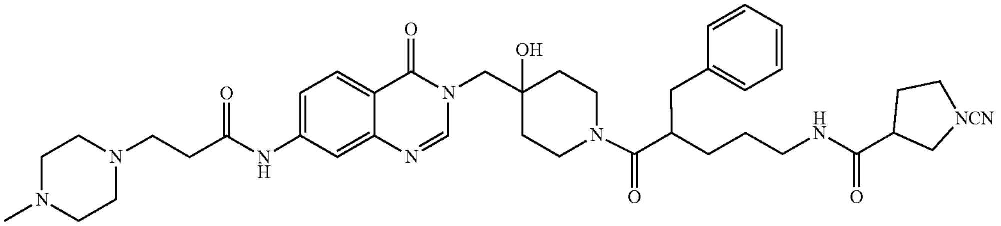 19 | + |
| 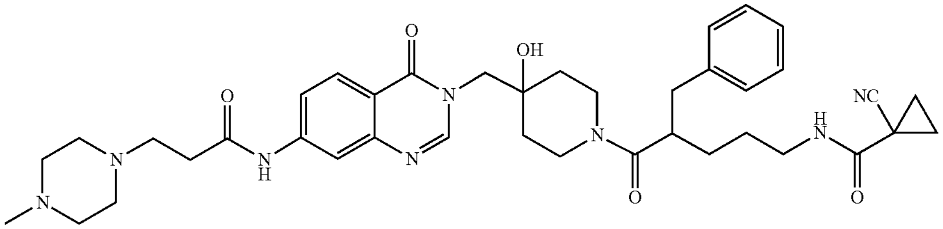 20 | ++ |

TABLE 1-continued
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (nM) |
|---|---|
| 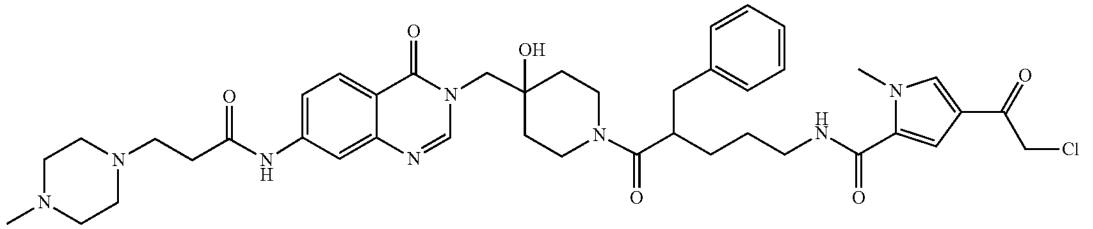<br>21 | + |
| 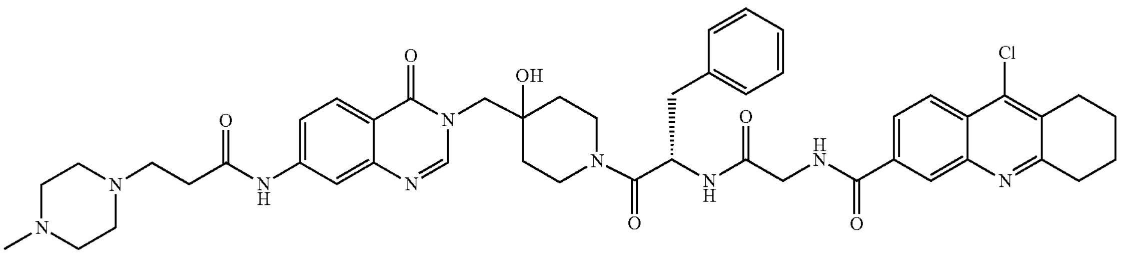<br>22 | ++++ |
| 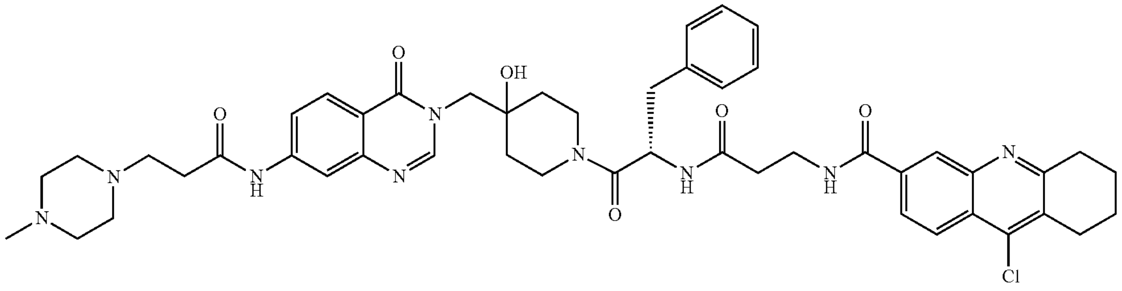<br>23 | ++++ |
| 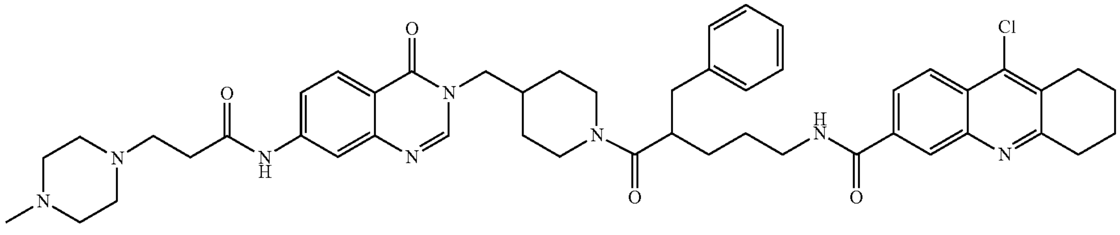<br>24 | + |

TABLE 1-continued
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (nM) |
|---|---|
| 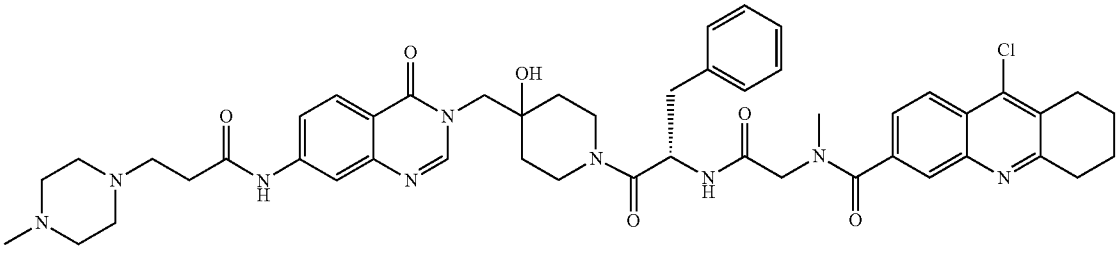 25 | ++++ |
| 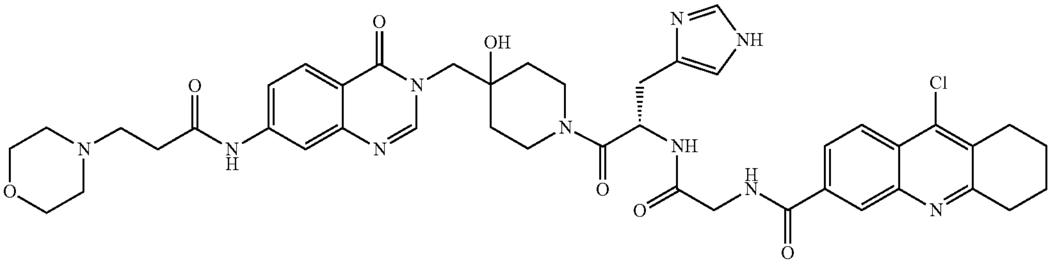 26 | ++++ |
| 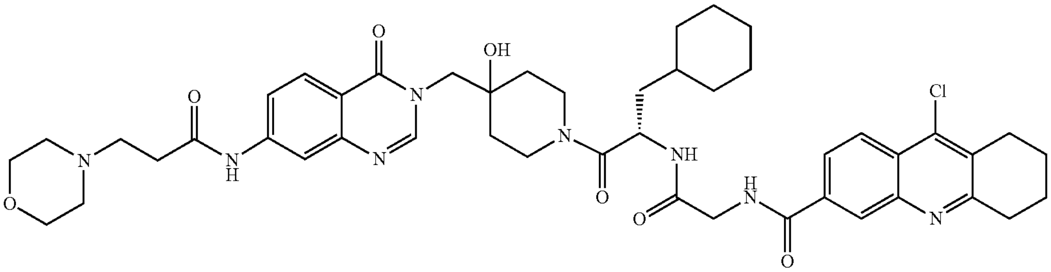 27 | ++++ |
| 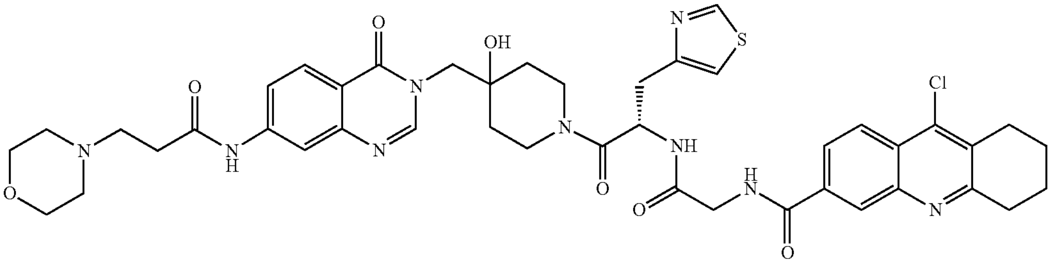 28 | ++++ |

TABLE 1-continued
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (nM) |
|---|---|
| 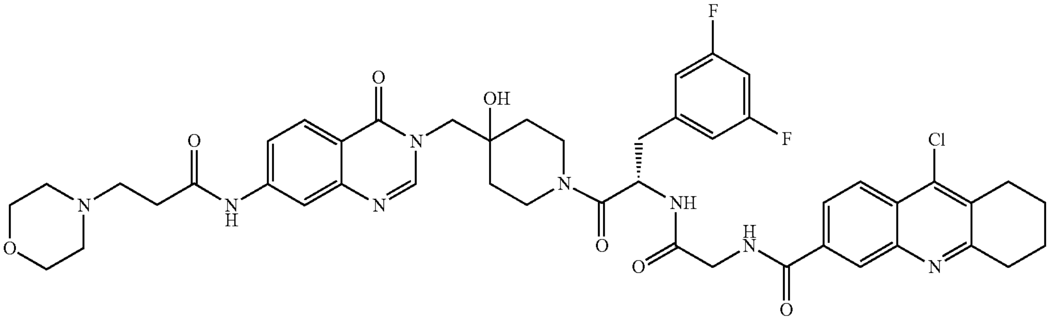 29 | ++++ |
| 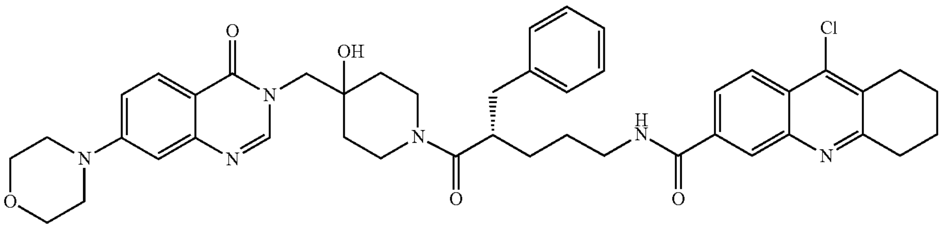 30 | ++ |
| 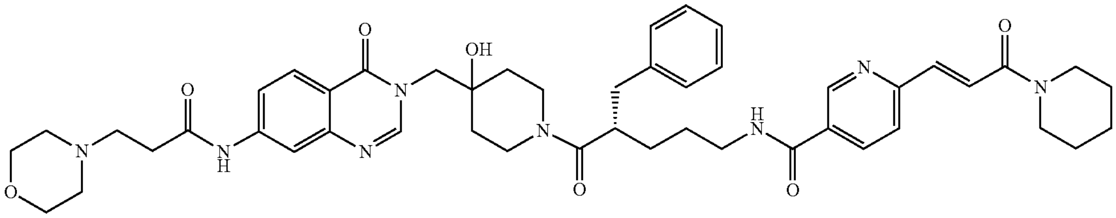 31 | + |
| 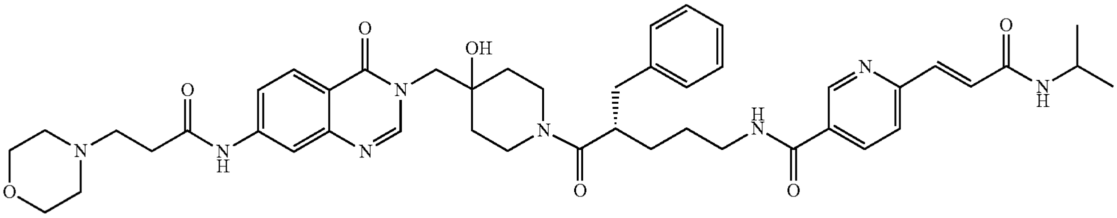 32 | + |
| 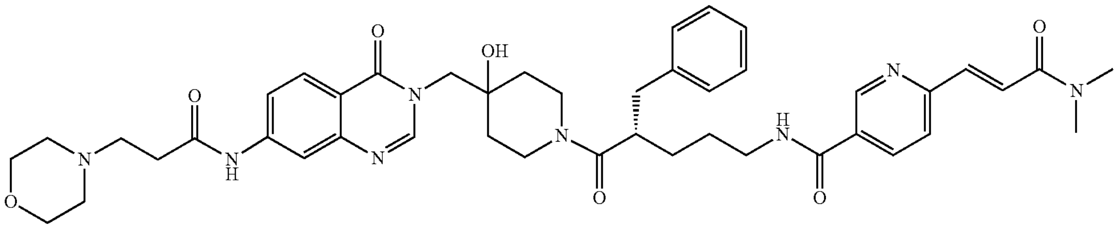 33 | + |

TABLE 2
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (μM) |
|---|---|
| 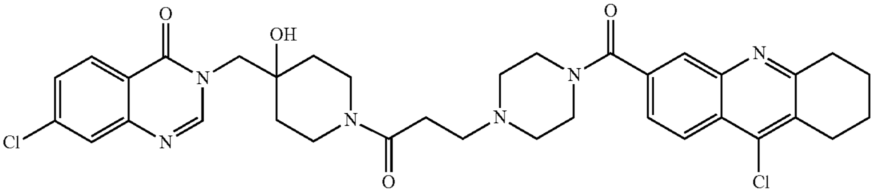 34 | ++ |
| 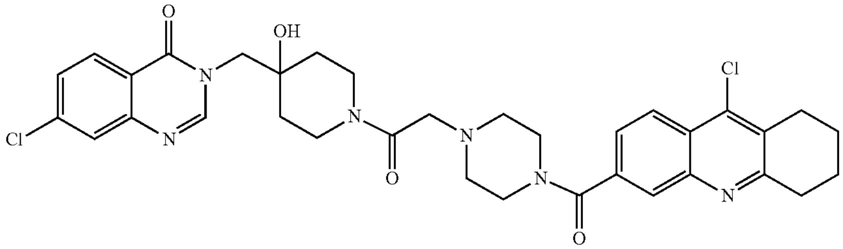 35 | +++ |
| 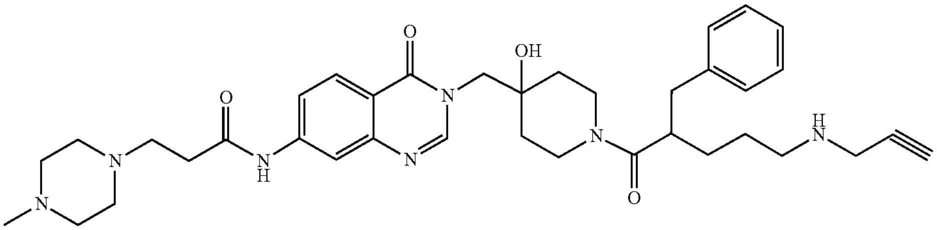 36 | +++ |
| 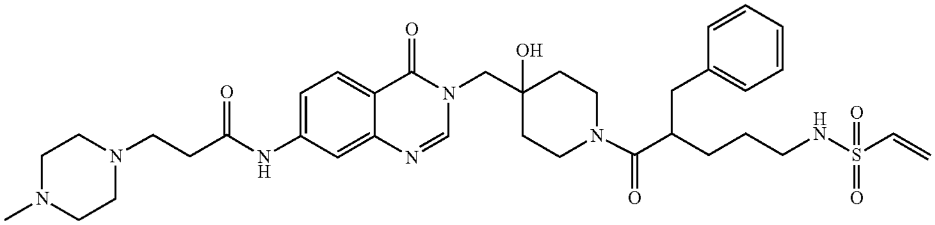 37 | +++ |
| 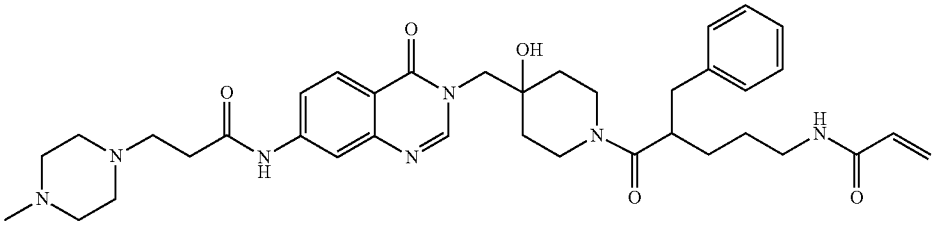 38 | ++++ |

TABLE 2-continued
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (μM) |
|---|---|
| 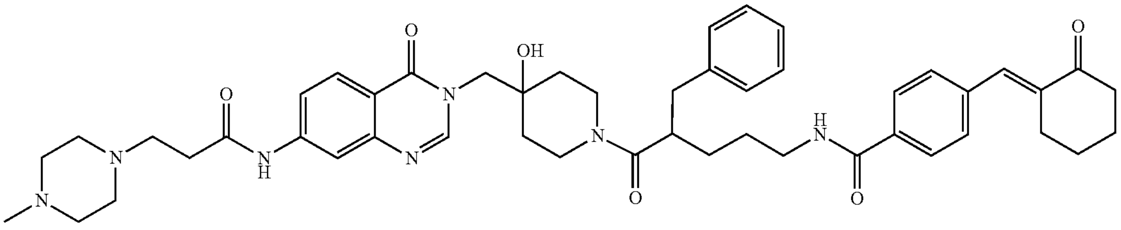 39 | +++ |
| 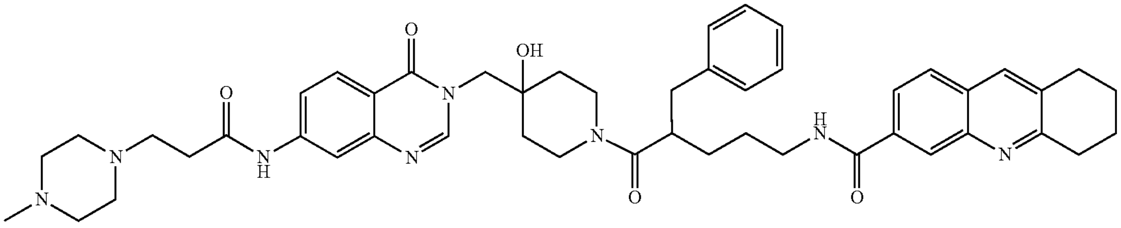 40 | ++ |
| 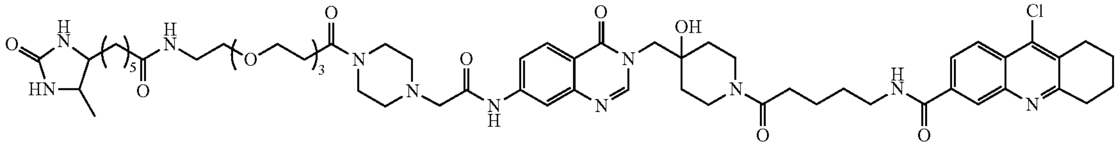 41 | +++ |
| 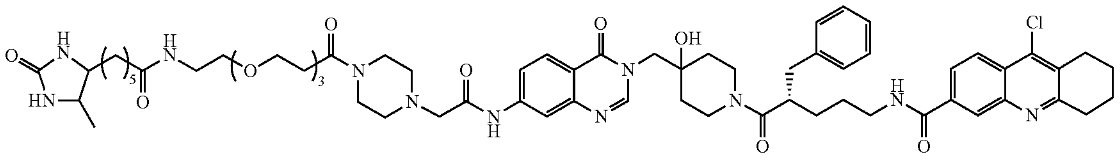 42 | ND |

TABLE 3
| USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed. | |
|---|---|
| Compound | $IC_{50}$ (μM) |
| 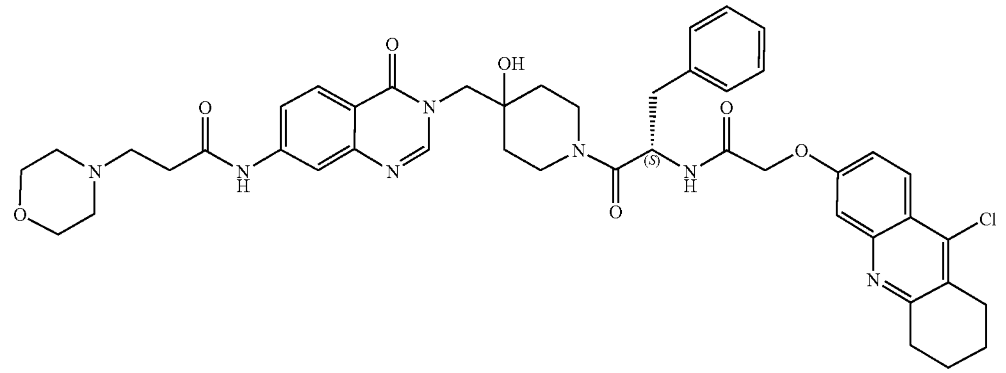 43 | ++ |
| 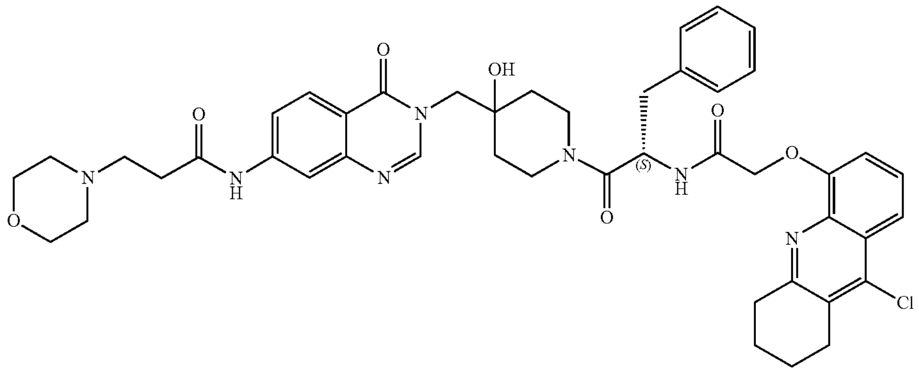 44 | +++ |
| 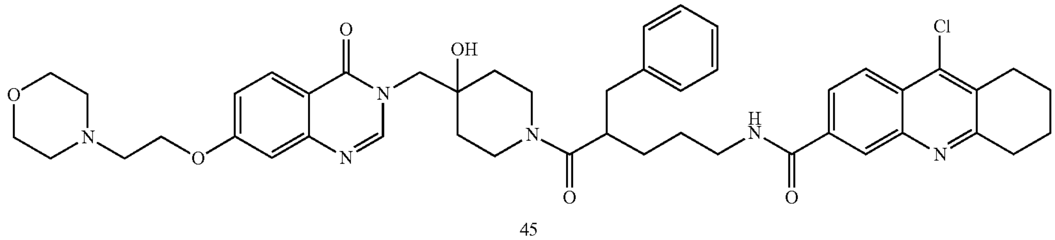 [SMILES: O=C(NCCCC(Cc1ccccc1)C(=O)N1CCC(O)(Cn2cnc3cc(OCCN4CCOCC4)ccc3c2=O)CC1)c1ccc2c(Cl)c3c(nc2c1)CCCC3] 45 | +++ |
| 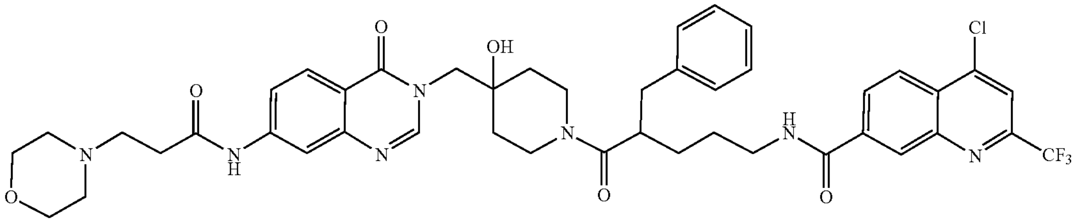 46 | ++ |

TABLE 3-continued
| USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed. | |
|---|---|
| Compound | $IC_{50}$ (μM) |
| 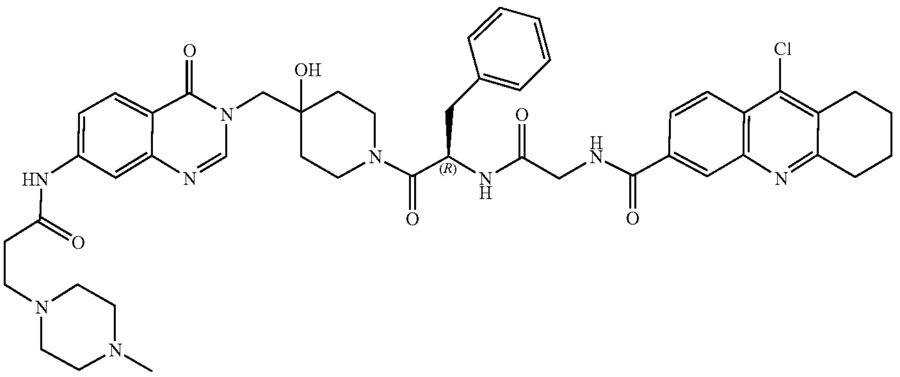<br>47 | +++ |
| 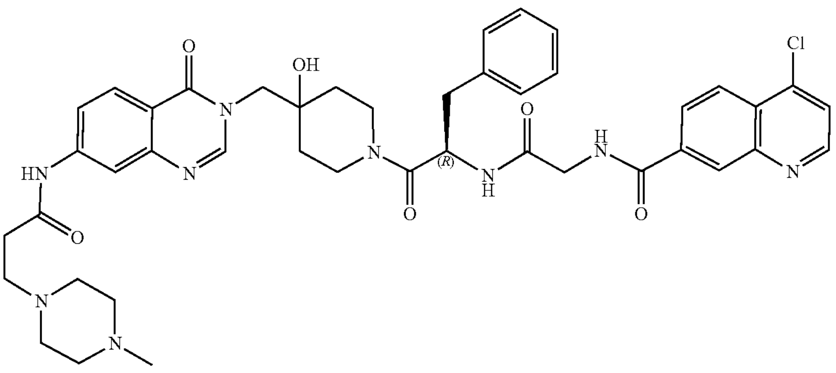<br>48 | +++ |
| 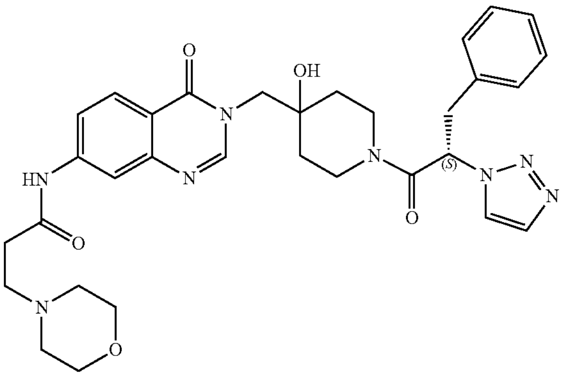<br>49 | + |

TABLE 3-continued
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (μM) |
|---|---|
| 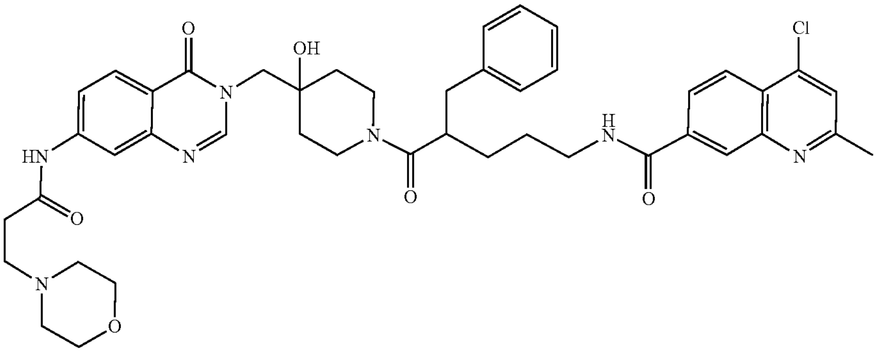 50 | + |
| 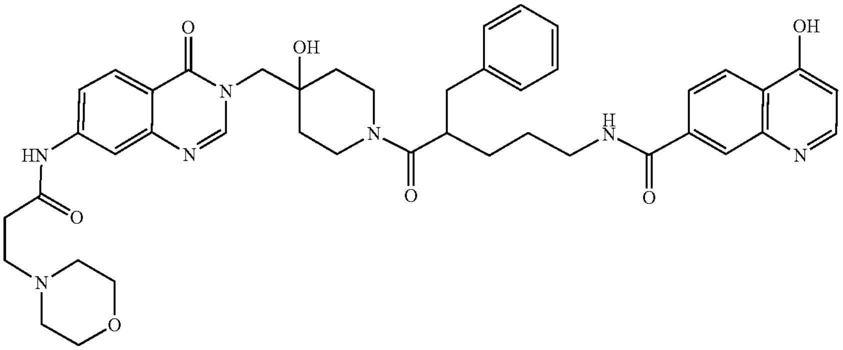 51 | + |
| 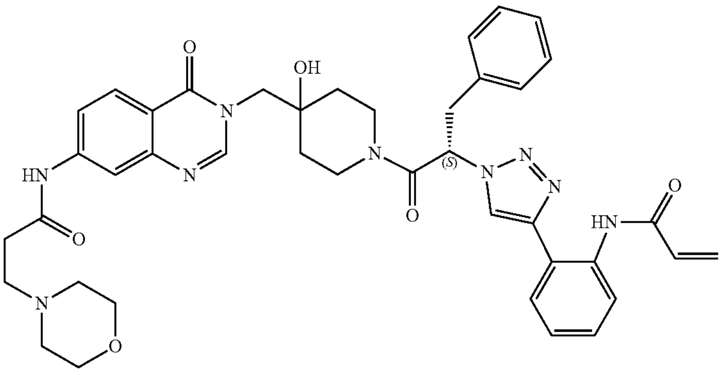 52 | + |

TABLE 3-continued
| USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed. | |
|---|---|
| Compound | $IC_{50}$ (μM) |
| 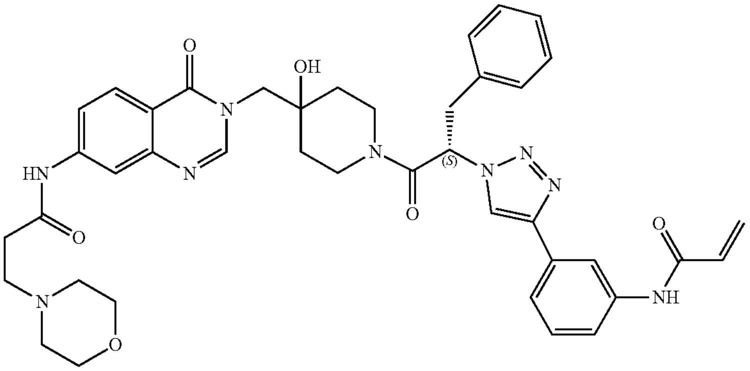 53 | + |
| 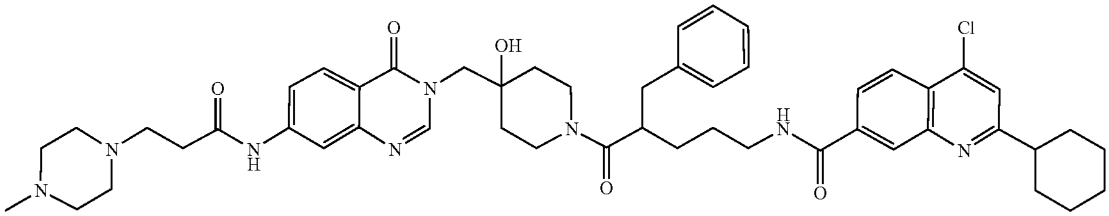 54 | +++ |
| 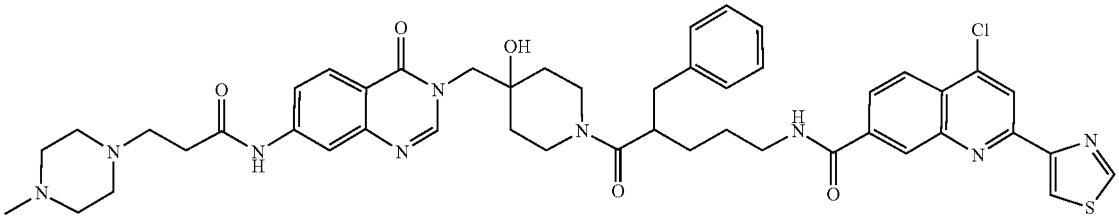 55 | +++ |
| 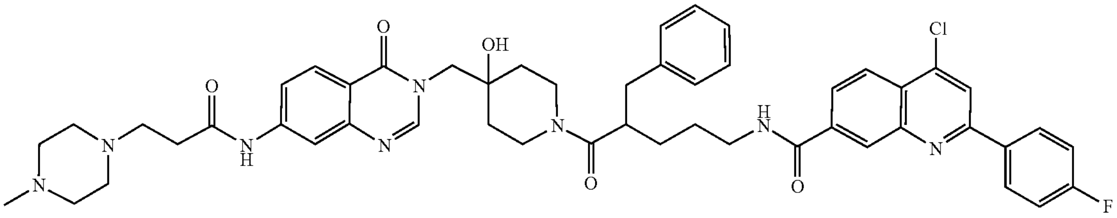 56 | +++ |
| 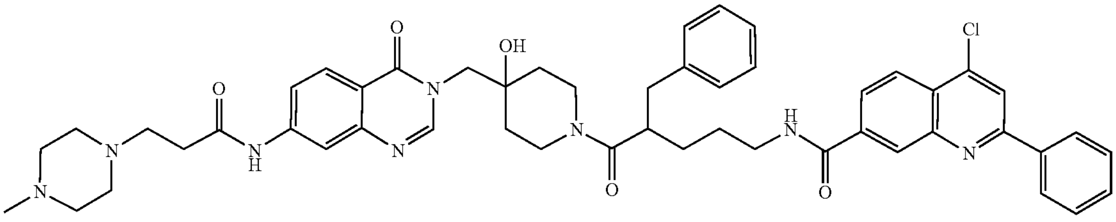 57 | ++ |

TABLE 3-continued
USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.
| Compound | $IC_{50}$ (μM) |
|---|---|
| 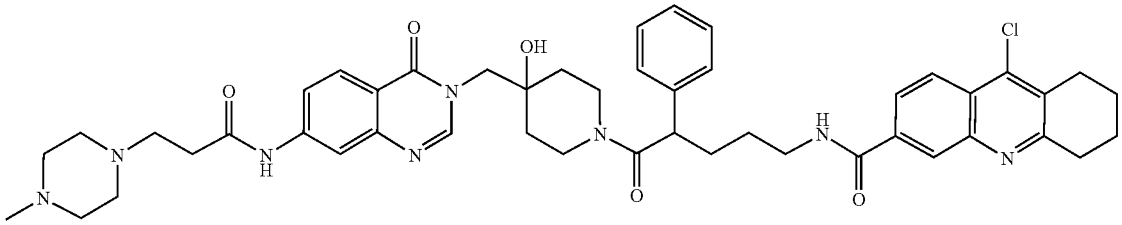 58 | + |
| 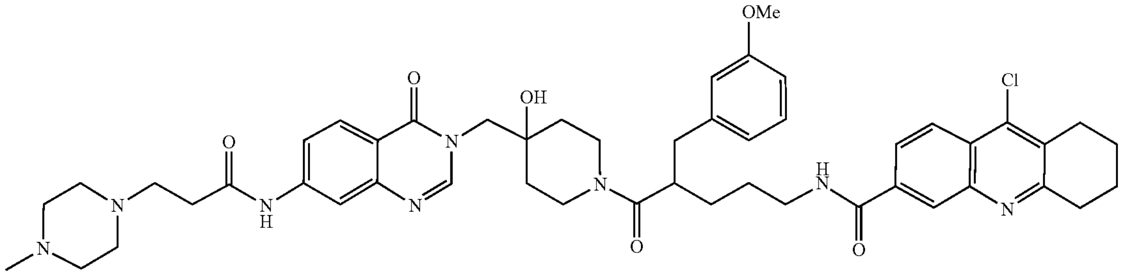 59 | + |
| 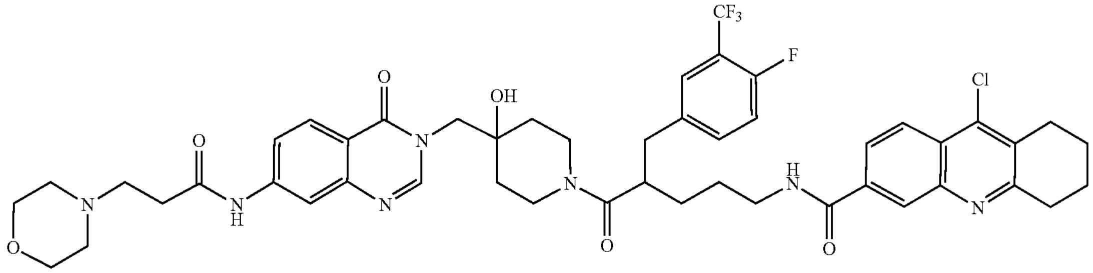 60 | +++ |
| 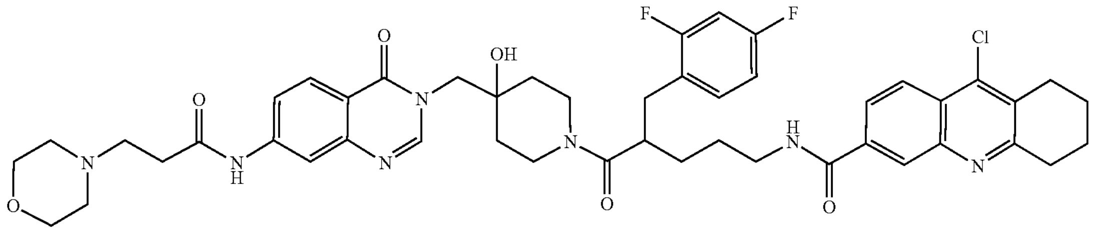 61 | +++ |

TABLE 3-continued

USP7 activity of exemplary compounds in USP7 assay. ++++ indicates an $IC_{50}$ of less than about 20 nM, +++ indicates an $IC_{50}$ from about 20 nM to about 100 nM, ++ indicates an $IC_{50}$ from about 100 nM to about 1 μM, and + indicates an $IC_{50}$ greater than 1 μM. ND refers to not disclosed.

| Compound | $IC_{50}$ (μM) |
| --- | --- |
| 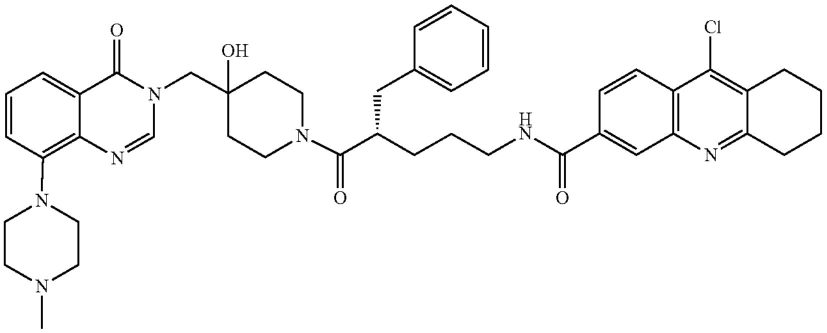 62 | +++ |
| 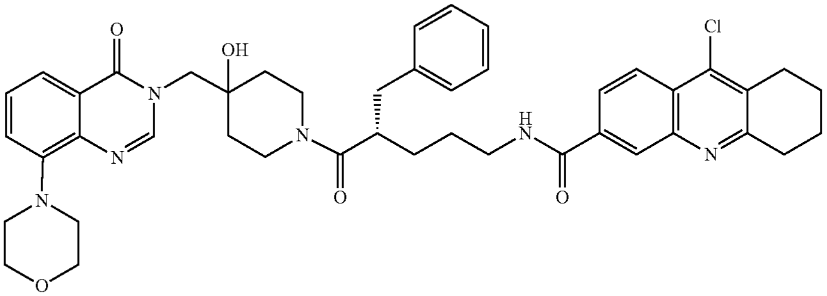 63 | +++ |

USP7 Cloning, Expression, and Purification

The constructs encoding USP7 full length (amino acids 1-1102) and catalytic domain (208-560) used were cloned as described (Lamberto, I. et al. Structure-Guided Development of a Potent and Article Structure-Guided Development of a Potent and Selective Non-covalent Active-Site Inhibitor of USP7. *Cell Chem. Biol.* 24, 1490-1500 (2017)). Both constructs were overexpressed in *E. coli* BL21 (DE3). Cells were grown at 37° C. to an OD of 0.9, cooled to 16° C., induced with 500 μM isopropyl-1-thio-D-galactopyranoside (IPTG), incubated overnight at 16° C., collected by centrifugation, and stored at −80° C. Cell pellets were sonicated in lysis buffer (25 mM Tris pH 8, 1 M NaCl, and 10 mM BME) supplemented with 10 μg/ml phenylmethanesulfonylfluoride (PMSF) and the resulting lysate was centrifuged at 30,000×g for 40 min. Ni-NTA beads (Qiagen) were mixed with lysate supernatant for 2 hours, and washed with lysis buffer supplemented with 25 mM imidazole. The bound protein was eluted with lysis buffer supplemented with 300 mM imidazole. The sample was then concentrated to 1 ml (30 kDa concentrator; Amicon Ultra, Millipore), and run on a Superdex 200 (GE healthcare) in buffer containing 25 mM HEPES pH 7.5, 200 mM NaCl, and 1 mM DTT. Fractions were pooled, concentrated and frozen at −80° C.

Ub-AMC Enzymatic and Kinetic Assays

Full length USP7 was tested for its activity in Ubiquitin-AMC assay in presence or absence of inhibitors. USP7 (5 nM) was pre-incubated for 6 hours at room temperature with different concentrations of inhibitors or DMSO as a control in 50 mM HEPES pH 7.5, 0.5 mM EDTA, 11 μM ovalbumin, and 5 mM DTT. Ubiquitin-AMC (Boston Biochem) was then added to a final concentration of 500 nM. The initial rate of the reaction was measured by collecting fluorescence data at one minute intervals over 30-minute period using a Clariostar fluorescence plate reader at excitation and emission wavelength of 345 and 445 nm respectively. The calculated initial rate values were plotted against inhibitor concentrations to determine $IC_{50}$s. All the experimental data were plotted using Prism GraphPad. All assays for each compound were performed at least twice for each compound.

To calculate the $k_i$ and $k_{inact}$ values for compound 1, the procedure above was used, but different concentrations of inhibitor were incubated with USP7 for different time points (5 min-3 hours) before adding Ubiquitin-AMC. To determine $k_{obs}$, the time course curves were fit to the equation $y=y_{max}(1-\exp(-k_{obs}\cdot x))$. The $k_{obs}$ values were then plotted against the inhibitor concentrations and fit to the equation $y=k_{inact}/(1+(k_i/x))$ to obtain the values for $k_i$ and $k_{inact}$.

MS Labeling

Purified USP7 catalytic domain was diluted to 20 μM in 10 μL labeling buffer (20 mM HEPES pH 7.5, 150 mM NaCl, 1 mM TCEP) and incubated for the indicated times with 50 μM (2.5×) compound. After incubation, samples were flash frozen in liquid nitrogen and stored at −80° C. until analysis.

Intact MS Analysis

Intact mass analysis was performed by injecting 5 μg USP7 catalytic domain onto a self-packed reversed phase column (1/32" O.D.×500 um I.D., 5 cm of POROS 10R2 resin). After desalting, protein was eluted with an HPLC gradient (0-100% B in 4 minutes, A=0.2M acetic acid in water, B=0.2 M acetic acid in acetonitrile, flow rate ~30 μL/min) into an LTQ ion trap mass spectrometer (ThermoFisher Scientific, San Jose, CA). Mass spectra were deconvoluted using MagTran1.03b2 software. Zhang, Z. & Marshall, A. G. A universal algorithm for fast and automated charge state deconvolution of electrospray mass-to-charge ratio spectra. *J. Am. Soc. Mass Spectrom.* 9, 225-233 (1998).

CE-MS Analysis

To identify sites of covalent modification, treated protein was reduced (10 mM dithiothreitol), alkylated (22.5 mM iodoacetamide), and digested with trypsin overnight at 37° C. Peptides were desalted using SP3 (Hughes, C. S. et al. Ultrasensitive proteome analysis using paramagnetic bead technology. *Mol. Syst. Biol.* 10, 757-757 (2014)), dried by vacuum centrifugation, and reconstituted in 1% formic acid/50% acetonitrile with 100 mM ammonium acetate. Peptides were then analyzed by CE-MS using a ZipChip CE system and autosampler (908 Devices, Boston, MA) interfaced to a QExactive HF mass spectrometer (ThermoFisher Scientific, San Jose, CA). Peptide solution was loaded for 30 seconds, and the mass spectrometer was operated in data dependent mode and subjected the 5 most abundant ions in each MS scan (60 k resolution, 3E6 target, lock mass enabled) to MS/MS (15 k resolution, 1E5 target, 100 ms max inject time). Dynamic exclusion was enabled with a repeat count of 1 and an exclusion time of 6 seconds. MS/MS data was extracted to .mgf using multipliers scripts (Alexander, W. M. et al. multipliers v2.0: A Python-based ecosystem for shared access and analysis of native mass spectrometry data. Proteomics 17, 15-16 (2017); Askenazi, M., et al. mzAPI: A new strategy for efficiently sharing mass spectrometry data. *Nat. Methods* 6, 240-241 (2009)) and searched against a forward-reverse human NCBI refseq database using Mascot version 2.6. Search parameters specified fixed carbamidomethylation of cysteine, and variable oxidation (methionine) and compound 6 modification (cysteine). Precursor mass tolerance was set to 10 ppm and product ion tolerance was 25 mmu. Spectral validation was performed using mzStudio. Ficarro, S., et al. mzStudio: A Dynamic Digital Canvas for User-Driven Interrogation of Mass Spectrometry Data. *Proteomes* 5, 20 (2017).

Cellular Assays with Exemplary USP7 Irreversible Inhibitors

Figure 1D:
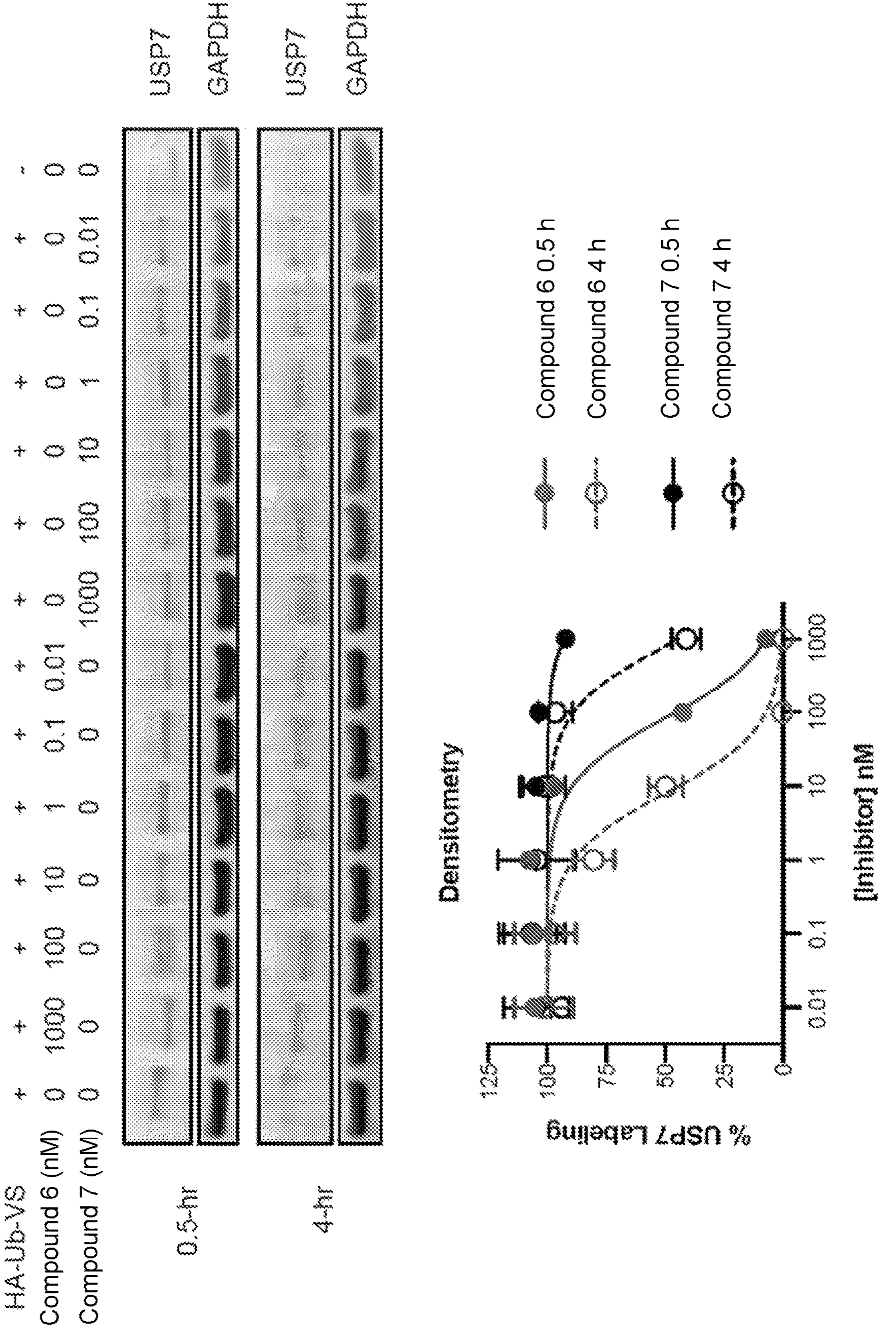
FIG. 1D depicts representative Western blots showing USP7 labeling by the DUB ABPP HA-Ub-VS in whole cell lysate after 30-minute or 4-hour pre-treatment with compound 6 or compound 7.
Figure 2A:
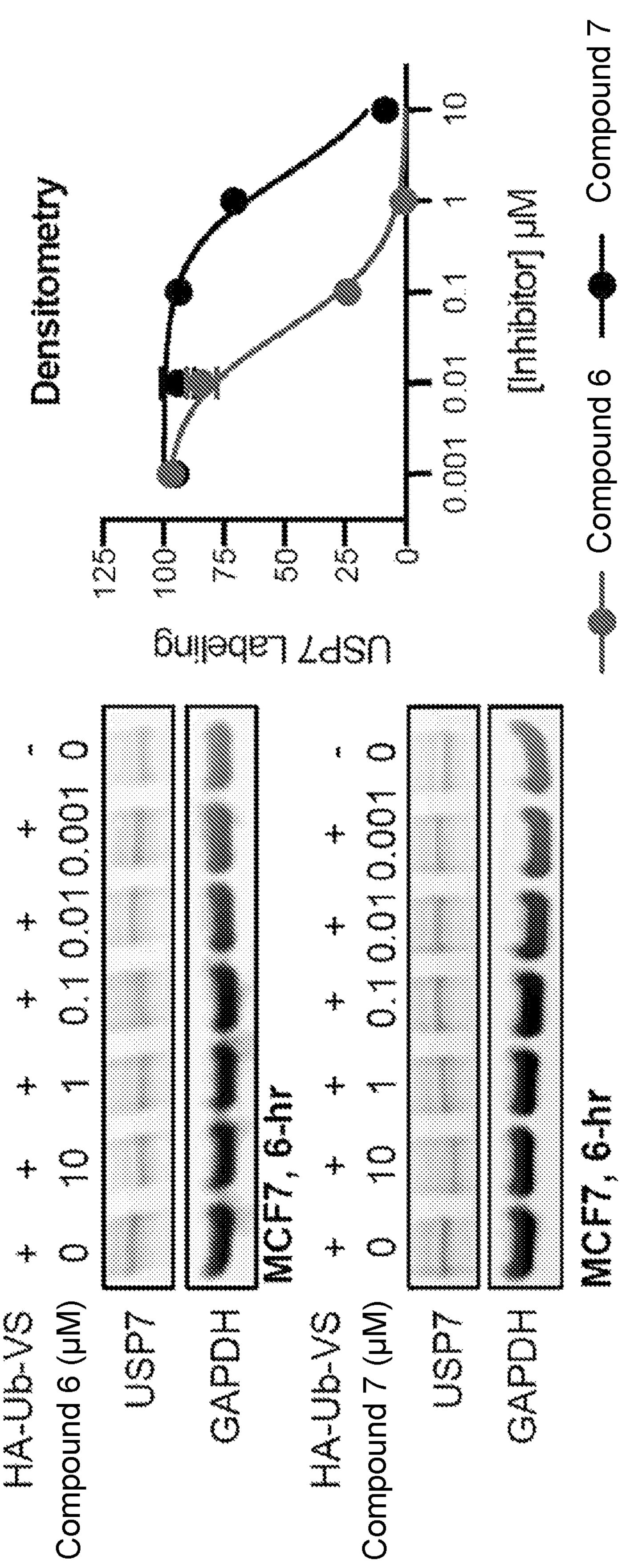
FIG. 2A depicts exemplary Western blots showing USP7 labeling by HA-Ub-VS after 6-hour cell treatment with compound 6 or compound 7.

To test USP7 target engagement in a cellular context, competitive activity-based protein profiling (ABPP) was used with MCF7 crude cell extracts and the DUB activity-based probe (ABP) hemagglutinin (HA)-ubiquitin vinylmethylsulfone (HA-Ub-VS). Compound 6 inhibited HA-Ub-VS labeling with $IC_{50}$ values of 85 and 8 nM following 30 min and 4 hr compound preincubations, respectively (FIG. 1D). Live cell treatment and competitive ABPP was also employed to demonstrate that compound 6 inhibits USP7 in cyto, with an $IC_{50}$ of 39 nM after 6 hr treatment (FIG. 2A). The enantiomer of compound 6, compound 7 (FIG. 1B), also demonstrated time-dependent USP7 inhibition, but with ~500-fold less potency against USP7 in experiments using purified enzyme, crude lysate, and live cell treatment (FIGS. 1C, 1D, and 2A). Compound 7 is thus a useful matched control for assessing the USP7-specific effects of compound 6. Compound 7 is also a useful USP7 inhibitor.

Figure 2B:
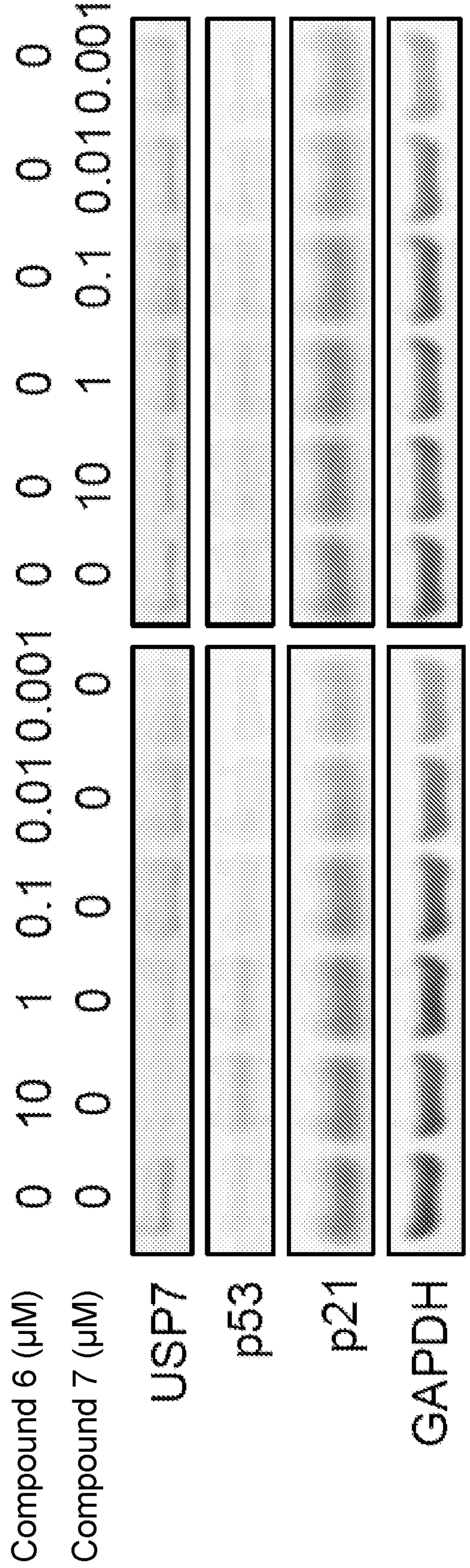
FIG. 2B depicts exemplary whole cell lysate Western blots of MCF7 cells after 2-hr treatment with compound 6 or compound 7.
Figure 2C:
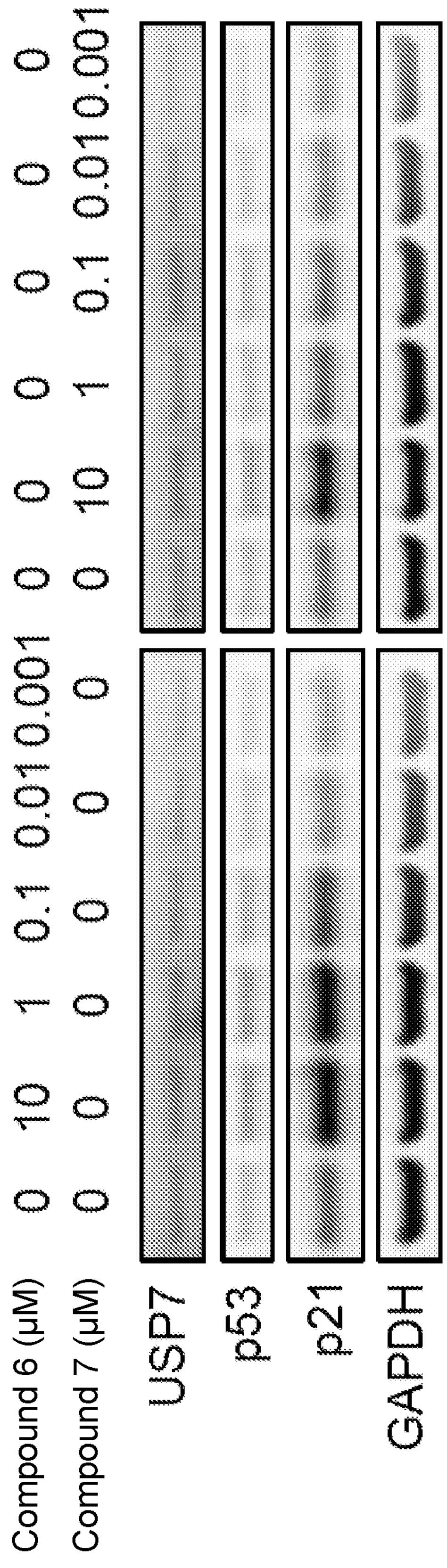
FIG. 2C depicts exemplary whole cell lysate Western blots of MCF7 cells after 16-hr treatment with compound 6 or compound 7.
Figure 2D:
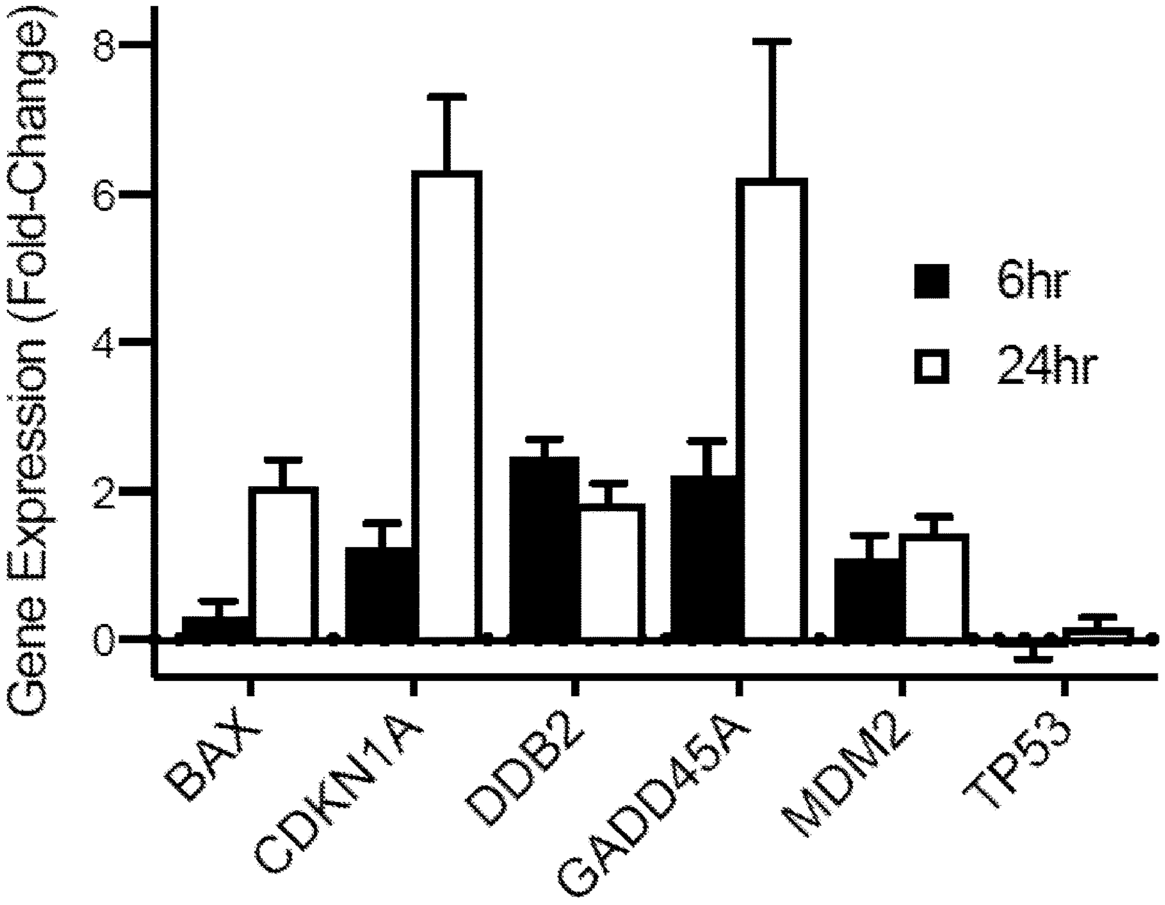
FIG. 2D depicts exemplary quantitative real-time PCR of MCF7 cells treated for 6 or 24 hours with 1 μM compound 6.
Figure 2E:
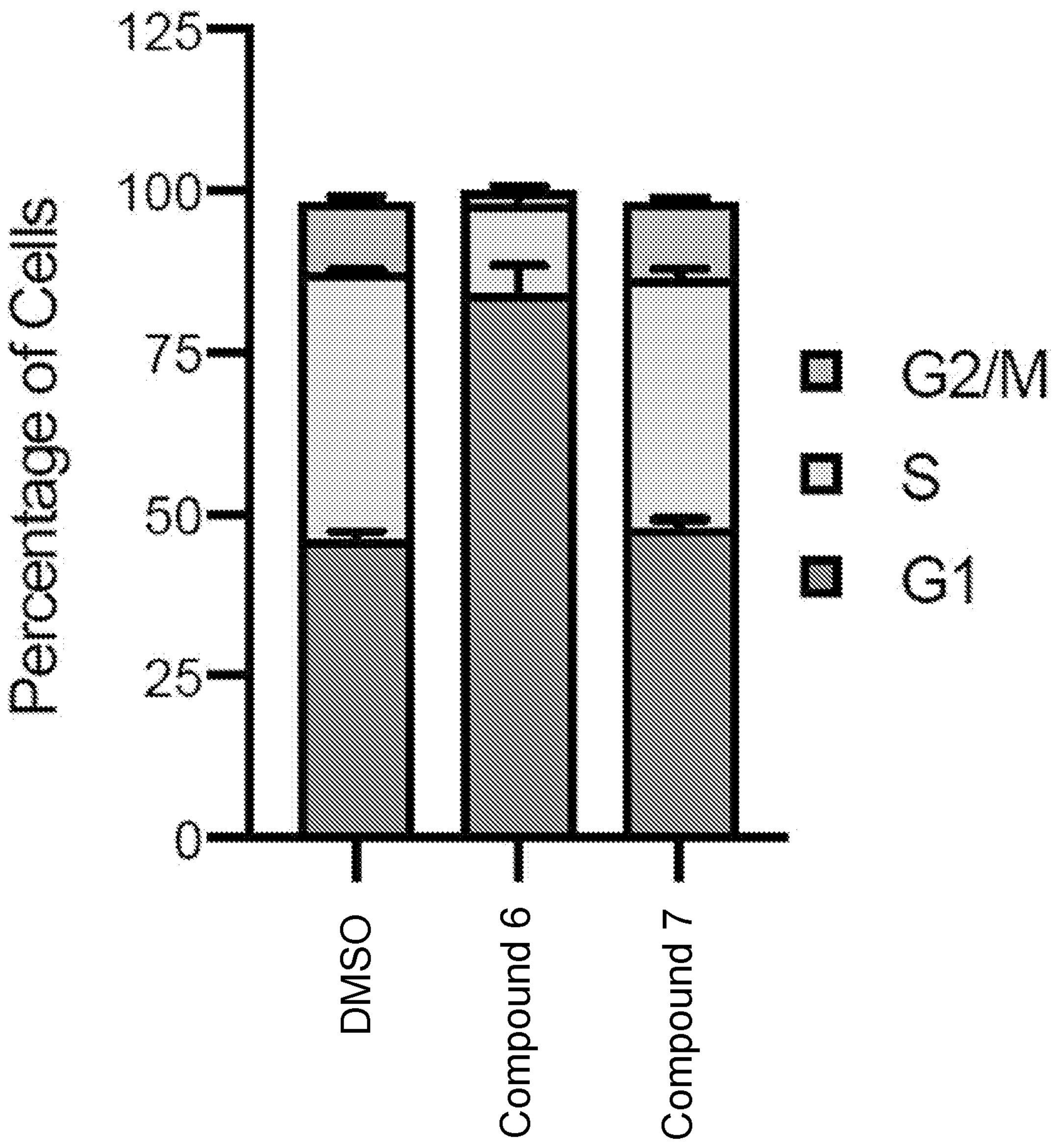
FIG. 2E depicts exemplary cell cycle analysis based on propidium iodide staining of MCF7 cells after 24-hr treatment with 1 μM compound 6 or compound 7.

To further confirm inhibition of cellular USP7, the impact was determined of compound 6 and of compound 7 on the MDM2-p53 signaling axis, the most well-validated pathway in its relation to USP7 DUB activity. As expected, treatment of MCF7 cells, which express wild-type TP53, with compound 6 induced rapid degradation of MDM2 within 2 hours, followed by increases in p53 and downstream p21 protein levels (FIGS. 2B and 2C) and stimulating transcription of p53 target genes related to both cell cycle arrest (CDKN1A and GADD45A) and apoptosis (BAX and DDB2) (FIG. 2D). Indeed, 1 μM compound 6 induced complete G1 arrest in MCF7 cells after 24 hours (FIG. 2E). In contrast, negative control compound 7 did not exert any of the same effects over the same range of concentrations (FIGS. 2B, 2C, and 2E). Due to negative feedback signaling, whereby p53 transcriptionally upregulates MDM2, after 24 hours of treatment with compound 6, p53 and p21 protein levels remained high, but MDM2 protein levels matched DMSO control (FIGS. 2B and 2C).

Example 3: Binding Mode of Exemplary Compounds

The search for potent and selective DUB inhibitors is of great interest to researchers interested in DUB biology. Despite advances in technology for DUB selectivity screening, including commercial DUB panels and ABPP methods, proteome-wide selectivity profiling has not previously been reported for DUB inhibitors. One of the most well-validated methods for proteome profiling is affinity chromatography, in which the small molecule of interest is conjugated to a solid resin via a solvent-exposed linker, exposed to native cell lysate, and enriched for any bound proteins. Terstappen, G. C., Schlüpen, C., Raggiaschi, R. & Gaviraghi, G. Target deconvolution strategies in drug discovery. *Nat. Rev. Drug Discov.* 6, 891-903 (2007). Drawbacks of this technique are that it requires that the affinity probe a) retain activity after conjugation of the linker, and b) bind irreversibly to target proteins either via crosslinking or covalent bond formation. The co-crystal structure of a selective USP7 inhibitor compound 42 bound to the USP7 catalytic domain showed that a) its piperazinyl moiety was solvent-exposed, providing a location for linker conjugation with activity retention, and b) its β-methyl group was located 5 Å from the active site, providing a potential site for irreversible binding to USP7. Further, Turnbull et al. had previously reported FT827, an irreversible USP7 inhibitor that binds in the same site as compound 42. Turnbull, A. P. et al. Molecular basis of USP7 inhibition by selective small-molecule inhibitors. *Nature* 550, 481-486 (2017). For these reasons, an affinity probe was developed based on compound 42 in order to perform proteome-wide profiling of compound 42 activity and determine whether targets other than USP7 may be mediating its observed p53-dependent activity. Stolte, B. et al. Genome-scale CRISPR-Cas9 screen identifies druggable dependencies in TP53 wild-type Ewing sarcoma. *J. Exp. Med.* jem.20171066 (2018).

Bivalent inhibitors, which combine two protein ligands via a synthetic linker, have the potential for markedly increased potency when compared to the parent ligands alone thanks to the additivity of their binding energies. Jencks, W. P. On the attribution and additivity of binding energies. *Proc. Natl. Acad. Sci.* 78, 4046-4050 (1981). While this strategy has been successfully applied in several instances for the kinases (Lamba, V. & Ghosh, I. New Directions in Targeting Protein Kinases: Focusing Upon True Allosteric and Bivalent Inhibitors. *Curr. Pharm. Des.*

18, 2936-2945 (2012)), design of irreversible bivalent probes is challenging, and FT827 possesses reduced affinity for USP7 compared to its reversible analog FT671. Similar results were found with several irreversible analogs of compound 42, but the use of the unusual 4-Cl-tetrahydroacridine warhead present in the previously reported non-selective USP7 inhibitor HBX-19818 (Reverdy, C. et al. Discovery of specific inhibitors of human USP7/HAUSP deubiquitinating enzyme. *Chem. Biol.* 19,467-477 (2012)) allowed development of inhibitors with similar or increased potency compared to compound 42. Compound 6's biochemical subnanomolar $IC_{50}$ is dramatically lower than that of compound 42 (nanomolar) or HBX-19818 (micromolar) alone, making it an example of a bivalent DUB inhibitor and an example of a bivalent inhibitor that binds irreversibly to the active site residue.

After confirming the biochemical and cellular activity of compound 6 and its inactive enantiomer compound 7, a number of linkers were conjugated to the piperazinyl moiety in order to achieve an active affinity probe based on the compound 42 and compound 6 scaffolds. Compound 6-DTB was a potent analog from this series, and this compound was chosen to pursue proteome-wide selectivity profiling of compound 6. By pre-treating cell lysates with native compound 6 to block compound 6-DTB labeling, specific targets of this compound series were annotated. Lanning, B. R. et al. A road map to evaluate the proteome-wide selectivity of covalent kinase inhibitors. *Nat. Chem. Biol.* 10, 760-767 (2014). Remarkably, compound 6 displayed exquisite selectivity for USP7 across the HEK 293 proteome even at high doses, results that are in contrast with many previous proteome-wide studies of covalent kinase inhibitors. Lanning, B. R. et al. A road map to evaluate the proteome-wide selectivity of covalent kinase inhibitors. *Nat. Chem. Biol.* 10, 760-767 (2014). This unexpected selectivity may be due to the low intrinsic reactivity of the 4-Cl-tetrahydroacridine warhead and the extended small molecule surface required for recognition by USP7. This compound 6 profiling data provided a high degree of confidence in the USP7-dependent effects of this compound and allowed determination of whether p53 signaling is a key determinant of cellular responses to USP7 inhibition.

Figure 3A:
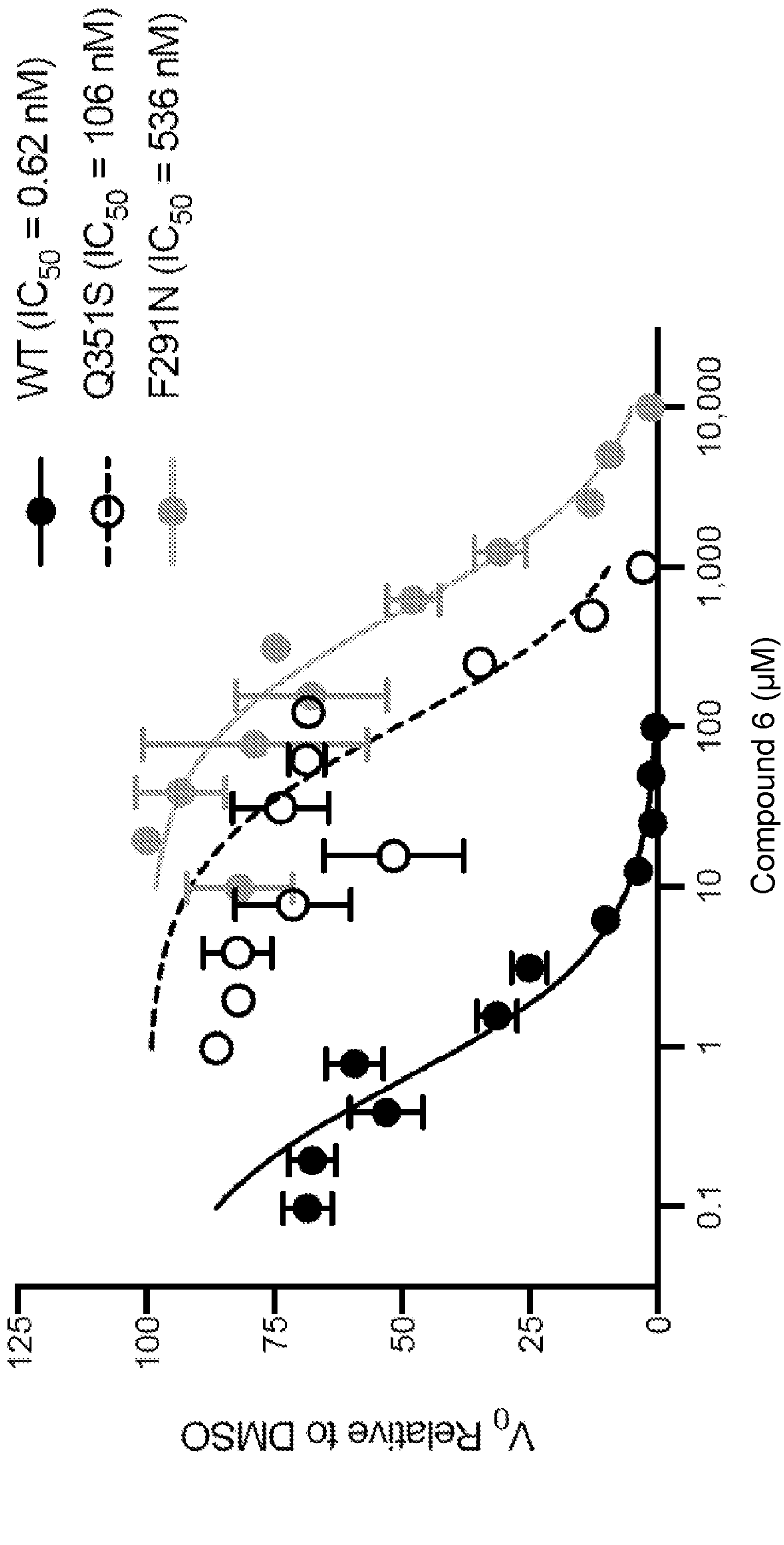
FIG. 3A depicts exemplary comparative Ub-AMC Michaelis-Menten curves of USP7-WT, USP7-Q351S, and USP7-F291N after 6-hr pre-incubation with compound 6.
Figure 3B:
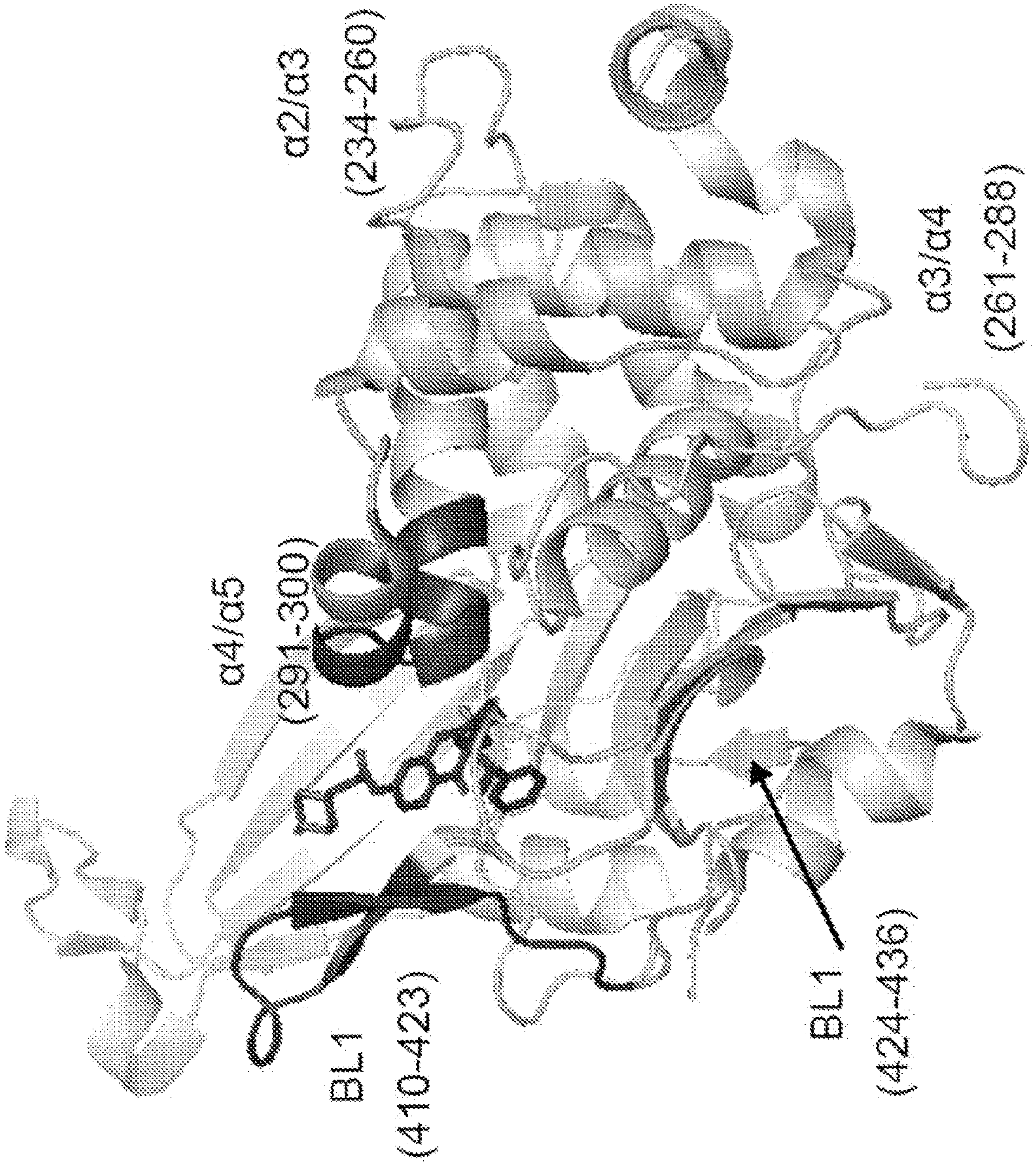
FIG. 3B depicts the structure of USP7 CD highlighting regions with increased or decreased hydrogen exchange after treatment with compound 6.
Figure 3C:
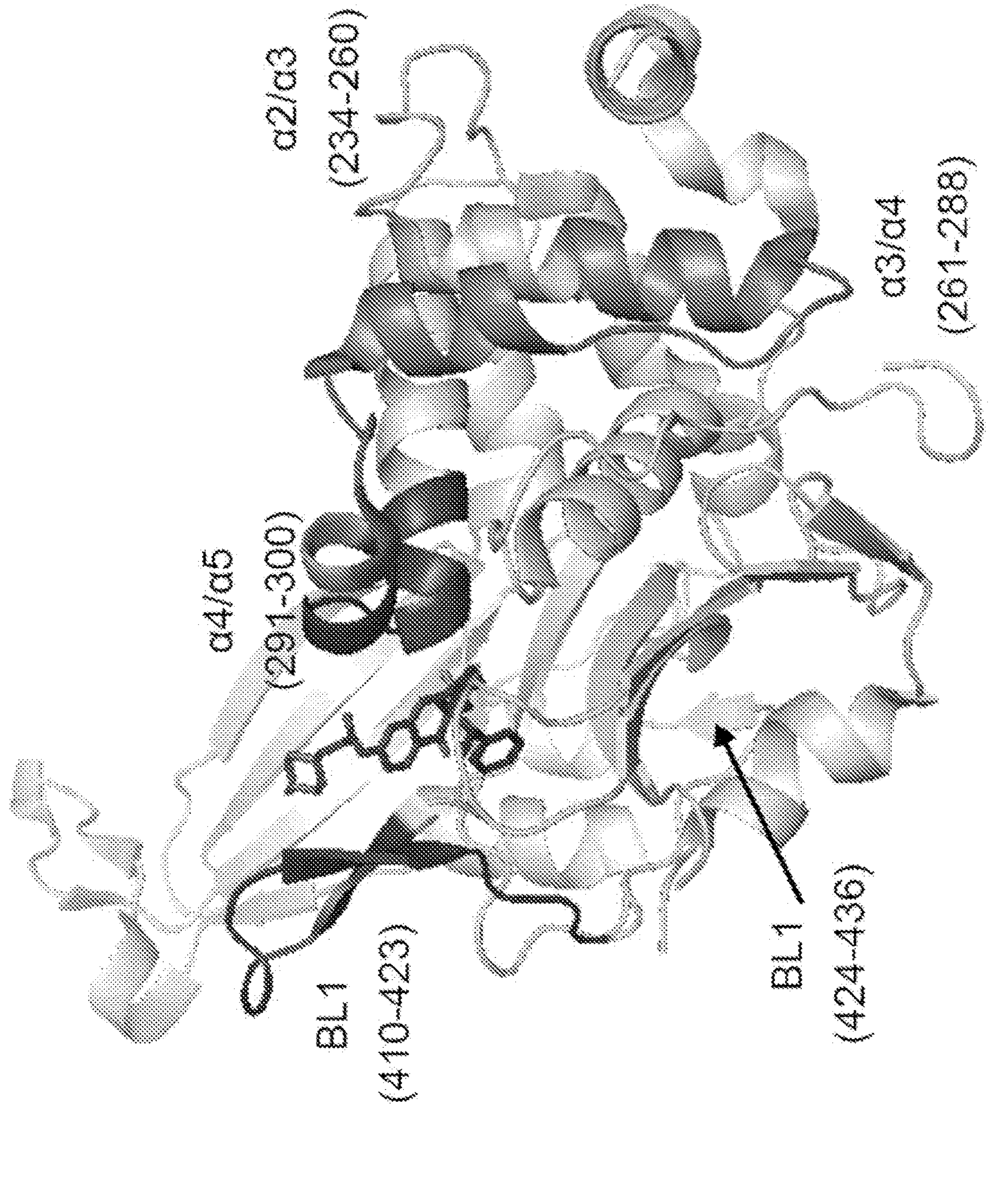
FIG. 3C depicts the structure of USP7 CD highlighting regions with increased or decreased hydrogen exchange after treatment with compound 1.

Compound 42 binds the S4-S5 pocket of USP7 (FIG. 1A). Without being bound by any theory, it was hypothesized that compound 6 was still binding this pocket. Unfortunately, extensive efforts to crystallize the USP7—compound 6 complex for structure determination by X-ray were unsuccessful. The binding mode was investigated using structure-activity-relationship (SAR) studies, USP7 mutant enzyme studies, hydrogen-deuterium exchange mass spectrometry (HDX), and molecular dynamics (MD) simulations. The 4-hydroxy-piperidine group of compound 42 forms hydrogen-bonding interactions with the sidechain carboxylic group of USP7 Q297 and the peptide backbone of V296 and is required for USP7 inhibition; replacement of the hydroxyl group with a hydrogen atom reduces potency >1,000-fold ($IC_{50}$=8 μM) in a purified enzyme biochemical assay. In addition, two compound 42-resistant USP7 mutants, F291N and Q351, are inhibited by compound 6 with 100-fold loss in potency compared to wild-type enzyme (FIG. 3A). To gain more direct structural information about the interaction of compound 6 with USP7, hydrogen exchange (HDX) was performed to monitor changes in protein dynamics. This technique was used to confirm that the binding mode observed with compound 42 in crystals is relevant in solution. Both compound 42 and compound 6 protected the BL1 and α-4/5 loops surrounding the S4-S5 pocket from exchange. Consistent with the benzyl moiety of compound 6 being buried in the S4 pocket, a compound 6 analog lacking the benzyl group (compound 1) does not protect β-sheet residues 410-423 that engage the benzyl group on compound 42. (FIG. 3B and FIG. 3C). While the regions of protection for compound 42 and compound 6 are similar enhanced exchange was observed in the region from α2 to α4 of USP7, putatively due to changes in dynamics resulting from covalent bond formation. The results were confirmed not to be unique to the catalytic domain only construct: the same regions of enhanced exchange/protection were observed with full-length enzyme. The data suggest that compound 6 possesses similar binding sites and a similar binding mode to that of compound 42.

Antibodies, Cell Lines, and Reagents

MDM2 (sc-965) antibody was obtained from Santa Cruz. P53 (9282s), p21 (2947s), GAPDH (2118s), and USP7 (4833s) antibodies were obtained from Cell Signaling Technology. Ub-AMC (U-550) and HA-Ub-VS (U-212) were obtained from Boston Biochem. Bio-Ub-PA (UbiQ-076) and Bio-Ub-VME (UbiQ-054) were obtained from UbiQ Bio. BAX (Hs00180269_m1), CDKN1A (Hs00355782_m1), DDB2 (Hs03044953 ml), GADD45A (Hs00169255_m1), GAPDH (402869), MDM2 (Hs00540450_s1), and TP53 (Hs01034249 ml) Taqman probes were obtained from Thermo-Fisher. MCF7 cells were a generous gift from Jean Zhao's laboratory. HEK 293AD, G401, G402, and MESSA were purchased from ATCC.

Cell Culture

MCF7 and MM1.S cells were cultured in RPMI-1640 growth medium supplemented with 10% FBS. HEK293AD cells were cultured in DMEM+10% FBS+1% antibiotics. A673 cells were cultured in DMEM+10% FBS+1 mM sodium pyruvate+1% PSQ. TC32 and TC71 cells were cultured in RPMI+10% FBS+1% PSQ. TC138 and CHLA258 cells were cultured in IMDM+20% Fetal Bovine Serum+4 mM L-Glutamine+1×ITS (5 μg/mL insulin, 5 μg/mL transferrin, 5 ng/mL selenous acid). All cell lines were maintained in 10 $cm^2$ tissue-culture treated dishes 37° C. in a 5% $CO_2$ incubator. All cell lines were verified *Mycoplasma*-free by the MycoAlert test kit.

HA-Ub-VS Labeling

HA-Ub-VS experiments were performed as previously described in Lamberto, I. et al. Structure-Guided Development of a Potent and Article Structure-Guided Development of a Potent and Selective Non-covalent Active-Site Inhibitor of USP7. *Cell Chem. Biol.* 24, 1490-1500 (2017). Briefly, target engagement lysis buffer (50 mM Tris pH 8.0, 150 mM NaCl, 5 mM $MgCl_2$, 0.5 mM EDTA, 0.5% NP-40, 10% glycerol, 1 mM TCEP, protease and phosphatase inhibitors) was added to cell pellets on ice. Lysate was cleared by centrifugation and diluted to 1.67 mg/mL. Where indicated, 30 μL lysate was then incubated with inhibitors or DMSO for the indicated timepoints. 1 μM HA-Ub-VS was then added to the lysate and incubated at RT for the indicated time points. Labeling reactions were quenched with 4×LDS sample buffer (Thermo Fisher B0007) supplemented with 10% BME, vortexed vigorously, and heated to 95° C. for 5 minutes. Samples were resolved by SDS-PAGE and analyzed by Western blot with the indicated antibodies.

Quantitative Real-Time PCR

After cell treatment under the indicated conditions, total cellular RNA was purified using a Qiagen RNEasy kit. 1 μg of RNA was then converted to cDNA using SuperScript III First-Strand Synthesis (Invitrogen). cDNA from each sample was then combined with the indicated TaqMan probe and 2× MasterMix in a 96-well Fast RT-PCR plate (Invitrogen). qPCR was performed on an Invitrogen 7500 Fast qPCR instrument and gene expression was calculated using the $2^{-\Delta\Delta ct}$ method on Graphpad Prism.

Cell Cycle Analysis

For propidium iodide (PI) staining, treated cells (~1 million per condition) were washed with cold PBS, then fixed in 80% ethanol overnight at −20° C. After fixing, cells were pelleted, washed with PBS, and reconstituted in 500 μL FxCycle PI/RNAse A staining solution (Thermo Fisher). Cells were stored overnight at 4° C. and analyzed using a BD Fortessa flow cytometer.

Hydrogen Deuterium Exchange Experiments

Hydrogen exchange experiments were performed as follows. A stock solution of USP7 catalytic domain at 50 pmol/μL in 20 mM Hepes (pH 7.5), 200 mM NaCl, 1 mM TCEP, 5% glycerol $H_2O$ was prepared. Deuterium exchange in USP7 catalytic domain alone was initiated by dilution with 15-fold D2O buffer (pD 7.5), at room temperature. At each deuterium exchange time point (from 10 s to 4 hours) an aliquot from the exchange reaction was removed and labeling was quenched by adjusting the pH to 2.5 with an equal volume of quench buffer (0.8% Formic Acid and 0.8M Guanidine Hydrochloride, $H_2O$). Quenched samples were immediately injected into the LC/MS system.

For the HDX MS experiments of USP7 bound to covalent compounds, each compound was individually incubated with USP7 as follows: compound 1 was incubated at RT for 60 min with USP7 at a protein:compound ratio of 1:10, ensuring that >99.97% was bound after dilution with $D_2O$. Compound 6 was mixed at a protein:compound ratio of 1:10, for 30 min at room temperature before dilution with $D_2O$. The same timecourse as for the protein alone was implemented for the compounds work (10 sec-4 h).

Mass Analysis

Each sample was online digested using a Poroszyme immobilized pepsin cartridge (2.1 mm×30 mm, Applied Biosystems) at 15° C. for 30 s, then injected into a custom Waters nanoACQUITY UPLC HDX Manager™ and analyzed on a XEVO G2 mass spectrometer (Waters Corp., USA). The average amount of back-exchange using this experimental setup was 20-30%, based on analysis of highly deuterated peptide standards. Deuterium levels were not corrected for back-exchange and are therefore reported as relative. Wales, T. E. & Engen, J. R. Hydrogen exchange mass spectrometry for the analysis of protein dynamics. *Mass Spectrom. Rev.* 25, 158-170 (2006). All experiments were performed in duplicate. The error of measuring the mass of each peptide averaged±0.15 Da in this experimental setup. The HDX-MS data were processed using PLGS 3.0 and DynamX 3.0 (Waters Corp., USA). The common peptides that were compared between the USP7 catalytic domain alone and bound to the compounds lead to a sequence coverage of 85.4% corresponding to 81 peptic peptides with compound 1 and 94% and 105 peptic peptides with compound 6 that were followed with hydrogen deuterium exchange uptake plots.

Example 4: Selectivity of Exemplary Compounds Among DUBs

Figure 4A:
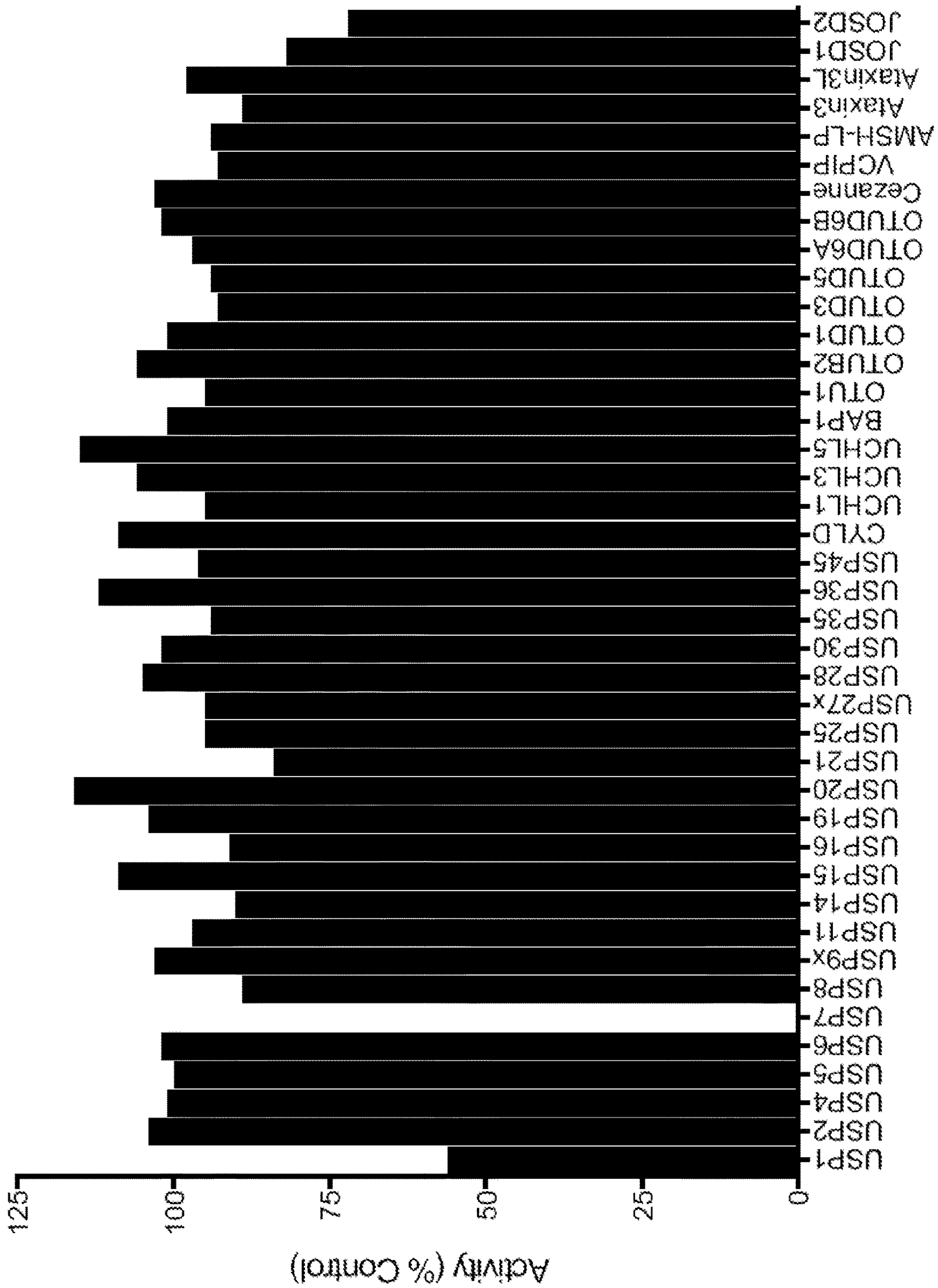
FIG. 4A depicts remaining activity of 41 purified recombinant DUBs against Ub-Rho after 15-minute pre-treatment with compound 6.
Figure 4B:
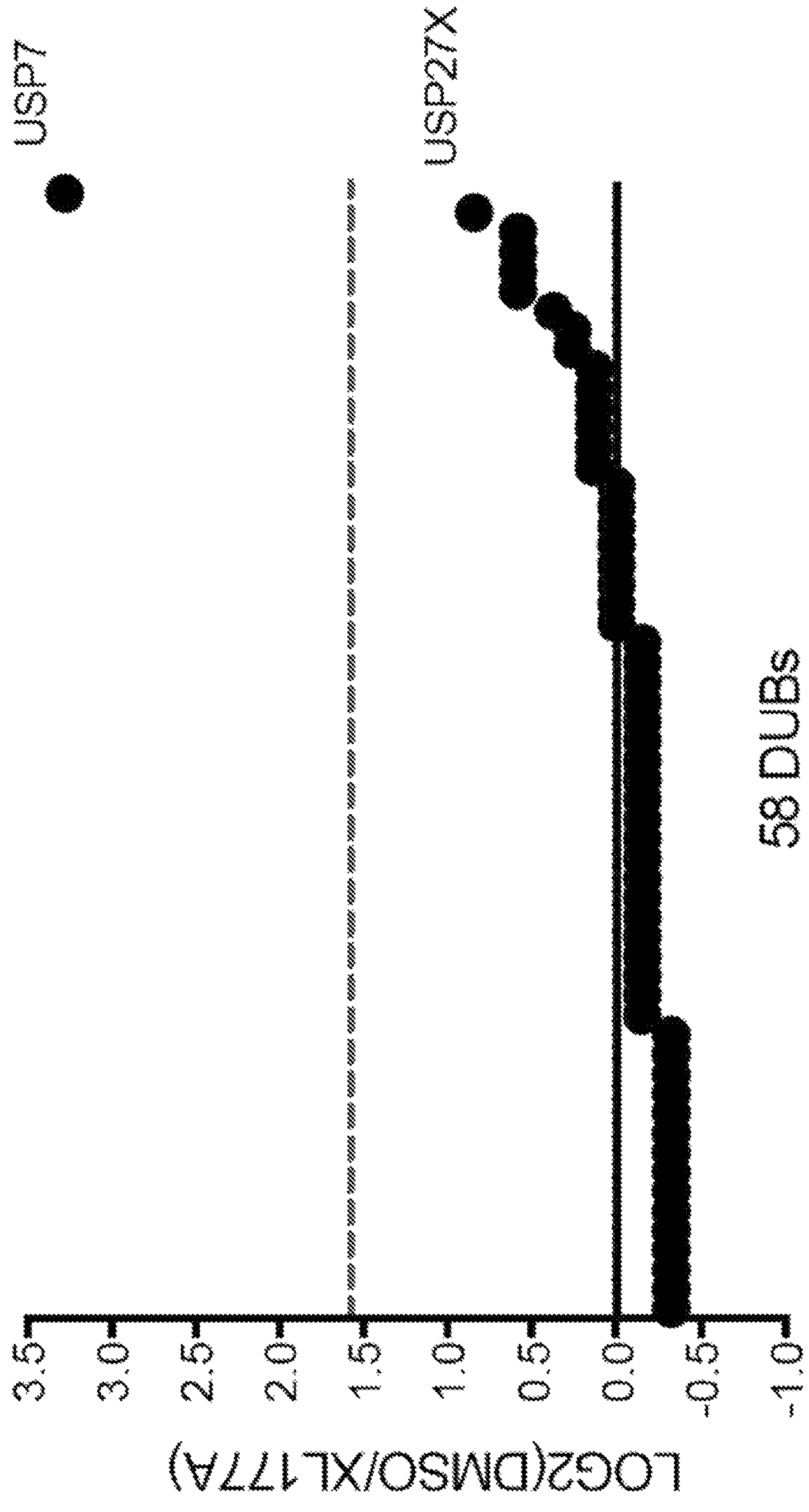
FIG. 4B depicts the ratio of Bio-Ub-PA/VME labeling for 59 DUBs in HEK293AD lysate between samples pre-treated for 5 hours with DMSO v. 1 μM compound 6. Dashed line represents 3-fold excess labeling of DMSO vs. compound 6 samples.

The active site binding pocket is highly conserved among DUBs, and an inhibitor mechanism that includes binding the conserved catalytic cysteine thus has the potential for broad DUB activity. The selectivity of compound 6 was first assessed by determining the inhibitory activity across a panel of 41 recombinant DUBs using in vitro activity assays. At a concentration of 1 μM (~1000-fold higher than its $IC_{50}$ for USP7), compound 6 completely inhibited USP7 enzymatic activity but did not exhibit significant activity against any other DUBs (FIG. 4A). The DUB enzymes in this panel primarily consist of only domains or binding partners that are sufficient for in vitro activity, and many DUBs are large multi-domain proteins and/or exist in macromolecular complexes. Furthermore, the standard conditions for this panel include compound pre-incubations of 15 minutes, limiting our ability to assess off-targets that are inhibited with time-dependent kinetics. Competitive ABPP was used with quantitative MS to explore the selectivity of compound 6 in a more native context. Briefly, either DMSO or compound 6 was pre-incubated with HEK293 crude cell extract for 5 hours. The lysate was then incubated with a 1:1 mixture of biotin-ubiquitin-propargylic acid (Bio-Ub-PA) and biotin-ubiquitin-vinyl methyl ester (Bio-Ub-VME), an ABP combination that maximized DUB biotin labeling in our hands. The labeled lysates were enriched by streptavidin resin, tandem mass tag (TMT)-labeled, combined and analyzed by LC/MS. Compound 6 significantly blocked USP7 labeling by DUB ABPs in a dose-dependent manner while remaining selective against 58 other DUBs (FIG. 4B).

In Vitro DUB Profiling

Compounds were screened using the Ubiquigent Drug Profiler SPT system. Each of 41 purified DUBs was incubated with compound for 15 minutes, then ubiquitin rhodamine 110 (Ub-Rho) was added and percent inhibition determined based on fluorescence relative to a DMSO control.

In Situ DUB Profiling

DUB profiling was performed using conditions similar to those in Lawson, A. P. et al. Identification of deubiquitinase targets of isothiocyanates using SILAC-assisted quantitative mass spectrometry. Oncotarget 5, (2017). HEK 293AD cells were lysed using target engagement lysis buffer (50 mM Tris pH 8.0, 150 mM NaCl, 5 mM $MgCl_2$, 0.5 mM EDTA, 0.5% NP-40, 10% glycerol, 1 mM TCEP, protease and phosphatase inhibitors), and the lysate was cleared by centrifugation. Samples were diluted to 2 mg/mL, and 1 mL lysate was incubated with the indicated concentration of compound 6 for 5 hours at RT. Excess inhibitor was removed using a 30K Amicon spin filter, then the resulting lysate was incubated with 1 μM each of Biotin-Ub-PA and Biotin-Ub-VME for 90 minutes at RT. SDS was added to a final concentration of 1.2%, and samples were heated to 80° C. for 5 minutes. After cooling to RT, 1×PBS was added to dilute the final SDS concentration to 0.2%. 100 μL streptavidin agarose slurry was added to each sample, followed by incubation at RT for 3 hours. After streptavidin enrichment, samples were washed vigorously (2×0.2% SDS, 3×PBS, 3×dd$H_2O$). After the final wash, all supernatant was removed using a flat-bottom tip, and the resin was flash frozen and stored at −80° C. until workup for TMT labeling.

Example 5: Proteomic Profiling of Exemplary Compounds

Figure 4C:
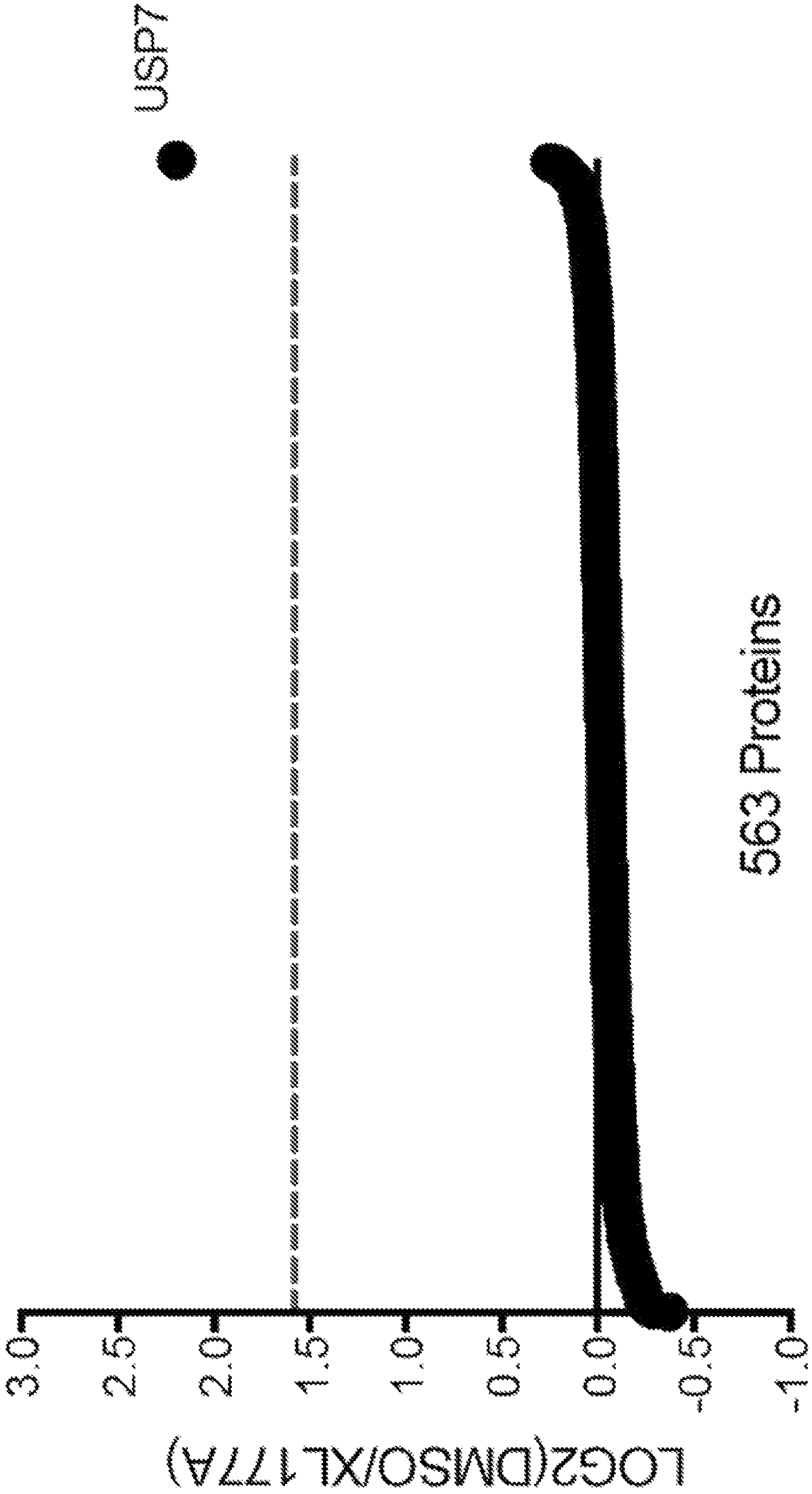
FIG. 4C depicts the ratio of compound 6-DTB labeling for 566 proteins in HEK293AD lysate between samples pre-treated for 5 hours with DMSO v. 1 μM compound 6. Dashed line represents 3-fold excess labeling of DMSO vs. compound 6 samples.

To define compound 6 specificity proteome-wide, binding partners were assessed using an unbiased chemical proteomics screen. First, compound 6-DTB was synthesized, an compound 6 analog with a desthiobiotin (DTB) affinity tag (compound 41), and demonstrated that it retained USP7 inhibitory activity against purified enzyme and native USP7. HEK293 cell lysates were treated with compound 6 for 5 hours at 1 μM or 10 μM, incubated with compound 6-DTB (compound 41), and quantified concentration-dependent blocking of compound 6-DTB binding throughout the proteome. In total, 566 proteins were detected as covalently modified by DTB-compound 6, but only USP7 exhibited >3-fold inhibition of labeling when treated with compound 6 at 1 μM or 10 μM (FIG. 4C). These data corroborate that compound 6 is highly specific for USP7 relative to other DUBs and further, the rest of the proteome. The tetrahydroacridine warhead of compound 6 is not commonly observed in irreversible inhibitors, and this data suggests a possible propensity to react specifically with DUBs over other target classes.

Taken together, these data demonstrate that compound 6 possesses good cellular permeability, highly potent target engagement with native USP7, and exquisite proteome-wide selectivity for USP7. Further, the data demonstrates that covalent targeting of the DUB catalytic cysteine is tractable for drug discovery. The USP7 probes have been assessed for binding partners in an unbiased fashion. This compound, in combination with compound 7, meets the criteria of potency, selectivity, and cellular activity set out by multiple organizations to describe well-characterized chemical probes. Frye, S. V. The art of the chemical probe. *Nat. Chem. Biol.* 6, 159-161 (2010); Workman, P. & Collins, I. Probing the Probes: Fitness Factors For Small Molecule Tools. *Chem. Biol.* 17, 561-577 (2010).

Compound 6-DUTB Profiling

HEK 293AD cells were lysed as described above, and the lysate was cleared by centrifugation. Samples were diluted to 10 mg/mL, and 200 μL lysate (2 mg protein total) was incubated with the indicated concentrations of compound 6 for 4 hours at RT, then 2 μM of Compound 42 for 4 additional hours. SDS was added to a final concentration of 1.2% (27.2 μL of a 10% stock), and denatured by heating to 80° C. for 5 minutes. After cooling to RT, 1125 μL 1×PBS was added to dilute the final SDS concentration to 0.2%. 50 μL streptavidin agarose slurry was added to each sample, followed by incubation at RT for 3 hours. After streptavidin enrichment, samples were washed vigorously (2×0.2% SDS, 3×PBS, 3×dd$H_2O$). After the final wash, all supernatant was removed using a flat-bottom tip, and the resin was flash frozen and stored at −80° C. until workup for TMT labeling.

Sample Prep for Mass Spectrometry Analysis

Streptavidin beads were resuspended in 95 μL 100 mM Tris pH 8.0. Each sample was denatured with 0.1% rapigest, reduced (10 mM dithiothreitol), alkylated (22.5 mM iodoacetamide), and digested with trypsin overnight at 37° C. To remove rapigest, recovered supernatants were acidified with 10% TFA, incubated at 37° C. for 45 minutes, and centrifuged at 14,000 rpm for 15 minutes at 4° C. Peptides were then desalted by C18, and dried by vacuum centrifugation. Dried peptides were reconstituted in 40 μL 50 mM pH 8.0 TEAB, and 2/5 units of TMT reagent was added and reactions incubated at RT for 1 hour. TMT reactions were pooled and treated with hydroxylamine according to the manufacturer's instructions. Peptide mixtures were then dried, reconstituted in 50 mM ammonium bicarbonate and desalted by SP3. Eluted peptides were then analyzed by nanoLC-MS as described (Ficarro, S. B. et al. Improved electrospray ionization efficiency compensates for diminished chromatographic resolution and enables proteomics analysis of tyrosine signaling in embryonic stem cells. *Anal. Chem.* 81, 3440-3447 (2009)) with a NanoAcquity UPLC system (Waters, Milford, MA) interfaced to a QExactive HF mass spectrometer (Thermofisher Scientific, San Jose, CA). TMT labeled peptides were injected onto a precolumn (4 cm POROS 10R2, Applied Biosystems, Framingham, MA), resolved on an analytical column (30 μm I.D.×50 cm packed with 5 μm Monitor C18) and introduced to the mass spectrometer by ESI (spray voltage=3.5 kV, flow rate~30 nL/min). The mass spectrometer was operated in data dependent mode such that the 15 most abundant ions in each MS scan (m z 300-2000, 120K resolution, target=3E6, lock mass for 445.120025 enabled) were subjected to MS/MS (m/z 100-2000, 30K resolution, target=1E5, max fill time=100 ms). Dynamic exclusion was selected with a repeat count of 1 and an exclusion time of 30 seconds. MS/MS data was extracted to .mgf using multipliers scripts (Alexander, W. M. et al. multipliers v2.0: A Python-based ecosystem for shared access and analysis of native mass spectrometry data. Proteomics 17, 15-16 (2017); Askenazi, M., et al. mzAPI: A new strategy for efficiently sharing mass spectrometry data. *Nat. Methods* 6, 240-241 (2009)) and searched against a forward-reverse human NCBI refseq database using Mascot version 2.6. Search parameters specified fixed carbamidomethylation of cysteine, fixed N-terminal and lysine TMT labelling, and variable oxidation (methionine). Additional multipliers scripts were used to filter results to 1% FDR and derive protein-level aggregate reporter ion intensities using peptides mapping uniquely into the genome.

Example 6: Genetic Studies of p53 Status with Exemplary Compounds

Several previous studies of USP7 inhibitors in cancer have found that TP53 status is not necessarily predictive of response to USP7 inhibition. Specifically, the USP7 inhibitors P5091 and GNE-6640 do not produce TP53-dependent cell killing in multiple myeloma or a panel of cancer cells, respectively. In a recently reported study, it was found that, while P5091 displayed equipotent activity against WT and TP53-KO Ewing Sarcoma cells, compound 42 was virtually inactive against TP53-KO Ewing Sarcoma cells. After profiling compound 6, this compound was tested against the same cells and found highly TP53-dependent cell killing, in line with results for compound 42. These findings provided strong evidence that selective inhibition of USP7 may be a viable strategy for targeting TP53-WT tumors. It was further found that a) compound 6 synergizes with multiple p53-targeting compounds in Ewing Sarcoma, and b) compound 6 induces a transcriptional profile that correlates strongly with Nutlin-3A. These results clearly demonstrate the importance of the MDM2-p53 axis in response to selective USP7 inhibitors. Meanwhile, several transcriptional targets of high-dose compound 6 were identified that differ from Nutlin-3A, so while p53 signaling should certainly be considered in subsequent studies of USP7 inhibitors, it is by no means the only pathway that may prove important.

Figure 5A:
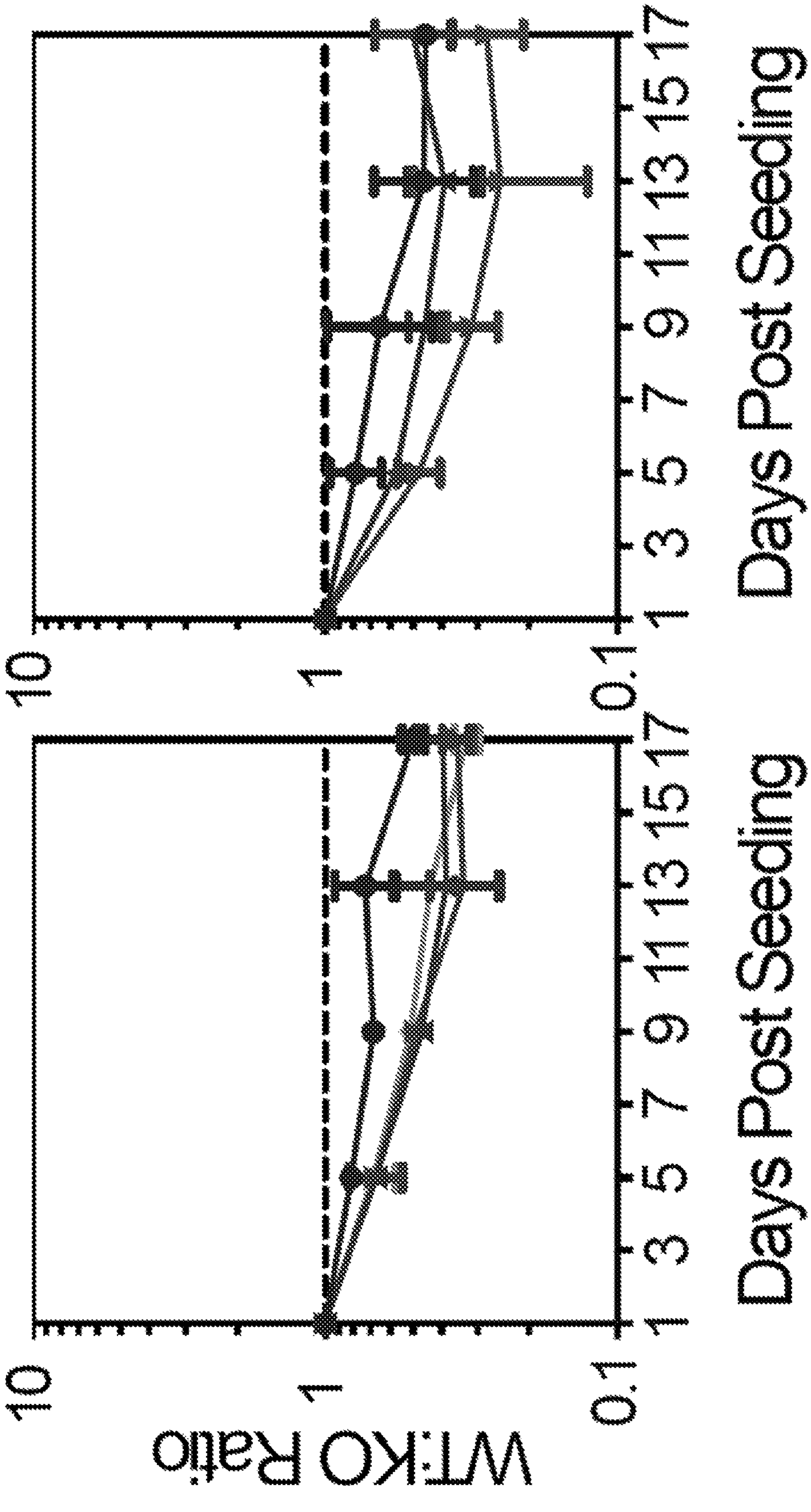
FIG. 5A depicts $\log_{10}$ ratio of A549-FF to A549-sgTP53-Renilla cells after treatment of an initial 1:1 mixture of the two cell lines with the indicated sgRNA for the indicated number of days.

While MDM2-p53 is the most well-validated substrate of USP7, the question of whether TP53 status (mutant versus wild-type) is a determinant of response to USP7 inhibition remains unanswered. Several studies investigating vulnerability of selected cancer types to pharmacological USP7 inhibition show little to no specificity for cell lines expressing functional p53. Kategaya, L. et al. USP7 small-molecule inhibitors interfere with ubiquitin binding. *Nature* 550, 534-538 (2017); Chauhan, D. et al. A Small Molecule Inhibitor of Ubiquitin-Specific Protease-7 Induces Apoptosis in Multiple Myeloma Cells and Overcomes Bortezomib Resistance. *Cancer Cell* 22, 345-358 (2013). To assess the functional role of p53 on USP7 modulation in TP53-WT cell lines, a dual luciferase reporter assay was employed to assess the comparative fitness of TP53-WT and TP53-KO cells in response to USP7 KO. Giacomelli, A. O. et al. Mutational processes shape the landscape of TP53 mutations in human cancer. *Nat. Genet.* 50, 1381-87 (2018). Briefly, Firefly (FF) luciferase was expressed in parental A549 and RKO cells and Renilla luciferase in stable TP53-KO A540 and RKO cells. The FF- and Renilla-expressing cells were mixed in a 1:1 ratio and then exposed to Cas9 and sgRNAs targeting MDM2, USP7, TP53, CDKN1A, LacZ, or FF luciferase for 17 days. Both sgMDM2 and sgUSP7 led to sustained reductions in the parental cells of both A549 and RKO (FIG. 5A), indicating that p53-KO improves the fitness of these cells in response to USP7 or MDM2 modulation. Thus, the cell killing effect of USP7 KO is, as with MDM2 KO, at least partially mediated by p53 in TP53-WT cells.

Dual Reporter Luciferase Competition Assay $p53^{WT}$ and $p53^{NULL}$ A549 cells constitutively expressing firefly luciferase or Renilla luciferase have been described in Giacomelli, A. O. et al. Mutational processes shape the landscape of TP53 mutations in human cancer. *Nat. Genet.* 50, 1381-87 (2018). Each cell line was infected with lentivirus encoding *S. pyrogenes* Cas9 under control of the human EF1alpha promoter (pLX311) and selected in blasticidin (InvivoGen) (1 mg/mL) (10 μg/mL). To perform the competition assay, Cas9-expressing p53w cells were mixed at a 1:1 ratio with complementarily-labeled Cas9-expressing $p53^{NULL}$ cells and seeded at 2,500 cells/well in 96-well dishes in 200 μL of normal culture media. The following day, cells were infected with an array of sgRNA-expressing lentiviruses (pXPR003). Twenty-four hours thereafter, the supernatant was removed and fresh media containing puromycin (InvivoGen) (1 μg/mL) was added to select for infected cells. Two days later, cells were split into two new replica plates, and incubated for four more days. One replica plate was subjected to a dual luciferase assay (Dyer, B. W., Ferrer, F. A., Kleindienst, D. K. & Rodriguez, R. A non-commercial dual luciferase enzyme assay system for reporter gene analysis. *Anal. Biochem.* 282, 158-161 (2000)) and luminescence readings were obtained using a Wallac EnVision (Perkin-Elmer). Readings from wells infected with experimental sgRNAs were normalized to wells infected with control sgRNAs, and firefly:Renilla luminescence ratios were calculated to estimate the relative effects of sgRNAs on $p53^{WT}$ versus $p53^{NULL}$ cells within a well. To continue the assay, the second replica plate was passaged at a 1/16 dilution. Giacomelli, A. O. et al. Mutational processes shape the landscape of TP53 mutations in human cancer. *Nat. Genet.* 50, 1381-87 (2018). The process of reading and re-plating the cells was repeated every 4 days.

Example 7: USP7 Inhibition with Exemplary Compounds in Cancer Cells

Figure 5B:
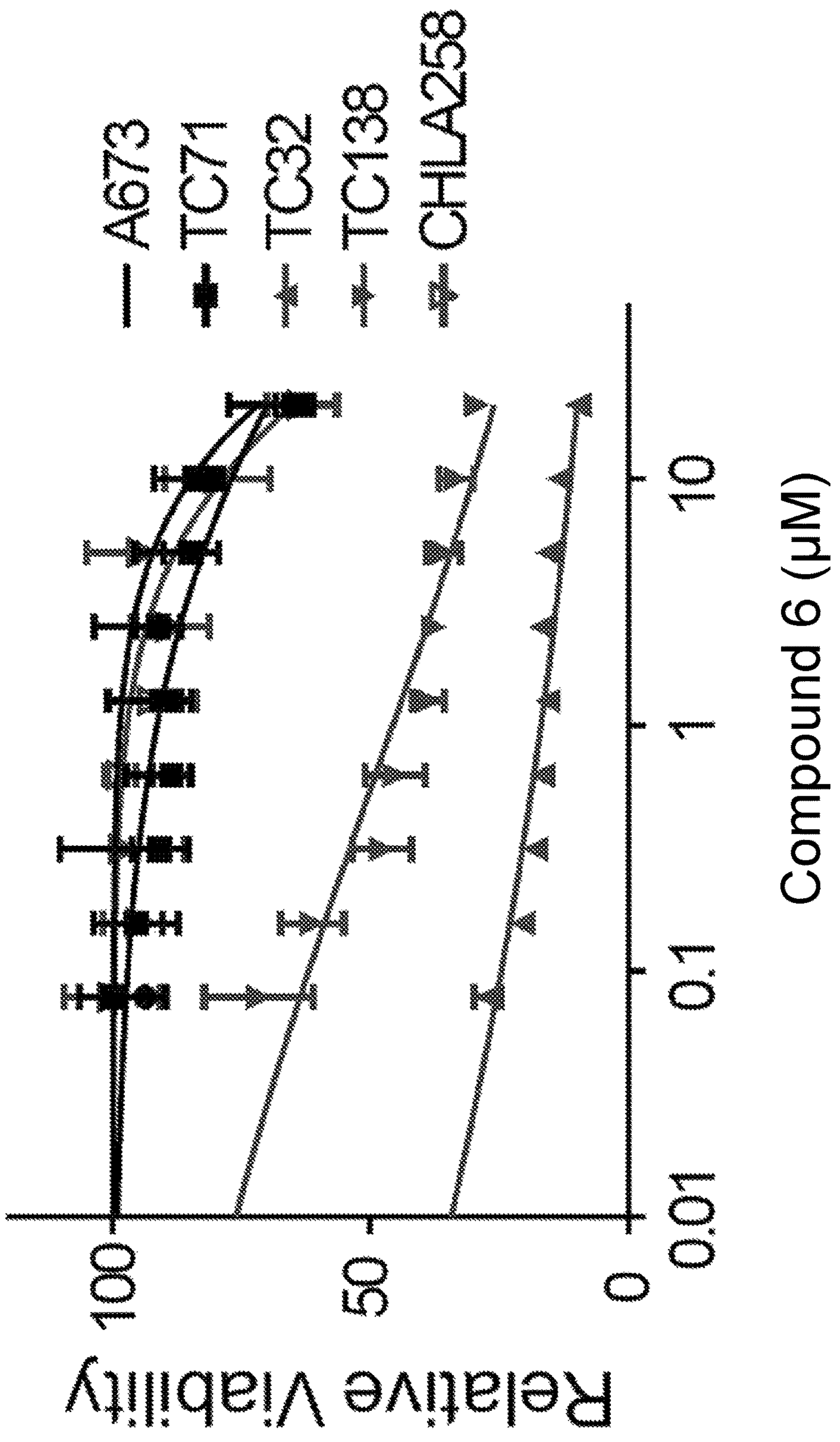
FIG. 5B depicts exemplary relative cell titer glo luminescence of a panel of p53-WT (gray) or p53-mutant (black) Ewing Sarcoma cell lines after treatment with compound 6 for 3 days.
Figure 5C:
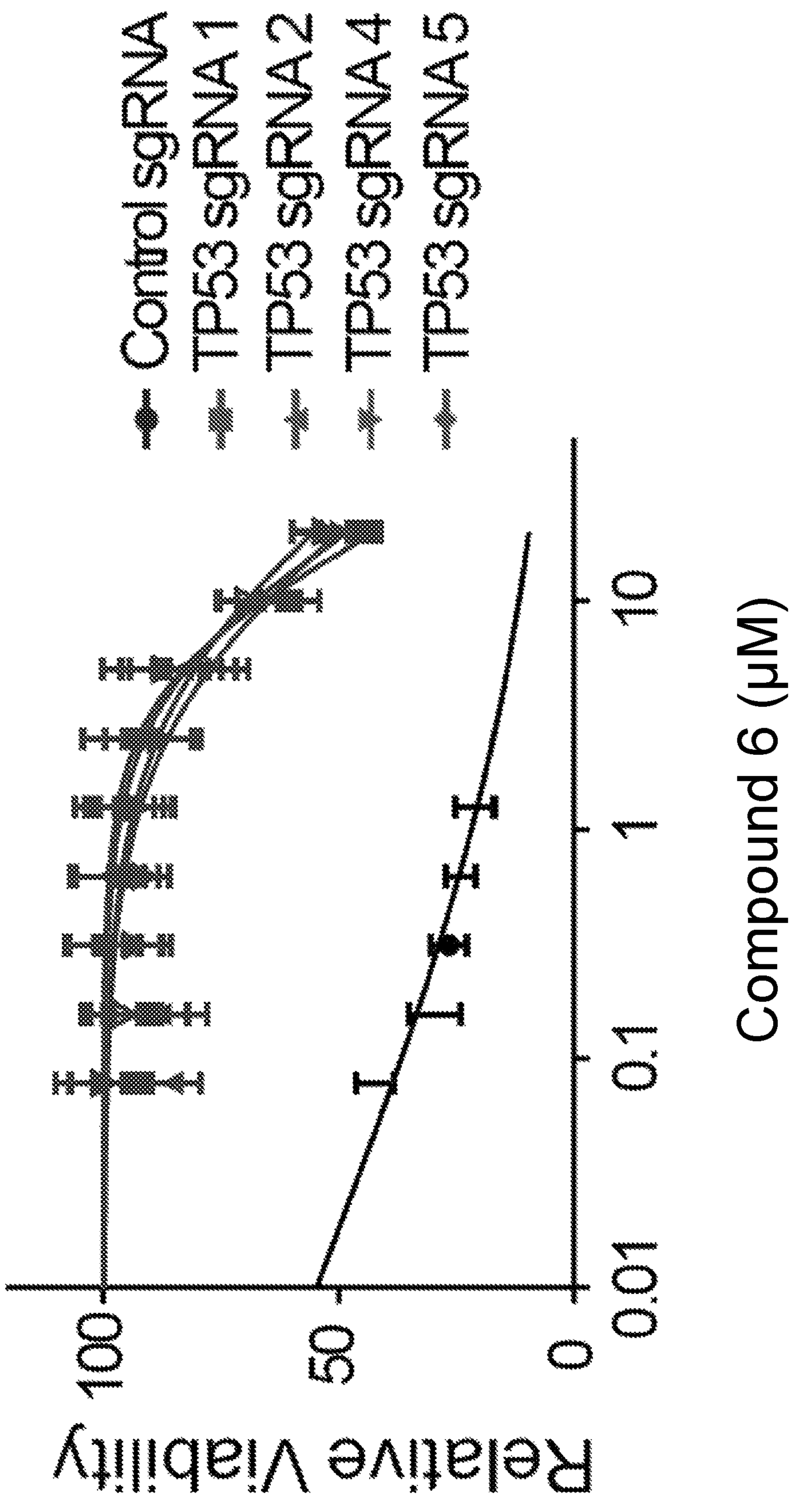
FIG. 5C depicts exemplary relative cell titer glo luminescence of TC32 cells expressing the indicated sgRNA after treatment with compound 6 for 3 days.

As an initial assessment of whether pharmacological inhibition of USP7 with compound 6 phenocopies RNAi knockdown and CRISPR knockout, the antiproliferative effect of compound 6 and compound 7 was investigated across panels of Ewing sarcoma (FIG. 5B) cancer cell lines containing examples of both TP53 WT and mutant lines and tested the MDM2 inhibitor Nutlin-3a side-by-side for comparison. Preferential growth suppression was observed of TP53 wild-type cell lines over mutant-TP53-expressing cells: growth of TP53 wild-type TC32 and TC138 cells was potently inhibited by compound 6, while neither TP53-mutant A673 or TC71 was substantially inhibited. Meanwhile, the inactive control compound 7 was approximately 100-fold less potent, consistent with the effects being USP7-dependent. The cytotoxic effect of compound 6 in TC32 cells was rescued by TP53 knockout, supporting the requirement for functional p53 for the observed anti-proliferative response (FIG. 5C). To compare the compound 6 results with effects of previously reported USP7 inhibitors, P5091 and GNE6640 were tested across the same set of cell lines and observed little to no specificity for TP53-WT expressing cells.

Ewing sarcoma tumors possess remarkably quiet genomes. The effect of pharmacological inhibition of USP7 was studied across panels of TP53-WT and mutant lines with more genetic heterogeneity and diverse oncogenic drivers. Findings of p53-dependence were also observed in small panels of other cell lines, including acute myeloid leukemia and B-cell lymphoma. Across 26 cell lines tested in total, there were three compound 6-sensitive TP53-mutant lines and two compound 6-resistant TP53-WT cells, indicating that other factors may also govern response to compound 6 in some cases.

Cell Proliferation

Cells were plated in 384-well culture-treated plates and allowed to settle overnight. After drug treatment and appropriate incubation time, cell viability was assessed using the CellTiter-Glo Luminescent Cell Viability Assay (Promega). Luminescence was read on a Fluostar Omega Reader (BMG Labtech).

TP53 Knockout

Lentivirus was produced by transfecting HEK-293T cells with the pLentiV2 vector (Addgene plasmid #52961) and the packaging plasmids pCMV8.9 and pCMV-VSVG according to the FuGENE 6 (Roche) protocol. For lentiviral transduction, Ewing sarcoma cells were incubated with 2 mL of virus and 8 μg/mL of polybrene (Sigma-Aldrich). Cells were selected in puromycin (Sigma-Aldrich) 48 hours after infection for single knockout experiments.

sgRNAs were designed using the Broad Institute's sgRNA designer tool. The following sequences were used as control or to target the respective genes:

```
sgTP53 #1:
                                  (SEQ ID NO: 1)
GCTTGTAGATGGCCATGGCG

sgTP53 #2:
                                  (SEQ ID NO: 2)
TCCTCAGCATCTTATCCGAG

sgTP53 #4:
                                  (SEQ ID NO: 3)
GCAGTCACAGCACATGACGG

sgTP53 #5:
                                  (SEQ ID NO: 4)
GTAGTGGTAATCTACTGGGA
```

Example 8: Combinations of DNA-Damaging Agents and Exemplary Compounds in Cancer Cells To investigate possible synergism of USP7 inhibition with other p53-dependent anti-proliferative small molecules, combination treatments of TC32 cells were performed with compound 6 and one of RG7388 (Ding, Q. et al. Discovery of RG7388, a potent and selective p53-MDM2 inhibitor in clinical development. *J. Med. Chem.* 56, 5979-5983 (2013)), GSK2830371 (Gilmartin, A. G. et al. Allosteric Wip1 phosphatase inhibition through flap-subdomain interaction. *Nat. Chem. Biol.* 10, 181-187 (2014); PPM1D/Wip1 inhibitor), or the DNA-damaging topoisomerase II inhibitors etoposide and doxorubicin. All four drugs showed strong synergy with compound 6 (combination index <0.6), indicating that USP7 inhibition may be a beneficial addition to certain DNA-damaging and p53 stabilizing chemotherapy regimens. It should be noted that MCF7 cells exhibited consistently lower sensitivity to compound 6 than TC32, and combination of compound 6 with GSK2830371, etoposide, or doxorubicin led to mixed synergy and antagonism in MCF7 cells. This indicates that there may be a spectrum of compound 6 sensitivity within p53-WT cell lines, which could be related to p53-dependent or p53-independent effects of USP7.

Drug Synergy Analysis Chou-Talalay Combination Index for Loewe Additivity

Loewe Additivity is a dose-effect approach that estimates the effect of combining two drugs based on the concentration of each individual drug that produces the same quantitative effect (Goldoni and Johansson, 2007). Chou and Talalay (Chou, 2006; Chou, 2010) showed that Loewe equations are valid for enzyme inhibitors with similar mechanisms of action—either competitive or non-competitive toward the substrate. They introduced the combination index (CI) scores to estimate the interaction between the two drugs. If CI<1, the drugs have a synergistic effect, and if CI>1, the drugs have an antagonistic effect. CI=1 means the drugs have an additive effect.

Example 9: Transcriptome Profiling with Exemplary Compounds

While directed studies of p53 transcriptional targets and TP53-knockout cell lines demonstrated that compound 6 exerts p53-dependent activity, there was interest in exploring the broader effects of USP7 inhibition in order to determine whether p53 was the major mediator of response to compound 6. To this end, MCF7 cells were treated for 24 hours with low or high doses of compound 6, compound 7, or the MDM2 inhibitor Nutlin-3A, then used high-throughput 3' Digital Gene Expression (DGE) RNA-seq to analyze the transcriptome-wide effects of these compounds. Overall, transcripts were detected for 7000-10,000 genes (7276 genes detected across all conditions). Compound 6 and Nutlin-3A demonstrated strongly correlated transcriptional profiles at both low (0.1 μM compound 6 and 1 μM Nutlin-3A) and high (1 μM compound 6 and M Nutlin-3A) doses, while compound 7 was highly correlated with the vehicle (DMSO)-treated control cells.

Figure 6A:
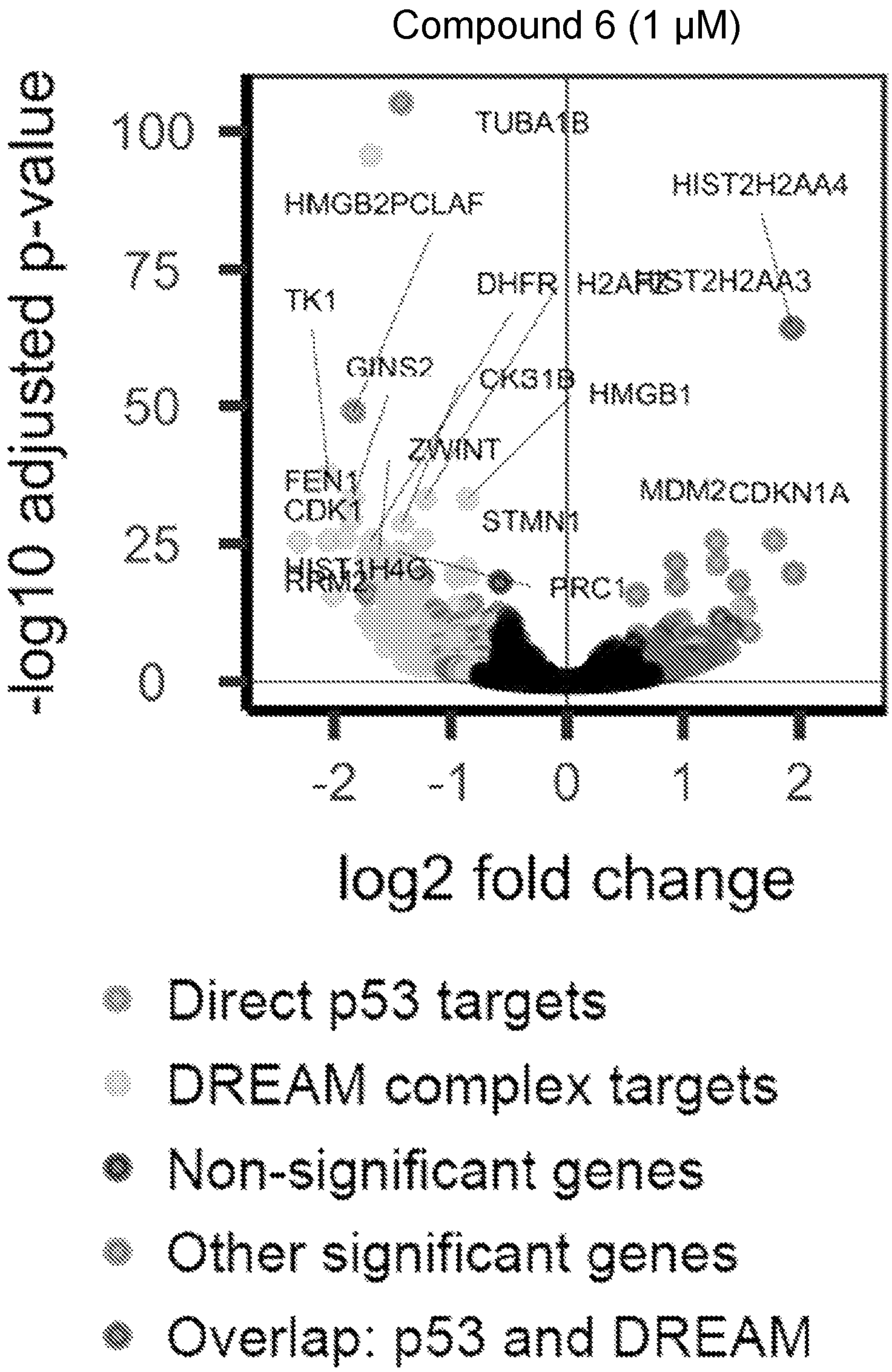
FIG. 6A depicts exemplary volcano plots of genes enriched or depleted after 24-hr treatment with 1 μM compound 6.
Figure 6B:
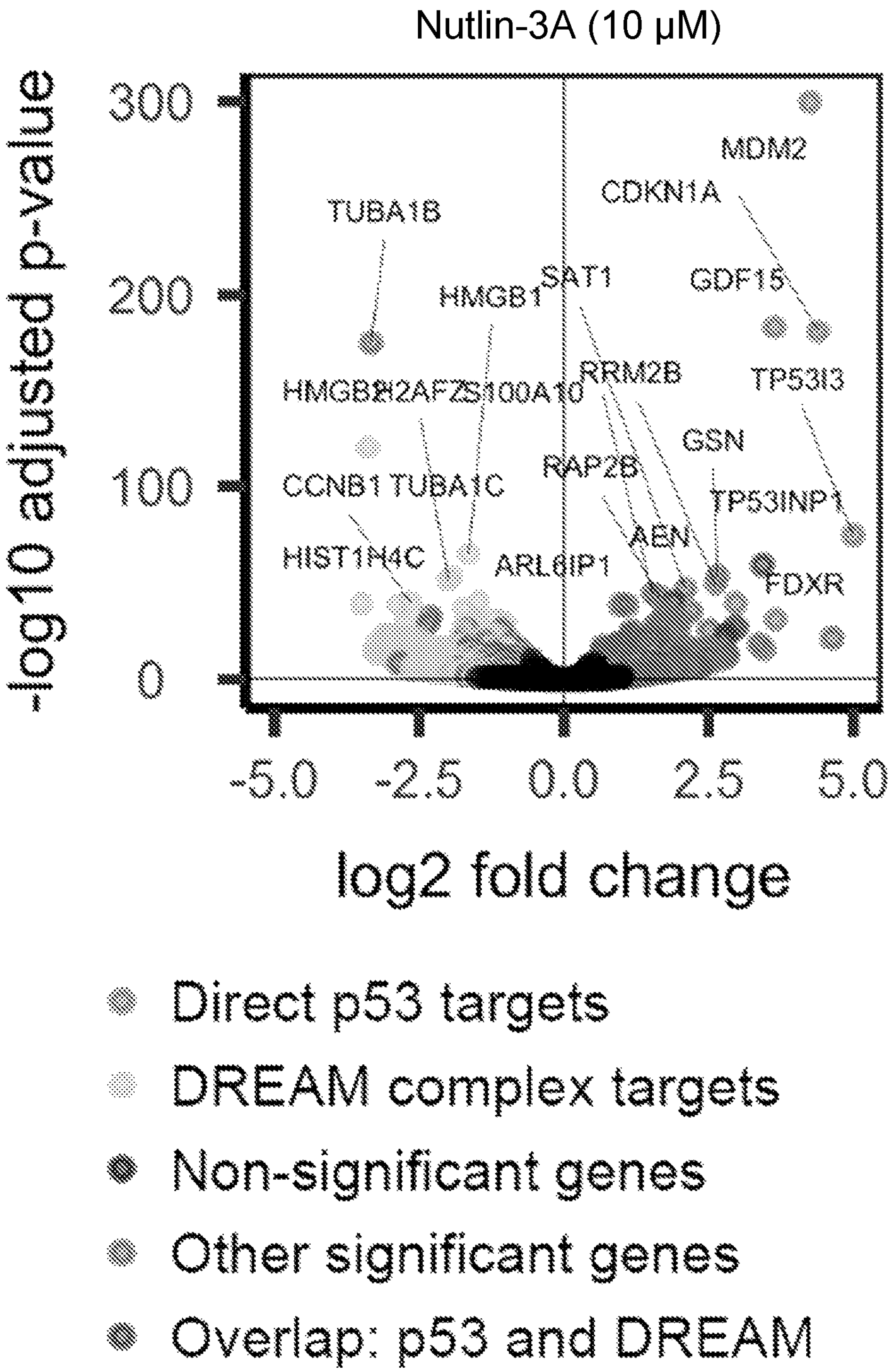
FIG. 6B depicts exemplary volcano plots of genes enriched or depleted after 24-hr treatment with 10 μM Nutlin-3A.
Figure 6C:
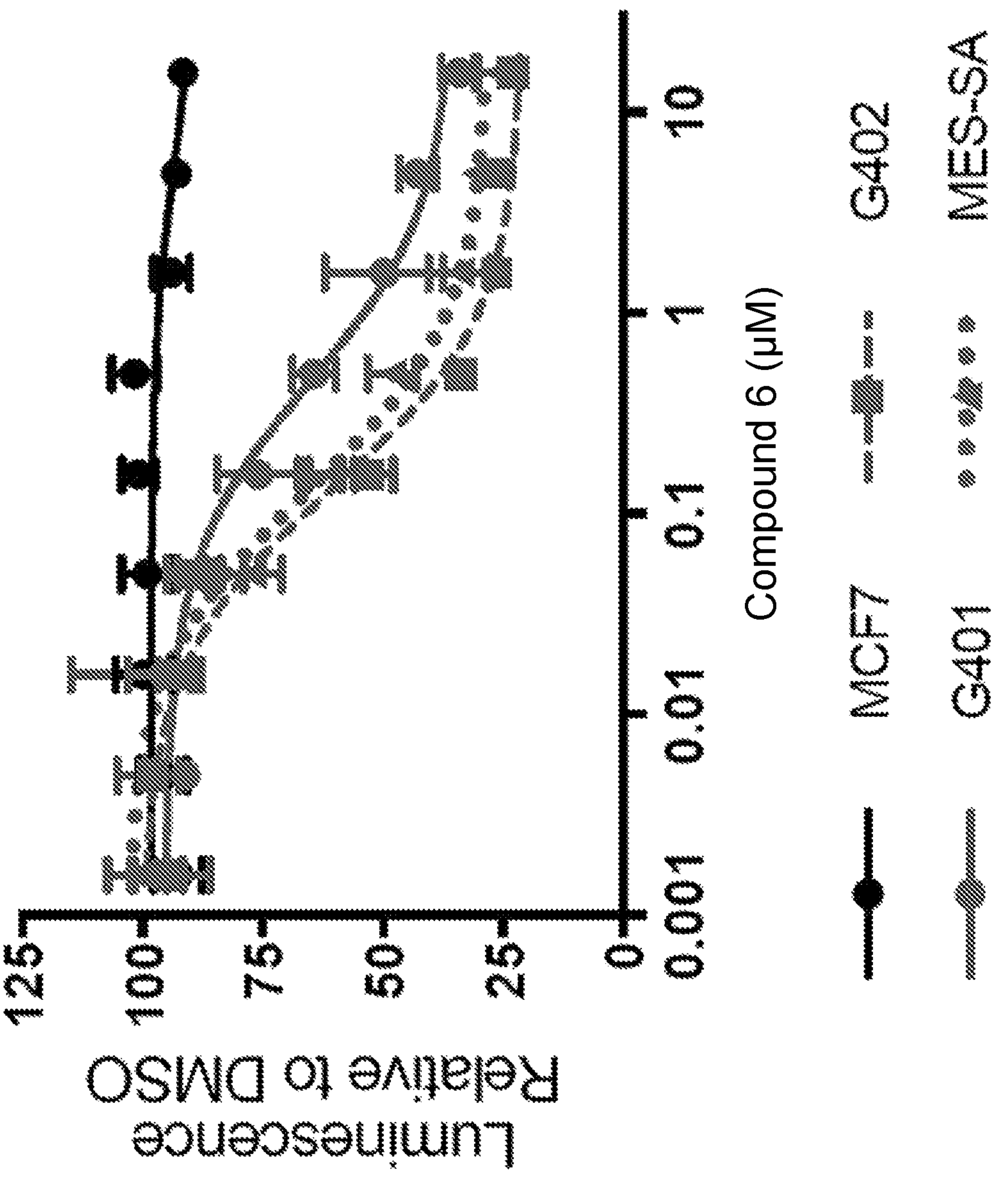
FIG. 6C depicts exemplary relative cell titer glo luminescence of a panel of p53-WT cell lines after treatment with compound 6 for 5 days.
Figure 6D:
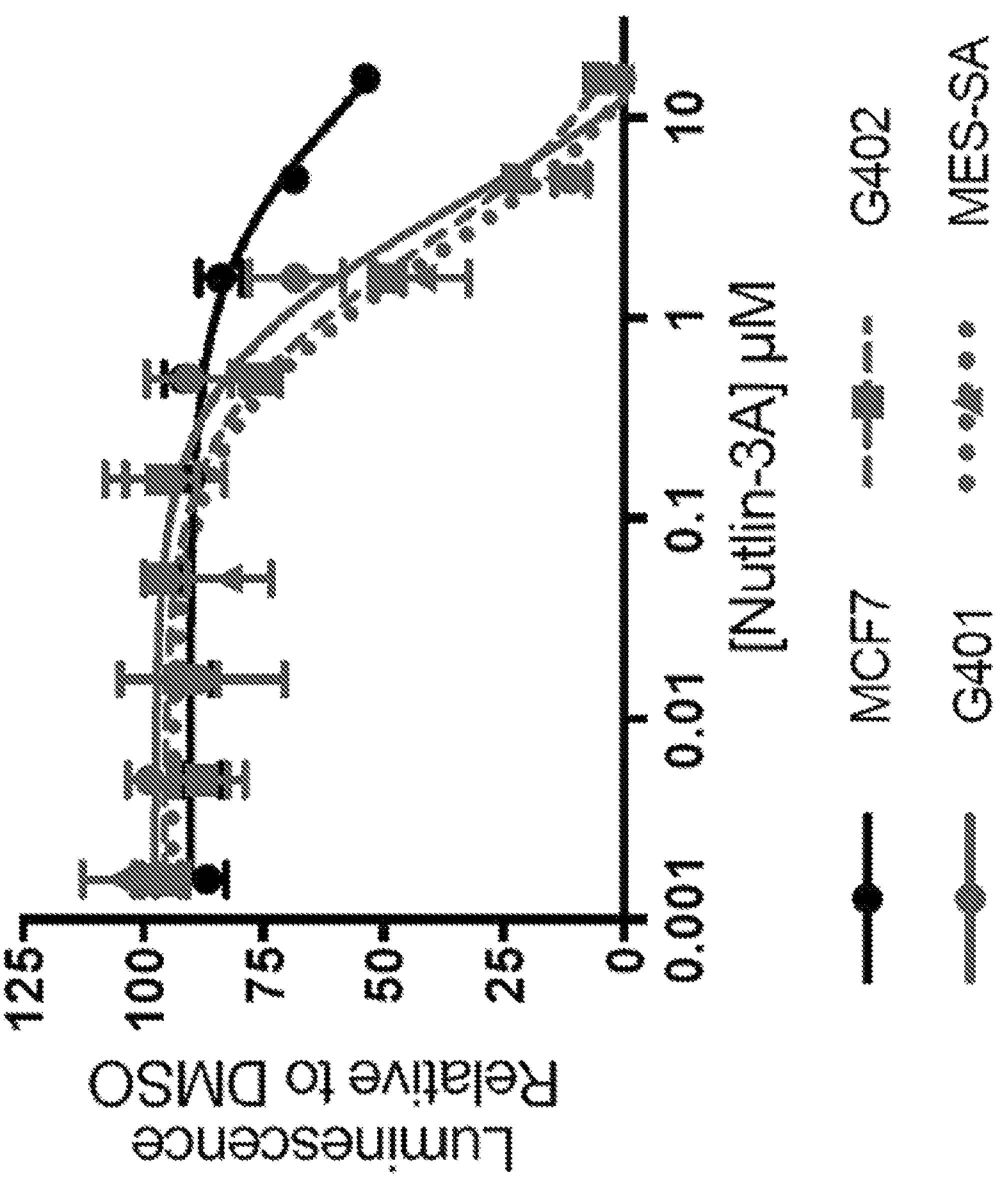
FIG. 6D depicts exemplary relative cell titer glo luminescence of a panel of p53-WT cell lines after treatment with Nutlin-3A for 5 days.

To identify specific gene sets that were enriched under different treatment conditions, the significantly upregulated and downregulated genes we rank ordered from all six cell treatments and used the Broad Institute's gene-set enrichment analysis (GSEA) tool. A recent meta-analysis of p53 target genes had been generated in part by RNA-seq data from Nutlin-3A-treated MCF7 cells (Ritorto, M. S. et al. Screening of DUB activity and specificity by MALDI-TOF mass spectrometry. *Nat. Commun.* 5, 4763 (2014)), and it was found that the upregulated genes from both low- and high-dose Nutlin-3A were enriched for the direct p53 target genes from this meta-analysis. The same report had also identified a set of dimerization partner, Retinoblastoma-like, E2F and multi-vulval class B (DREAM) complex target genes by combining p53 repression data (generated in part with Nutlin-3A-treated MCF7 cells) with cell cycle expression and DREAM component binding. Again, this DREAM target geneset was most strongly enriched in the downregulated genes from both Nutlin-3A treatments. Interestingly, it was found that the most highly enriched datasets for both low- and high-dose compound 6 were the p53 targets (upregulated genes) and the DREAM complex targets (downregulated genes) (FIG. 6A). These findings demonstrate that the broad transcriptional effects of compound 6 and Nutlin-3A are highly similar, indicating that p53 stabilization may be the most relevant phenotype of USP7 inhibition. There is, however, a set of genes upregulated by high-dose compound 6 that is not affected by Nutlin-3A.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound of Formula (I):

(I)

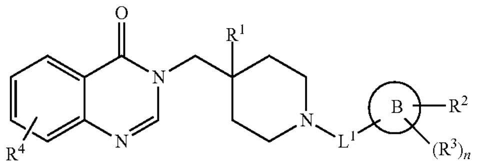

or a pharmaceutically acceptable salt thereof, wherein:

Ring B is cycloalkyl, heterocyclyl, aryl, or heteroaryl;

$L^1$ is —C(═O)alkyl-[$NR^5$C(═O)-alkyl]$_p$—$NR^5$C(═O), wherein each alkyl is independently substituted with one or more $R^7$, $R^1$ is H, —$OR^5$, or —$NR^5R^6$;

$R^2$ is

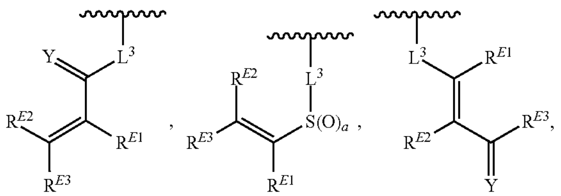

, , ,

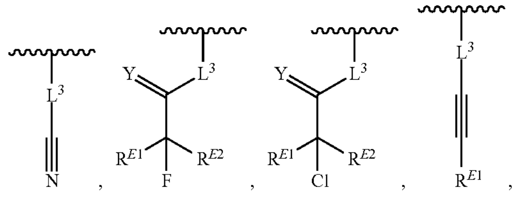

, , , ,

-continued

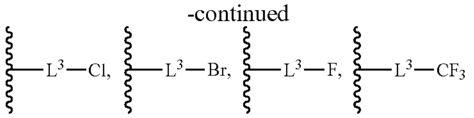

or absent;

$L^3$ is a bond, —$NR^5R^6$, alkyl, cycloalkyl, or heterocyclyl, wherein each alkyl is independently optionally substituted with one or more $R^8$, Y is O;

each $R^{E1}$, $R^{E2}$, and $R^{E3}$ is independently at each occurrence H, alkyl, —$OR^{11}$, —$NR^{11}R^{12}$, cycloalkyl, —$NR^5$C(═O) heterocyclyl, —C(═O)$NR^5$alkyl, C(═O)NR cycloalkyl, or —C(═O) heterocyclyl;

each $R^{11}$ and $R^{12}$ is independently at each occurrence H, alkyl, cycloalkyl, heterocyclyl, aryl, or heteroaryl; or $R^{11}$ and $R^{12}$ together form heterocyclyl or heteroaryl;

$R^3$ is alkyl, hydroxyl, $CF_3$, halo-$NR^5$C(═O)alkyl, —C(═O)$NR^5$alkyl, —$NR^5R^6$, cycloalkyl, heteroaryl, or aryl;

$R^4$ is alkyl, —$NR^5$C(═O)alkyl, —C(═O)$NR^5$alkyl, or —$NR^5R^6$, wherein each alkyl is independently optionally substituted with one or more $R^8$, wherein when $R^4$ is alkyl, it is optionally substituted with two $R^8$ substituents that, taken together, form cycloalkyl or heterocyclyl, wherein each cycloalkyl or heterocyclyl is independently optionally substituted with one or more $R^9$;

each $R^5$ and $R^6$ is independently H, alkenyl, or alkyl;

each $R^7$ is independently at each occurrence-$NR^5R^6$, alkylamine, cycloalkyl, carbocycloalkyl, aryl, aralkyl, heterocyclyl, heterocyclylalkyl, heteroaryl, or heteroaralkyl, wherein each amine, cycloalkyl, aryl, heterocyclyl, or heteroaryl is independently optionally substituted with one or more $R^{10}$;

each $R^8$ is independently at each occurrence-$NR^5R^6$, cycloalkyl, or heterocyclyl;

each $R^9$ is independently at each occurrence H, alkenyl, or alkyl;

each $R^{10}$ is independently at each occurrence halogen, —$OR^5$, —$NR^5R^6$, alkenyl, or alkyl;

n is 0, 1, 2, 3, or 4; and p is 0, 1, 2, 3, or 4.

2. The compound of claim 1 having the following structural formula:

(Ia)

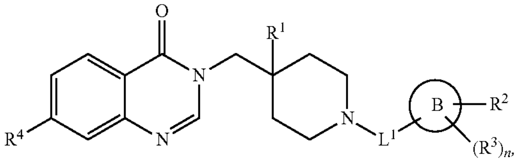

or (Ib)

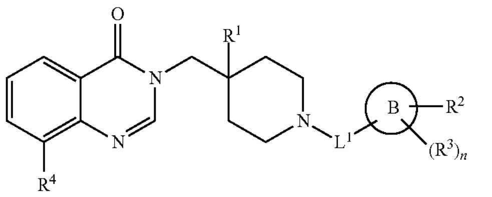

or a pharmaceutically acceptable salt thereof.

3. The compound of claim 1 having the following structural formula:

(Ic)

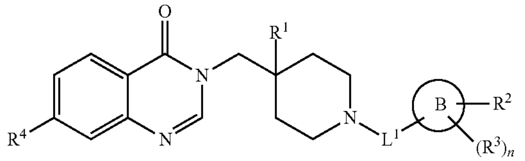

or a pharmaceutically acceptable salt thereof, wherein:

Ring B is cycloalkyl, heterocyclyl, aryl, or heteroaryl;

$L^1$ is a —C(═O)alkyl-[$NR^5$C(═O)-alkyl], —$NR^5$C(═O), wherein each alkyl is independently optionally substituted with one or more $R^7$, $R^1$ is H, —$OR^5$, or —$NR^5R^6$;

$R^2$ is

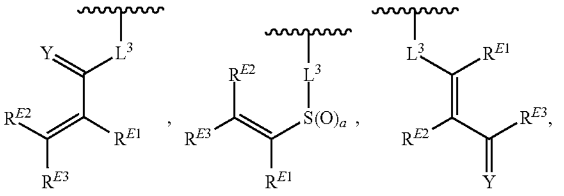

-continued

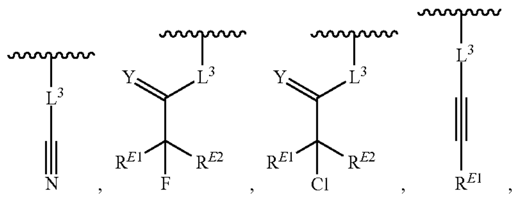

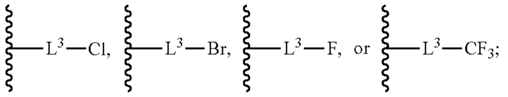

$L^3$ is a bond, —$NR^5R^6$, alkyl, cycloalkyl, or heterocyclyl, wherein each alkyl is independently optionally substituted with one or more $R^8$, Y is O;

each $R^{E1}$, $R^{E2}$, and $R^{E3}$ is independently at each occurrence H, alkyl, —$OR^{11}$, —$NR^{11}R^{12}$, cycloalkyl, —$NR^5$C(═O) heterocyclyl, —C(═O)$NR^5$alkyl, C(═O)$NR^5$cycloalkyl, or —C(═O) heterocyclyl;

each $R^{11}$ and $R^{12}$ is independently at each occurrence H, alkyl, cycloalkyl, heterocyclyl, aryl, or heteroaryl, or $R^{11}$ and $R^{12}$ together form heterocyclyl or heteroaryl;

$R^3$ is alkyl, —$NR^5$C(═O)alkyl, —C(═O)$NR^5$alkyl, or —$NR^5R^6$, $R^4$ is alkyl, —$NR^5$C(═O)alkyl, —C(═O)$NR^5$alkyl, or —$NR^5R^6$, wherein each alkyl is independently optionally substituted with one or more $R^8$, wherein when $R^4$ is alkyl, it is optionally substituted with two $R^8$ substituents that, taken together, form cycloalkyl or heterocyclyl, wherein each cycloalkyl or heterocyclyl is independently optionally substituted with one or more $R^9$;

each $R^5$ and Re is independently H, alkenyl, or alkyl;

each $R^7$ is independently at each occurrence-$NR^5R^6$, alkylamine, cycloalkyl, carbocycloalkyl, aryl, aralkyl, heterocyclyl, heterocyclylalkyl, heteroaryl, or heteroaralkyl, wherein each amine, cycloalkyl, aryl, heterocyclyl, or heteroaryl is independently optionally substituted with one or more $R^{10}$;

each $R^8$ is independently at each occurrence-$NR^5R^6$, cycloalkyl, or heterocyclyl;

each $R^9$ is independently at each occurrence H, alkenyl, or alkyl;

each $R^{10}$ is independently at each occurrence halogen, —$OR^5$, —$NR^5R^6$, alkenyl, or alkyl;

n is 0, 1, 2, 3, or 4; and p is 0, 1, 2, 3, or 4.

4. The compound of claim 1, having the following structural formula:

(IIIa)

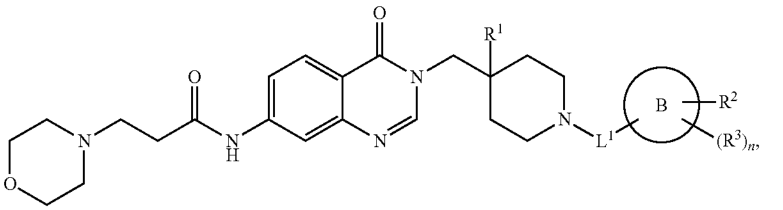

or (IIIb)

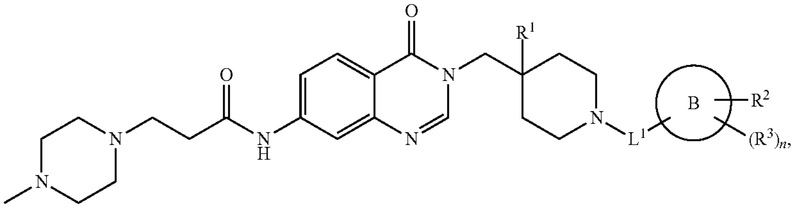

or a pharmaceutically acceptable salt thereof.

5. The compound of claim 1, having the following structural formula:

(IVa)

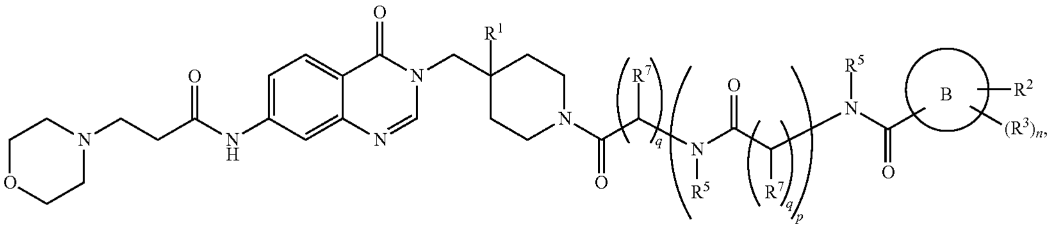

or (IVb)

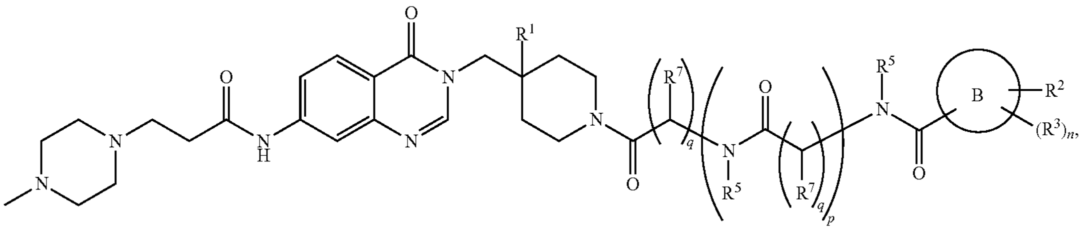

or a pharmaceutically acceptable salt thereof, wherein q is 1, 2, 3, 4, 5, or 6.

6. The compound of claim 1, wherein ring B is cycloalkyl, heterocyclyl, or heteroaryl.

7. The compound of claim 1, wherein each $R^7$ is independently at each occurrence aralkyl, heterocyclylalkyl, or heteroaralkyl.

8. The compound of claim 7, wherein each aryl, heterocyclyl, or heteroaryl of $R^7$ is substituted with one of more $R^{10}$; and $R^{10}$ is independently at each occurrence halogen, —$OR^5$, —$NR^5R^6$, or alkyl.

9. The compound of claim 1, wherein $R^2$ is

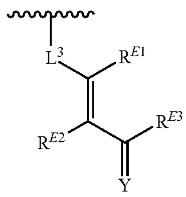

,

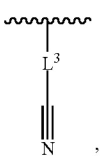

,

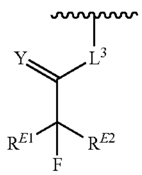

,

-continued

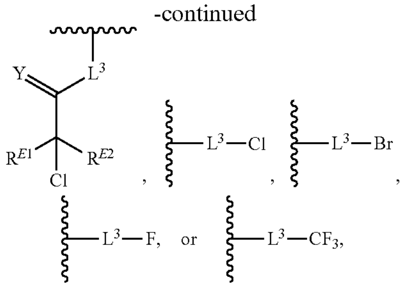

10. The compound of claim 9, wherein each $R^{E1}$, $R^{E2}$, and $R^{E3}$ is independently at each occurrence H or —$NR^{11}R^{12}$.

11. The compound of claim 10, wherein each $R^{11}$ and $R^{12}$ is independently at each occurrence H, alkyl, cycloalkyl, or heterocyclyl;

or $R^{11}$ and $R^{12}$ together form heterocyclyl or heteroaryl.

12. The compound of claim 9, wherein $L^3$ is a bond, —$NR^5R^6$, or heterocyclyl.

13. The compound of claim 1, wherein $R^1$ is H or —$OR^5$.

14. The compound of claim 1, wherein each $R^3$ is independently selected from $CF_3$, alkyl, hydroxyl, cycloalkyl, heteroaryl, and aryl; and n is 1, 2, 3, or 4.

15. The compound of claim 1, wherein

Ring B is heterocyclyl or heteroaryl;

$L^1$ is —C(=O)alkyl-[$NR^5$C(=O)-alkyl]—$NR^5$C(=O), wherein each alkyl is independently substituted with one or more $R^7$;

$R^1$ is H or —$OR^5$;

$R^2$ is

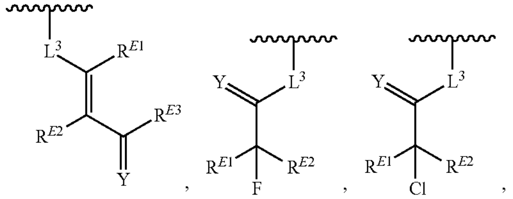

-continued

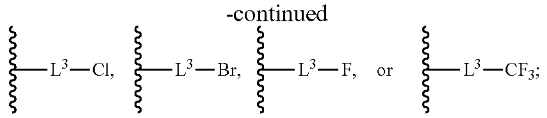

$L^3$ is a bond;

Y is O;

each $R^{E1}$, $R^{E2}$, and $R^{E3}$ is independently at each occurrence H, alkyl, —$OR^{11}$, or —$NR^{11}R^{12}$, each $R^{11}$ and $R^{12}$ is independently at each occurrence H or alkyl; or $R^{11}$ and $R^{12}$ together form heterocyclyl;

$R^4$ is alkyl, —$NR^5$C(=O)alkyl, —C(=O)$NR^5$alkyl, or —$NR^5R^6$, wherein each alkyl is independently optionally substituted with one or more $R^8$, wherein when $R^4$ is alkyl, it is optionally substituted with two $R^8$ substituents that, taken together, form cycloalkyl or heterocyclyl, wherein each cycloalkyl or heterocyclyl is independently optionally substituted with one or more $R^9$;

each $R^5$ and Re is H;

each $R^7$ is independently at each occurrence carbocycloalkyl, aralkyl, heterocyclylalkyl, or heteroaralkyl;

each $R^9$ is independently at each occurrence H or alkyl;

n is 0; and p is 0, 1, or 2.

16. The compound of claim 1, wherein $R^4$ is

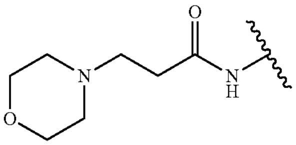

or

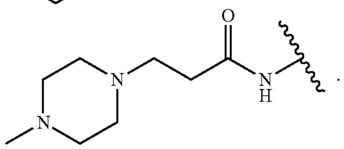

17. The compound of claim 1, wherein ring B is heteroaryl.

18. A compound, or a pharmaceutically acceptable salt thereof, wherein the compound is selected from:

| Compound | |
|---|---|
| 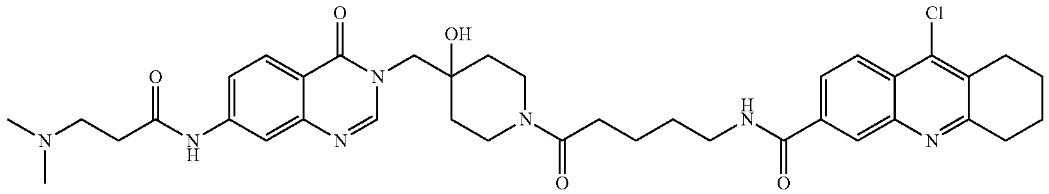 , | 2 |
| 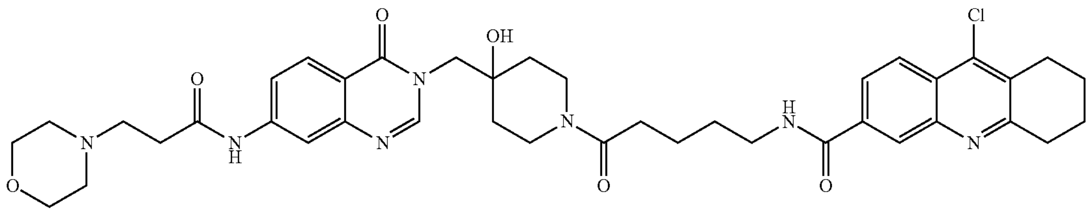 , | 3 |

-continued
| Compound |
| --- |
| 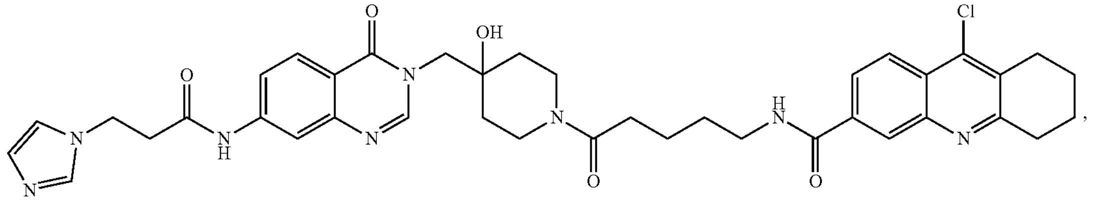 4 |
| 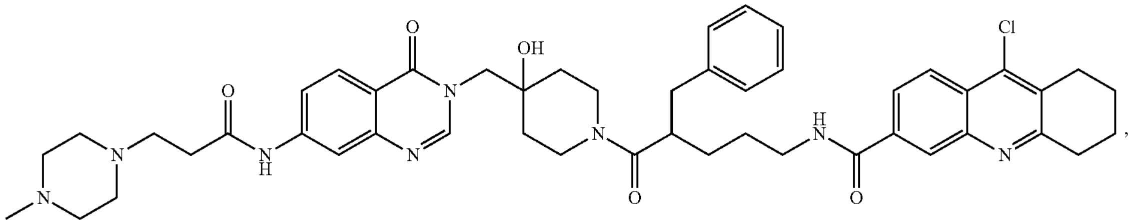 5 |
| 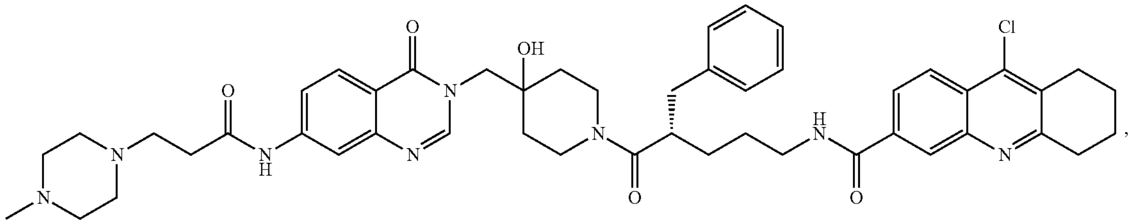 6 |
| 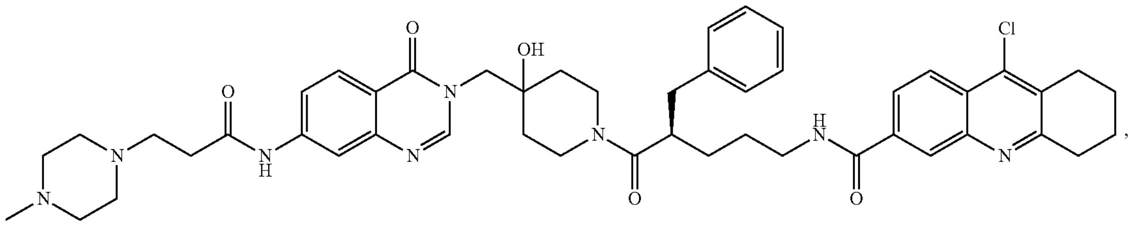 7 |
| 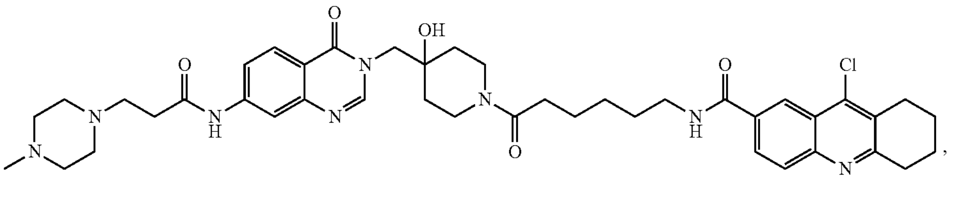 11 |
| 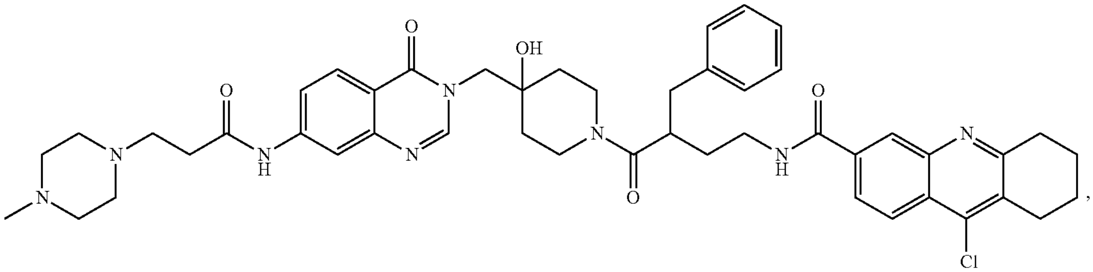 12 |

-continued
| Compound |
| --- |
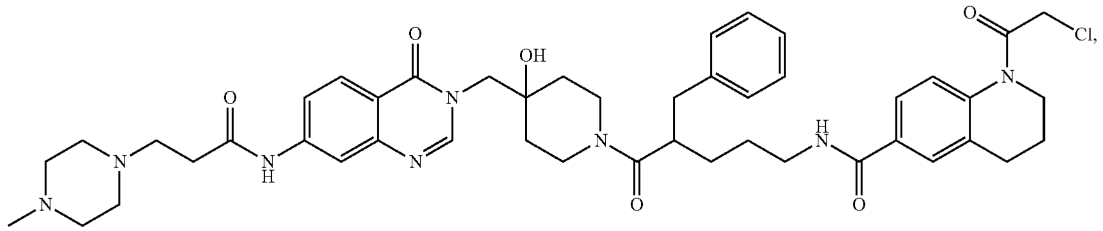
13
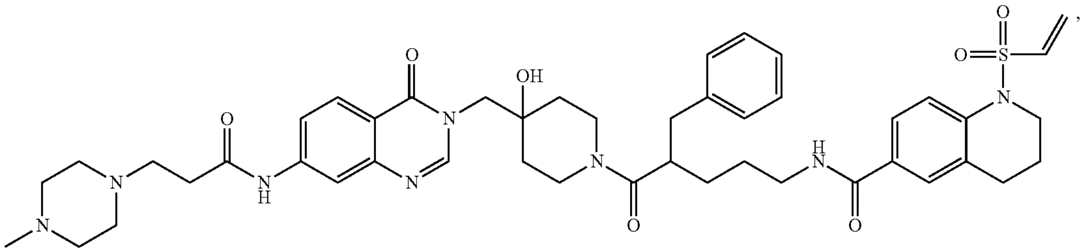
14
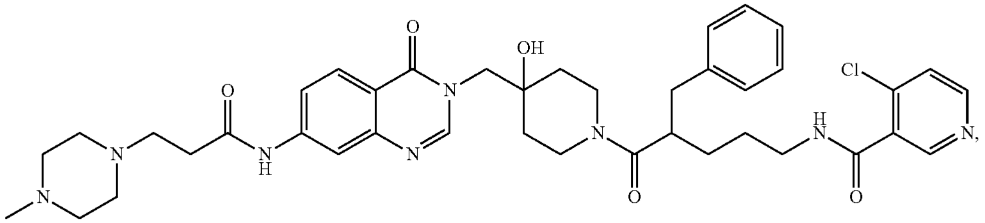
15
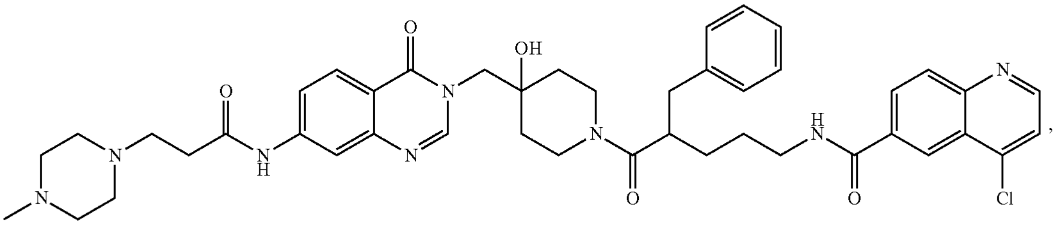
16
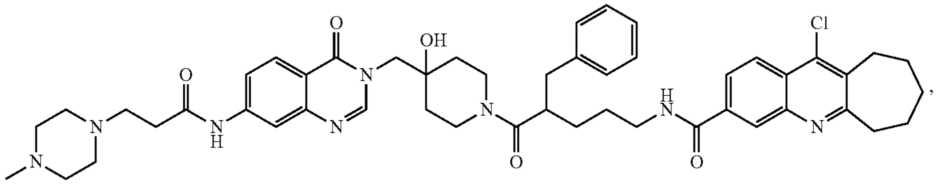
17
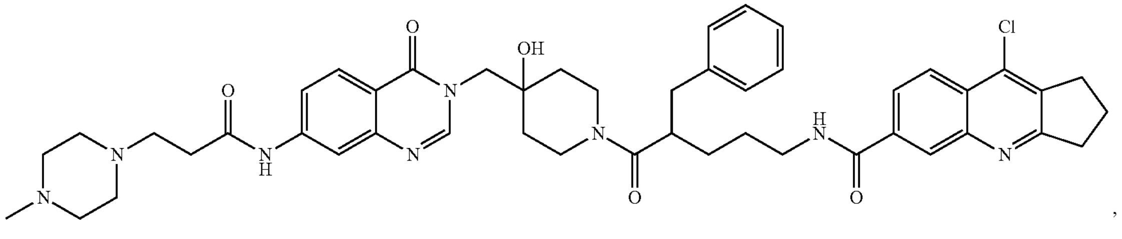
18

-continued
| Compound |
| --- |
19
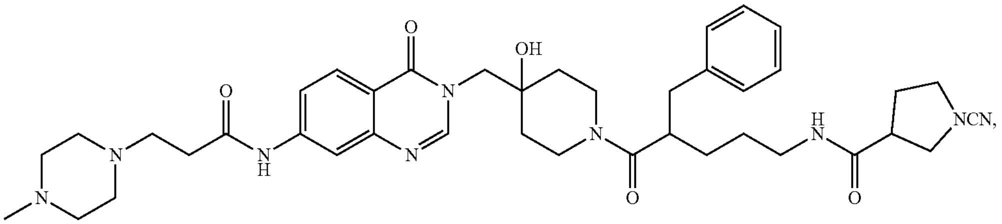
20
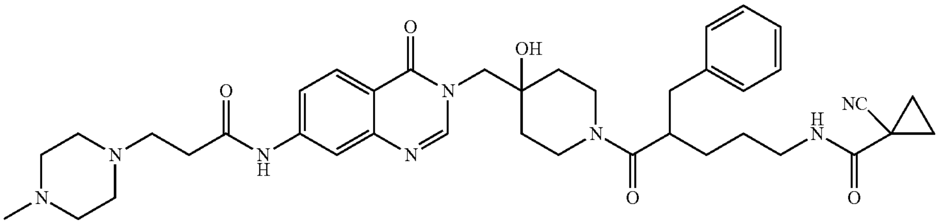
,
21
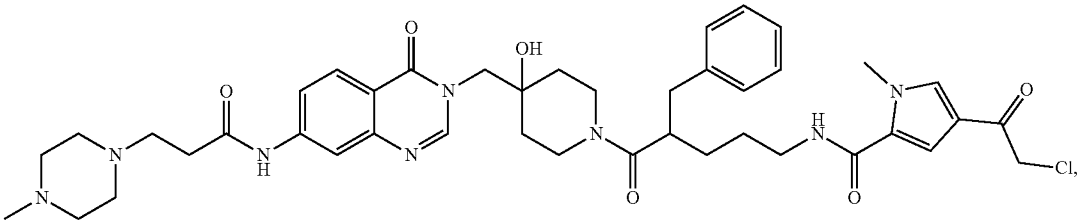
22
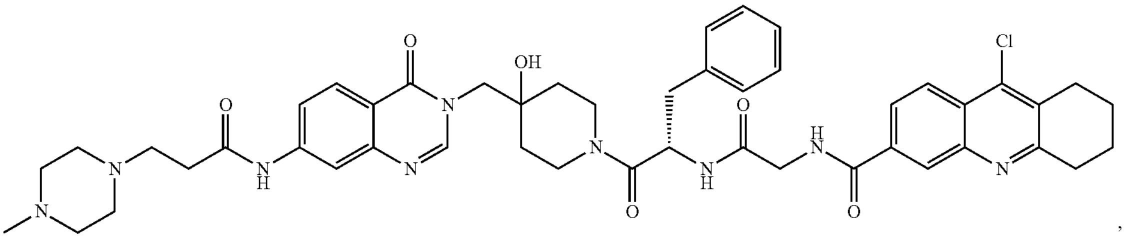
,
23
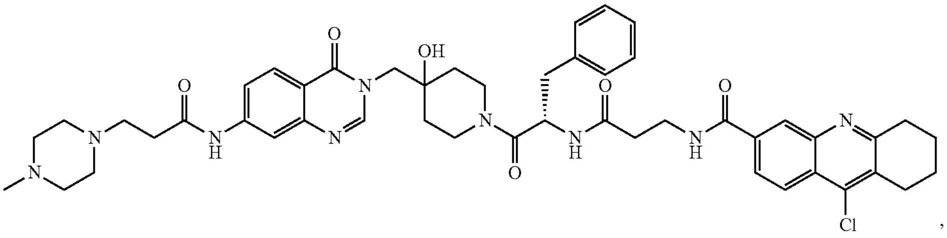
,
24
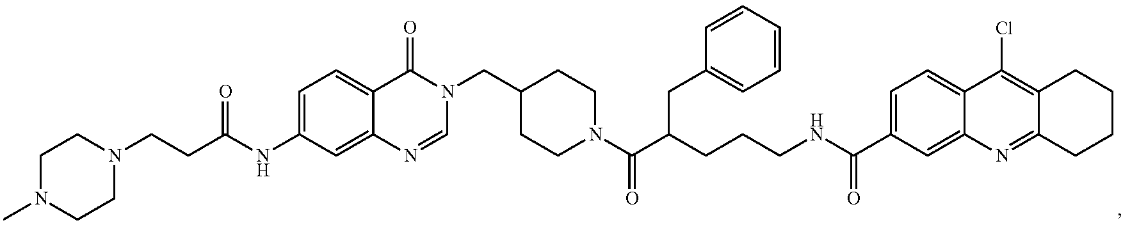
, -continued
| Compound |
|---|
| 25 |
| 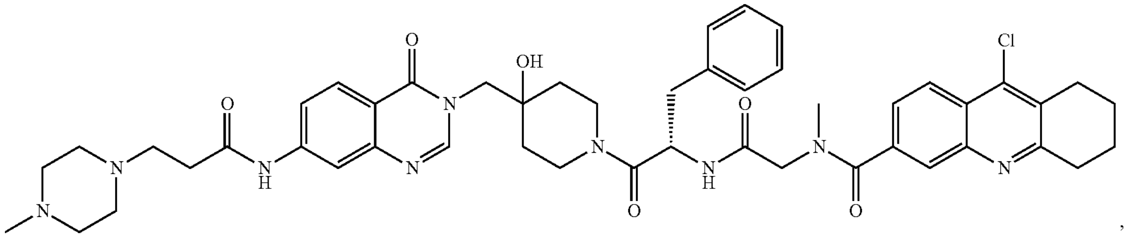 , |
| 26 |
| 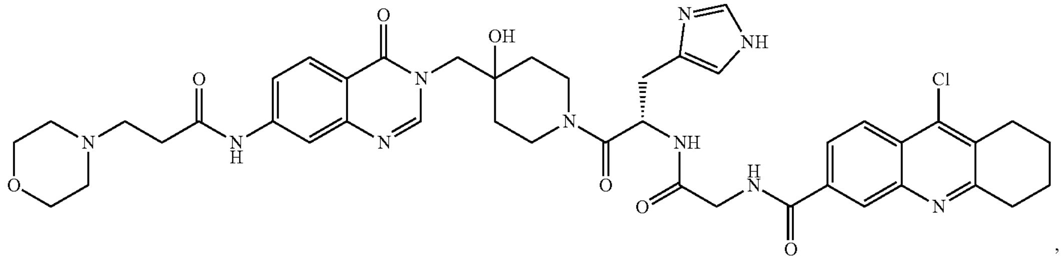 , |
| 27 |
| 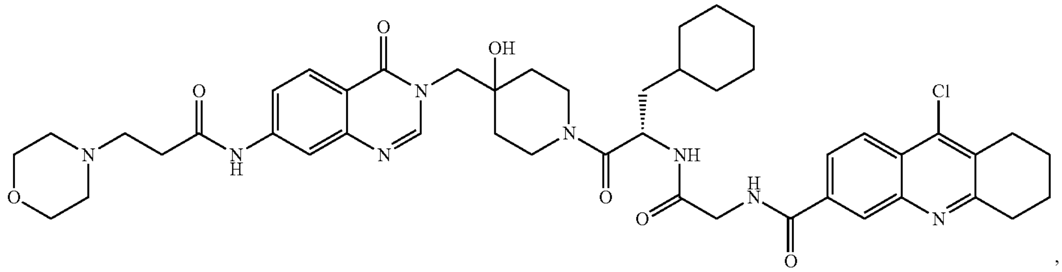 , |
| 28 |
| 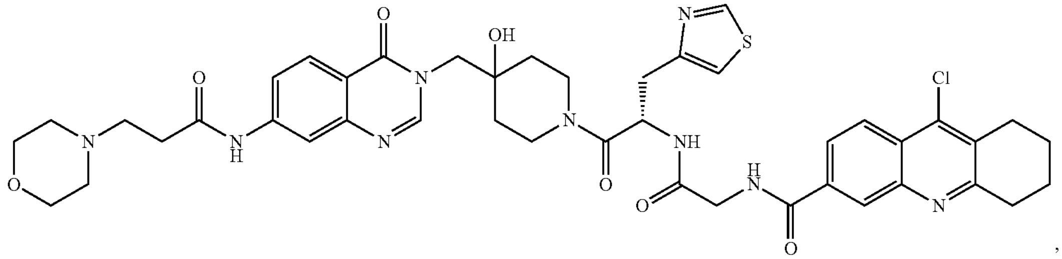 , |
| 29 |
| 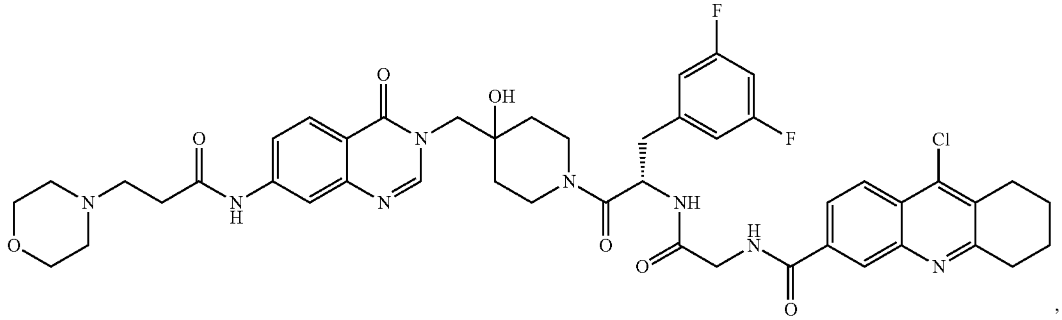 , |

-continued
| Compound |
|---|
| 30 |
| 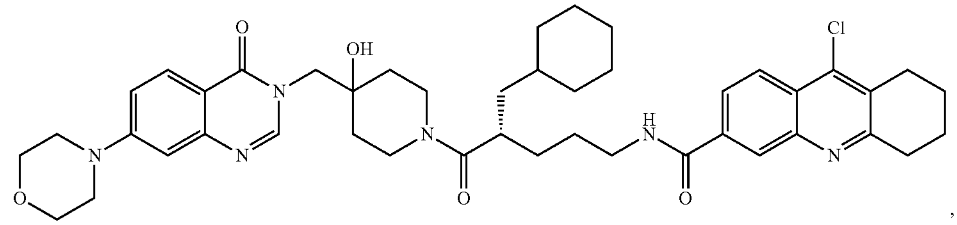 , |
| 31 |
| 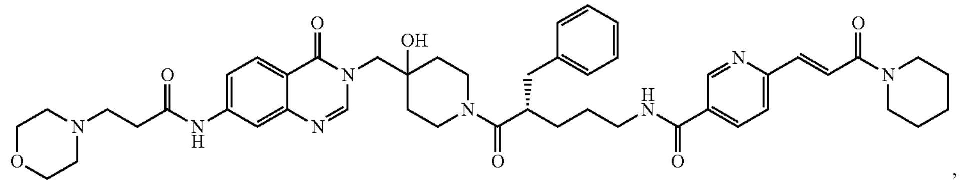 , |
| 32 |
| 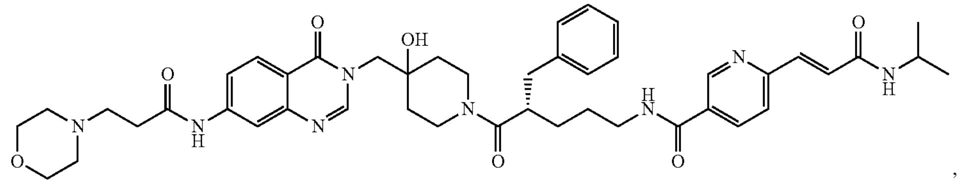 , |
| 34 |
| 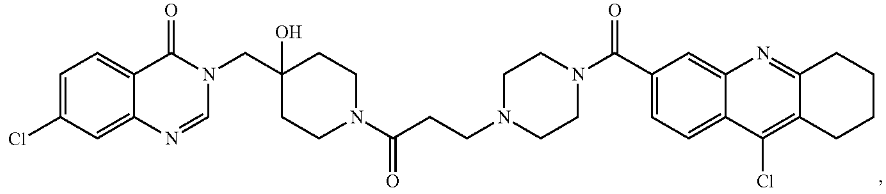 , |
| 35 |
| 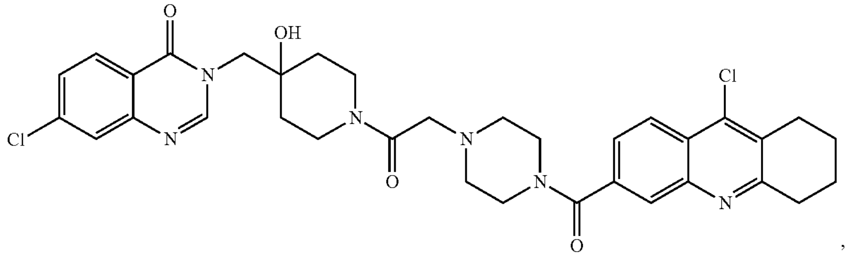 , |
| 36 |
| 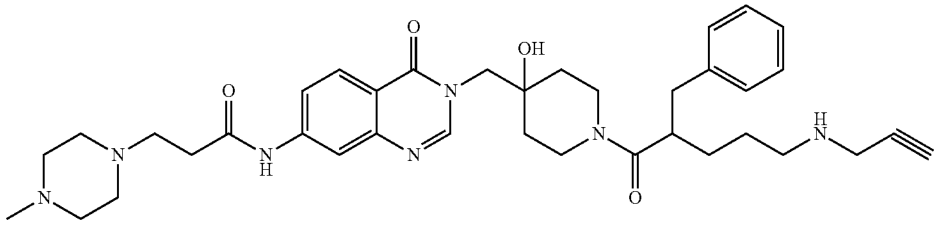 , |

-continued
| Compound |
| --- |
37
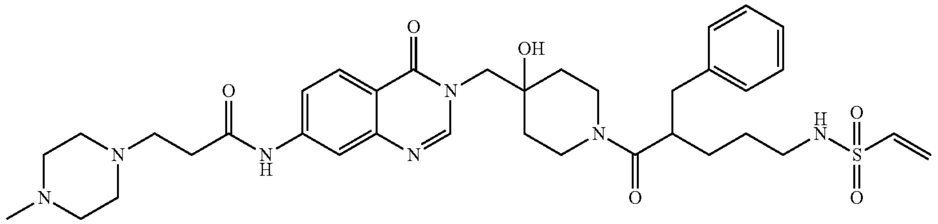
,
38
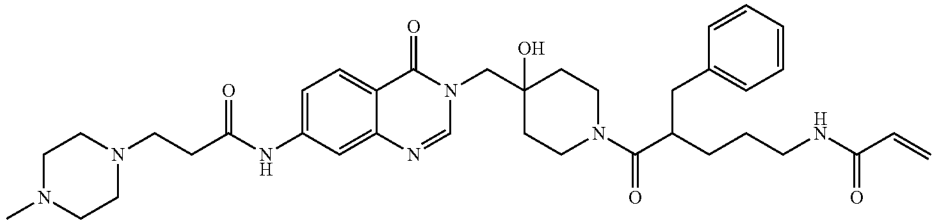
,
40
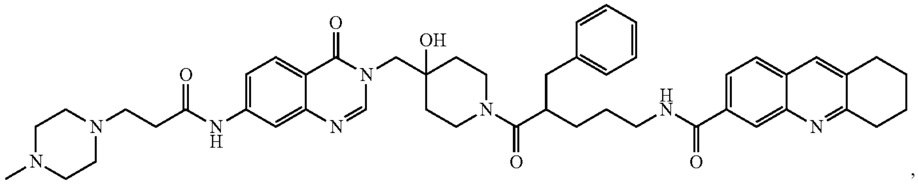
,
41
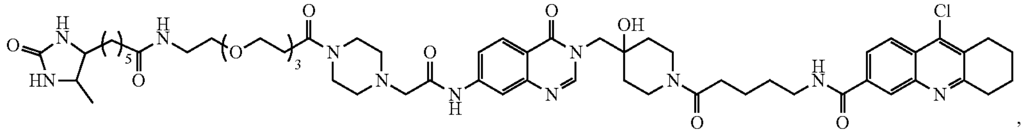
,
42
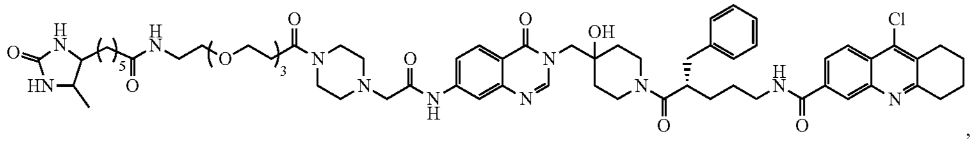
,
43
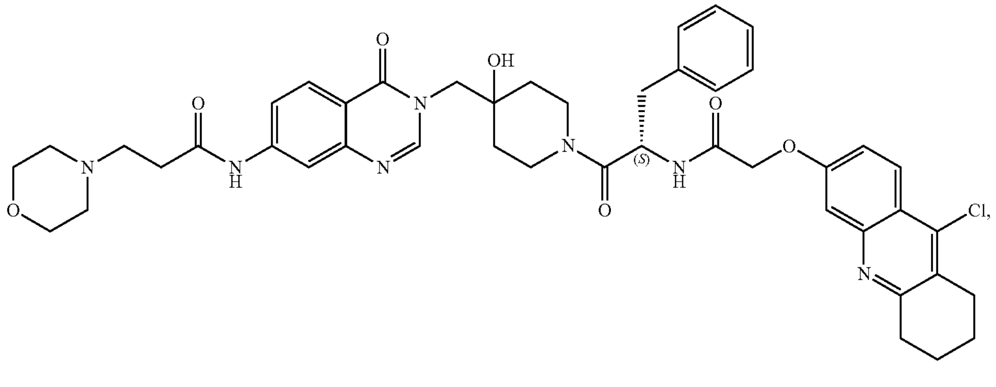

-continued
| Compound |
|---|
44
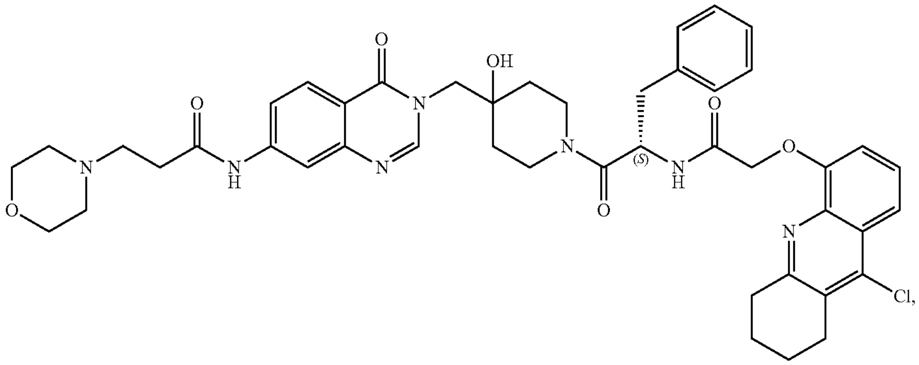
45
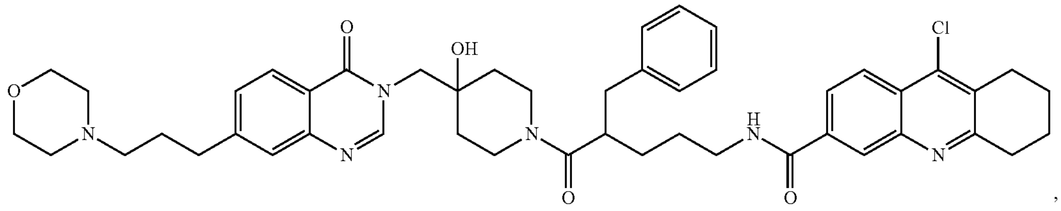
,
46
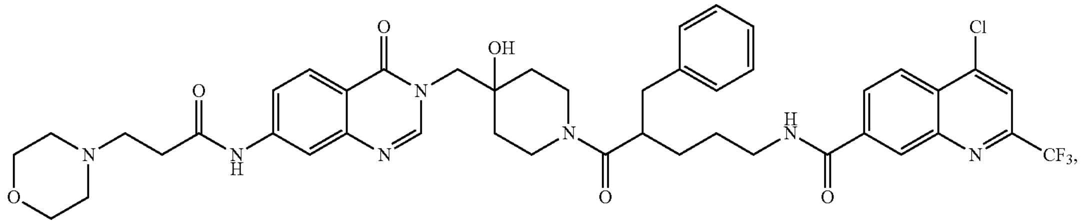
47
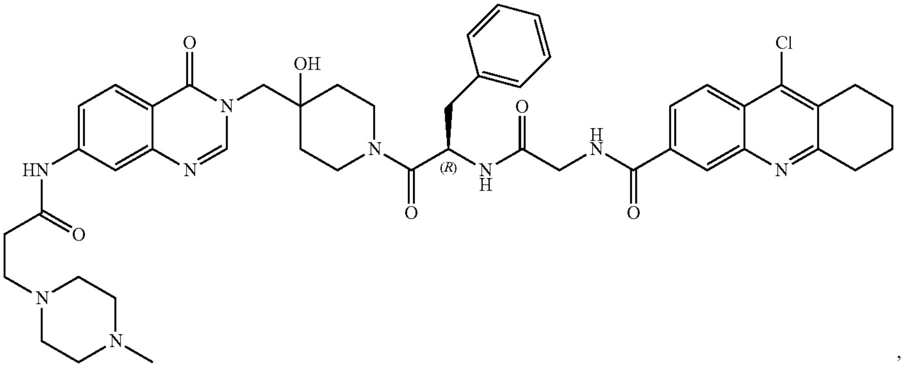
, -continued
| Compound |
| --- |
48
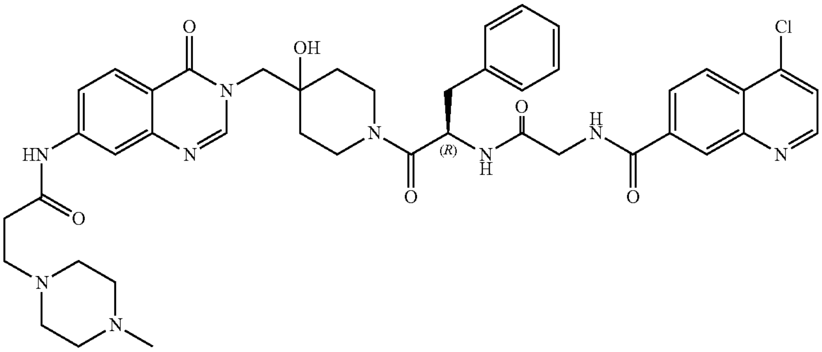
,
49
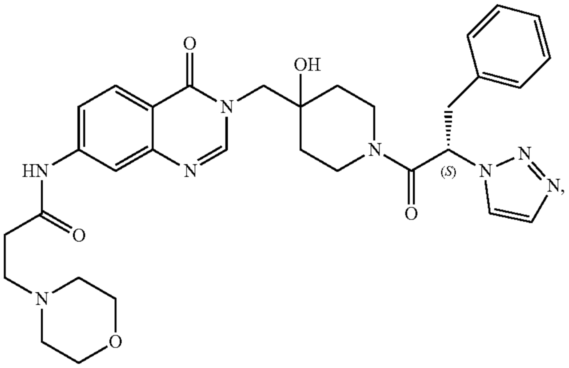
50
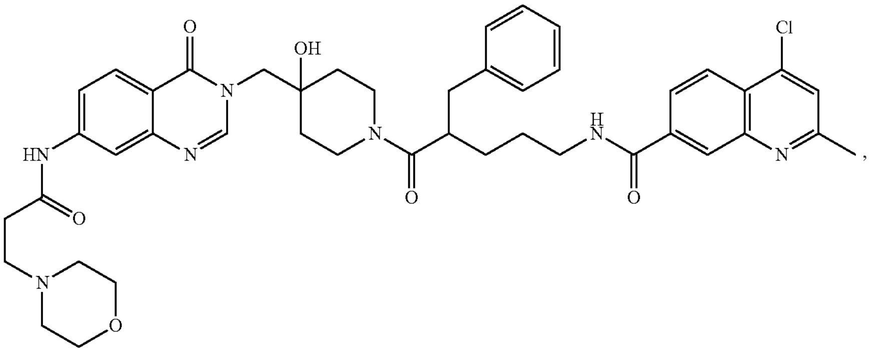
51
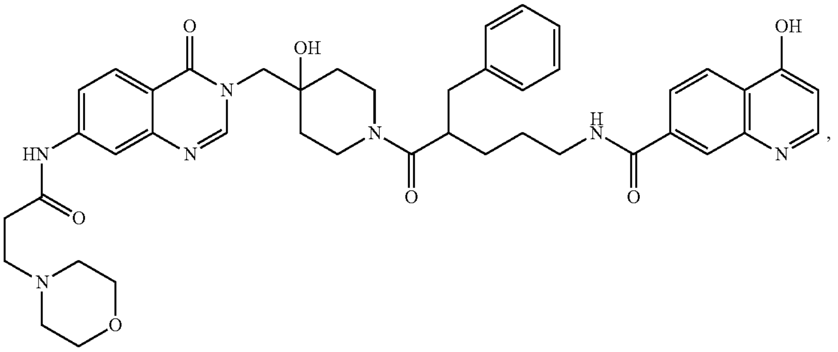

-continued
| Compound |
| --- |
| 52<br>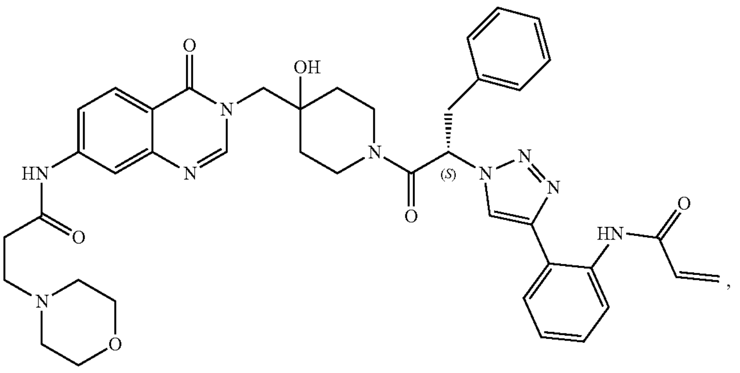 |
| 53<br>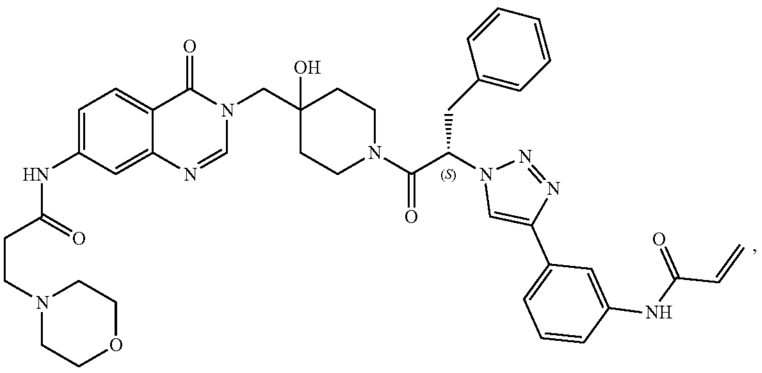 |
| 54<br>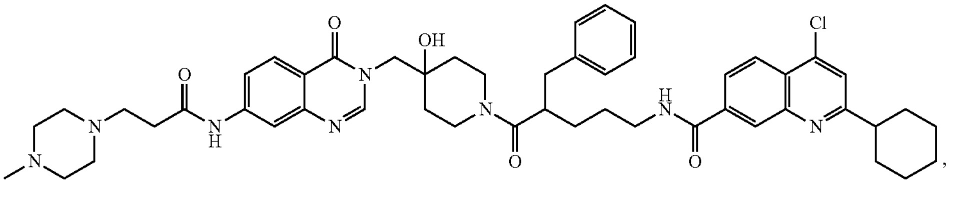 |
| 55<br>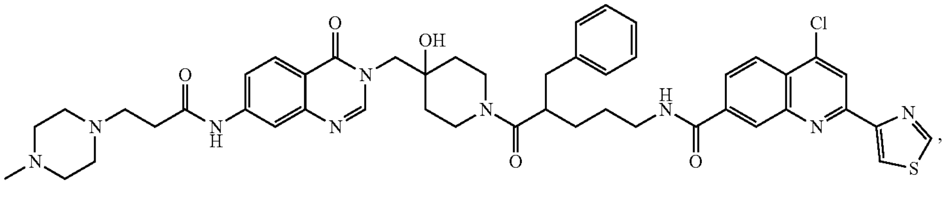 |
| 56<br>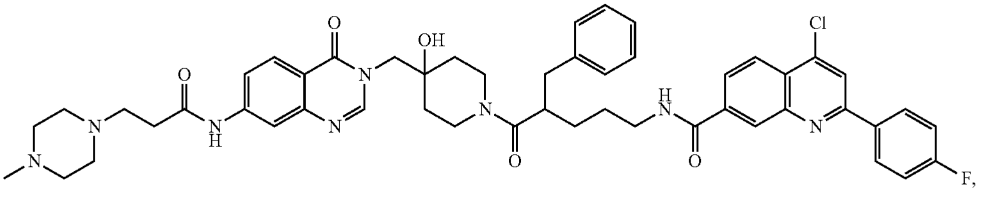 |

-continued
| Compound |
| --- |
57
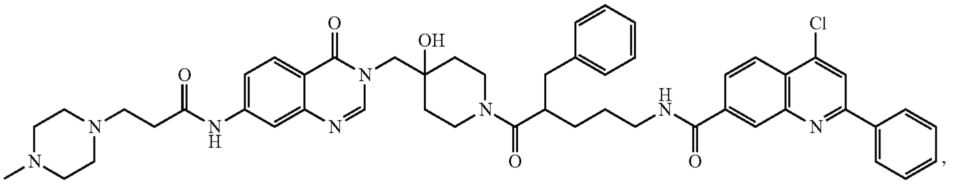
58
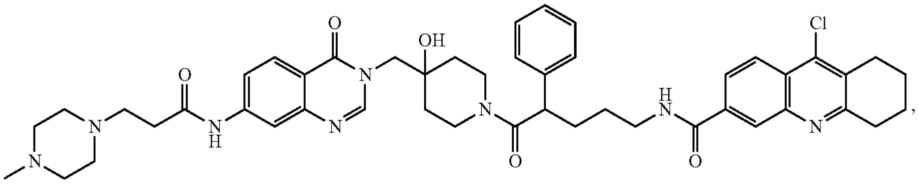
59
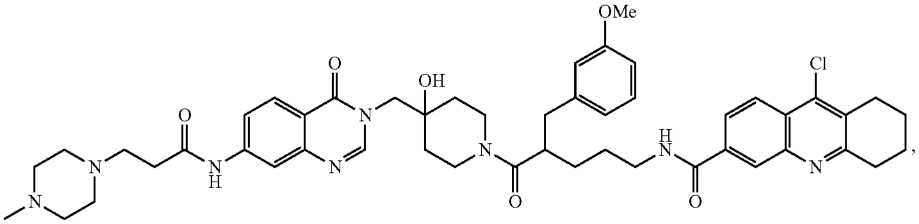
60
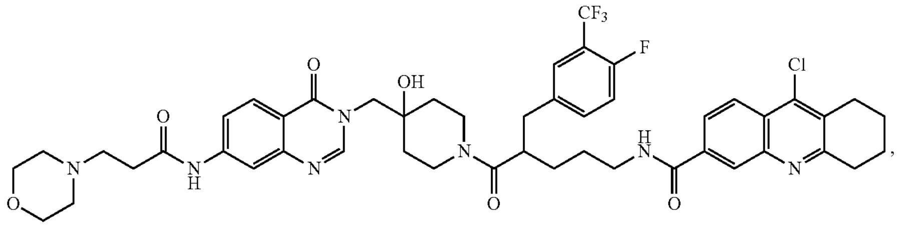
61
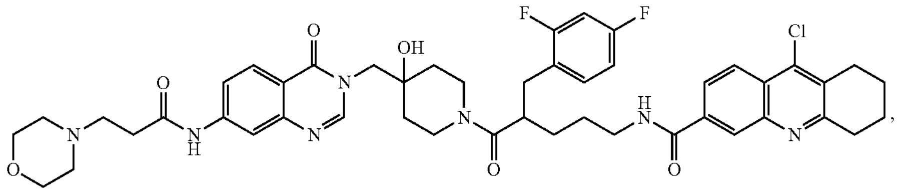
62
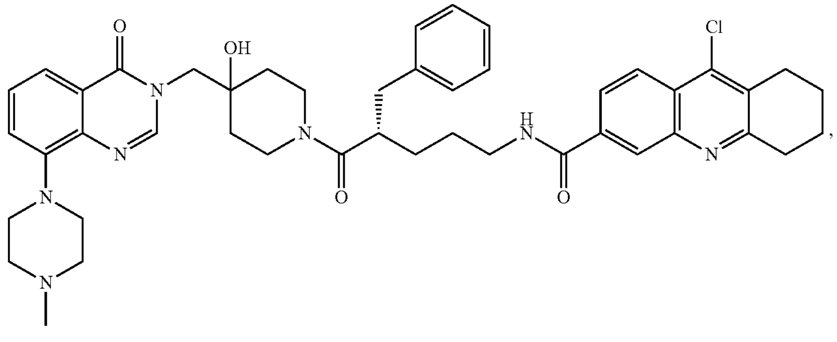
and -continued
| Compound | |
|---|---|
| 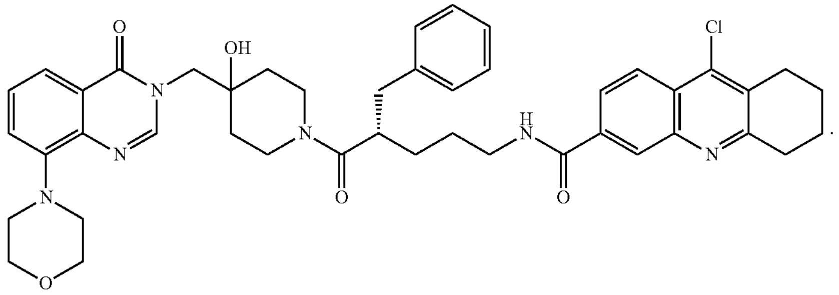 | 63 |
* * * * *

```
                         SEQUENCE LISTING


<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

gcttgtagat ggccatggcg                                              20


<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 2

tcctcagcat cttatccgag                                                20


<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

gcagtcacag cacatgacgg                                                20


<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

gtagtggtaa tctactggga                                                20
```